(12) United States Patent
Martin et al.

(10) Patent No.: US 6,472,404 B1
(45) Date of Patent: Oct. 29, 2002

(54) HIV PROTEASE INHIBITORS

(75) Inventors: Joseph Armstrong Martin, Harpenden (GB); Sally Redshaw, Hitchin (GB); Steven Swallow, Hitchin (GB); Gareth John Thomas, Welwyn (GB)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/999,082

(22) Filed: Nov. 20, 2001

(30) Foreign Application Priority Data

Nov. 22, 2000 (GB) .............................................. 0028483

(51) Int. Cl.$^7$ .................. A61K 31/472; C07D 217/02; C07D 401/12
(52) U.S. Cl. ........................ 514/307; 546/148; 546/145; 544/584; 544/61; 544/128; 544/355; 544/363; 544/406; 514/19; 514/227.8; 514/235.2; 514/249; 514/253
(58) Field of Search .............................. 514/307, 227.8, 514/235.2, 249, 253; 546/146, 145; 544/58.4, 61, 128, 355, 363, 406

(56) References Cited

FOREIGN PATENT DOCUMENTS

| EP | 432 695 | 6/1991 |
| EP | 604 185 A1 | 6/1994 |

OTHER PUBLICATIONS

Munroe, J.E. et al. : Potent, orally bioavailable HIV–1 protease inhibitors containing noncoded–D–amino acids. Bioorg. & Medic. Chem. Lett. vol. 5, pp. 2897–2902, 1995.*
Park, C. et al. : Beta–Methanesulfonyl–l–valine as a novel, unnatural amino acid surrogate for P2 in the design of HIV protease inhibitors. Bioorg. & Medic. Chem. Lett. vol. 6, pp. 585–588, 1996.*
Munroe et al., *Bioorganic & Medicinal Chem. Letters*, vol. 5, No. 23, pp. 2897–2902 (1995.
Park et al., *Bioorganic & Medicinal Chem. Letters*, vol. 6, pp. 585–588 (1996).
A. F. Abdel–Magid et al., *Tetrahedron Letters*, vol. 31(39), pp. 5595–5598 (1990).
Anwer Basha et al., *Tetrahedron Letters*, vol. 48, pp. 171–4174 (1977).
Kevin S. Webb, *Tetrahedron Letters*, vol. 35(21), pp. 3457–3460 (1994).
Norman M. Olken et al., *J.Med. Chem.*, vol. 35, p. 1137–1144 (1992).
Dawei Ma et al., *J. Am. Chem. Soc.*, vol. 120, pp. 12459–12467 (1998).
Gerald Pattenden et al., *J. Chem. Soc. Perkin Trans.*, vol. 1(10), pp. 1215–1221 (1992).
Edmund D. Matayoshi et al., *Science*, vol. 247, pp. 954–958 (1990).
A. H. Cook et al., *J. Chem. Soc.*, vol. 17(9), pp. 1022–1028 (1949).
N. Choy et al., *Organic Preprations & Procedures Int.*, vol. 28(2), pp. 173–177 (1996).
Pauwels, et al., *J. Virol. Methods*, vol. 20, pp. 309–321 (1988).
Abstract of EP 594,540.

\* cited by examiner

Primary Examiner—Charanjit S. Aulakh
(74) Attorney, Agent, or Firm—George W. Johnston; Dennis P. Tramaloni

(57) ABSTRACT

The present invention discloses novel isoquinoline carboxamide derivatives which are HIV protease inhibitors or prodrugs thereof, a process for their manufacture, pharmaceutical compositions and the use of such compounds in medicine. In particular, the compounds are hydroxyethylamine tripeptide mimetics which act as inhibitors of the HIV aspartyl protease, an essential enzyme in the replicative life cycle of HIV. Consequently, the compounds of this invention may be advantageously used in the treatment of HIV infection, either alone or in combination with other inhibitors of HIV viral replication or with pharmacoenhancers such as cytochrome P450 inhibitors.

17 Claims, No Drawings

HIV PROTEASE INHIBITORS

BACKGROUND OF THE INVENTION

The human immunodeficiency virus HIV is the causative agent of acquired immunodeficiency syndrome (AIDS), a disease characterised by the destruction of the immune system, particularly of the CD4+ T-cell, with attendant susceptibility to opportunistic infections. HIV infection is also associated with a precursor AIDs-related complex (ARC), a syndrome characterised by symptoms such as persistent generalised lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes. In particular, much effort has been directed towards the inhibition of HIV protease and the HIV protease inhibitors (PIs) saquinavir, ritonavir, nelfinavir, indinavir, amprenavir and lopinavir have been approved for treatment of HIV infections. Because of the emergence of resistant virus during monotherapy, current clinical practice is to use such protease inhibitors in combination therapy, typically with RT inhibitors.

The emergence of resistant virus can be attributed to errors introduced by the HIV reverse transcriptase, in conjunction with a high virus replication rate. It is likely that mutations that lead to resistant virus occur spontaneously but remain undetectable until initiation of therapy leads to a selective pressure for the emergence of virus with replicative advantage over the wildtype population. In the context of HIV protease inhibition, accumulation of mutations that lead to a reduction in inhibitor binding while maintaining sufficient substrate turnover can lead to drug resistance. Although the onset of drug resistance can be delayed to some extent by the use of combinations of drugs, there remains a need for more effective HIV protease inhibitors that retain activity against PI-resistant and multi-PI resistant viruses.

SUMMARY OF THE INVENTION

This invention is concerned with novel HIV protease inhibitors or prodrugs thereof, a process for their manufacture, pharmaceutical compositions and the use of such compounds in medicine. In particular, the compounds are hydroxyethylamine tripeptide mimetics which act as inhibitors of the HIV aspartyl protease, an essential enzyme in the replicative life cycle of HIV. Consequently, the compounds of this invention may be advantageously used in the treatment of HIV infection, either alone or in combination with other inhibitors of HIV viral replication or with pharmacoenhancers such as cytochrome P450 inhibitors. This object could be achieved with the novel compounds of the general formula I

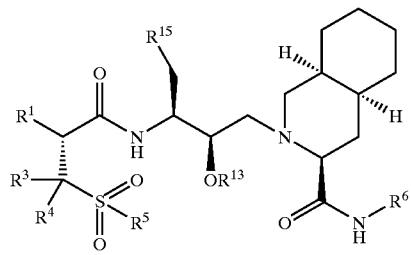

DETAILED DESCRIPTION OF THE INVENTION

The present invention comprises novel compounds of general formula I

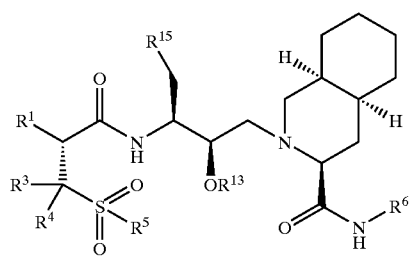

wherein $R^1$ is H, hydroxy or $NHR^2$ wherein $R^2$ is H, alkyl, alkenyl, alkynyl, arylalkyl, heterocyclylalkyl, cycloalkyl alkyl carbonyl, cycloalkyl carbonyl, aryl carbonyl, heterocyclyl carbonyl, heterocyclyl alkyl carbonyl, aryl alkyl carbonyl, alkyl oxy carbonyl, aryl alkyl oxy carbonyl, heterocyclyl alkyl oxy carbonyl, aryl heterocyclyl sulfonyl, alkyl sulfonyl, aryl sulfonyl, heterocyclyl sulfonyl or a group of the formula

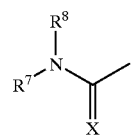

wherein X is O or S and
$R^7$ and $R^8$ independently are H, alkyl, aryl, heterocyclyl, aryl alkyl, heterocyclyl alkyl or $R^7$ and $R^8$ together with the nitrogen atom to which they are attached form a saturated ring optionally containing a further hetero atom or a group

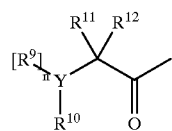

wherein when n=0, Y represents O or S and $R^{10}$ is H, alkyl, aryl alkyl, heterocyclyl alkyl, aryl, heterocyclyl or when n=1, Y represents N, $R^9$ is H or alkyl and $R^{10}$ H, alkyl, aryl alkyl, heterocyclyl alkyl, aryl, heterocyclyl or $R^9$ and $R^{10}$ taken together with the heteroatom to which they are attached form a heterocycle, $R^{11}$ and $R^{12}$ independently are H or alkyl or $R^{11}$ and $R^{12}$ taken together with the carbon atom to which they are attached form a cycle, $R^3$, $R^4$ independently are alkyl or taken together with the carbon atom to which they are attached form a carbocycle, $R^5$ is alkyl, aryl alkyl, heterocyclyl alkyl or $R^4$ and $R^5$ taken together with the carbon and sulfur atom to which they are attached form a heterocycle and $R^6$ is alkyl, aryl alkyl, heterocyclyl alkyl, alkyl oxy alkyl, hydroxy alkyl, amino alkyl, fluoro alkyl and $R^{13}$ is H or the residue of an inorganic or an organic ester and $R^{15}$ is aryl and pharmaceutically acceptable salts thereof, with the proviso that, if $R^3$, $R^4$ and $R^5$ are methyl, $R^6$ is tert.-butyl, $R^{13}$ is H and if $R^{15}$ is phenyl $R^2$ is not benzyl oxycarbonyl and not 2-quinoline carbonyl.

The term alkyl defines an optionally substituted straight or branched alkyl chain carrying 1 to 6 carbon atoms, preferably 1 to 4 carbon atoms.

The term alkenyl defines an optionally substituted straight or branched alkenyl chain carrying 2 to 6 carbon atoms, preferably 2 to 4 carbon atoms.

The term alkynyl defines an optionally substituted straight or branched alkynyl chain carrying 2 to 6 carbon atoms, preferably 2 to 4 carbon atoms.

Alkyl accordingly preferably stands for methyl, ethyl, n-propyl, i-propyl, n-butyl, i-butyl and tert.-butyl.

Alkenyl accordingly preferably is vinyl, 1-propenyl, 2-propenyl, i-propenyl, and butenyl and its isomers.

Alkynyl accordingly preferably is ethynyl, propynyl and its isomers, and butynyl and its isomers.

Suitable substituents of alkyl, alkenyl or alkynyl can be selected from one or more of aryl, heterocyclyl, carboxy, cyano, alkoxy, cycloalkyl oxy, aryl oxy, heterocyclyl oxy, hydroxy, alkyl carbonyl, cycloalkyl carbonyl, aryl carbonyl, heterocyclyl carbonyl, alkoxy carbonyl, cycloalkyl oxy carbonyl, aryl oxy carbonyl, heterocyclyl oxy carbonyl, amino carbonyl, alkyl amino carbonyl, dialkyl amino carbonyl, cycloalkyl amino carbonyl, aryl amino carbonyl, heterocyclyl amino carbonyl, amino, alkyl amino, dialkyl amino, alkenyl amino, alkynyl amino, cycloalkyl amino, aryl amino, heterocyclyl amino, alkyl carbonyl amino, dialkyl carbonyl amino, cycloalkyl carbonyl amino, aryl carbonyl amino, heterocyclyl carbonyl amino, alkoxy carbonyl amino, cycloalkyl oxy carbonyl amino, aryloxy carbonyl amino, heterocylyl oxy carbonyl amino, alkyl amino carbonyl amino, dialkyl amino carbonyl amino, cycloalkyl amino carbonyl amino, aryl amino carbonyl amino, heterocyclyl amino carbonyl amino alkyl sulfonyl amino, cycloalkyl sulfonyl amino, aryl sulfonyl amino, heterocyclyl sulfonyl amino, nitro, alkyl sulfonyl, cycloalkyl sulfonyl, aryl sulfonyl, heterocyclyl sulfonyl, thio, alkyl thio, cycloalkyl thio, aryl thio, heterocyclyl thio or halogen.

In all cases above where there are NH groups, the free hydrogen may also be substituted, preferably with lower alkyl.

Cycloalkyl has the meaning of an optionally substituted cycloalkyl group containing 3 to 8 carbon atoms, preferably 3 to 6 carbon atoms e.g. cyclopropyl, cyclobutyl, cyclopentyl, cyclohexyl, cycloheptyl and cyclooctyl or adamantyl which can also be benz-fused to an optionally substituted saturated, partially unsaturated or aromatic monocyclic, bicyclic or tricyclic heterocycle or carbocycle, e.g. to phenyl.

The term aryl denotes optionally substituted phenyl and naphthyl, both optionally benz-fused to an optionally substituted saturated, partially unsaturated or aromatic monocyclic, bicyclic or tricyclic heterocycle or carbocycle e.g. to cyclohexyl or cyclopentyl.

The term heterocyclyl stands for an optionally substituted saturated, partially unsaturated or aromatic monocyclic, bicyclic or tricyclic heterocycle which contains one or more hetero atoms selected from nitrogen, oxygen and sulfur which can also be benz-fused to an optionally substituted saturated, partially unsaturated or aromatic monocyclic, bicyclic or tricyclic carbocycle or heterocycle.

Examples of suitable heterocycles are oxazolyl, isoxazolyl, furyl, tetrahydrofuryl, 1,3-dioxolanyl, dihydropyranyl, thienyl, pyrazinyl, isothiazolyl, isoquinolinyl, indolyl, indazolyl, quinolinyl, dihydrooxazolyl, pyrimidinyl, benzofuranyl, tetrazolyl, pyrrolidinonyl, (N-oxide)-pyridinyl, pyrrolyl, triazolyl e.g. 1,2,4-triazolyl, pyrazolyl, benzotriazolyl, piperidinyl, morpholinyl, thiazolyl, pyridinyl, dihydrothiazolyl, imidazolidinyl, pyrazolinyl, benzothienyl, piperazinyl, imidazolyl, thiadiazolyl e.g. 1,2,3-thiadiazolyl, and benzothiazolyl.

Suitable substituents for cycloalkyl, aryl, heterocyclyl can be selected from those named for alkyl, in addition, however, alkyl, alkenyl and alkynyl are substituents to be added to the selection.

The term halogen stands for fluorine, chlorine, bromine and iodine.

The term residue of an inorganic ester stands for a sulfate of the formula —$SO_2OH$ or a phosphate of the formula —$PO(OH)_2$.

The term residue of an organic ester defines an acyl group as e.g. described in the European Patent Application EP A1 0 594 540 for group $R_1$.

Suitable residues of an organic ester are defined in $R^{13}$ as being a group of formula

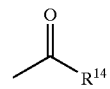

wherein $R^{14}$ is alkyl, alkenyl, cycloalkyl, aryl, aryl alkyl heterocyclyl, a group —$CH^2(CH_2CH_2O)_mCH_3$, wherein m is an integer from 0 to 10, or a carbonyl group-linked radical of an aminoacid.

With the exception that the alkyl and the alkenyl chain can carry up to 20 carbon atoms the meaning of the terms alkyl, alkenyl, cycloalkyl, aryl, heterocyclyl is the same as outlined above.

The term "carbonyl group-linked radical of an aminoacid" stands for a radical of a natural or unnatural amino acid selected from e.g. glycine, alanine, leucine, isoleucine, phenylalanine, lysine, methionine, threonine, tryptophan, valine, serine, glutamine, etc which is linked to the carbonyl group of

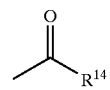

Any functional (i.e. reactive) group present in a side-chain may be protected, with the protecting group being a group which is known per se, for example, as described in "Protective Groups in Organic Synthesis", 2$^{nd}$ Ed., T. W. Greene and P. G. M. Wuts, John Wiley & Sons, New York, N.Y., 1991. For example, an amino group can be protected by a tert-butoxycarbonyl (BOC), formyl, trityl, benzyloxycarbonyl (Z), 9-fluorenylmethyloxcarbonyl (FMOC), trifluoroacetyl, 2-(biphenylyl)isopropoxycarbonyl or isobornyloxycarbonyl group or in the form of a phthalimido group; or a hydroxyl group can be protected by a tert-butyldimethylsilyl, tetrahydropyranyl, 4-methoxybenzyl, or benzyl or acetate etc; or a carboxyl group can be protected in the form of an ester, for example as a methyl or benzyl or tert. butyl ester. The protecting group may be retained in the final compound or optionally removed by techniques known in the art.

The compounds of this invention are characterized by a core structure with fixed stereochemistry as shown in general formula The residues $R^1$ to $R^{15}$ in compounds of this invention may contain one or more asymmetric carbon atoms and may therefore occur as single enantiomers, racemates and racemic mixtures, individual diastereomers and diastereomeric mixtures. Furthermore, where a compound of the invention contains an olefinic double bond, this can have the (E) or (Z) configuration. Also, each chiral centre may be of the R or S configuration. All such isomeric forms of these compounds are embraced by the present invention.

Compounds of formula (I) which are acidic can form pharmaceutically acceptable salts with bases such as alkali metal hydroxides, e.g. sodium hydroxide, potassium hydroxide and the like; alkaline earth metal hydroxides, e.g. calcium hydroxide, barium hydroxide, magnesium hydroxide and the like; with organic bases e.g. N-ethyl piperidine, dibenzylaminen and the like. Those compounds of formula (I) which are basic can form pharmaceutically acceptable salts with inorganic acids, e.g. hydrohalic acids such as hydrochloric acid and hydrobromic acid, sulphuric acid, nitric acid, phosphoric acid and the like; and with organic acids, e.g. acetic acid, tartaric acid, succinic acid, fumaric acid, maleic acid, malic acid, salicylic acid, citric acid, methanesulphonic acid, p-toluene sulphonic acid and the like. The formation and isolation of such salts can be carried out according to methods known in the art.

Preferred compounds of formula (I) are those having the formula

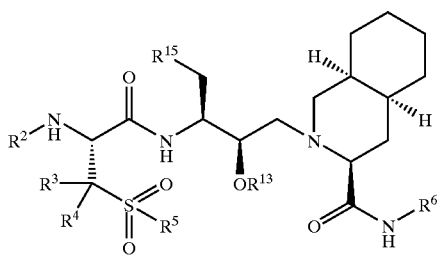

II wherein $R^2$, $R^3$, $R^4$, $R^5$, $R^6$, $R^{13}$ and $R^{15}$ are as above.

In a further preferred embodiment $R^3$, $R^4$ and $R^5$ have the meaning of methyl, $R^6$ has the meaning of tert-butyl or hydroxy tert-butyl and $R^{15}$ has the meaning of phenyl.

In a further preferred embodiment $R^2$ is alkyl carbonyl, cycloalkyl carbonyl, aryl carbonyl, heterocyclyl carbonyl, heterocyclyl alkyl carbonyl or a group of the formula

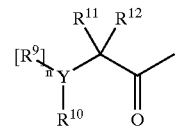

wherein when n=0, Y represents O or S and $R^{10}$ alkyl, aryl alkyl, heterocyclyl alkyl, aryl, heterocyclyl or when n=1, Y represents N, $R^9$ is H and $R^{10}$ is alkyl, aryl alkyl, heterocyclyl alkyl, aryl, heterocyclyl and wherein $R^{11}$ and $R^{12}$ independently are H.

Still further preferred are compounds wherein $R^3$, $R^4$ and $R^5$ are methyl, $R^6$ is tert-butyl, $R^{15}$ is phenyl and $R^2$ is alkyl carbonyl, cycloalkyl carbonyl, aryl carbonyl, heterocyclyl carbonyl, heterocyclyl alkyl carbonyl or a group of the formula

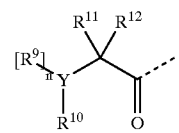

wherein when n=0, Y represents O or S and $R^{10}$ is alkyl, aryl alkyl, heterocyclyl alkyl, aryl, heterocyclyl or when n=1, Y represents N, $R^9$ is H and $R^{10}$ is alkyl, aryl alkyl, heterocyclyl alkyl, aryl, heterocyclyl and wherein $R^{11}$ and $R^{12}$ independently are H.

Still further preferred are compounds wherein $R^3$, $R^4$, $R^5$ are methyl, $R^6$ is tert-butyl, $R^{15}$ is phenyl and $R^2$ is aryl carbonyl, heterocyclyl carbonyl, or a group of the formula

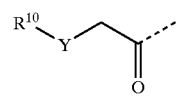

wherein Y represents O, NH, S, CH$_2$ and $R^{10}$ is aryl or heterocyclyl.

In a still further preferred embodiment $R^{13}$ has the meaning of H.

Examples of compounds of formula I or II with the meaning of $R^{13}$ is H are set out in table A below.

TABLE A

| Ex | Name | Structures |
|---|---|---|
| 1 | 2-[3(S)-[[N-Benzoyl-3-(methanesulfonyl)-L-valyl]amino]-2(R)-hydroxy-4-phenylbutyl]-N-benzyl-1,2,3,44a(S),5,6,7,8,8a(S)-decahydro-3(S)-isoquinolinecarboxamide | 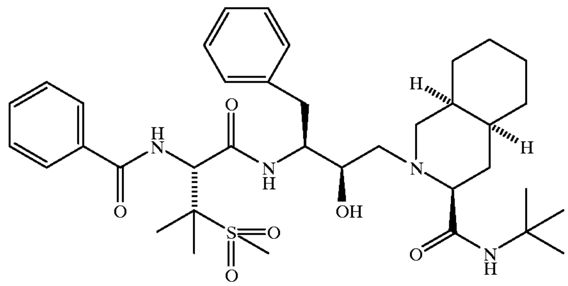 |
| 2 | N-tert-Butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 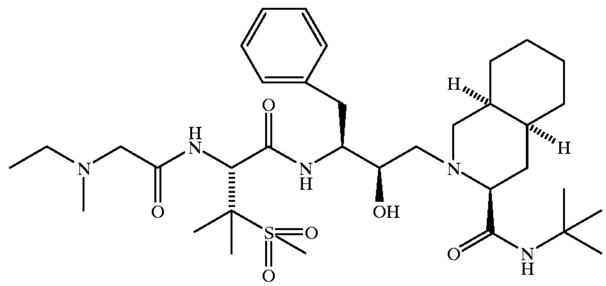 |
| 3 | N-tert-Butyl-1,2,3,4,4a(S),5,6,7,8,8a(S)-decahydro-2-[2(R)-hydroxy-3(S)-[[3-(methanesulfonyl)-N-[2-(3-pyridyloxy)acetyl]-L-valyl]amino]-4-phenylbutyl]-3(S)-isoquinolinecarboxamide | 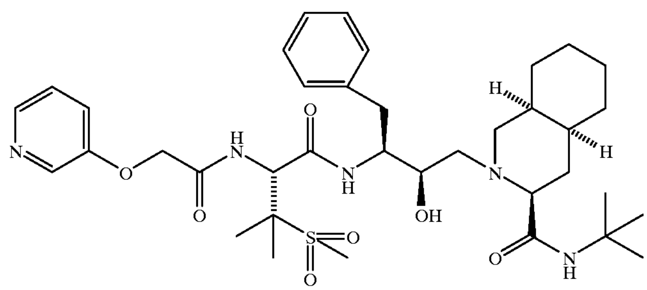 |
| 4 | N-tert-Butyl-1,2,3,4,4a(S),5,6,7,8,8a(S)-decahydro-2-[2(R)-hydroxy-3(S)-[[3-(methanesulfonyl)-N-(methoxycarbonyl)-L-valyl]amino]-4-phenylbutyl]-3(S)-isoquinlinecarboxamide | 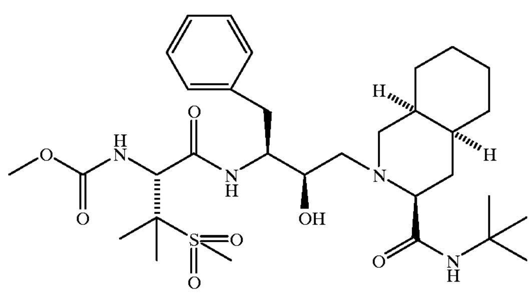 |
| 5 | 2-[3(S)-[[N,3-Bis(methanesulfonyl)-L-valyl]amino]-2(R)-hydroxy-4-phenylbutyl]-N-tert-butyl-1,2,3,4,4a(S),5,6,7,8a(S)-decahydro-3(S)-isoquinolinecarboxamide | 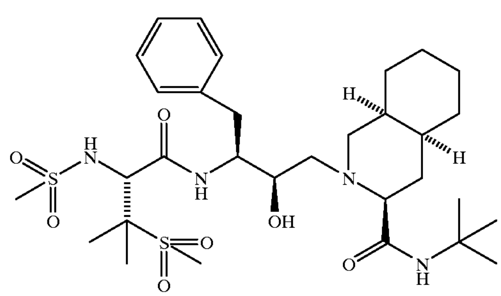 |

TABLE A-continued

| Ex | Name | Structures |
|---|---|---|
| 6 | 2-[3(S)-[[N-Acetyl-3-(methanesulfonyl)-L-valyl]amino]-2 (R)-hydroxy-4-phenylbutyl]-N-tert-butyl-1,2,3,4,4a(S),5,6,7,8,8a(S)-decahydro-3(S)-isoquinolinecarboxamide | 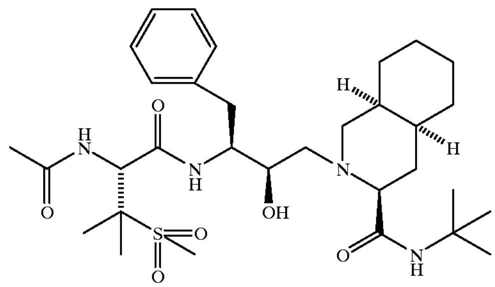 |
| 7 | N-tert-Butyl-1,2,3,4,4a(S),5,6,7,8,8a(S)-decahydro-2-[2(R)-hydroxy-3(S)-[[3-(methanesulfonyl)-N-[(3-pyridyl)carbonyl]-L-valyl]amino]-4-phenylbutyl]-3(S)-isoquinolinecarboxamide | 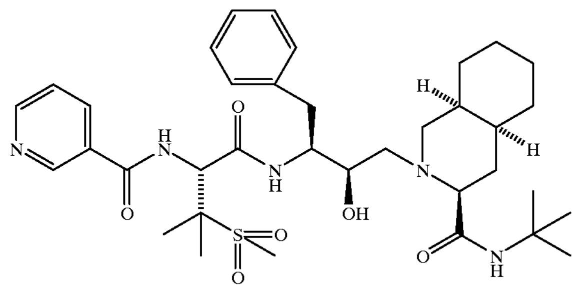 |
| 8 | N-tert-Butyl-1,2,3,4,4a(S),5,6,7,8,8a(S)-decahydro-2-[2(R)-hydroxy-3(S)-[[3-(methanesulfonyl)-N-propionyl-L-valyl]amino]-4-phenylbutyl]-3(S)-isoquinolinecarboxamide | 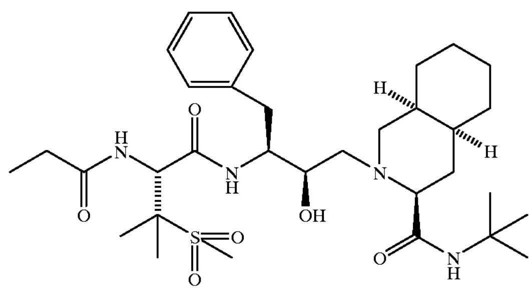 |
| 9 | 2-[3(S)-[[N-Butyryl-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 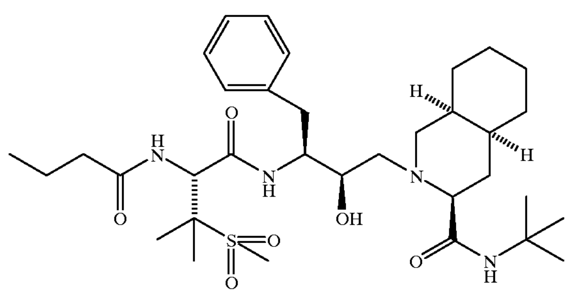 |
| 10 | N-tert-Butyl-1,2,3,4,4a(S),5,6,7,8,8a(S)-decahydro-2-[2(R)-hydroxy-3(S)-[[N-isobutyryl-3-(methanesulfonyl)-L-valyl]amino]-4-phenylbutyl]-3(S)-isoquinolinecarboxamide | 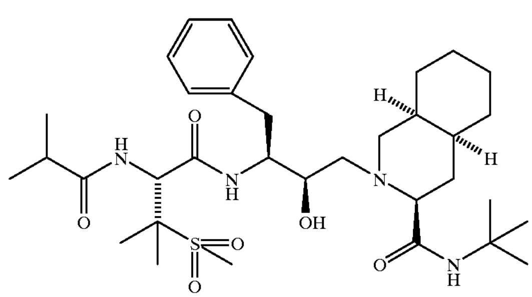 |

TABLE A-continued

| Ex | Name | Structures |
|---|---|---|
| 11 | 2-[3(S)-[[N-Benzoyl-3-(ethanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 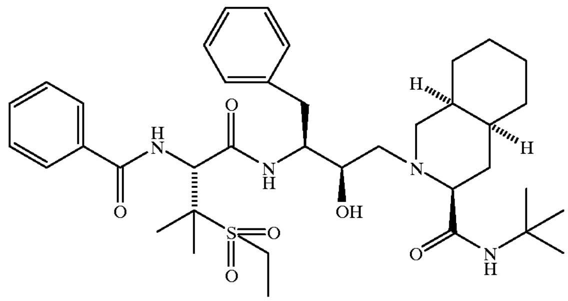 |
| 12 | 2-[3(S)-[[N-Acetyl-3-(ethanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 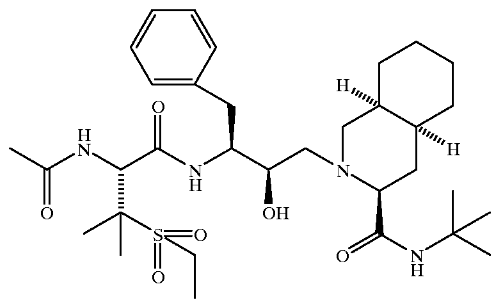 |
| 13 | N-tert-Butyl-1,2,3,4,4a(S),5,6,7,8,8a(S)-decahydro-2-[2(R)-hydroxy-3(S)-[[3-(methanesulfonyl)-N-(2-thenoyl)-L-valyl]amino]-4-phenylbutyl]-3(S)-isoquinolinecarboxamide | 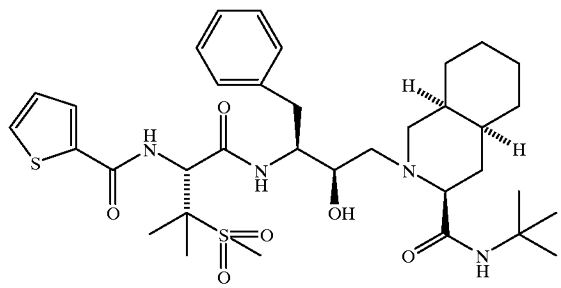 |
| 14 | N-tert-Butyl-1,2,3,4,4a(S),5,6,7,8,8a(S)-decahydro-2-[2(R)-hydroxy-3(S)-[[3-(methanesulfonyl)-N-(2-phenoxyacetyl)-L-valyl]amino]-4-phenylbutyl]-3(S)-isoquinolinecarboxamide | 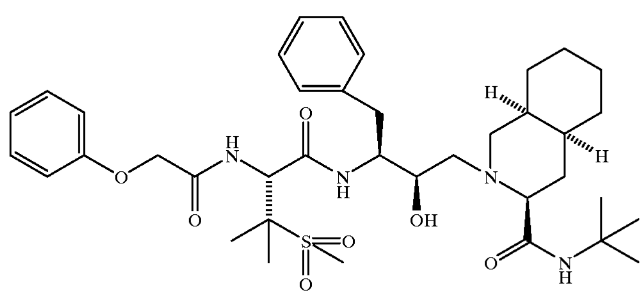 |
| 15 | N-tert-Butyl-1,2,3,4,4a(S),5,6,7,8,8a(S)-decahydro-2-[2(R)-hydroxy-3(S)-[[3-(methanesulfonyl)-N-[(2-pyrazinyl)carbonyl]-valyl]amino]-4-phenylbutyl]-3(S)-isoquinolinecarboxamide | 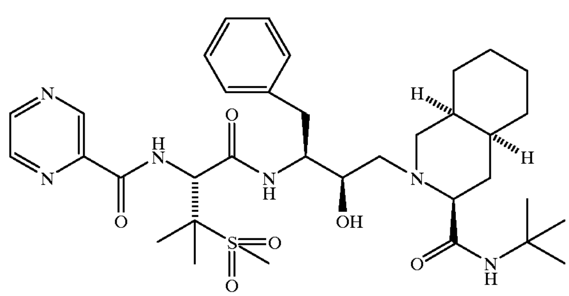 |

TABLE A-continued

| Ex | Name | Structures |
|----|------|------------|
| 16 | N-tert-Butyl-2-[3(S)-[[N-[(6-chloro-3-pyridyl)carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 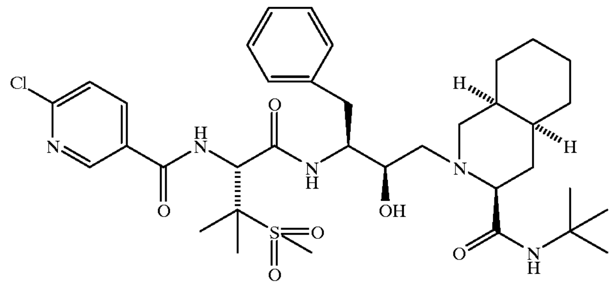 |
| 17 | N-tert-Butyl-1,2,3,4,4a(S),5,6,7,8,8a(S)-decahydro-2-[2(R)-hydroxy-3(S)-[[N-[(1-hydroxy-1-cyclopropyl)carbonyl]-3-(methanesulfonyl)-L-valyl]amino]-4-phenylbutyl]-3(S)-isoquinolinecarboxamide | 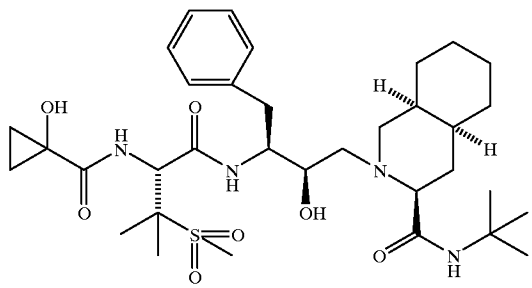 |
| 18 | N-tert-Butyl-1,2,3,4,4a(S),5,6,7,8,8a(S)-decahydro-2-[2(R)-hydroxy-3(S)-[[3-(methanesulfonyl)-N-[(1,2,3-thiadiazol-4-yl)carbonyl]-L-valyl]amino]-4-phenylbutyl]-3(S)-isoquinolinecarboxamide | 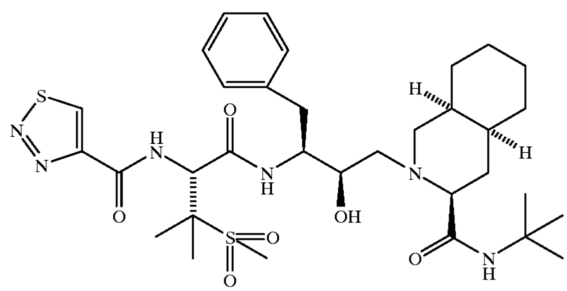 |
| 19 | N-tert-Butyl-2-[3(S)-[[N-(5-chloro-2-furoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 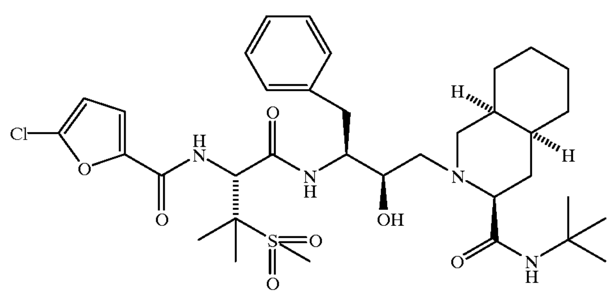 |
| 20 | N-tert-Butyl-1,2,3,4,4a(S),5,6,7,8,8a(S)-decahydro-2-[2(R)-hydroxy-3(S)-[[3-(methanesulfonyl)-N-[(5-isoxazolyl)carbonyl]-L-valyl]amino]-4-phenylbutyl]-3(S)-isoquinolinecarboxamide | 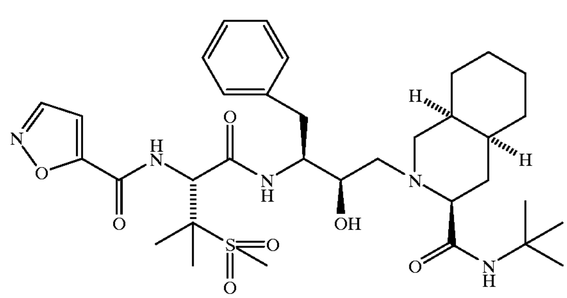 |

TABLE A-continued

| Ex | Name | Structures |
|---|---|---|
| 21 | N-tert-Butyl-1,2,3,4,4a(S),5,6,7,8,8a(S)-decahydro-2-[2(R)-hydroxy-3(S)-[[3-(methanesulfonyl)-N-[(3-methyl-4-isoxazolyl)carbonyl]-L-valyl]amino]-4-phenylbutyl]-3(S)-isoquinolinecarboxamide | 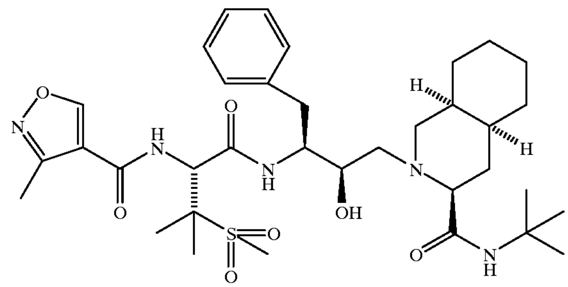 |
| 22 | N-tert-Butyl-1,2,3,4,4a(S),5,6,7,8,8a(S)-decahydro-2-[2(R)-hydroxy-3(S)-[[3-(methanesulfonyl)-N-[(5-methyl-3-isoxazolyl)carbonyl]-L-valyl]amino]-4-phenylbutyl]-3(S)-isoquinolinecarboxamide | 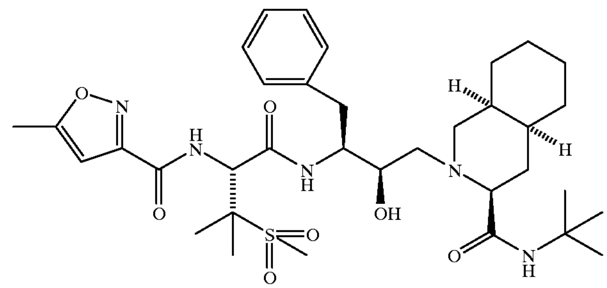 |
| 23 | N-tert-Butyl-1,2,3,4,4a(S),5,6,7,8,8a(S)-decahydro-2-[2(R)-hydroxy-3(S)-[[N-(2-hydroxy-2-ethylbutyryl)-3-(methanesulfonyl)-L-valyl]amino]-4-phenylbutyl]-3(S)-isoquinolinecarboxamide | 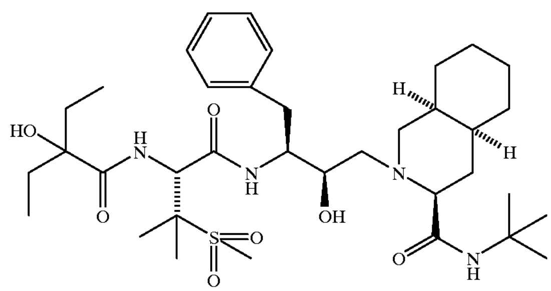 |
| 24 | N-tert-Butyl-1,2,3,4,4a(S),5,6,7,8,8a(S)-decahydro-2-[2(R)-hydroxy-3(S)-[[3-(methanesulfonyl)-N-(2-methoxyacetyl))-L-valyl]amino]-4-phenylbutyl]-3-(S)-isoquinolinecarboxamide | 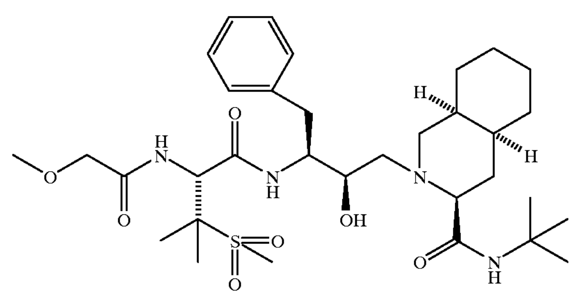 |
| 25 | N-tert-Butyl-2-[3(S)-[[N-(2-ethoxyacetyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 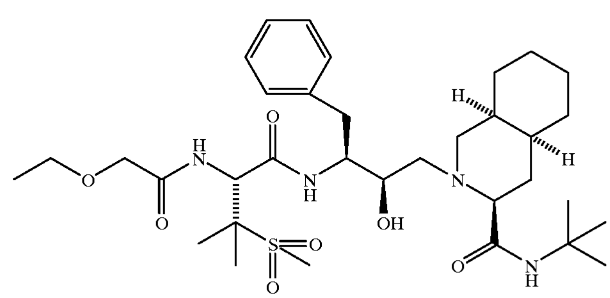 |

TABLE A-continued

| Ex | Name | Structures |
|---|---|---|
| 26 | N-tert-Butyl-1,2,3,4,4a(S),5,6,7,8,8a(S)-decahydro-2-[2(R)-hydroxy-3(S)-[[N-(2-hydroxyacetyl)-3-(methanesulfonyl)-L-valyl]amino]-4-phenylbutyl]-3(S)-isoquinolinecarboxamide | 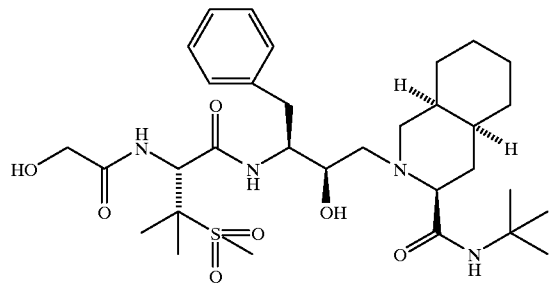 |
| 27 | N-tert-Butyl-1,2,3,4,4a(S),5,6,7,8,8a(S)-decahydro-2-[2(R)-hydroxy-3(S)-[[N-(2-hydroxy-2-methylpropionyl)-3-(methanesulfonyl)-L-valyl]amino]-4-phenylbutyl]-3(S)-isoquinolinecarboxamide | 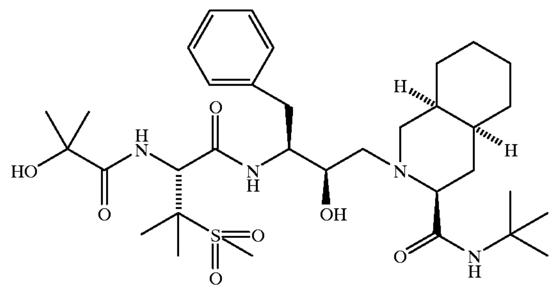 |
| 28 | N-tert-Butyl-2-[3(S)-[[N-(3-furoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 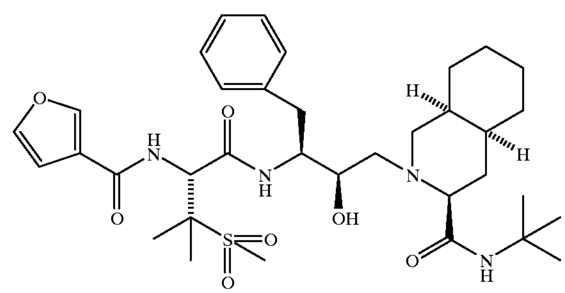 |
| 29 | N-tert-Butyl-1,2,3,4,4a(S),5,6,7,8,8a(S)-decahydro-2-[2(R)-hydroxy-3(S)-[[3-(methanesulfonyl)-N-[(4-pyridyl)carbonyl]-L-valyl]amino]-4-phenylbutyl]-3(S)-isoquinolinecarboxamide | 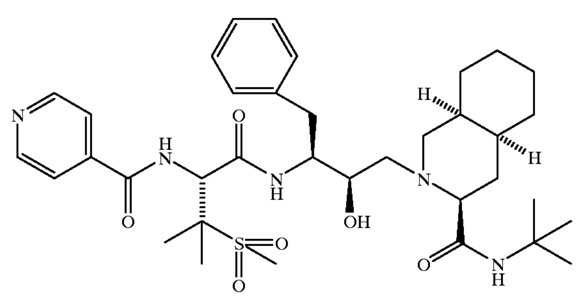 |
| 30 | N-tert-Butyl-1,2,3,4,4a(S),5,6,7,8,8a(S)-decahydro-2-[2(R)-hydroxy-3(S)-[[N-(2(S)-hydroxypropionyl)-3-(methanesulfonyl)-L-valyl]amino]-4-phenylbutyl]-3(S)-isoquinolinecarboxamide | 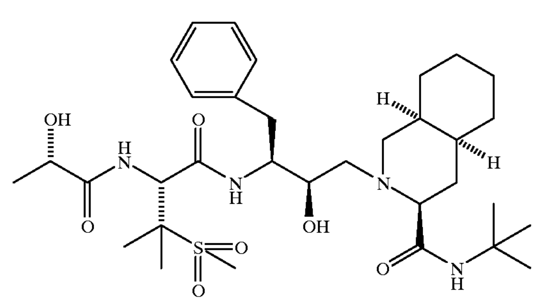 |

TABLE A-continued

| Ex | Name | Structures |
|---|---|---|
| 31 | N-tert-Butyl-1,2,3,4,4a(S),5,6,7,8,8a(S)-decahydro-2-[2(R)-hydroxy-3(S)-[[N-(2(R)-hydroxypropionyl)-3-(methanesulfonyl)-L-valyl]amino]-4-phenylbutyl]-3(S)-isoquinolinecarboxamide | 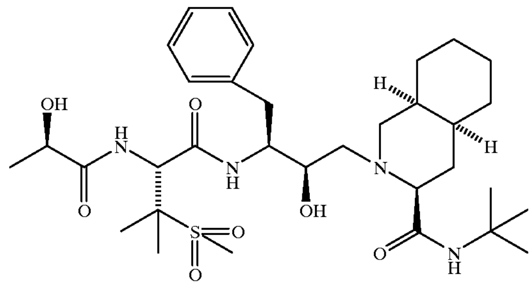 |
| 32 | 2-[3(S)-[[N-(5-Bromo-2-furoyl)-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 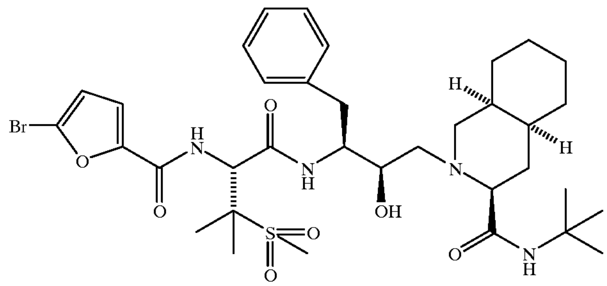 |
| 33 | N-tert-Butyl-1,2,3,4,4a(S),5,6,7,8,8a(S)-decahydro-2-[2(R)-hydroxy-3(S)-[[3-(methanesulfonyl)-N-(4,5-dimethyl-2-furoyl)-L-valyl]amino]-4-phenylbutyl]-3(S)-isoquinolinecarboxamide | 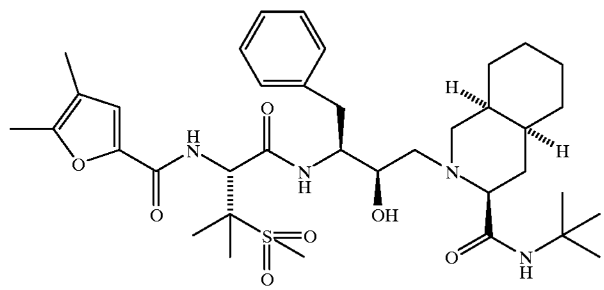 |
| 34 | N-tert-Butyl-2-[3(S)-[[N-[5-(trifluoromethyl)-2-furoyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 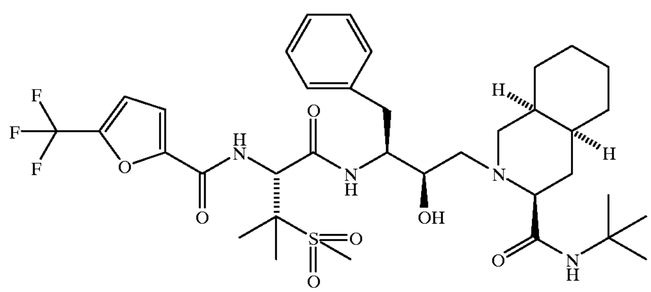 |
| 35 | N-tert-Butyl-1,2,3,4,4a(S),5,6,7,8,8a(S)-decahydro-2-[2(R)-hydroxy-3(S)-[[3-(methanesulfonyl)-N-(5-methyl-2-theonyl)-L-valyl]amino]-4-phenylbutyl]-3(S)-isoquinolinecarboxamide | 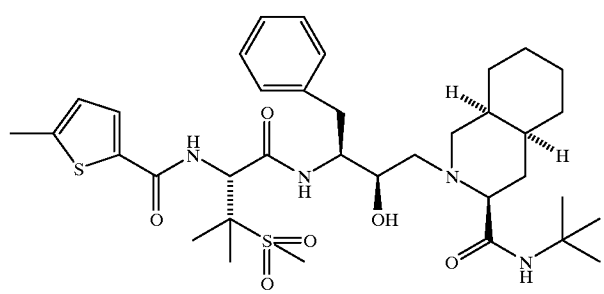 |

TABLE A-continued

| Ex | Name | Structures |
|---|---|---|
| 36 | N-tert-Butyl-2-[3(S)-[[N-(5-chloro-2-thenoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 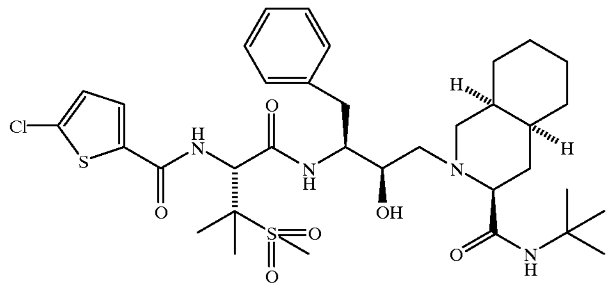 |
| 37 | 2-[3(S)-[[N-(5-Acetyl-2-thenoyl)-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 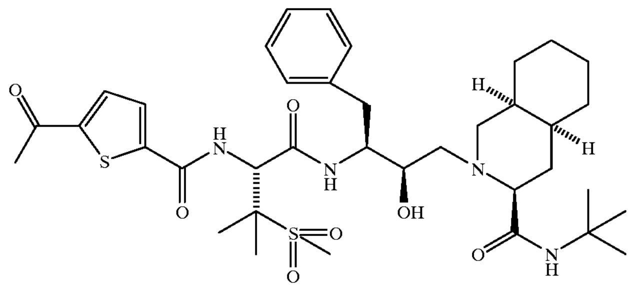 |
| 38 | N-tert-Butyl-2-[3(S)-[[N-(5-tert-butyl-2-thenoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 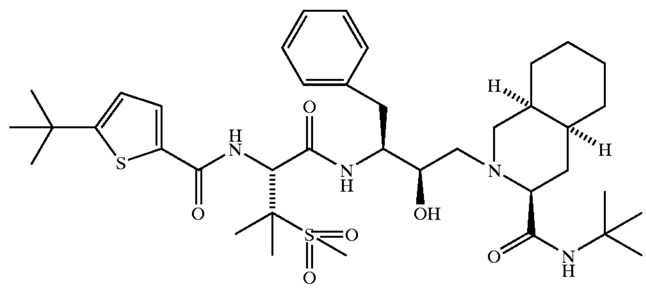 |
| 39 | N-tert-Butyl-2-[3(S)-[[N-(3-cyanobenzoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 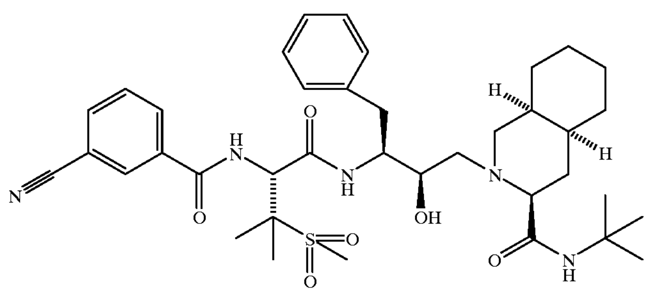 |
| 40 | N-tert-Butyl-2-[3(S)-[[N-(3-fluorobenzoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 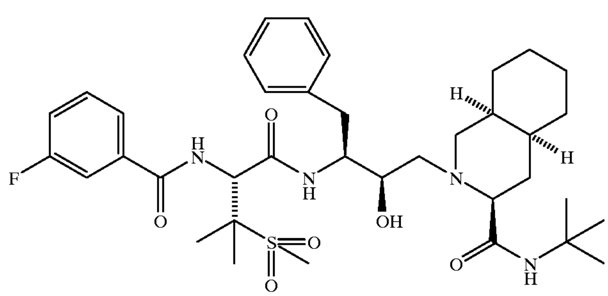 |

TABLE A-continued

| Ex | Name | Structures |
|----|------|------------|
| 41 | N-tert-Butyl-2-[3(S)-[[N-(4-cyanobenzoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 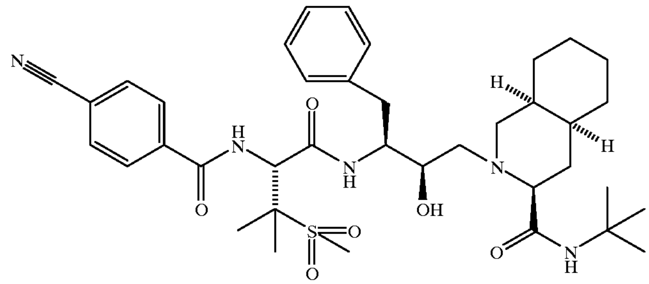 |
| 42 | N-tert-Butyl-2-[3(S)-[[N-(4-fluorobenzyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 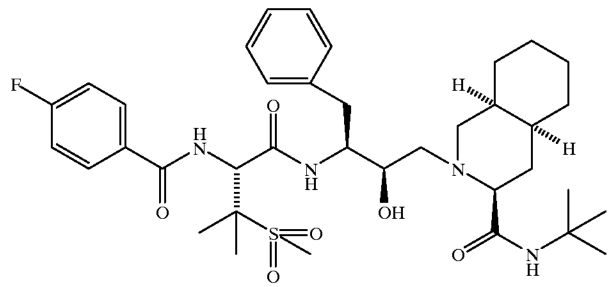 |
| 43 | N-tert-Butyl-2-[3(S)-[[N-[[6-(trifluoromethyl)-3-pyridyl]carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 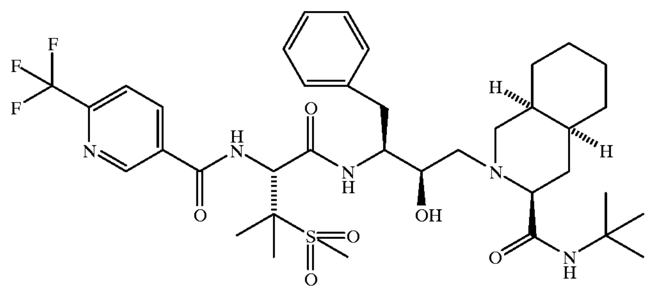 |
| 44 | N-tert-Butyl-2-[3(S)-[[N-[(6-cyano-3-pyridyl)carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 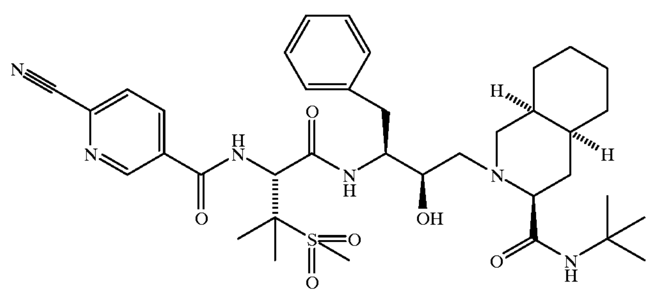 |
| 45 | N-tert-Butyl-1,2,3,4,4a(S),5,6,7,8,8a(S)-decahydro-2-[2(R)-hydroxy-3(S)-[[3-(methanesulfonyl)-N-[(1,5-dimethyl-3-pyrazolyl)carbonyl]-L-valyl]amino]-4-phenylbutyl]-3(S)-isoquinolinecarboxamide | 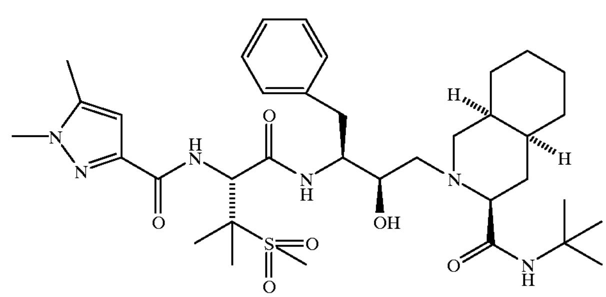 |

TABLE A-continued

| Ex | Name | Structures |
|---|---|---|
| 46 | N-tert-Butyl-2-[3(S)-[[N-[(1-tert-butyl-5-methyl-3-pyrazolyl)carbonyl]3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 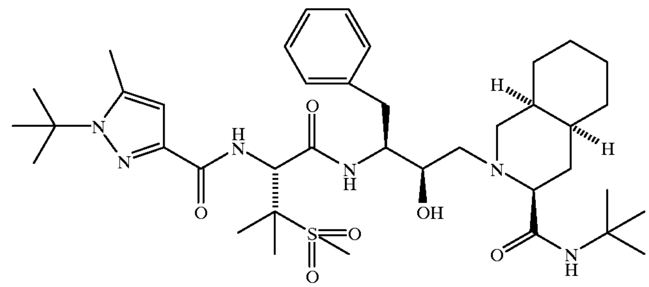 |
| 47 | N-tert-Butyl-2-[3(S)-[[N-(cyclopropylcarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 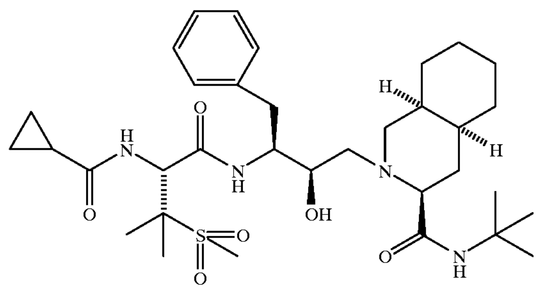 |
| 48 | N-tert-Butyl-2-[3(S)-[[N-(cyclobutylcarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 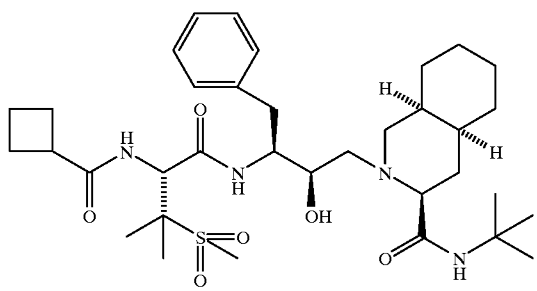 |
| 49 | N-tert-Butyl-2-[3(S)-[[N-(cydohexylcarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 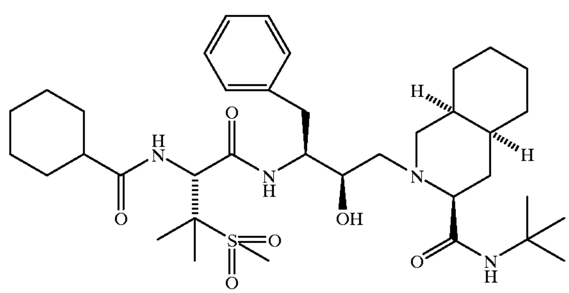 |
| 50 | N-tert-Butyl-1,2,3,4,4a(S),5,6,7,8,8a(S)-decahydro-2-[3(S)-[[N-(tetrahydro-3(RS)-furoyl)-3-(methanesulfonyl)-L-valyl]amino]-2(R)-hydroxy-4-phenylbutyl]-3(S)-isoquinolinecarboxamide(1:1 mixture of diastereoisomers) | 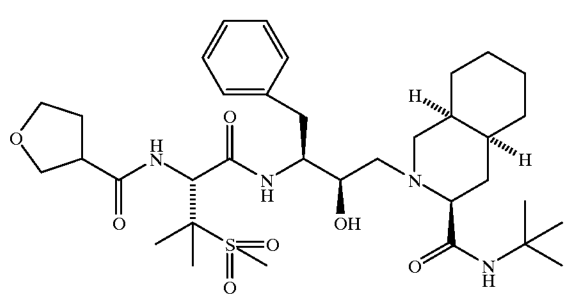 |

TABLE A-continued

| Ex | Name | Structures |
|---|---|---|
| 51 | N-tert-Butyl-2-[N-[(2-chloro-6-methyl-4-pyridyl)carbonyl]-3(S)-[[3-(methanesulfonyl)-L-valyl) amino]-2(R)-hydroxy-4-phenylbutyl]-1,2,3,4,4a(S),5,6,7,8,8a(S)-decahydro-3(S)-isoquinolinecarboxamide | 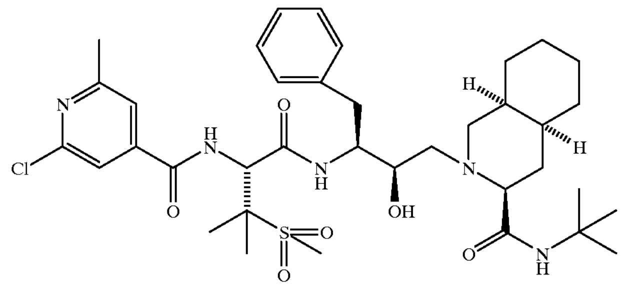 |
| 52 | N-tert-Butyl-2-[3(S)-[[N-[(2-chloro-4-pyridyl)carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 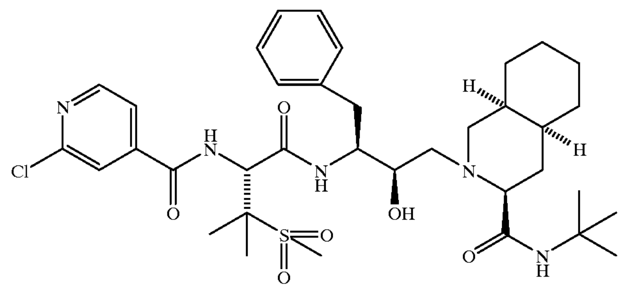 |
| 53 | N-tert-Butyl-2-[[N-(2-furoyl)-3(S)-[[3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 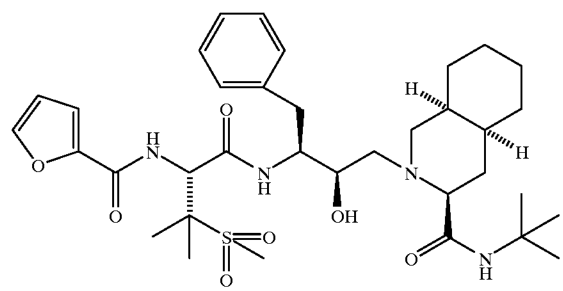 |
| 54 | N-tert-Butyl-1,2,3,4,4a(S),5,6,7,8,8a(S)-decahydro-2-[2(R)-hydroxy-3(S)-[[3-(methanesulfonyl)-N-(3-methylbenzoyl)-L-valyl]amino]-4-phenylbutyl]-3(S)-isoquinolinecarboxamide | 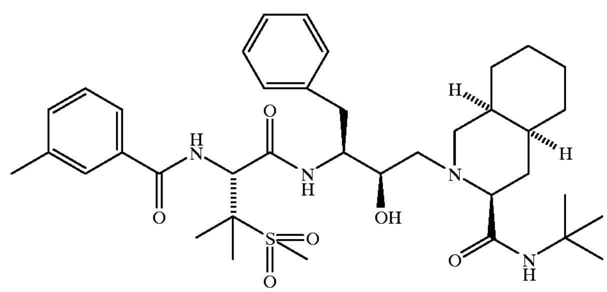 |
| 55 | N-tert-Butyl-1,2,3,4,4a(S),5,6,7,8,8a(S)-decahydro-2-[2(R)-hydroxy-3(S)-[[3-(methanesulfonyl)-N-(3-methylbenzoyl)-L-valyl]amino]-4-phenylbutyl]-3(S)-isoquinolinecarboxamide | 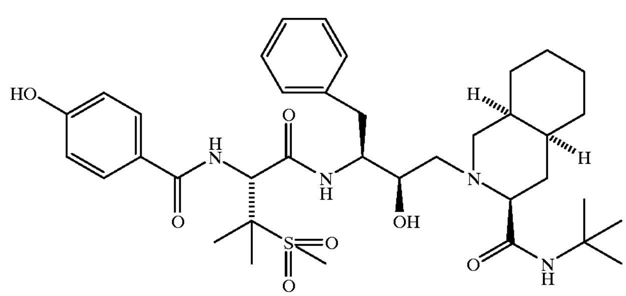 |

TABLE A-continued

| Ex | Name | Structures |
|---|---|---|
| 56 | N-tert-Butyl-1,2,3,4,4a(S),5,6,7,8,8a(S)-decahydro-2-[2(R)-hydroxy-3(S)-[[3-(methanesulfonyl)-N-(3-methylbenzoyl)-L-valyl]amino]-4-phenylbutyl]-3(S)-isoquinolinecarboxamide | 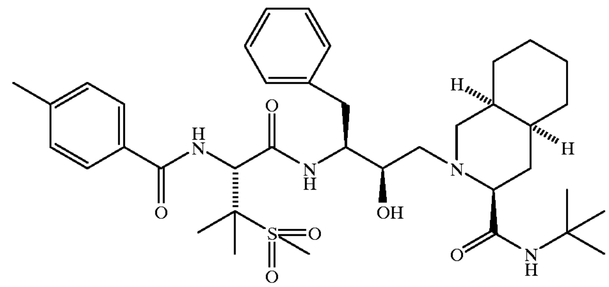 |
| 57 | N-tert-Butyl-1,2,3,4,4a(S),5,6,7,8,8a(S)-decahydro-2-[2(R)-hydroxy-3(S)-[[3-(methanesulfonyl)-N-[(5-methyl-3-pyridyl)carbonyl]-L-valyl]amino]-4-phenylbutyl]-3(S)-isoquinolinecarboxamide | 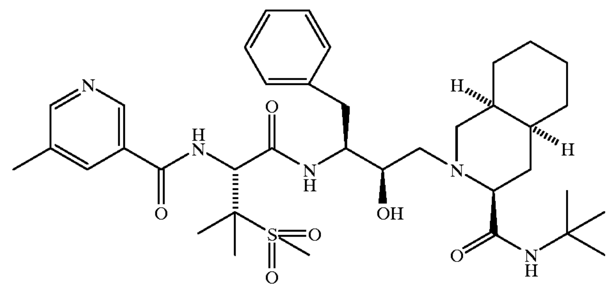 |
| 58 | N-tert-Butyl-2-[3(S)-[[N-(cyclopentylcarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 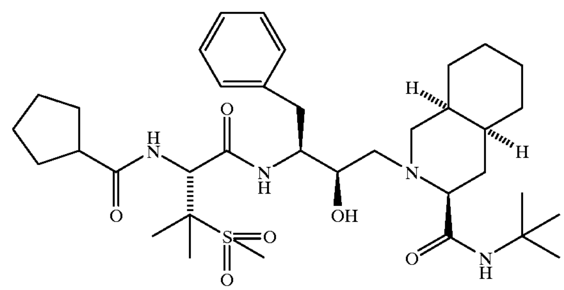 |
| 59 | N-tert-Butyl-1,2,3,4,4a(S),5,6,7,8,8a(S)-decahydro-2-[2(R)-hydroxy-3(S)-[[3-(methanesulfonyl)-N-[(2,5-dimethyl-3-pyrazolyl)carbonyl]-L-valyl]amino]-4-phenylbutyl]-3(S)-isoquinolinecarboxamide | 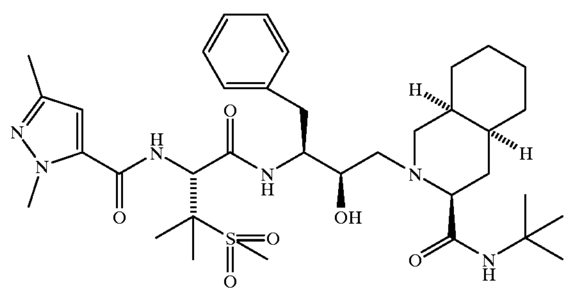 |
| 60 | N-tert-Butyl-1,2,3,4,4a(S),5,6,7,8,8a(S)-decahydro-2-[2(R)-hydroxy-3(S)-[[3-(methanesulfonyl)-N-pivaloyl-L-valyl]amino]-4-phenylbutyl]-3(S)-isoquinolinecarboxamide | 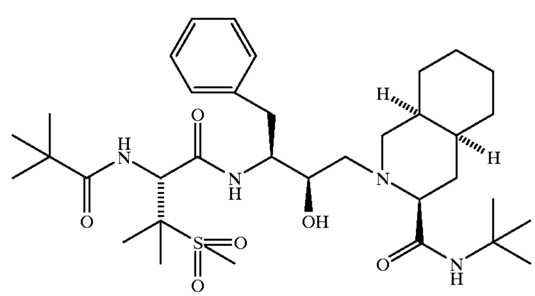 |

TABLE A-continued

| Ex | Name | Structures |
|---|---|---|
| 61 | N-tert-Butyl-1,2,3,4,4a(S),5,6,7,8,8a(S)-decahydro-2-[2(R)-hydroxy-3(S)-[[3-(methanesulfonyl)-N-[(4-methyl-2-thiazolyl)carbonyl]-L-valyl]amino]-4-phenylbutyl]-3(S)-isoquinolinecarboxamide | 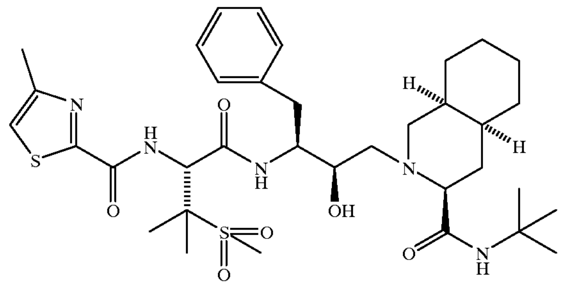 |
| 62 | N-tert-Butyl-1,2,3,4,4a(S),5,6,7,8,8a(S)-decahydro-2-[2(R)-hydroxy-3(S)-[[3-(methanesulfonyl)-3-methyl-N-[2-(1-pyrrolyl)acetyl]-L-valyl]amino]-4-phenylbutyl]-3(S)-isoquinolinecarboxamide | 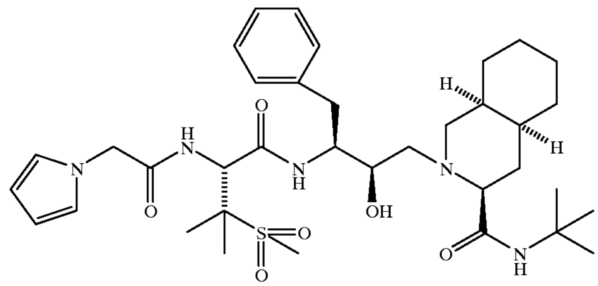 |
| 63 | N-tert-Butyl-2-[3(S)-[[N-[2-(diethylamino) acetyl]-3-(methanesulfonyl)-3-methyl-L-valyl]amino]-2(R)-hydroxy-4-phenylbutyl]-1,2,3,4,4a(S),5,6,7,8,8a(S)-decahydro3(S)-isoquinolinecarboxamide | 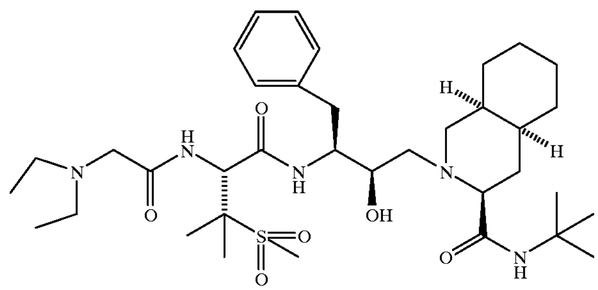 |
| 64 | N-tert-Butyl-1,2,3,4,4a(S),5,6,7,8,8a(S)-decahydro-2-[2(R)-hydroxy-3(S)-[[3-(methanesulfonyl)-3-methyl-N-[2-(1-pyrazolyl)acetyl]-L-valyl]amino]-4-phenylbutyl]-3(S)-isoquinolinecarboxamide | 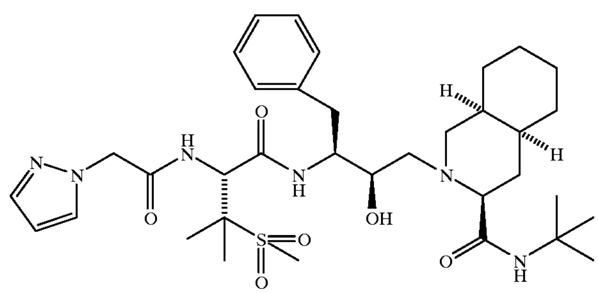 |
| 65 | N-tert-Butyl-1,2,3,4,4a(S),5,6,7,8,8a(S)-decahydro-2-[2(R)-hydroxy-3(S)-[[N-[2-(1-imidazolyl)acetyl]-3-(methanesulfonyl)-3-methyl-L-valyl]amino]-4-phenylbutyl]-3(S)-isoquinolinecarboxamide | 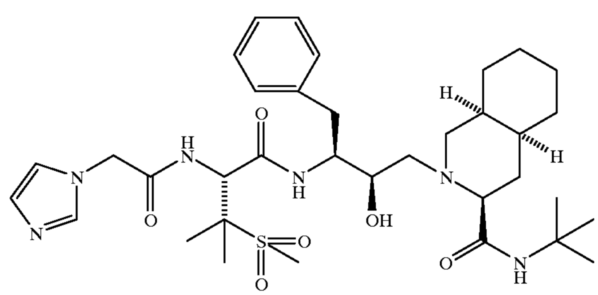 |

TABLE A-continued

| Ex | Name | Structures |
|---|---|---|
| 66 | N-tert-Butyl-1,2,3,4,4a(S),5,6,7,8,8a(S)-decahydro-2-[2(R)-hydroxy-3(S)-[[3-(methanesulfonyl)-N-[2-(1-pyrrolidinyl)acetyl]-L-valyl]amino]-4-phenylbutyl-3(S)-isoquinolinecarboxamide | 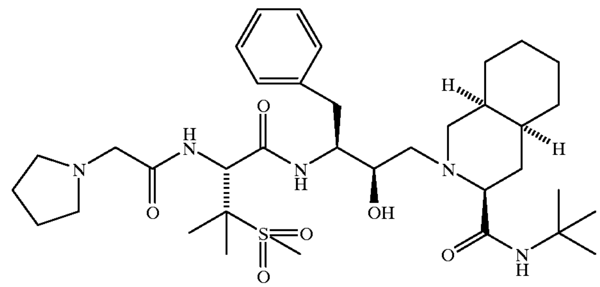 |
| 67 | N-tert-Butyl-1,2,3,4,4a(S),5,6,7,8,8a(S)-decahydro-2-[2(R)-hydroxy-3(S)-[[3-(methanesulfonyl)-N-(2-morpholinoacetyl)-L-valyl]amino]-4-phenylbutyl]-3(S)-isoquinolinecarboxamide | 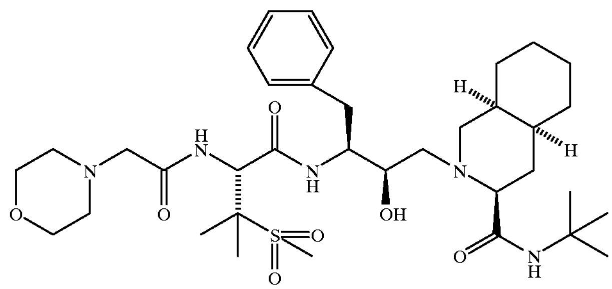 |
| 68 | N-tert-Butyl-1,2,3,4,4a(S),5,6,7,8,8a(S)-decahydro-2-[2(R)-hydroxy-3(S)-[[3-(methanesulfonyl)-N-(3-thenoyl)-L-valyl]amino]-4-phenylbutyl]-3(S)-isoquinolinecarboxamide | 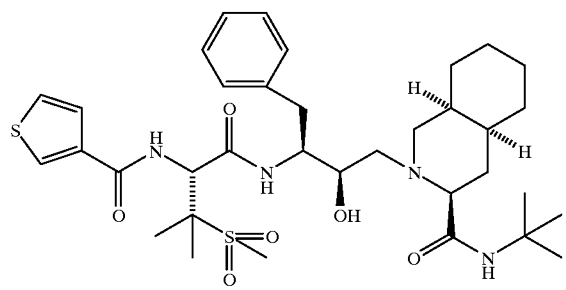 |
| 69 | N-tert-Butyl-1,2,3,4,4a(S),5,6,7,8,8a(S)-decahydro-2-[2(R)-hydroxy-3(S)-[[3-(methanesulfonyl)-N-[(5-thiazolyl)carbonyl]-L-valyl]amino]-4-phenylbutyl]-3(S)-isoquinolinecarboxamide | 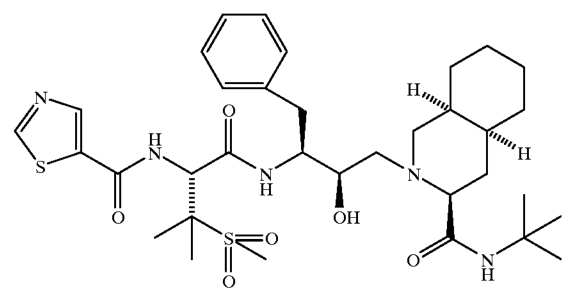 |
| 70 | N-tert-Butyl-1,2,3,4,4a(S),5,6,7,8,8a(S)-decahydro-2-[2(R)-hydroxy-3(S)-[[3-(methanesulfonyl)-N-[(6-methyl-3-pyridyl)carbonyl]-L-valyl]amino]-4-phenylbutyl]-3(S)-isoquinolinecarboxamide | 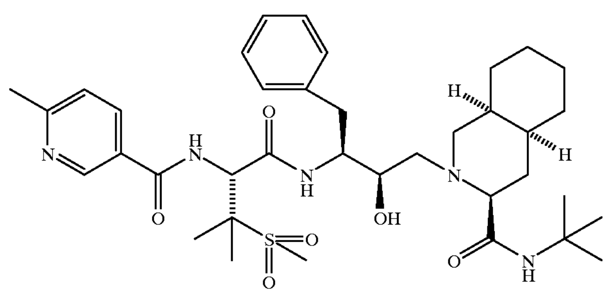 |

TABLE A-continued

| Ex | Name | Structures |
|---|---|---|
| 71 | N-tert-Butyl-1,2,3,4,4a(S),5,6,7,8,8a(S)-decahydro-2-[2(R)-hydroxy-3(S)-[[3-(methanesulfonyl)-N-[N-methyl-N-phenylglycyl]-L-valyl]amino]-4-phenylbutyl]-3(S)-isoquinolinecarboxamide | 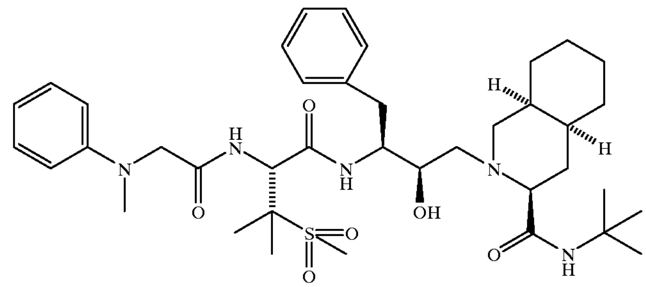 |
| 72 | N-tert-Butyl-1,2,3,4,4a(S),5,6,7,8,8a(S)-decahydro-2-[2(R)-hydroxy-3(S)-[[N-(2-isopropoxyacetyl)-3-(methanesulfonyl)-L-valyl]amino]-4-phenylbutyl]-3(S)-isoquinolinecarboxamide | 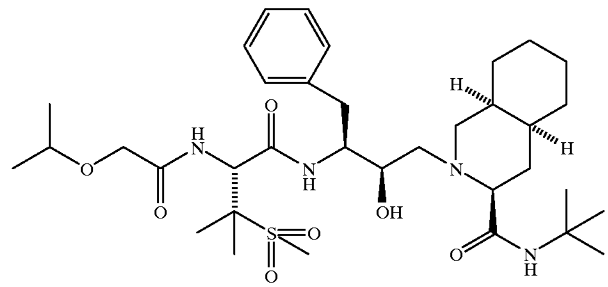 |
| 73 | N-tert-Butyl-1,2,3,4,4a(S),5,6,7,8,8a(S)-decahydro-2-[2(R)-hydroxy-3(S)-[[3-(methanesulfonyl)-N-[(2-pyridyl)carbonyl]-L-valyl]amino]-4-phenylbutyl]-3(S)-isoquinolinecarboxamide | 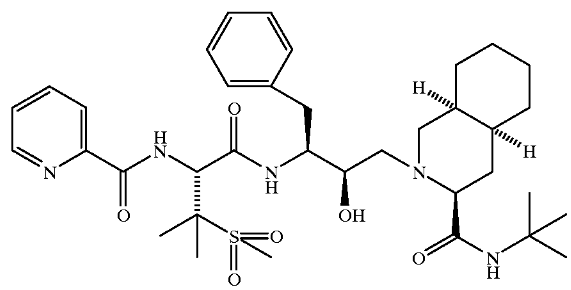 |
| 74 | N-tert-Butyl-1,2,3,4,4a(S),5,6,7,8,8a(S)-decahydro-2-[2(R)-hydroxy-3(S)-[[3-(methanesulfonyl)-N-[(2-methyl-4-thiazolyl)carbonyl]-L-valyl]amino]-4-phenylbutyl]-3(S)-isoquinolinecarboxamide | 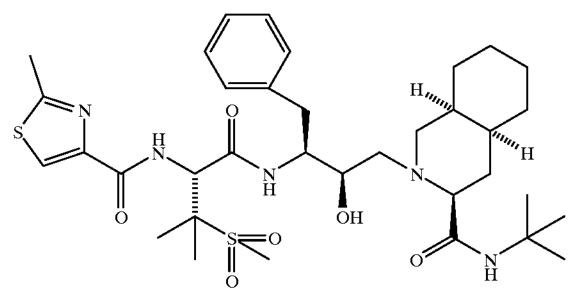 |
| 75 | N-tert-Butyl-1,2,3,4,4a(S),5,6,7,8,8a(S)-decahydro-2-[2(R)-hydroxy-3(S)-[[3-(methanesulfonyl)-N-(3-phenylpropionyl)-L-valyl]amino]-4-phenylbutyl]-3(S)-isoquinolinecarboxamide | 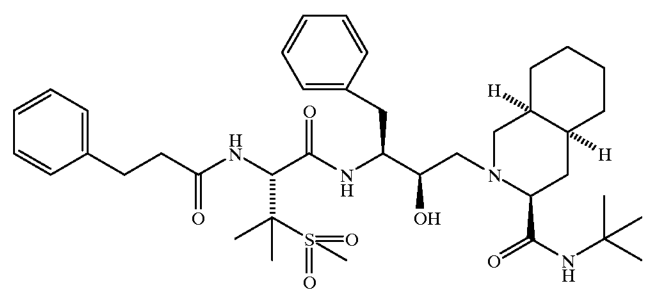 |

TABLE A-continued

| Ex | Name | Structures |
|---|---|---|
| 76 | (E)-N-tert-Butyl-1,2,3,4,4a(S),5,6,7,8,8a(S)-decahydro-2-[2(R)-hydroxy-3(S)-[[3-(methanesulfonyl)-N-(3-phenylacryloyl)-L-valyl]amino]-4-phenylbutyl]-3(S)-isoquinolinecarboxamide | 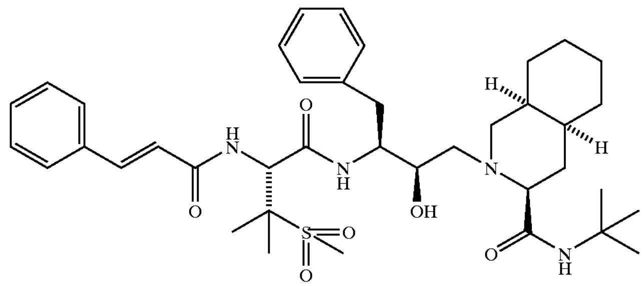 |
| 77 | N-tert-Butyl-2-[3(S)-[[N-[2-(pentafluorophenoxy)acetyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 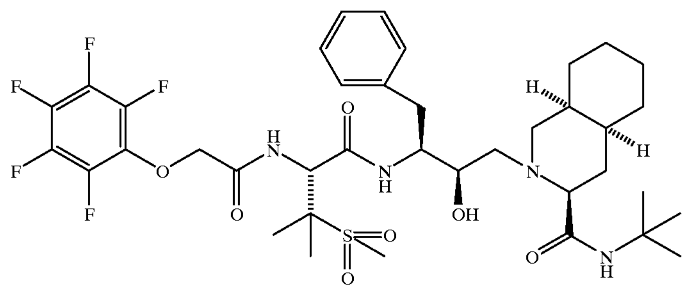 |
| 78 | 2-[3(S)-[[N-[[(2-Benzofuryl)carbonyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 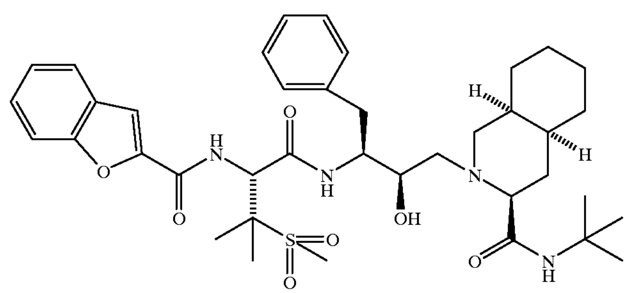 |
| 79 | N-tert-Butyl-1,2,3,4,4a(S),5,6,7,8,8a(S)-decahydro-2-[2(R)-hydroxy-3(S)-[[3-(methanesulfonyl)-N-[2-(phenylthio)acetyl]-L-valyl]amino]-4-phenylbutyl]-3(S)-isoquinolinecarboxamide | 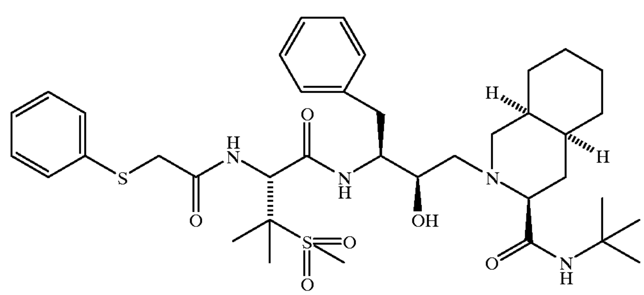 |
| 80 | N-tert-Butyl-1,2,3,4,4a(S),5,6,7,8,8a(S)-decahydro-2-[2(R)-hydroxy-3(S)-[[3-(methanesulfonyl)-N-(2-methyl-2-phenoxypropionyl)-L-valyl]amino]-4-phenylbutyl]-3(S)-isoquinolinecarboxamide | 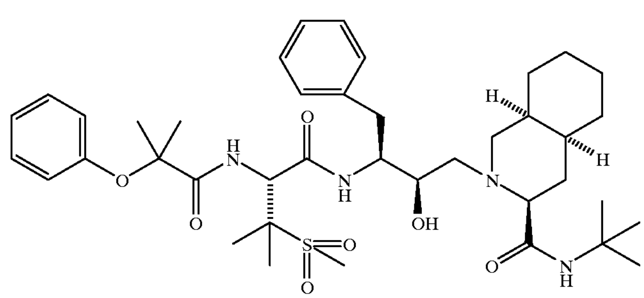 |

TABLE A-continued

| Ex | Name | Structures |
|----|------|------------|
| 81 | N-tert-Butyl-1,2,3,4,4a(S),5,6,7,8,8a(S)-decahydro-2-[2(R)-hydroxy-3(S)-[[3-(methanesulfonyl)-N-[2-(2-naphthyloxy)acetyl]-L-valyl]amino]-4-phenylbutyl]-3(S)-isoquinolinecarboxamide | 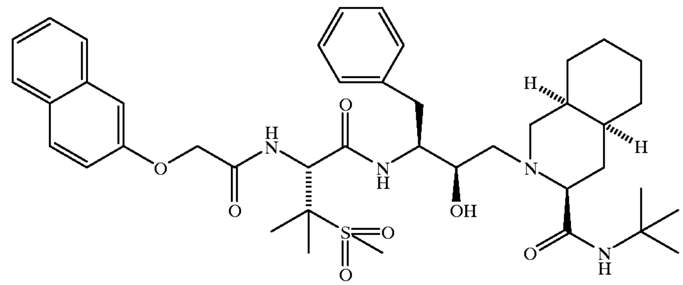 |
| 82 | N-tert-Butyl-1,2,3,4,4a(S),5,6,7,8,8a(S)-decahydro-2-[2(R)-hydroxy-3(S)-[[3-(methanesulfonyl)-N-[2-(1-naphthyloxy)acetylamino]-L-valyl]amino]-4-phenylbutyl]-3(S)-isoquinolinecarboxamide | 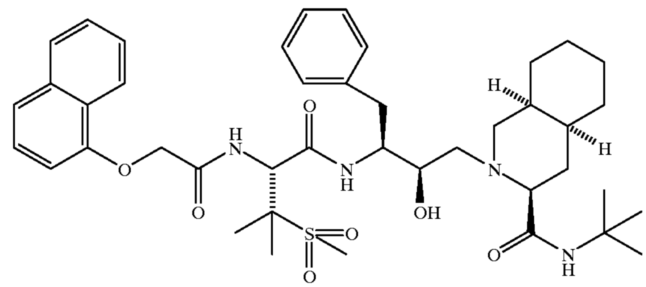 |
| 83 | N-tert-Butyl-1,2,3,4,4a(S),5,6,7,8,8a(S)-decahydro-2-[2(R)-hydroxy-3(S)-[[3-(methanesulfonyl)-N-(5-methyl-2-furoyl)-L-valyl]amino]-4-phenylbutyl]-3(S)-isoquinolinecarboxamide | 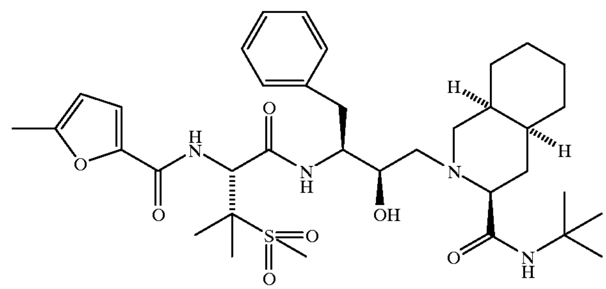 |
| 84 | N-tert-Butyl-1,2,3,4,4a(S),5,6,7,8,8a(S)-decahydro-2-[2(R)-hydroxy-3(S)-[[2-[2-(dimethylamino)acetyl]-3-(methanesulfonyl)-L-valyl]amino]-4-phenylbutyl]-3(S)-isoquinolinecarboxamide | 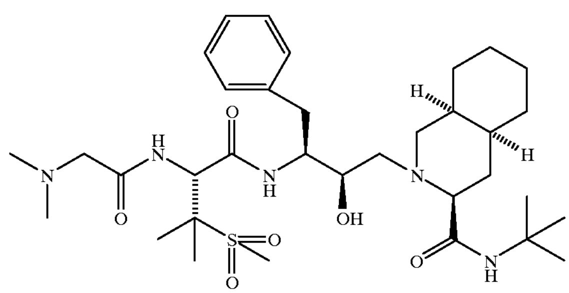 |
| 85 | N-tert-Butyl-1,2,3,4,4a(S),5,6,7,8,8a(S)-decahydro-2-[2(R)-hydroxy-3(S)-[[3-(methanesulfonyl)-N-(3,5-dimethoxybenzoyl)-L-valyl]amino]-4-phenylbutyl]-3(S)-isoquinolinecarboxamide | 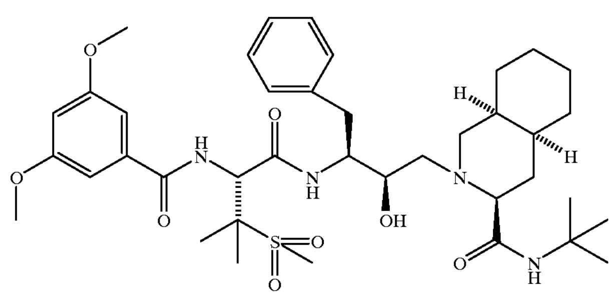 |

TABLE A-continued

| Ex | Name | Structures |
|---|---|---|
| 86 | N-tert-Butyl-1,2,3,4,4a(S),5,6,7,8,8a(S)-decahydro-2-[2(R)-hydroxy-N-[(2-indolyl)carbonyl]-3(S)-[[3-(methanesulfonyl)-L-valyl]amino]-4-phenylbutyl]-3(S)-isoquinolinecarboxamide | 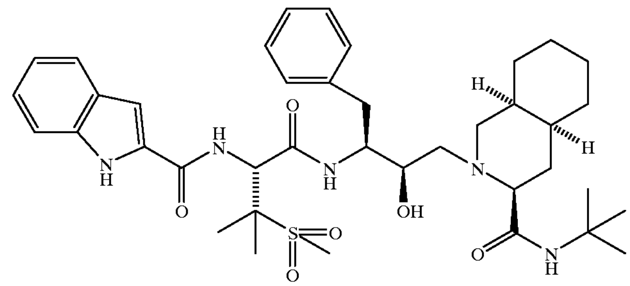 |
| 87 | N-tert-Butyl-1,2,3,4,4a(S),5,6,7,8,8a(S)-decahydro-2-[2(R)-hydroxy-3(S)-[[-3-(methanesulfonyl)-N-[1-methyl-2-indolyl)carbonyl]-L-valyl]amino]-4-phenylbutyl]-3(S)-isoquinolinecarboxamide | 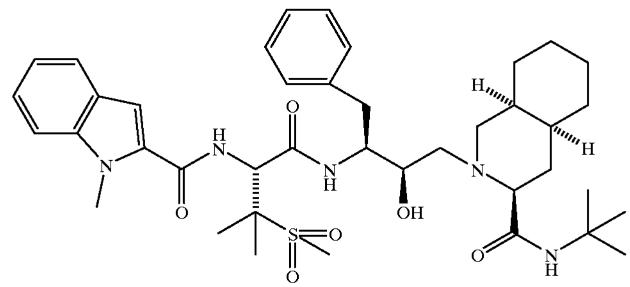 |
| 88 | 2-[3(S)-[[N-[(1-Benzothiophen-2-yl)carbonyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 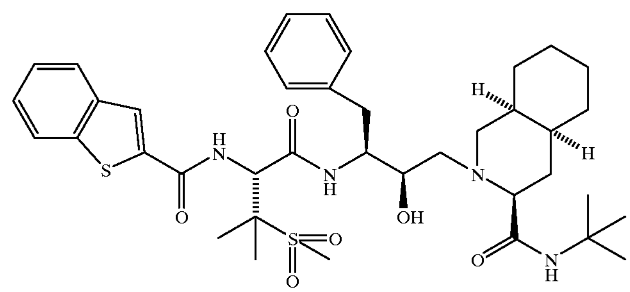 |
| 89 | N-tert-Butyl-1,2,3,4,4a(S),5,6,7,8,8a(S)-decahydro-2-[2(R)-hydroxy-3(S)-[[3-(methanesulfonyl)-N-(propoxycarbonyl)-L-valyl]amino]-4-phenylbutyl]-3(S)-isoquinolinecarboxamide | 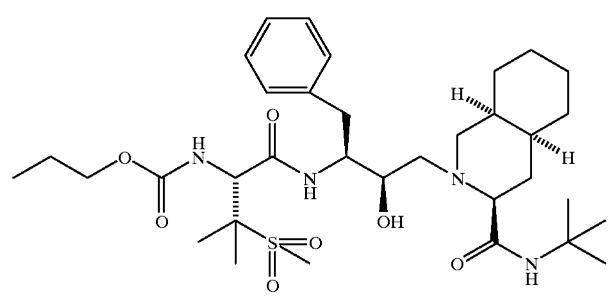 |
| 90 | N-tert-Butyl-1,2,3,4,4a(S),5,6,7,8,8a(S)-decahydro-2-[2(R)-hydroxy-3(S)-[[N-(isopropoxycarbonyl)-3-(methanesulfonyl)-L-valyl]amino]-4-phenylbutyl]-3(S)-isoquinolinecarboxamide | 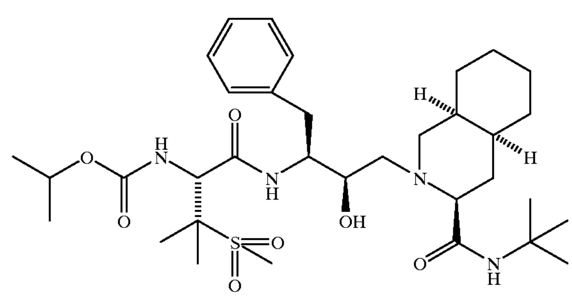 |

TABLE A-continued

| Ex | Name | Structures |
|---|---|---|
| 91 | N-tert-Butyl-2-[3(S)-[[N-(ethoxycarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 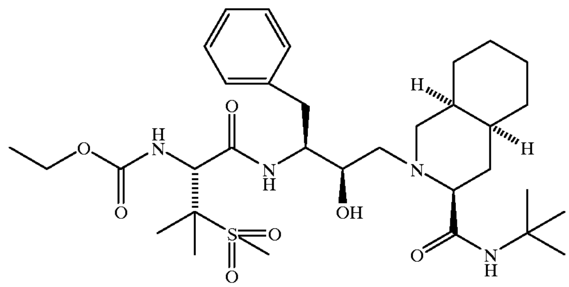 |
| 92 | N-tert-Butyl-1,2,3,4,4a(S),5,6,7,8,8a(S)-decahydro-2-[2(R)-hydroxy-3(S)-[[N-[2-(isopropylamino)acetyl]-3-(methanesulfonyl)-L-valyl]amino]-4-phenylbutyl]-3(S)-isoquinolinecarboxamide | 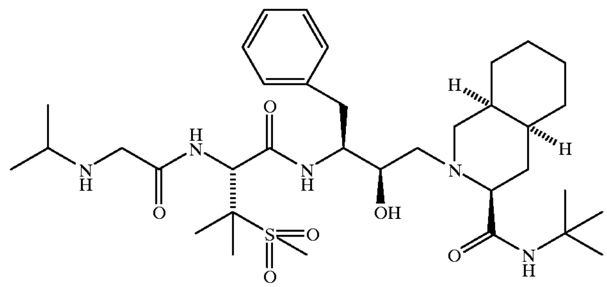 |
| 93 | N-tert-Butyl-1,2,3,4,4a(S),5,6,7,8,8a(S)-decahydro-2-[2(R)-hydroxy-3(S)-[[3-(methanesulfonyl)-N-( N-phenylglycyl)-L-valyl]amino]-4-phenylbutyl]-3(S)-isoquinolinecarboxamide | 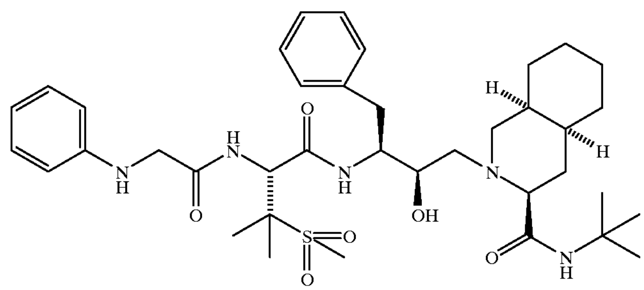 |
| 94 | N-tert-Butyl-1,2,3,4,4a(S),5,6,7,8,8a(S)-decahydro-2-[2(R)-hydroxy-3(S)-[[3-(methanesulfonyl)-N-(N-methylglycyl)-L-valyl]amino]-4-phenylbutyl]-3(S)-isoquinolinecarboxamide | 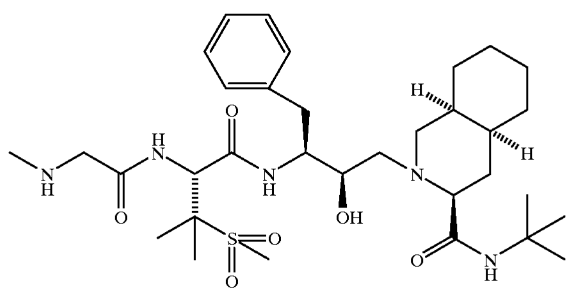 |
| 95 | N-tert-Butyl-1,2,3,4,4a(S),5,6,7,8,8a(S)-decahydro-1-[2(R)-hydroxy-3(S)-[3-(methanesulfonyl)butyramido]-4-phenylbutyl]-2(S)-piperazinecarboxamide | 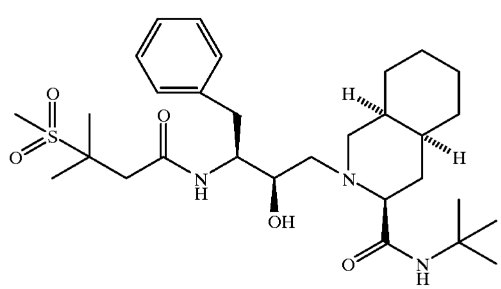 |

TABLE A-continued

| Ex | Name | Structures |
|---|---|---|
| 96 | 2-[3(S)-[3-(Ethanesulfonyl)-3-methylbutyramido]-2(R)-hydroxy-4-phenylbutyl]-1,2,3,4,4a(S),5,6,7,8,8a(S)-decahydro-3(S)-isoquinolinecarboxamide | 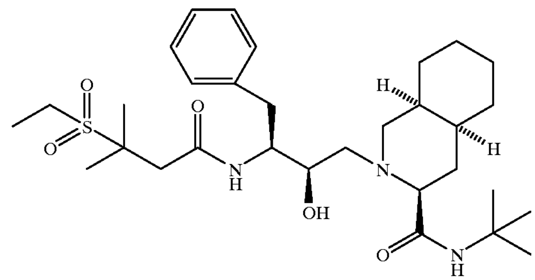 |
| 97 | 2-[3(S)-[3-(Benzenesulfonyl)-3-methylbutyramido]-2(R)-hydroxy-4-phenylbutyl]-N-tert-butyl-1,2,3,4,4a(S),5,6,7,8,8a(S)-decahydro-3(S)-isoquinolinecarboxamide | 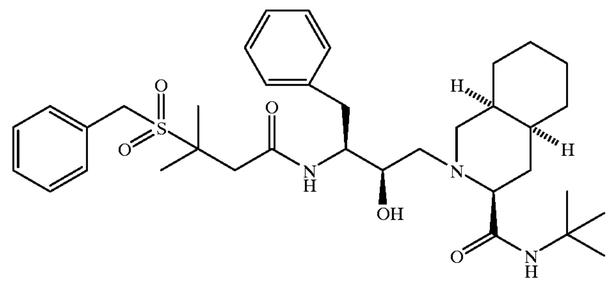 |
| 98 | N-tert-Butyl-1,2,3,4,4a(S),5,6,7,8,8a(S)-decahydro-2-[3(S)-[[N-[2-(tetrahydro-2(RS)-methyl-1, 1-dioxo-2-thienyl)acetyl]-3-(methanesulfonyl)-L-valyl]amino]-2(R)-hydroxy-4-phenylbutyl]-3(S)-isoquinolinecarboxamide (mixture of diastereoisomers) | 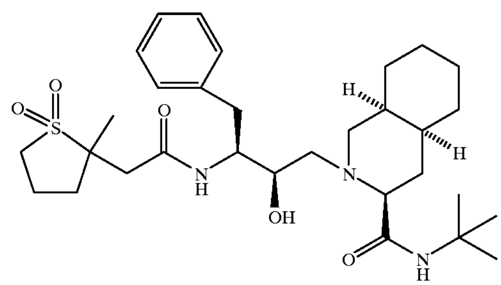 |
| 99 | N-tert-Butyl-1,2,3,4,4a(S),5,6,7,8,8a(S)-decahydro-2-[2(R)-hydroxy-3(S)-[2(R)-hydroxy-3-(methanesulfonyl)-3-methylbutyramido]-4-phenylbutyl]-3(S)-isoquinolinecarboxamide | 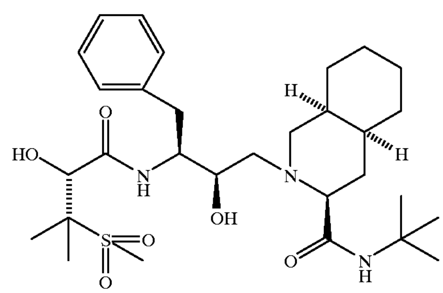 |
| 100 | N-tert-Butyl-1,2,3,4,4a(S),5,6,7,8,8a(S)-decahydro-2-[2(R)-hydroxy-3(S)-[[N-(dimethylcarbamoyl-3-(methanesulfonyl)-L-valyl]amino]-4-phenylbutyl]-3(S)-isoquinolinecarboxamide | 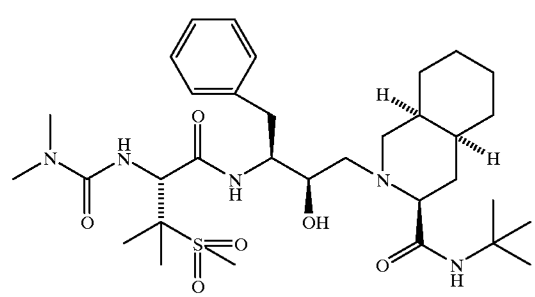 |

TABLE A-continued

| Ex | Name | Structures |
|---|---|---|
| 101 | N-tert-Butyl-2-[3(S)-[[N-(diethylcarbamoyl)-3-(methanesulfonyl)-L-valyl]amino]-2(R)-hydroxy-4-phenylbutyl)-1,2,3,4,4a(S),5,6,7,8,8a(S)-decahydro-3(S)-isoquinolinecarboxamide | 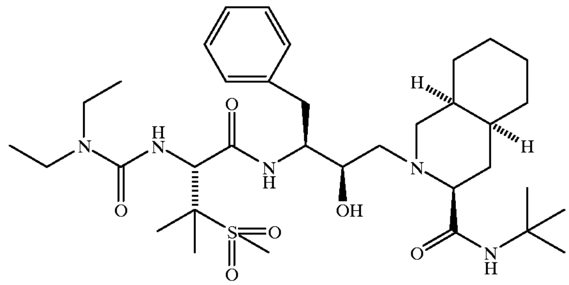 |
| 102 | N-tert-Butyl-2-[3(S)-[[N-(N-ethyl-N-methylcarbamoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 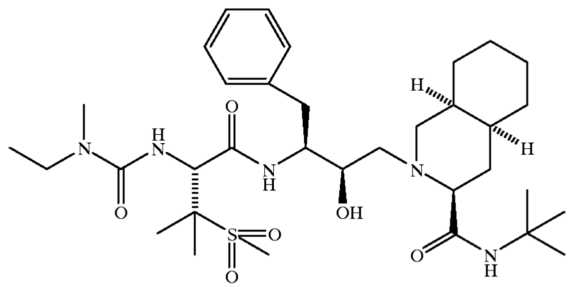 |
| 103 | N-tert-Butyl-1,2,3,4,4a(S),5,6,7,8,8a(S)-decahydro-2-[2(R)-hydroxy-3(S)-[[3-(methanesulfonyl)-N-(N-methyl-N-propylcarbamoyl)-L-valyl]amino]-4-phenylbutyl]-3(S)-isoquinolinecarboxamide | 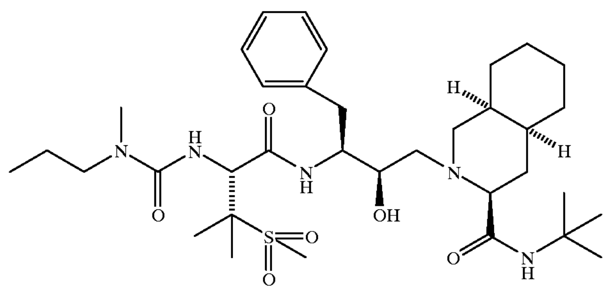 |
| 104 | N-tert-Butyl-1,2,3,4,4a(S),5,6,7,8,8a(S)-decahydro-2-[2(R)-hydroxy-3(S)-[[3-(methanesulfonyl)-N-[(1-pyrrolidinyl)carbonyl]-L-valyl]amino]-4-phenylbutyl]-3(S)-isoquinolinecarboxamide | 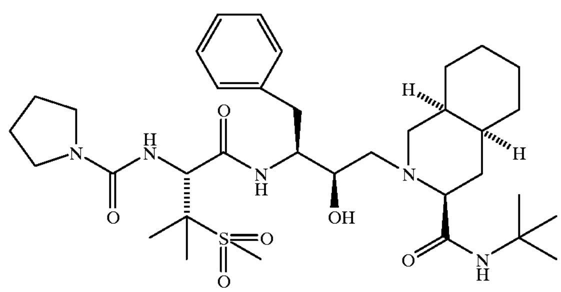 |
| 105 | N-tert-Butyl-1,2,3,4,4a(S),5,6,7,8,8a(S)-decahydro-2-[2(R)-hydroxy-3(S)-[[3-(methanesulfonyl)-N-(piperidinocarbonyl)-L-valyl]amino]-4-phenylbutyl]-3(S)-isoquinolinecarboxamide | 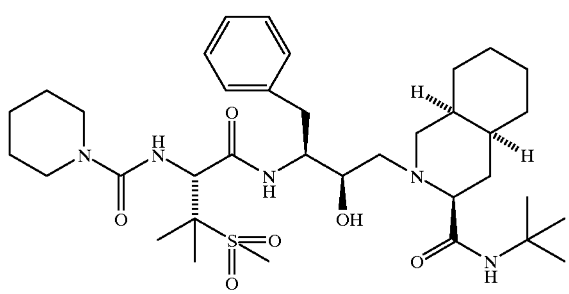 |

TABLE A-continued

| Ex | Name | Structures |
|---|---|---|
| 106 | N-tert-Butyl-1,2,3,4,4a(S),5,6,7,8,8a(S)-decahydro-2-[2(R)-hydroxy-3(S)-[[3-(methanesulfonyl)-N-(morpholinocarbonyl)-L-valyl]amino]-4-phenylbutyl]-3(S)-isoquinolinecarboxamide | 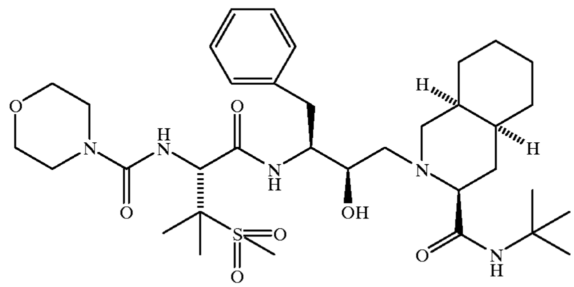 |
| 107 | N-tert-Butyl-1,2,3,4,4a(S),5,6,7,8,8a(S)-decahydro-2-[2(R)-hydroxy-3(S)-[[3-(methanesulfonyl)-N-[(1-piperazinyl)carbonyl]-L-valyl]amino]-4-phenylbutyl]-3(S)-isoquinolinecarboxamide | 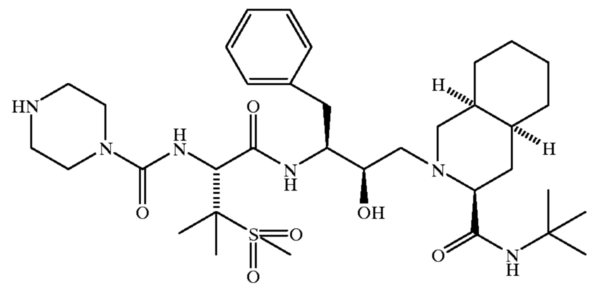 |
| 108 | N-tert-Butyl-1,2,3,4,4a(S),5,6,7,8,8a(S)-decahydro-2-[2(R)-hydroxy-3(S)-[[3-(methanesulfonyl)-N-[(4-methyl-1-piperazinyl)carbonyl]-L-valyl]amino]-4-phenylbutyl]-3(S)-isoquinolinecarboxamide | 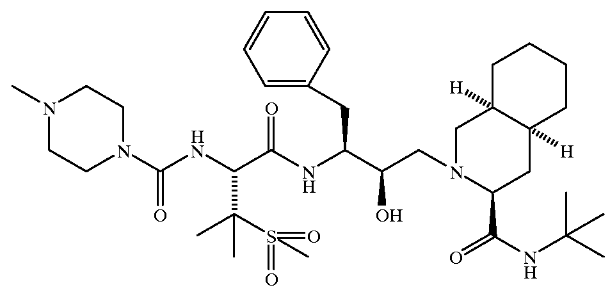 |
| 109 | N-tert-Butyl-1,2,3,4,4a(S),5,6,7,8,8a(S)-decahydro-2-[3(S)-[[N-[(tetrahydro-1,4-thiazin-4-yl)carbonyl]-3-(methanesulfonyl)-L-valyl]amino]-2(R)-hydroxy-4-phenylbutyl]-3(S)-isoquinolinecarboxamide | 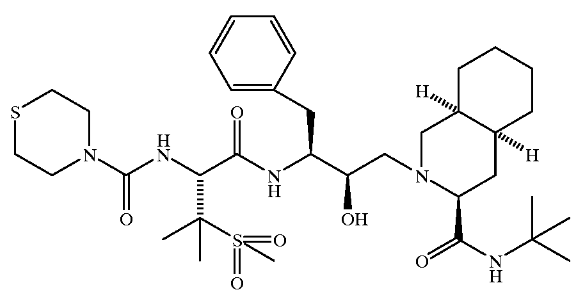 |
| 110 | N-tert-Butyl-1,2,3,4,4a(S),5,6,7,8,8a(S)-decahydro-2-[2(R)-hydroxy-3(S)-[[N-isopropyl-3-(methanesulfonyl)-L-valyl]amino]-4-phenylbutyl]-3(S)-isoquinolinecarboxamide | 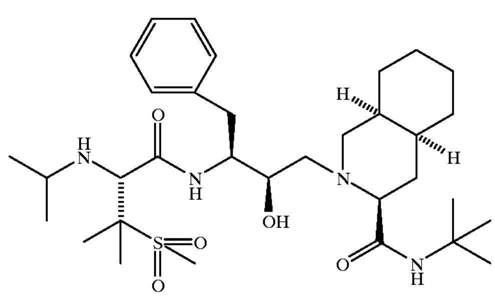 |

TABLE A-continued

| Ex | Name | Structures |
|---|---|---|
| 111 | N-tert-Butyl-2-[3(S)-[[N-ethyl-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 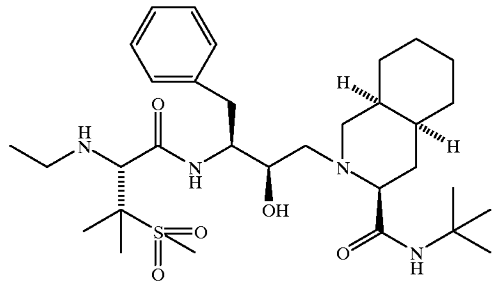 |
| 112 | 2-[3(S)-[[N-Benzyl-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 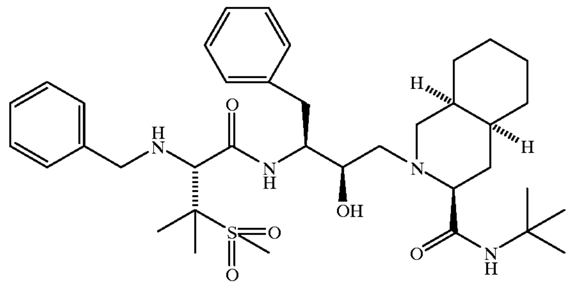 |
| 113 | N-tert-Butyl-1,2,3,4,4a(S),5,6,7,8,8a(S)-decahydro-2-[2(R)-hydroxy-3(S)-[[3-(methanesulfonyl)-N-methyl-L-valyl]amino]-4-phenylbutyl]-3(S)-isoquinolinecarboxamide | 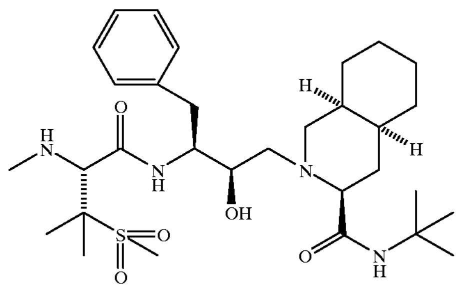 |
| 114 | N-tert-Butyl-2-[3(S)-[[N-(2-furfuryl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 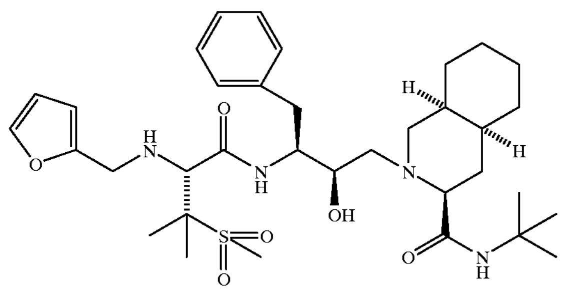 |
| 115 | N-tert-Butyl-1,2,3,4,4a(S),5,6,7,8,8a(S)-decahydro-2-[2(R)-hydroxy-3(S)-[[3-(methanesulfonyl)-N-(5-methyl-2-furfuryl)-L-valyl]amino]-4-phenylbutyl]-3(S)-isoquinolinecarboxamide | 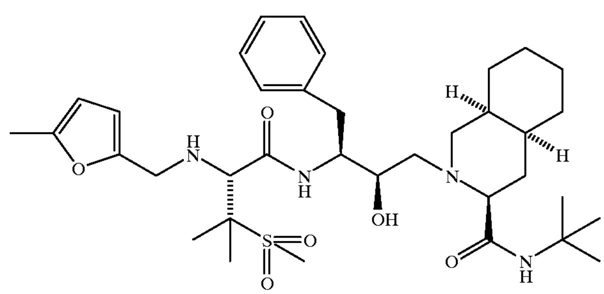 |

TABLE A-continued

| Ex | Name | Structures |
|---|---|---|
| 116 | N-tert-Butyl-2-[3(S)-[[N-(2-fluorobenzyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 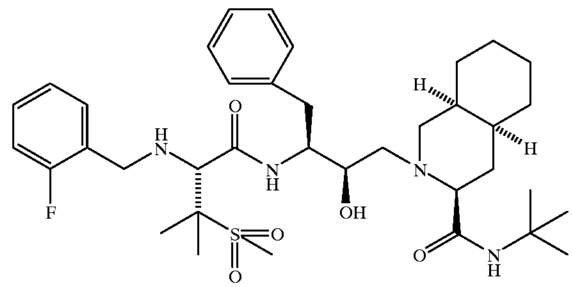 |
| 117 | N-tert-Butyl-2-[3(S)-[[N-(2-chlorobenzyl)-3-(methanesulfonyl)-L-valyl]amino]-3(R)-hydroxy-4-phenylbutyl]-1,2,3,4,4a(S),5,6,7,8,8a(S)-decahydro-3(S)-isoquinolinecarboxamide | 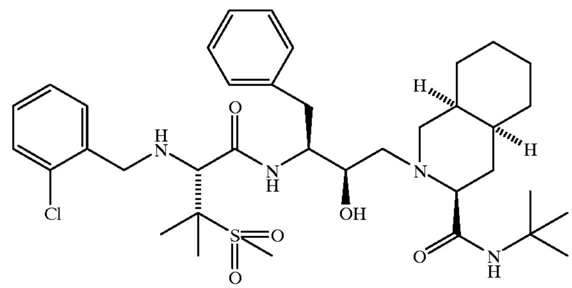 |
| 118 | N-tert-Butyl-1,2,3,4,4a(S),5,6,7,8,8a(S)-decahydro-2-[2(R)-hydroxy-3(S)-[[3-(methanesulfonyl)-N-(2-methoxybenzyl)-L-valyl]amino]-4-phenylbutyl]-3(S)-isoquinolinecarboxamide | 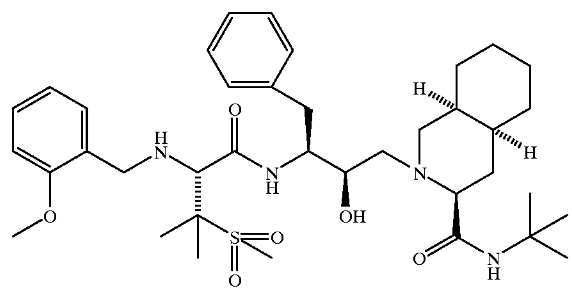 |
| 119 | N-tert-Butyl-1,2,3,4,4a(S),5,6,7,8,8a(S)-decahydro-2-[2(R)-hydroxy-3(S)-[[N-(2-hydroxybenzyl)-3-(methanesulfonyl)-L-valyl]amino]-4-phenylbutyl]-3(S)-isoquinolinecarboxamide | 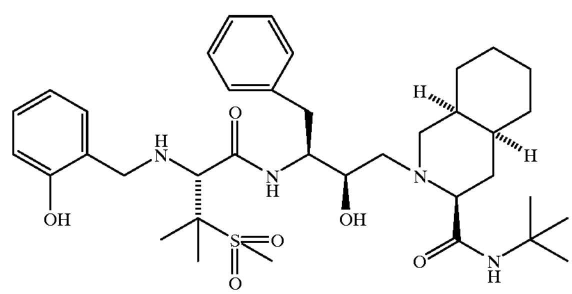 |
| 120 | N-tert-Butyl-1,2,3,4,4a(S),5,6,7,8,8a(S)-decahydro-2-[2(R)-hydroxy-3(S)-[[3-(methanesulfonyl)-N-(2-methylbenzyl)-L-valyl]amino]-4-phenylbutyl]-3(S)-isoquinolinecarboxamide | 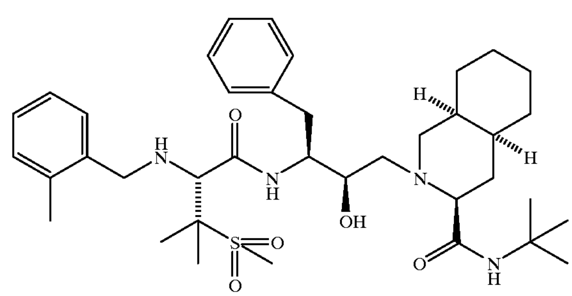 |

TABLE A-continued

| Ex | Name | Structures |
|----|------|------------|
| 121 | N-tert-Butyl-2-[3(S)-[[N-(3-fluorobenzyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 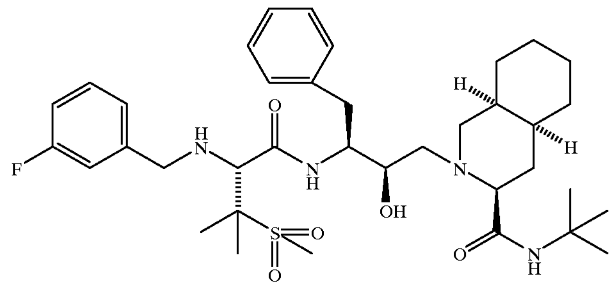 |
| 122 | N-tert-Butyl-2-[3(S)-[[N-(3-chlorobenzyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 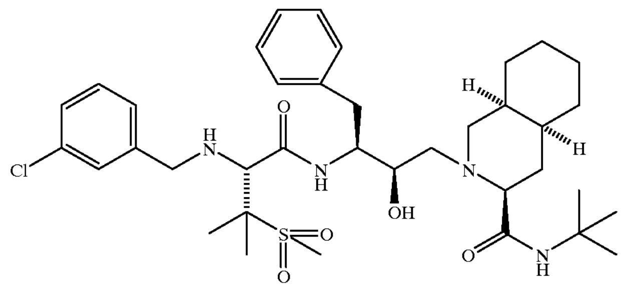 |
| 123 | N-tert-Butyl-1,2,3,4,4a(S),5,6,7,8,8a(S)-decahydro-2-[2(R)-hydroxy-3(S)-[[N-(3-hydroxybenzyl)-3-(methanesulfonyl)-L-valyl]amino]-4-phenylbutyl]-3(S)-isoquinolinecarboxamide | 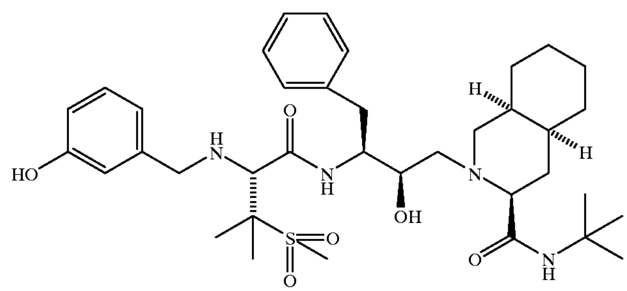 |
| 124 | N-tert-Butyl-1,2,3,4,4a(S),5,6,7,8,8a(S)-decahydro-2-[2(R)-hydroxy-3(S)-[[3-(methanesulfonyl)-N-(5-methyl-2-thenyl)-L-valyl]amino]-4-phenylbutyl]-3(S)-isoquinolinecarboxamide | 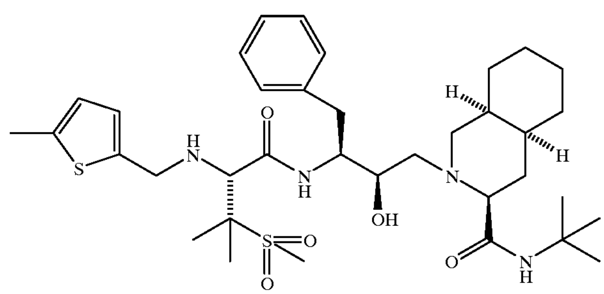 |
| 125 | N-tert-Butyl-1,2,3,4,4a(S),5,6,7,8,8a(S)-decahydro-2-[2(R)-hydroxy-3(S)-[[3-(methanesulfonyl)-N-[(2-pyridyl)methyl]-L-valyl]amino]-4-phenylbutyl]-3(S)-isoquinolinecarboxamide | 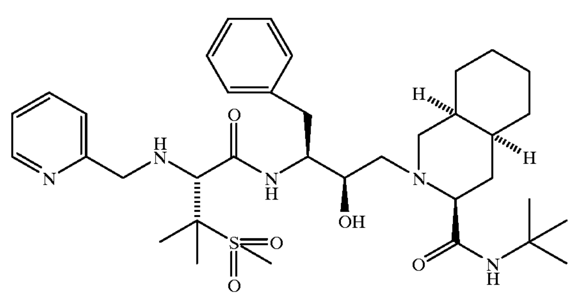 |

TABLE A-continued

| Ex | Name | Structures |
|---|---|---|
| 126 | N-tert-Butyl-1,2,3,4,4a(S),5,6,7,8,8a(S)-decahydro-2-[2(R)-hydroxy-3(S)-[[N-(4-hydroxybenzyl)-3-(methanesulfonyl)-L-valyl]amino]-4-phenylbutyl]-3(S)-isoquinolinecarboxamide | 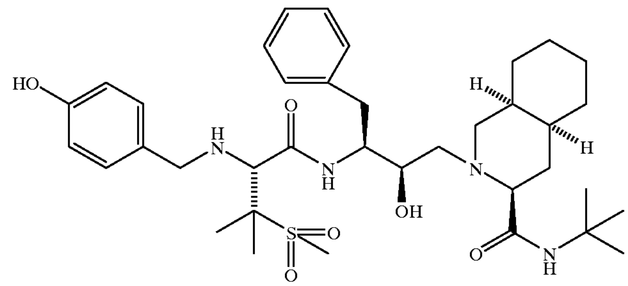 |
| 127 | N-tert-Butyl-1,2,3,4,4a(S),5,6,7,8,8a(S)-decahydro-2-[2(R)-hydroxy-3(S)-[[3-(methanesulfonyl)-N-(4-methylbenzyl)-L-valyl]amino]-4-phenylbutyl]-3(S)-isoquinolinecarboxamide | 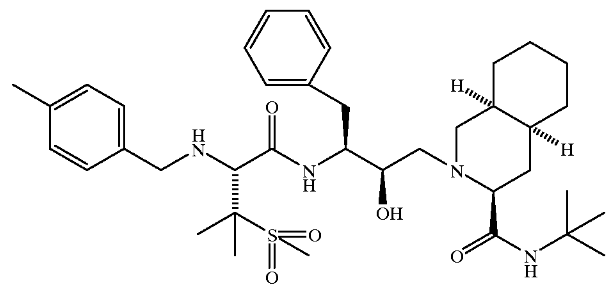 |
| 128 | N-tert-Butyl-1,2,3,4,4a(S),5,6,7,8,8a(S)-decahydro-2-[2(R)-hydroxy-3(S)-[[3-(methanesulfonyl)-N-(2,2-dimethylpropyl)-L-valyl]amino]-4-phenylbutyl]-3(S)-isoquinolinecarboxamide | 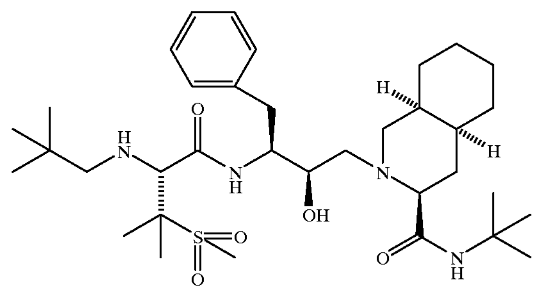 |
| 129 | N-tert-Butyl-1,2,3,4,4a(S),5,6,7,8,8a(S)-decahydro-2-[2(R)-hydroxy-3(S)-[[N-isobutyl-3-(methanesulfonyl)-L-valyl]amino]-4-phenylbutyl]-3(S)-isoquinolinecarboxamide | 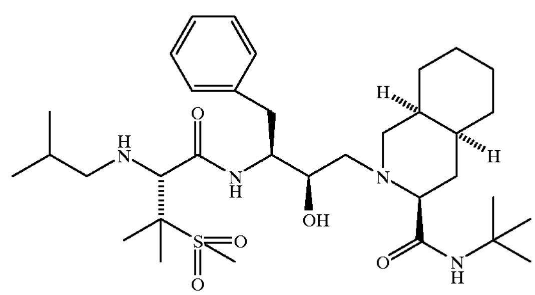 |
| 130 | N-tert-Butyl-1,2,3,4,4a(S),5,6,7,8,8a(S)-decahydro-2-[2(R)-hydroxy-3(S)-[[3-(methanesulfonyl)-N-(2-phenylethylyl))-L-valyl]amino]-4-phenylbutyl]-3(S)-isoquinolinecarboxamide | 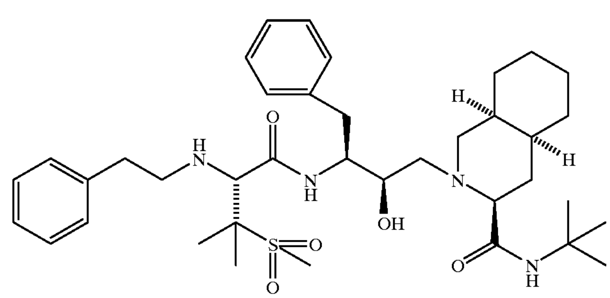 |

TABLE A-continued

| Ex | Name | Structures |
|---|---|---|
| 131 | N-tert-Butyl-2-[3(S)-[[N-(2,6-difluorobenzyl)-3-(methanesulfonyl)-N-L-valyl]amino]-2(R)-hydroxy-4-phenylbutyl]-1,2,3,4,4a(S),5,6,7,8,8a(S)-decahydro-3(S)-isoquinolinecarboxamide | 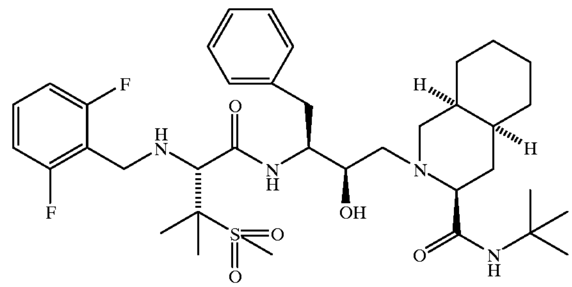 |
| 132 | N-tert-Butyl-2-[3(S)-[[N-(3-furfuryl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 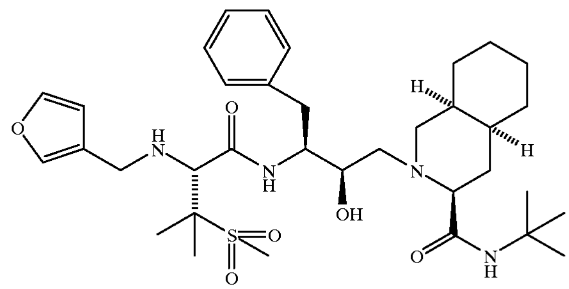 |
| 133 | N-tert-Butyl-2-[3(S)-[[N-(cyclopropylmethyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 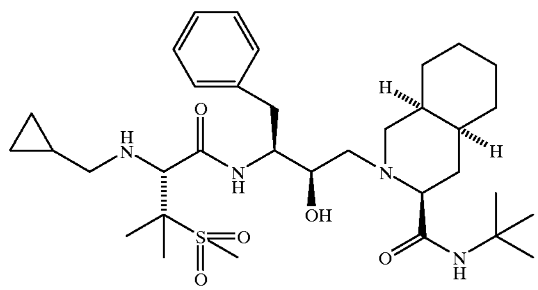 |
| 134 | N-tert-Butyl-1,2,3,4,4a(S),5,6,7,8,8a(S)-decahydro-2-[2(R)-hydroxy-3(S)-[[3-(methanesulfonyl)-N-[(2-methyl-4-imidazolyl)methyl]-L-valyl]amino]-4-phenylbutyl]-3(S)-isoquinolinecarboxamide | 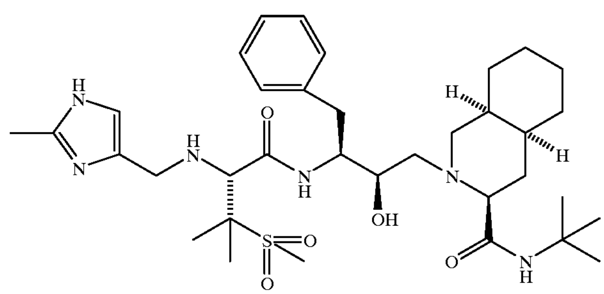 |
| 135 | N-tert-Butyl-1,2,3,4,4a(S),5,6,7,8,8a(S)-decahydro-2-[2(R)-hydroxy-3(S)-[[3-(methanesulfonyl)-N-[(5-methyl-4-imidazolyl)methyl]-L-valyl]amino]-4-phenylbutyl]-3(S)-isoquinolinecarboxamide | 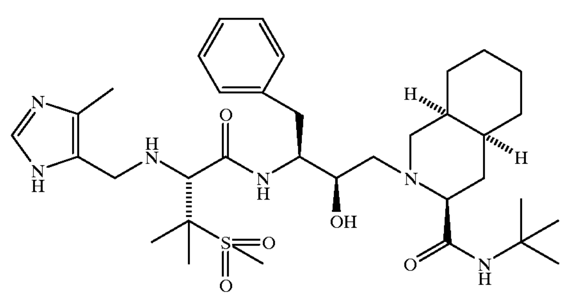 |

TABLE A-continued

| Ex | Name | Structures |
|---|---|---|
| 136 | N-tert-Butyl-1,2,3,4,4a(S),5,6,7,8,8a(S)-decahydro-2-[2(R)-hydroxy-3(S)-[[3-(methanesulfonyl)-N-[(1-methyl-2-imidazolyl)methyl]-L-valyl]amino]-4-phenylbutyl]-3(S)-isoquinolinecarboxamide | 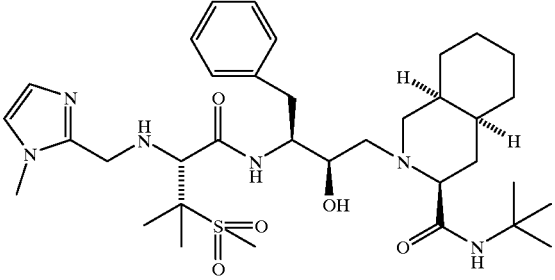 |
| 137 | N-tert-Butyl-1,2,3,4,4a(S),5,6,7,8,8a(S)-decahydro-2-[2(R)-hydroxy-3(S)-[[3-(methanesulfonyl)-N-(2-thiazolyl)-L-valyl]amino]-4-phenylbutyl]-3(S)-isoquinolinecarboxamide | 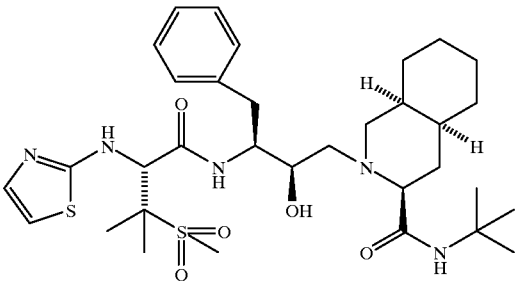 |
| 138 | N-tert-Butyl-1,2,3,4,4a(S),5,6,7,8,8a(S)-decahydro-2-[2(R)-hydroxy-3(S)-[[3-(methanesulfonyl)-N-(4-methyl-2-thiazolyl)-L-valyl]amino]-4-phenylbutyl]-3(S)-isoquinolinecarboxamide | 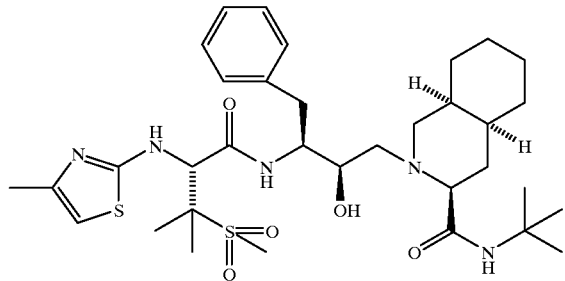 |
| 139 | N-tert-Butyl-1,2,3,4,4a(S),5,6,7,8,8a(S)-decahydro-2-[2(R)-hydroxy-3(S)-[[3-(methanesulfonyl)-N-(4-phenyl-2-thiazolyl)-L-valyl]amino]-4-phenylbutyl]-3(S)-isoquinolinecarboxamide | 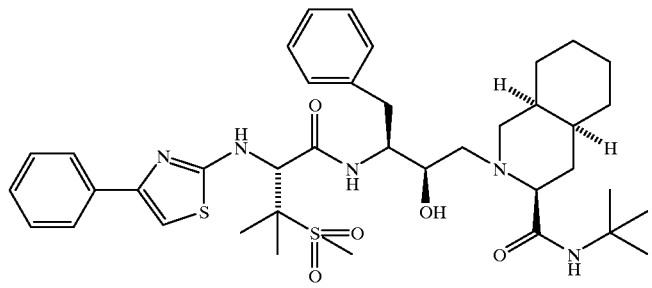 |
| 140 | N-tert-Butyl-2-[3(S)-[[N-[4-(ethoxycarbonyl)-2-thiazolyl]-3-(methanesulfonyl)-L-valyl]amino]-2(R)-hydroxy-4-phenylbutyl]-1,2,3,4,4a(S),5,6,7,8,8a(S)-decahydro3(S)-isoquinolinecarboxamide | 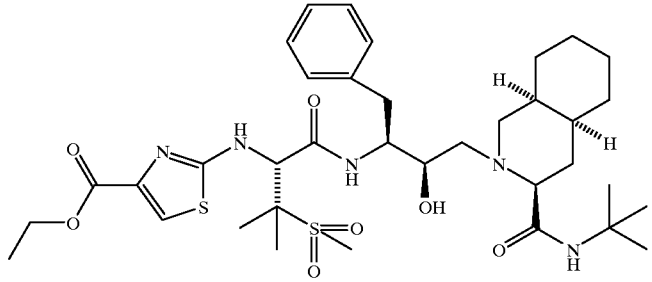 |

TABLE A-continued

| Ex | Name | Structures |
|---|---|---|
| 141 | 2-[3(S)-[[N-4-(Acetoxymethyl)-2-thiazolyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 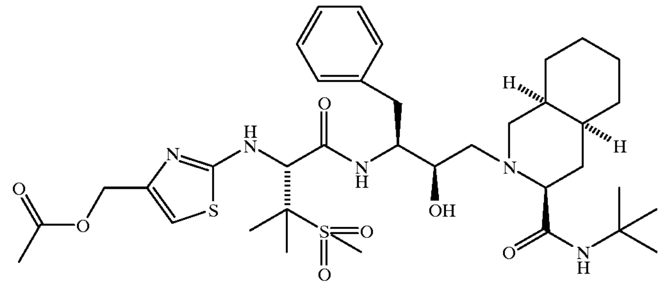 |
| 142 | N-tert-Butyl-1,2,3,4,4a(S),5,6,7,8,8a(S)-decahydro-2-[2(R)-hydroxy-3(S)-[[3-(methanesulfonyl)-N-[4-[(methoxycarbonyl)methyl]-2-thiazolyl]-L-valyl]amino]-4-phenylbutyl]-3(S)-isoquinolinecarboxamide | 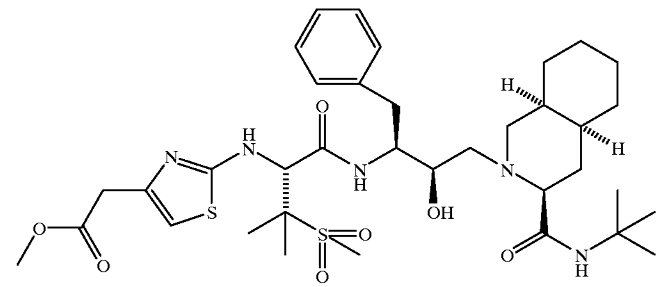 |
| 143 | N-tert-Butyl-1,2,3,4,4a(S),5,6,7,8,8a(S)-decahydro-2-[2(R)-hydroxy-3(S)-[[N-[4-(hydroxymethyl)-2-thiazolyl]-3-(methanesulfonyl)-L-valyl]amino]-4-phenylbutyl]-3(S)-isoquinolinecarboxamide | 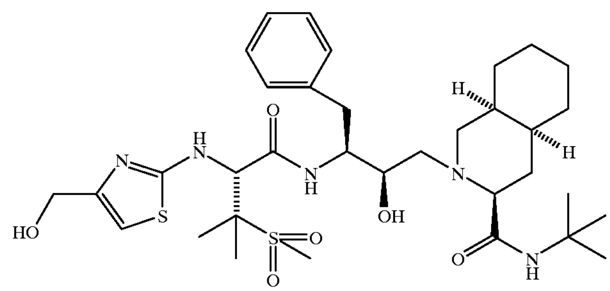 |
| 144 | N-tert-Butyl-1,2,3,4,4a(S),5,6,7,8,8a(S)-decahydro-2-[3(S)-[2(R)-(2,3-dihydro-2-oxo-1H-imidazol-2-yl)-3-(methanesulfonyl)-3-methylbutyramido]-2(R)-hydroxy-4-phenylbutyl]-3(S)-isoquinolinecarboxamide | 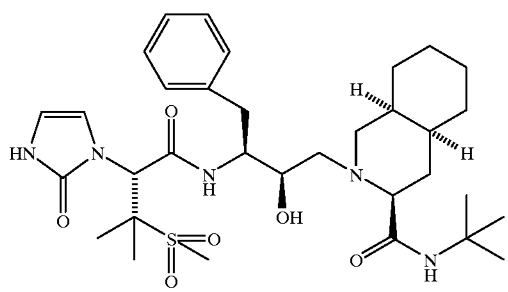 |
| 145 | N-Benzyl-1,2,3,4,4a(S),5,6,7,8,8a(S)-decahydro-2-[2(R)-hydroxy-3(S)-[[3-(methanesulfonyl)-N-(methoxycarbonyl)-L-valyl]amino]-4-phenylbutyl]-3(S)-isoquinolinecarboxamide | 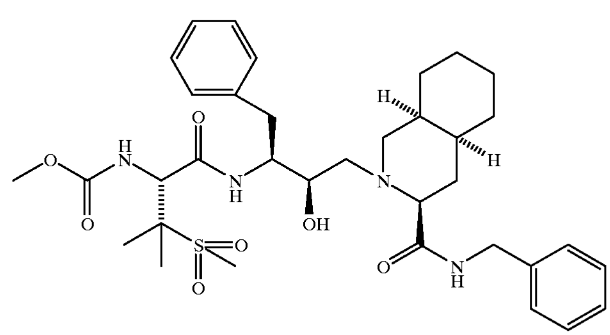 |

TABLE A-continued

| Ex | Name | Structures |
|---|---|---|
| 156 | N-tert-Butyl-2-[3(S)-[[N-[2-(3-fluorophenoxy)acetyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 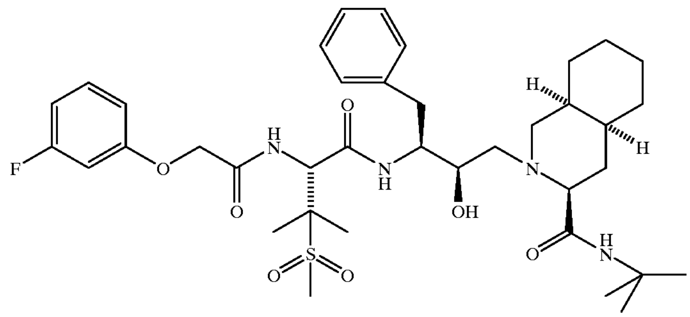 |
| 157 | N-tert-Butyl-2-[3(S)-[[N-[2-(4-fluorophenoxy)-acetyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 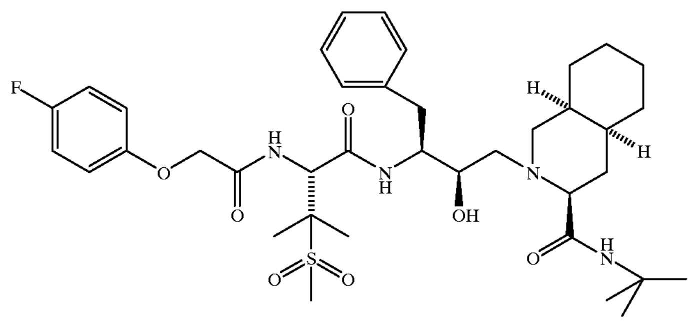 |
| 158 | (E)-N-tert-Butyl-1,2,3,4,4a(S),5,6,7,8,8a(S)-decahydro-2-[2(R)-hydroxy-3(S)-[[3-(methanesulfonyl)-N-[3-(4-pyridyl)acroyl]-L-valyl]amino]-4-phenylbutyl]-3(S)-isoquinolinecarboxamide | 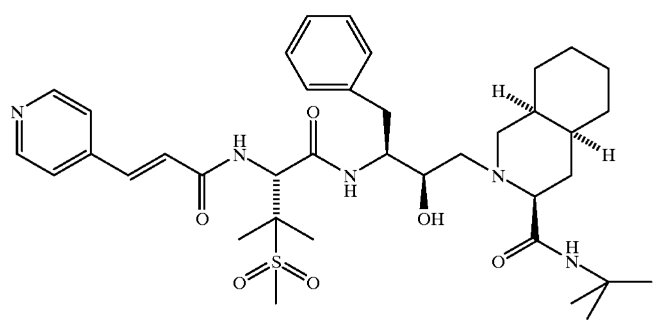 |
| 159 | N-tert-Butyl-1,2,3,4,4a(S),5,6,7,8,8a(S)-decahydro-2-[2(R)-hydroxy-3(S)-[(3-(methanesulfonyl)-N-[(6-quinolinyl)carbonyl]-L-valyl]amino]-4-phenylbutyl]-3(S)-isoquinolinecarboxamide | 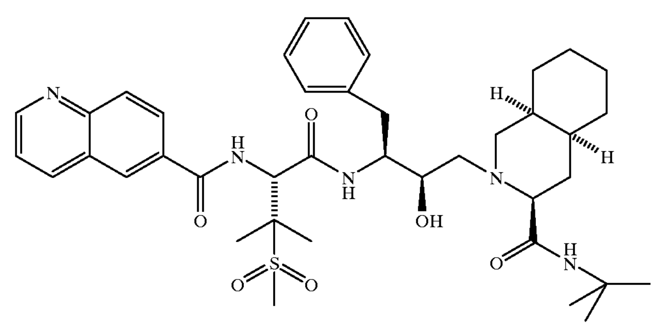 |

TABLE A-continued

| Ex | Name | Structures |
|---|---|---|
| 160 | 2-[3(S)-[[N-[(6-Benzothiazolyl)carbonyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 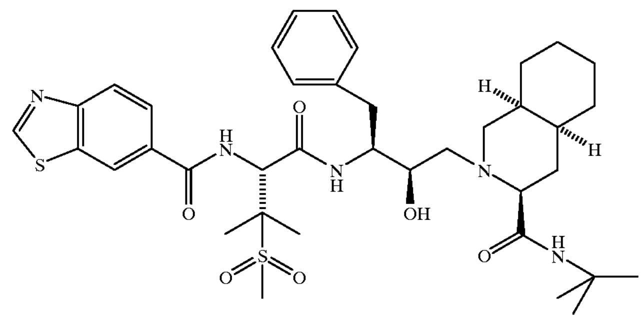 |
| 161 | (E)-N-tert-Butyl-1,2,3,4,4a(S),5,6,7,8,8a(S)-decahydro-2-[2(R)-hydroxy-3(S)-[[3-(methanesulfonyl)-N-[3-(2-pyridyl)acroyl]-L-valyl]amino]-4-phenylbutyl]-3(S)-isoquinolinecarboxamide | 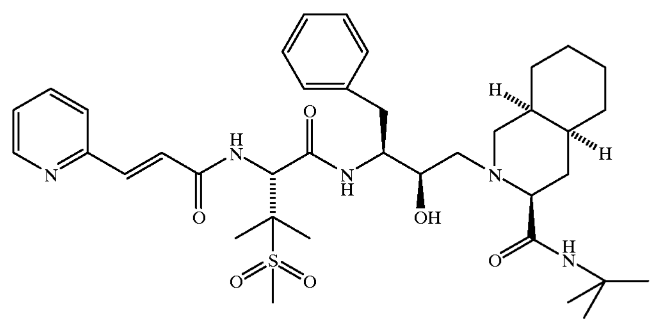 |
| 162 | (E)-N-tert-Butyl-1,2,3,4,4a(S),5,6,7,8,8a(S)-dehydro-2-[2(R)-hydroxy-3(S)-[[3-(methanesulfonyl)-N-[3-(3-pyridyl)acroyl]-L-valyl]amino]-4-phenylbutyl]-3(S)-isoquinolinecarboxamide | 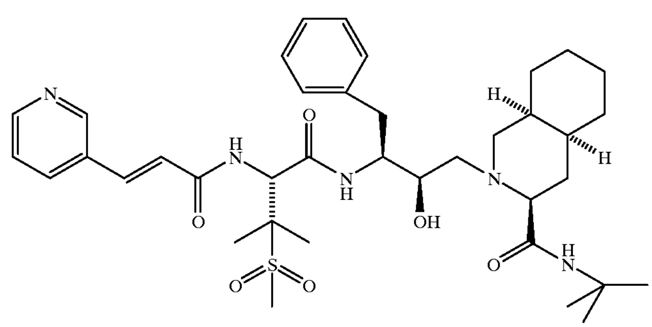 |
| 163 | N-tert-Butyl-1,2,3,4,4a(S),5,6,7,8,8a(S)-decahydro-2-[2(R)-hydroxy-3(S)-[[3-(methanesulfonyl)-N-[(2-quinoxalinyl)carbonyl]-L-valyl]amino]-4-phenylbutyl]-3(S)-isoquinolinecarboxamide | 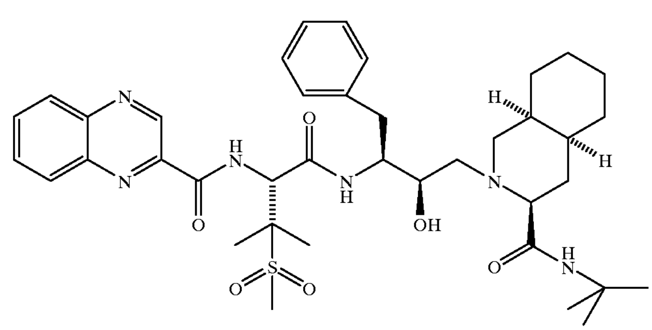 |

TABLE A-continued

| Ex | Name | Structures |
|---|---|---|
| 164 | N-tert-Butyl-1,2,3,4,4a(S),5,6,7,8,8a(S)-decahydro-2-[2(R)-hydroxy-3(S)-[[3-(methanesulfonyl)-N-[(pyrido[4,3-b]pyridin-2-yl)carbonyl]-L-valyl]amino]-4-phenylbutyl]-3(S)-isoquinolinecarboxamide | 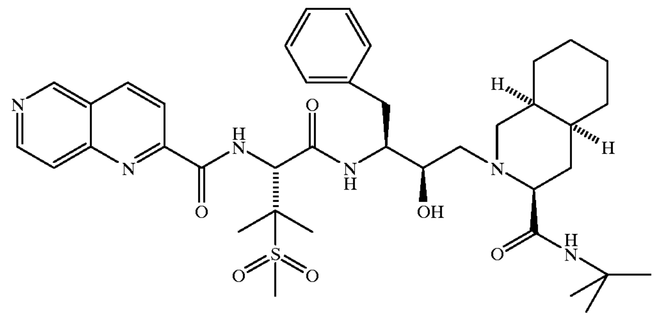 |
| 165 | (E)-N-tert-Butyl-1,2,3,4,4a(S),5,6,7,8,8a(S)-decahydro-2-[2(R)-hydroxy-3(S)-[[N-[3-(3-indolyl)acroyl]-3-(methanesulfonyl)-L-valyl]amino]-4-phenylbutyl]-3(S)-isoquinolinecarboxamide | 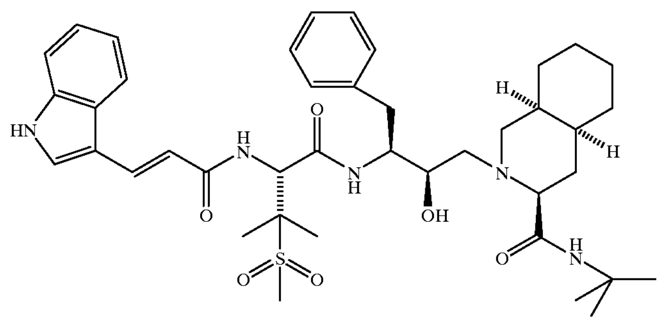 |
| 166 | (E)-2-[3(S)-[[N-[3-(1,3-Benzodioxol-5-yl)acroyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 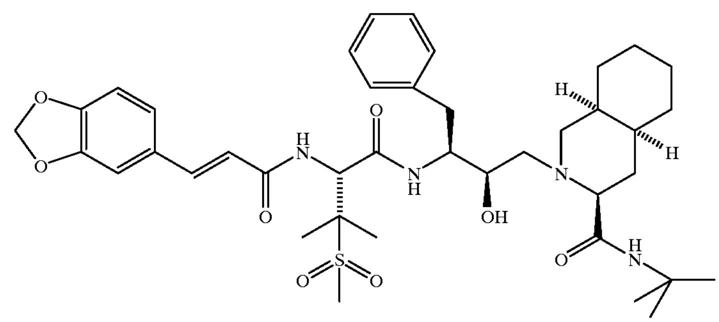 |
| 167 | N-tert-Butyl-1,2,3,4,4a(S),5,6,7,8,8a(S)-decahydro-2-[2(R)-hydroxy-3(S)-[[3-(methanesulfonyl)-N-[(3-quinolyl)carbonyl]-L-valyl]amino]-4-phenylbutyl]-3(S)-isoquinolinecarboxamide | 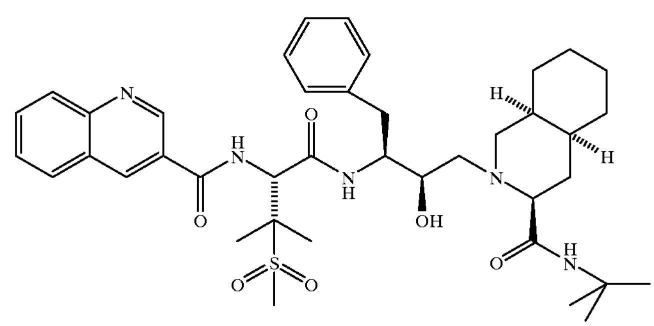 |

TABLE A-continued

| Ex | Name | Structures |
|---|---|---|
| 168 | 2[3(S)-[[N-(Benzylcarbamoyl)-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 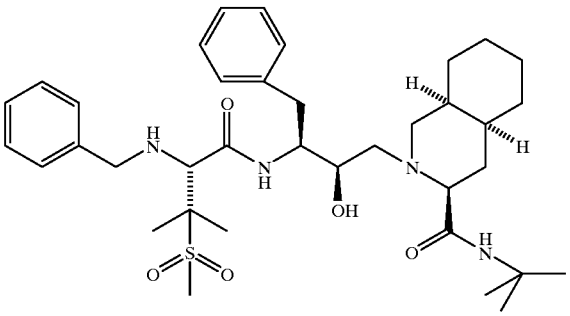 |
| 169 | N-tert-Butyl-1,2,3,4,4a(S),5,6,7,8,8a(S)-decahydro-2-[2(R)-hydroxy-3(S)-[[3-(methanesulfonyl)-N-[N-methyl-N-[(4-pyridyl)methyl]carbamoyl]-L-valyl]amino]-4-phenylbutyl]-3(S)-isoquinolinecarboxamide | 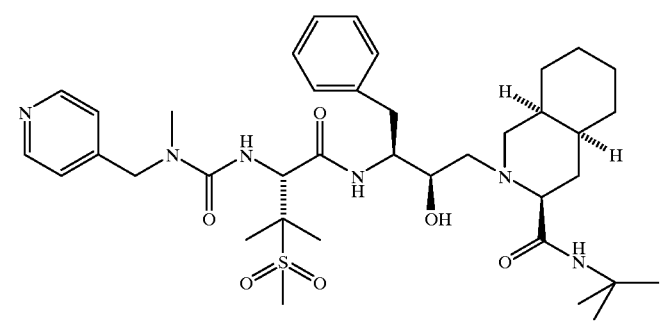 |
| 170 | N-tert-Butyl-1,2,3,4,4a(S),5,6,7,8,8a(S)-decahydro-2-[2(R)-hydroxy-3(S)-[[3-(methanesulfonyl)-N-[N-methyl-N-[(3-pyridyl)methyl]carbamoyl]-L-valyl]amino]-4-phenylbutyl]-3(S)-isoquinolinecarboxamide | 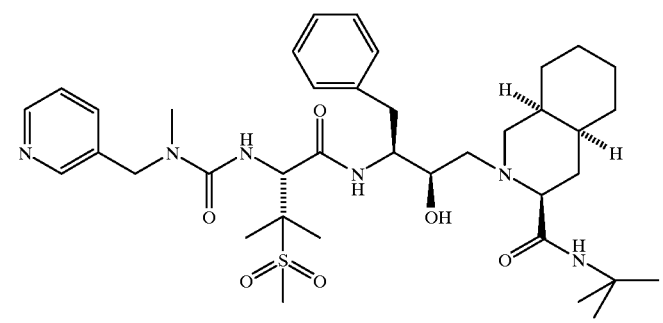 |
| 171 | N-tert-Butyl-1,2,3,4,4a(S),5,6,7,8,8a(S)-decahydro-2-[2(R)-hydroxy-3(S)-[[3-(methanesulfonyl)-N-[(5-methyl-2-furfuryl)carbamoyl]-L-valyl]amino]-4-phenylbutyl]-3(S)-isoquinolinecarboxamide | 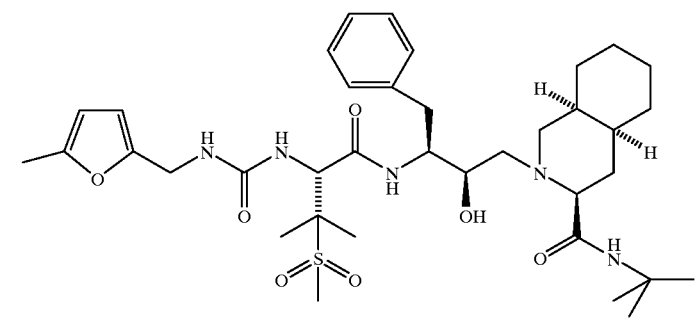 |

TABLE A-continued

| Ex | Name | Structures |
|---|---|---|
| 172 | N-tert-Butyl-2-[3(S)-[[N-[2-(4-fluorobenzylamino)acetyl]-3-(methanesulfonyl)-L-valyl]amino]-2(R)-hydroxy-4-phenylbutyl]-1,2,3,4,4a(S).5.6.7.8.8a(S)-decahydro-3(S)-isoquinolinecarboxamide | 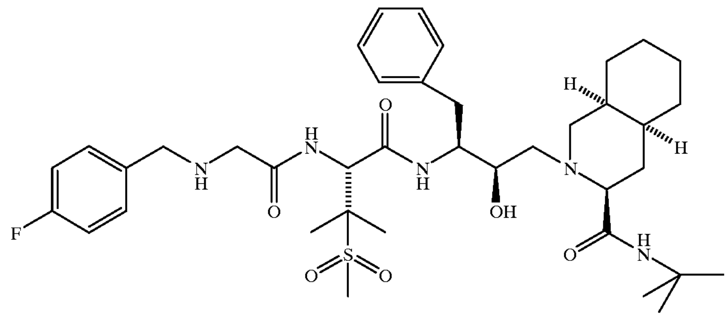 |
| 173 | 2-[3(S)-[[N-[2-(Benzylamino)acetyl]-3-(methanesulfonyl)-L-valyl]amino]-2(R)-hydroxy-4-phenylbutyl]-N-tert-butyl-1,2,3,4,4a(S).5.6.7.8.8a(S)-decahydro-3(S)-isoquinolinecarboxamide | 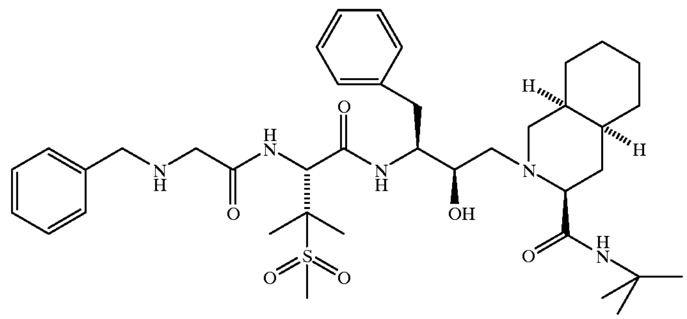 |

In another preferred embodiment $R^{13}$ has the meaning of —SO$_2$OH, —PO(OH)$_2$ or of a group

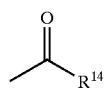

wherein $R^{14}$ is alkyl, alkenyl, cycloalkyl, aryl, aryl alkyl, heterocyclyl, a group —CH$_2$ (CH$_2$CH$_2$O)$_m$CH$_3$, wherein m is an integer from 0 to 10, or a carbonyl group-linked radical of an aminoacid.

Examples of compounds of formula I or II with $R^{13}$ not being H are set out in Table B below.

TABLE B

| Ex | Name | Structures |
|---|---|---|
| 146 | N-tert-Butyl-1,2,3,4,4s(S),5,6,7,8,8a(S)-decahydro-2-[2(R)-(isobutyryloxy)-3(S)-[[3-(methanesulfonyl)-N-[(3-pyridyl)carbonyl]-L-valyl]amino]-4-phenylbutyl]-3(S)-isoquinolinecarboxamide | 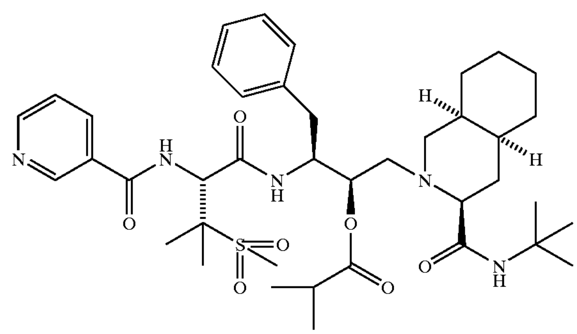 |

TABLE B-continued

| Ex | Name | Structures |
|----|------|------------|
| 147 | N-tert-Butyl-1,2,3,4,4a(S),5,6,7,8,8a(S)-decahydro-2-[2(R)-(isobutyryloxy)-3(S)-[[3-(methanesulfonyl)-N-[2-(3-pyridyloxy)acetyl]-L-valyl]amino]-4-phenylbutyl]-3(S)-isoquinolinecarboxamide | 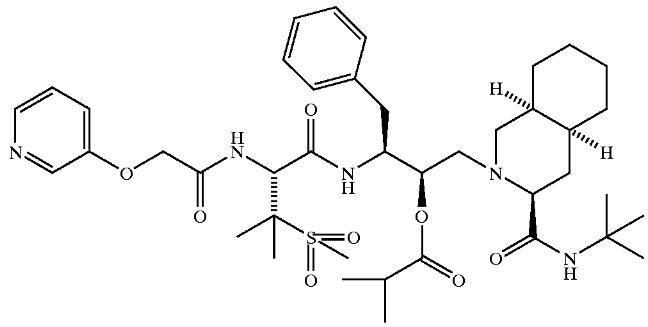 |
| 148 | N-tert-Butyl-1,2,3,4,4a(S),4,5,6,8,8(a)-decahydro-2-[3(S)-[[3-(methanesulfonyl)-N-[(3-pyridyl)carbonyl]-L-valyl]amino]-4-phenyl-2(R)-(L-valyloxy)butyl]-3(S)-isoquinolinecarboxamide | 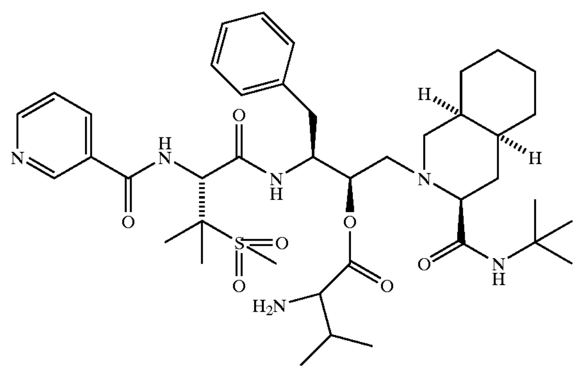 |
| 149 | N-tert-Butyl-1,2,3,4,4a(S),5,6,7,8,8a(S)-decahydro-2-[3(S)-[[N-[(2-indolyl)carbonyl]-3-(methanesulfonyl)-L-valyl]amino]-2(R)-[4-(morpholinomethyl)benzoyloxy]-4-phenylbutyl]-3(S)-isoquinolinecarboxamide | 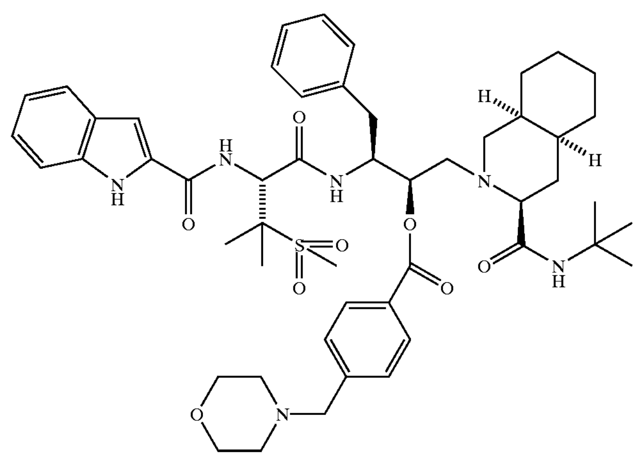 |

TABLE B-continued

| Ex | Name | Structures |
|---|---|---|
| 150 | N-tert-Butyl-2-[3(S)-[[N-(3-cyanobenzoyl)-3-(methanesulfonyl)-L-valyl]amino]-2(R)-[2-[2-(2-methoxyethoxy)ethoxy]acetoxy]-4-phenylbutyl]-1,2,3,4,4a(S),5,6,7,8,8a(S)-decahydro-3(S)-isoquinolinecarboxamide | 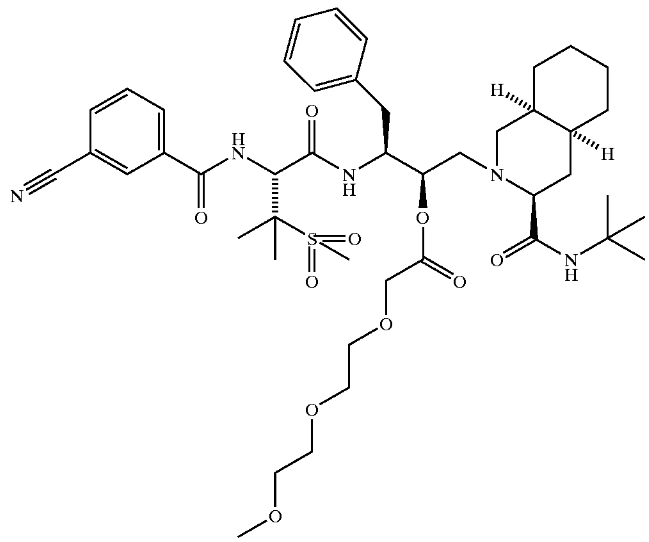 |
| 151 | N-tert-Butyl-2-[2(R)-(3-carboxypropionyloxy)-3(S)-[[3-(methanesulfonyl)-N-[(3-pyridyl)carbonyl]-L-valyl]amino]-4-phenylbutyl]-1,2,3,4,4a(S),5,6,7,8,8a(S)decahydro-3(S)-isoquinolinecarboxamide | 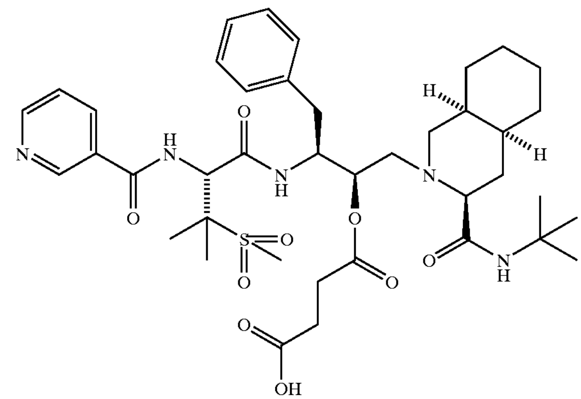 |

Further preferred compounds of formula (I) are those having the formula

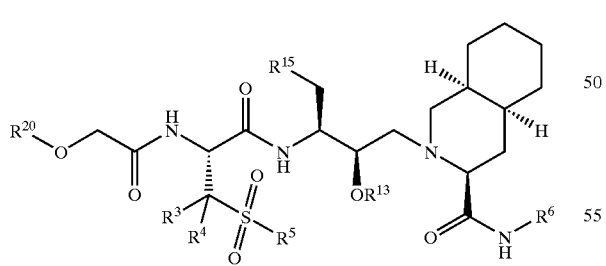

X wherein $R^3$, $R^4$, $R^5$, $R^6$, $R^{13}$ and $R^{15}$ are as above and $R^{20}$ is heterocyclyl.

More preferred compounds of formula (X) are those where $R^3$, $R^4$ and $R^5$ are methyl, $R^6$ is tert-butyl, $R^{13}$ is H and $R^{15}$ is phenyl.

Examples of such preferred compounds of formula (X) are listed below.

N-tert-Butyl-1,2,3,4,4a(S),5,6,7,8,8a(S)-decahydro-2-[2(R)-hydroxy-3(S)-[[3-(methanesulfonyl)-N-[2-(3-pyridyloxy)acetyl]-L-valyl]amino]-4-phenylbutyl]-3(S)-isoquinolinecarboxamide N-tert-Butyl-1,2,3,4,4a(S),5,6,7,8,8a(S)-decahydro-2-[2(R)-hydroxy-3(S)-[[3-(methanesulfonyl)-N-[2-(2-pyridyloxy)acetyl]-L-valyl]amino]-4-phenylbutyl]-3(S)-isoquinolinecarboxamide N-tert-Butyl-1,2,3,4,4a(S),5,6,7,8,8a(S)-decahydro-2-[2(R)-hydroxy-3(S)-[[3-(methanesulfonyl)-N-[2-(6-methyl-3-pyridyloxy)acetyl]-L-valyl]amino]-4-phenylbutyl]-3(S)-isoquinolinecarboxamide N-tert-Butyl-1,2,3,4,4a(S),5,6,7,8,8a(S)-decahydro-2-[2(R)-hydroxy-3(S)-[[3-(methanesulfonyl)-N-[2-(3-pyrazinyloxy)acetyl]-L-valyl]amino]-4-phenylbutyl]-3(S) -isoquinolinecarboxamide 2-(2-Hydroxy-3-{3-methanesulfonyl-3-methyl-2-[2-(pyrimidin-2-yloxy)-acetylamino]butyrylamino}-4-phenyl-butyl)-decahydro-isoquinoline-3-carboxylic acid tert-butylamide Most preferred compound is N-tert-Butyl-1,2,3,4,4a(S),5,6,7,8,8a(S)-decahydro-2-[2(R)-hydroxy-3(S)-[[3-(methanesulfonyl)-N-[2-(3-pyridyloxy)acetyl]-L-valyl]amino]-4-phenylbutyl]-3(S)-isoquinolinecarboxamide its pharmaceutically acceptable salts and esters.

The hydroxyethylamine compounds provided by the present invention are potent inhibitors, or prodrugs thereof, of the HIV aspartyl protease, an essential enzyme in the replicative cycle of the HIV virus. They accordingly are therapeutically active substances in the treatment of HIV-mediated diseases and therefore can be used as medicaments, either alone or combined with other therapeutically active agents.

The hydroxyethylamine compounds provided by the present invention are, in particular, useful in combating HIV disease states such as AIDS.

Compounds of the invention with formula I wherein $R^1$ is $NHR^2$ can be prepared from a compound of formula III

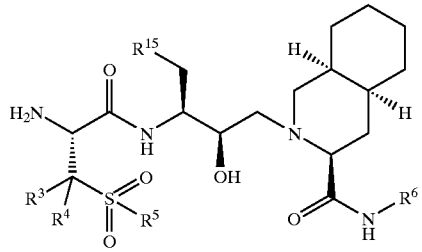

III wherein $R^3$, $R^4$, $R^5$, $R^6$ and $R^{15}$ are as above.

For a compound of formula I wherein $R^1$ is $NHR^2$ in which $R^2$ is alkyl carbonyl, cycloalkyl carbonyl, aryl carbonyl, heterocyclyl carbonyl, heterocyclyl alkyl carbonyl, aryl alkyl carbonyl, alkyl oxy carbonyl, aryl alkyl oxy carbonyl, heterocyclyl alkyl oxy carbonyl, sulfonyl, alkyl sulfonyl, aryl sulfonyl, heterocyclyl sulfonyl, or a group of formula

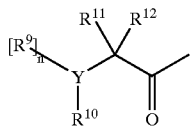

wherein $R^9$, $R^{10}$, $R^{11}$, and $R^{12}$ are as above.

the compound of formula III is reacted with an appropriate acid derivative such as an acyl halide, mixed anhydride etc.

Alternatively when n=1, Y represents N, $R^9$ is H and $R^{10}$ is alkyl, aryl alkyl, heterocyclyl alkyl, the compound of formula III is reacted with N-protected glycine, deprotected and reacted with an aldehyde or ketone under reductive conditions as described in embodiment b) of the process For a compound of formula I wherein $R^1$ is $NHR^2$ in which $R^2$ is, alkyl, alkenyl, alkynyl, arylalkyl, heterocyclylalkyl, cycloalkyl, a compound of formula III is reacted with an aldehyde or ketone under reductive conditions.

For a compound of formula I wherein $R^1$ is $NHR^2$ in which $R^2$ is a group of formula

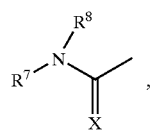

in which X, $R^7$ and $R^8$ have the same meaning as described previously, a compound of formula III is reacted with reagents described in the art for the formation of ureas and thioureas.

For a compound of formula I wherein $R^1$ is $NHR^2$ in which $R^2$ is a heterocycle a compound of formula III is reacted according to methods described in the art for the formation of heterocycles. For example, in the case where $R^2$ is thiazole, by using the Hansch synthesis according to Scheme 1, by converting a compound of formula III into the thiourea IV followed by reaction of IV with the required α-haloketone or α-haloaldehyde Scheme 1

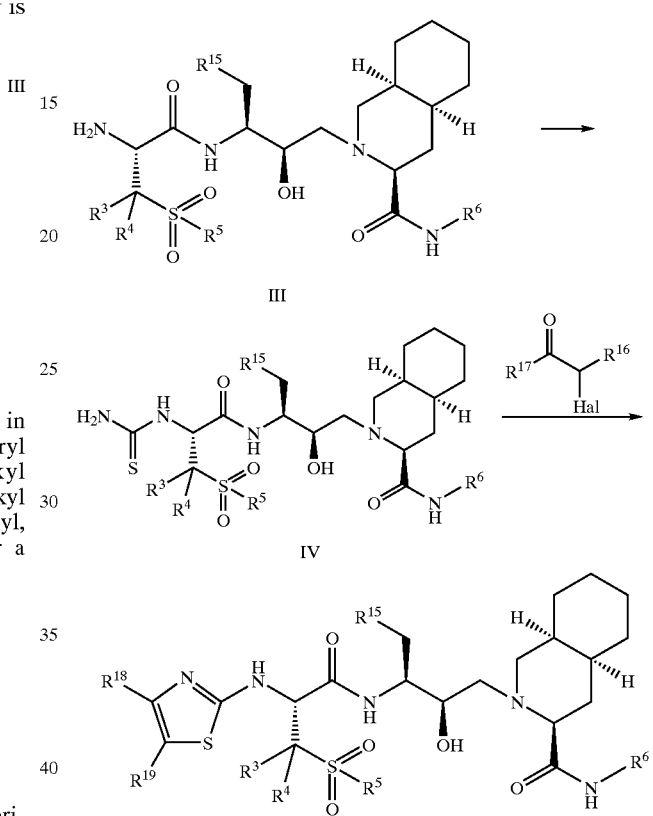

in said scheme, $R^2$, $R^3$, $R^4$, $R^5$, $R^6$ and $R^{15}$ are as previously described; $R^{16}$ has the meaning of H. alkyl, alkoxy carbonyl, aryl, heterocyclyl; $R^{17}$ has the meaning of H, alkyl, aryl, heterocyclyl; $R^{18}$ is the same as $R^{16}$; and $R^{19}$ is the same as $R^{17}$. Hal has the meaning of a halogen atom selected of, chlorine, bromine and iodine.

For a compound of formula I wherein $R^1$ is $NHR^2$ in which $R^2$ is aryl, a compound of formula III is reacted with aryl halides under transition metal catalysed conditions known in the art. Alternatively the amino acid derived from deprotection of compounds V (Scheme 3) can be reacted with aryl halides under similar conditions prior to coupling with compounds of formula VI (Scheme 3).

For a compound of formula I in which $R^6$ is alkyl, aryl alkyl, heterocyclyl alkyl, alkyl oxy alkyl, hydroxy alkyl, amino alkyl, fluoro alkyl, a compound of formula IVa (Scheme 2) is reacted with the appropriate amine under conditions of Lewis acid catalysis Scheme 2

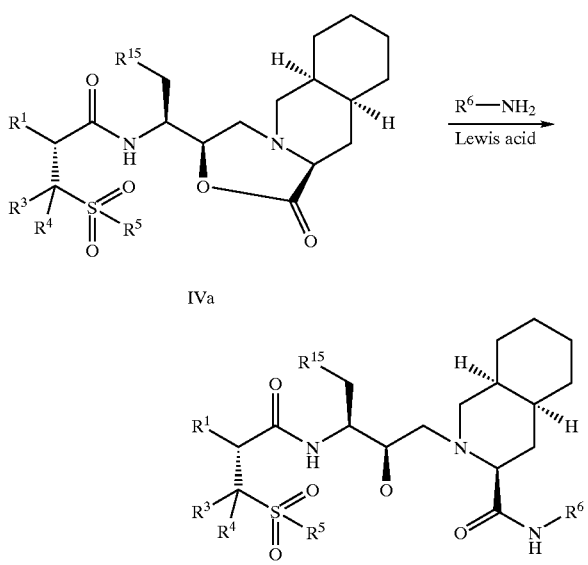

IVa in said scheme $R^1$, $R^3$, $R^4$, $R^5$, $R^6$ and $R^{15}$ are as previously described.

For a compound of formula I in which $R^{13}$ has the meaning of —$SO_2OH$, —$PO(OH)_2$, or a group

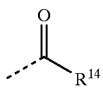

wherein $R^{14}$ is as previously described,
a compound of formula I in which $R^{13}$ is H is reacted with the appropriate activated acid derivative or, in the case of an amino acid, an amino-protected form thereof, according to methods described in the art for the formation of esters.

In accordance with embodiment a) of the process, suitable reagents which yield alkyl carbonyl, cycloalkyl carbonyl, aryl carbonyl, heterocycly carbonyl, aryl alkyl carbonyl, heterocycly alkyl carbonyl, alkyl oxy carbonyl, aryl alkyl oxy carbonyl, heterocyclyl alkyl oxy carbonyl, sulfonyl, alkyl sulfonyl, aryl sulfonyl, or heterocyclyl sulfonyl amines or a group of formula

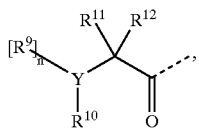

wherein $R^9$, $R^{10}$, $R^{11}$ and $R^{12}$ are as previously described,
are the corresponding acids or reactive derivatives thereof, such as the corresponding acid halides (e.g. acid chlorides), acid anhydrides, mixed anhydrides, activated esters etc. The reaction of III with the aforementioned reagents is carried out in accordance with methods described in the art for example in text books on organic chemistry such as J. March (1992) "Advanced Organic Chemistry: Reactions, Mechanisms and Structure", $4^{th}$ ed. John Wiley & Sons. Thus when an acid is used, the reaction is preferably carried out in the presence of condensation agents such as N-ethyl-N'(3-dimethylaminopropyl)carbodiimide hydrochloride (EDAC.HCl) in the presence of hydroxybenzotriazole (HOBT). This reaction is conveniently carried out in an inert organic solvent such as tetrahydrofuran (THF), dichloromethane or dimethylformamide at a temperature from −10° C. to +25° C. When a reactive derivative is used the reaction can be carried out in an inert solvent such as dichloromethane or tetrahydrofuran in the presence of an organic base (e.g. N-ethylmorpholine, triethylamine etc) at a temperature from −10° C. to 25° C.

In accordance with embodiment b) of the process, reaction of compounds of formula III with an aldehyde or ketone can be carried out according to methods described in the art for the reductive amination of aldehydes and ketones. For example, text books on organic chemistry such as J. March (1992) "Advanced Organic Chemistry: Reactions, Mechanisms and Structure", $4^{th}$ ed. John Wiley & Sons can be consulted. Thus, for example, the reaction is conveniently carried out with sodiumtriacetoxyborohydride in an inert halogenated solvent such as dichloroethane in the presence of acetic acid according to the method described by A. F. Abdel-Magid et al; Tetrahedron Letters 1990, 31, 5595.

In accordance with embodiment c) of the process, the reaction can be carried out according to methods known in the art, for example in text books on organic chemistry such as J. March (1992) "Advanced Organic Chemistry: Reactions, Mechanisms and Structure", $4^{th}$ ed. John Wiley & Sons. Thus, for example, for a compound in which X is O, the reaction can be carried out by reaction of compounds of formula III with para-nitrophenylchloroformate in the presence of an inorganic base such as sodium hydrogen carbonate followed by reaction with an amine $R^7R^8NH$ in the presence of an organic base such as triethylamine where $R^7$ and $R^8$ have the significance given earlier. (See for example N. Choy et al. Org. Prep. Proced. Int. 1996, 28(2), 173–7). The reaction is conveniently carried out in an inert polar solvent such as acetonitrile at a temperature between 0° C. and 25° C. When X is O or S and one of $R^7$ or $R^8$ is H the reaction can be conveniently carried out by the reaction of a compound of formula III with an isocyanate ($R^7N=C=O$ or $R^8N=C=O$) or isothiocyanate ($R^7N=C=S$ or $R^8N=C=S$) according to methods described in the art.

In accordance with embodiment d) of the process, the reaction can be carried out according to methods described in text books on heterocyclic chemistry such as T. L. Gilchrist (1992) "Heterocyclic Chemistry", $2^{nd}$ ed. John Wiley and Sons. For example when $R^2$ is thiazole, the reaction can be carried out by heating a mixture of compound IV and the α-halocarbonyl compound in an appropriate solvent such as an alkanol (e.g. ethanol). Compound IV can be readily prepared from compound III according to known methods, for example by reaction with benzoyl isothiocyanate in refluxing acetone followed by hydrolysis with an inorganic base such as potassium carbonate in a mixture of a polar organic solvent and water. (See for example N. M. Olken et al J. Med. Chem. 1992, 35, 1137).

In accordance with embodiment e) of the process, the reaction of amino acids (derived from compounds of formula V by deprotection) with aryl halides, e.g. bromobenzene, can be carried out in the presence of copper salts, e.g copper iodide in dimethyl acetamide. See for example D. Ma et al, J. Amer. Chem. Soc 1998, 120, 12467.

In accordance with embodiment f) of the process, the reaction of compounds of formula IVa with amines $R^6NH_2$ is carried out using methods described in the art for example using a reagent derived from the amine and an aluminium derived Lewis acid, e.g. trimethylaluminium, at ambient temperature in an inert solvent such as dichloromethane or toluene. (See for example S. M. Weinreb et al, Tetrahedron Letters 1977, 4171)

In accordance with embodiment g) of the process, the reaction can be carried out according to methods known in the art for the formation of esters, see for example text books on organic chemistry such as J. March (1992) "Advanced Organic Chemistry: Reactions, Mechanisms and Structure", 4th ed. John Wiley & Sons. For example the reaction is conveniently carried out at ambient temperature using the carboxylic acid derivative and a peptide coupling reagent such as EDAC.HCl in an inert solvent such as dichloromethane in the presence of 4-dimethylaminopyridine as a catalyst. Alternatively the acyl halide can be used in an inert solvent in the presence of pyridine and 4-dimethylaminopyridine as a catalyst at a temperature between 0° C. and 25° C.

Compounds of formula III which are used as starting materials in embodiments a–e are either known as can be prepared according to Scheme 3. Thus reaction of a compound of formula V with a compound of formula VI can be carried out in accordance with methods known in peptide chemistry to give a compound of formula VII (see J. Jones (1994), "The Chemical Synthesis of Peptides", Oxford University Press). The term "amino protecting group" (Prot) as used herein refers to groups employed in peptide chemistry such as a tert-butoxycarbonyl group (BOC) or a 9-fluorenylmethyloxycarbonyl group (FMOC). The preferred amino protecting group (Prot) for this reaction is a 9-fluorenylmethyloxycarbonyl group. This reaction is preferably carried out by reaction of a compound of formula V with a chloroformate (e.g. isobutylchloroformate) in the presence of an organic base such as N-ethylmorpholine to generate a mixed anhydride which is subsequently reacted with compounds of formula VI. The reaction is conveniently carried out in an inert solvent such as an ether (e.g. diethyl ether, tetrahydrofuran, etc) or an aliphatic halogenated solvent (e.g. dichloromethane) at a low temperature, suitably at about −10° C. to 5° C. Conversion of compounds of formula VII into compounds of formula III is carried out using known methods employed in peptide chemistry for the deprotection of the amino group of amino acids. For example when the amino protecting group is FMOC the reaction is conveniently conducted by reaction of compounds of formula VII with piperidine in dimethylformamide or dichloromethane at room temperature.

Scheme 3

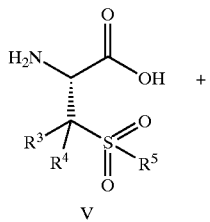

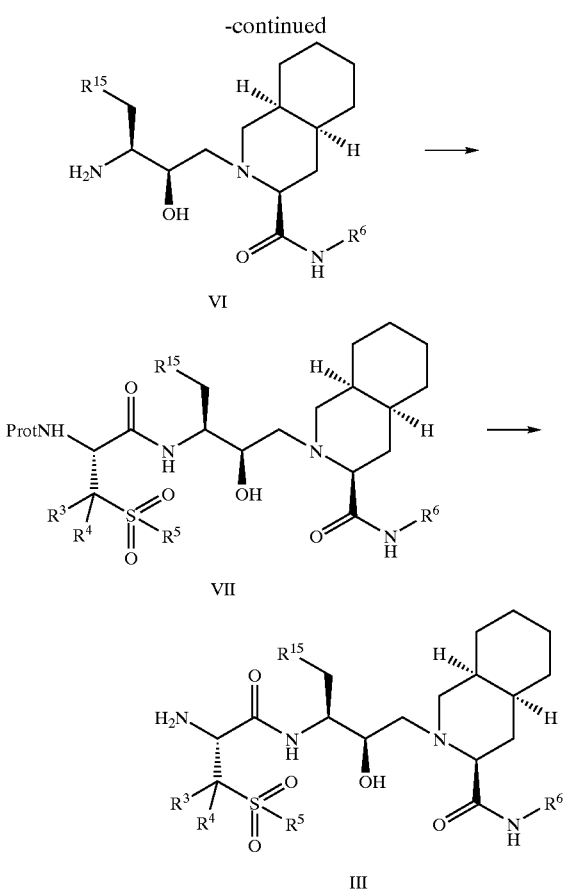

in said scheme $R^3$, $R^4$, $R^5$, $R^6$ and $R^{15}$ have the meaning previously described.

Compounds of formula V where $R^3$ and $R^4$ are methyl can be prepared from penicillamine according to Scheme 4.

Scheme 4

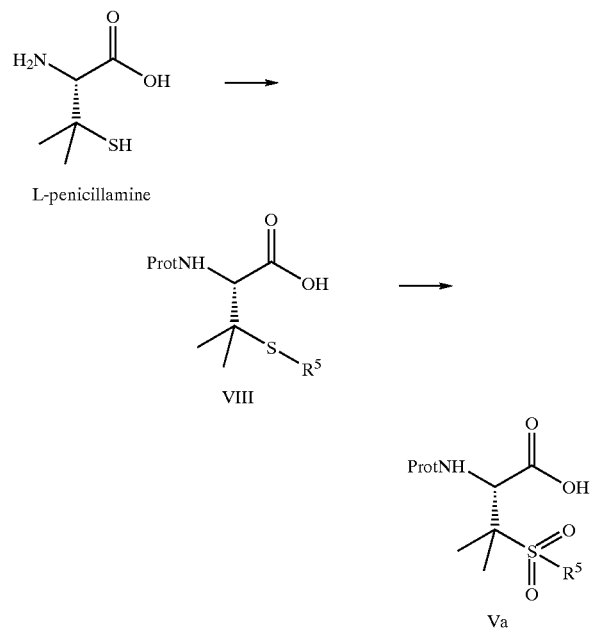

in said scheme R⁵ is as previously described.

Thus reaction of L-penicillamine with an alkyl halide R⁵X, where R⁵ has the significance given earlier and X is a halogen (e.g. bromide), in the presence of an inorganic base such as potassium carbonate, followed by reaction with a reagent for introducing amino acid protecting groups (e.g. FMOCONSu or BOC₂O) gives compounds of formula VIII. The reaction can be carried out at room temperature in a mixed solvent system consisting of water and an organic solvent preferably dioxane. Compounds of formula VIII are oxidized to compounds of formula Va according to known procedures preferably by reaction with Oxone (K. S. Webb, Tetrahedron Lett. 1994, 35(21), 3457–60).

Other compounds of formula V can be prepared by analogous routes from penicillamine analogues described in the art.

Compounds of formula VI can be prepared according to the known procedures described in the art, for example EP 432695 A2.

Compounds of formula I in which R¹ is hydroxy can be prepared according to methods described in the art, for example A. N. Cook et al; J. Chem. Soc. 1949, 1022. For example, deprotection of the amino acids V followed by diazotization, hydrolysis, and coupling to compounds of formula VI according to the methods described above gives compounds of formula I in which R¹ is hydroxy.

Compounds of formula I in which R¹ is H can be prepared from compounds of formula VI and compounds of formula IX (Scheme 5) in a manner analogous to that already described. Compounds of formula IX can be prepared from the appropriate acrylic acid and thiol according to methods decribed in the art and outlined in Scheme 5 (See for example G. Pattenden et al, J. Chem. Soc., Perkin Trans. 1, 1992, (10), 1215–21)

Scheme 5

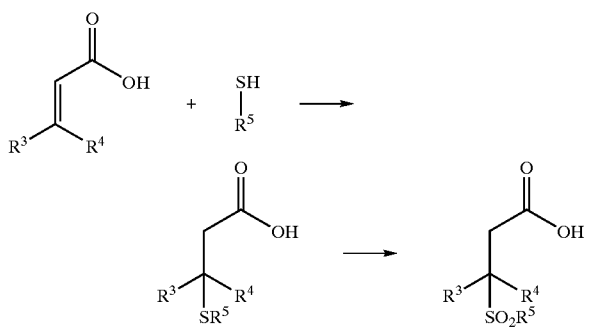

in said scheme R³, R⁴ and R⁵ are as previously described.

The starting materials of formula V, VI, IX and their reactive derivatives, insofar as they are not known compounds or analogues of known compounds, can be prepared in a similar manner to the known compounds or as described in the examples hereinafter or by analogy thereto. Moreover, the reagents used in embodiments a–g are generally known compounds.

Reagents required for the introduction of groups of formula

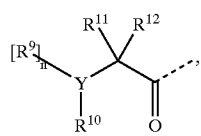

wherein R⁹, R¹⁰, R¹¹ and R¹² are as previously described are the corresponding carboxylic acids, or activated derivatives thereof, which themselves are known compounds or can be readily prepared by analogy to known compounds. For example when n=0, Y represents O or S and R¹⁰ is aryl or heterocyclyl the reagent is prepared by reaction of the appropriate alcohol (e.g. 3-hydroxypyridine) with tert-butylbromoacetate under basic conditions (e.g. sodium hydride in dimethylformamide or potassium carbonate in acetone) followed by acid-catalysed deprotection (e.g. hydrochloric acid in ether, hydrobromic acid in acetic acid or trifluoroacetic acid in dichloromethane). Similarly, when n=1 and Y represents N, the reagent can be prepared by similar methods in which the amine R⁹R¹⁰NH is used instead of the alcohol and without added base. Alternatively, glycine t-butyl ester can be reductively aminated with an aldehyde or ketone under analogous conditions to those described above in embodiment b) of the process, followed by acid catalysed deprotection of the carboxylic acid group; preferably with HBr in acetic acid.

Assay Methods

HIV Protease Inhibition Assay

HIV protease inhibitory activity was assessed using an adaptation of the method of Matayoshi. et al. [Matayoshi E. D. et al (1990). Science. 247. 954–958]

Crude HIV-1 protease was prepared from E. coli pPTΔN. Cultures were grown at 30° in M9 medium supplemented with 0.2% casamino acids, 100 μg/ml ampicillin and 25 μg/ml thiamine until $OD_{600}$=0.5–0.6, and the temperature was raised to 42° to induce expression of the protease. After 1.5 hours, the cells were harvested and the pellets stored at −70° until required.

The protease was prepared by lysis of the cells in a French pressure cell followed by precipitation of the enzyme with ammonium sulfate at 30% saturation.

The assay was based on intramolecular fluorescence energy transfer using a quenched fluorogenic substrate DABCYL-Ser.Gln.Asn.Tyr.Pro.Ile.Val.Gln.-EDANS, the peptide sequence of which was derived from one of the natural polypeptide processing sites of HIV-1 protease.

The peptide substrate was dissolved in spectroscopic grade dimethyl sulphoxide (DMSO) to give a stock solution of 500 μM. Inhibitors were dissolved in a 1:9 mixture of DMSO:0.1% aqueous Tween 20 to give inhibitor concentrations 20× more concentrated than the desired final concentration. The assay buffer comprised 0.1M sodium acetate pH 4.7, 8 mM EDTA, 0.2 M NaCl.

10 μl HIV-1 protease diluted in a 1:1 mixture of 0.1% Tween:assay buffer (concentration adjusted to give approximately 20% substrate turnover) was added to a mixture comprising 455 μl assay buffer, 25 μl inhibitor solution, 10 μl substrate solution.

Tubes were incubated for 2 hours at 37° and the reaction was terminated by the addition of 500 μl of a 2:1 mixture of DMSO:50 mM Tricine pH 8.5. Fluorescence was measured in a fluorescence spectrophotometer, excitation λ=340 nm, emission λ=492 nm.

Antiviral Assay Method

Anti-HIV antiviral activity was assessed using an adaptation of the method of Pauwels et al. [Pauwels et al., 1988, J. Virol. Methods 20: 309–321]. The method is based on the ability of compounds to protect HIV-infected T lymphoblastoid cells (MT4 cells) from cell-death mediated by the infection. The endpoint of the assay was calculated as the concentration of compound at which the cell viability of the culture was preserved by 50% ('50% inhibitory concentration', $IC_{50}$). The cell viability of a culture was determined by the uptake of soluble, yellow 3-[4,5-dimethylthiazol-2-yl]-2,5-diphenyltetrazolium bromide (MTT) and its reduction to a purple insoluble formazan salt. After solubilization, spectrophotometric methods were employed to measure the amount of formazan product.

MT4 cells were prepared to be in logarithmic-phase growth and a total of $2 \times 10^6$ cells infected with either the wild type or site directed mutant clones of HIV-HXB2 at a multiplicity of approximately 0.0001 infectious units of virus per cell in a total volume of between 200–500 µl. The cells were incubated with virus for one hour at 37° C. then washed in 0.01 M phosphate buffered saline, pH 7.2, and resuspended in culture medium for incubation in culture with serial dilutions of test compound. The culture medium used was RPMI 1640 without phenol red, supplemented with penicillin, streptomycin, L-glutamine and 10% fetal calf serum (GM10).

Test compounds were prepared as 2 mM solutions in dimethyl sulphoxide (DMSO). Four replicate, serial 2-fold dilutions in GM10 were then prepared and 50 microliter amounts placed in 96-well plates over a final concentration range of 625–1.22 nm. Fifty microliters GM10 and $3.75 \times 10^4$ infected cells were then added to each well. Control cultures containing no cells (blank), uninfected cells (100% viability; 4 replicates) and infected cells without compound (total virus-mediated cell death; 4 replicates) were also prepared. The cultures were then incubated at 37° C. in a humidified atmosphere of 5% $CO_2$ in air for 5 days.

A fresh solution of 5 mg/mL MTT was prepared in 0.01 M phosphate buffered saline, pH 7.2 and 20 µL added to each culture. The cultures were further incubated as before for 2 hours. They were then mixed by pipetting up and down, and 170 microliters of Triton X-100 in acidified isopropanol (10% v/v Triton X-100 in 1:250 mixture of concentrated HCl in isopropanol) were added and the cultures were mixed again by pipetting up and down. When the formazan deposit was fully solubilized by further mixing, the absorbance (OD) of the cultures was measured at 540 nm and 690 nm wavelength (690 nm readings were used as blanks for artefacts between wells). The percent protection for each treated culture was then calculated from the equation:

$$\text{Protection} = \frac{\text{(OD drug-treated cultures)} - \text{(OD untreated virus control cultures)}}{\text{(OD uninfected cultures)} - \text{(OD untreated virus control cultures)}} \times 100\%$$

The $IC_{50}$ was then obtained from graph plots of percentage protection versus $\log_{10}$ drug concentration.

The $IC_{50}$ of the compounds of the present invention is as a rule in the range of 1 nM to 10,000 nM, preferably in the range of 1 nM to 60 nM.

Some representative activity data is given in table 9 below.

TABLE 9

| Example number | Enzyme inhibitory $IC_{50}$ (nM) | Antiviral $IC_{50}$ (nM) |
| --- | --- | --- |
| 3 | 0.6 | 17 |
| 4 | 2.8 | 14 |
| 7 | 2.3 | 21 |
| 16 | 1.0 | 12 |
| 28 | 1.0 | 21 |
| 40 | 1.4 | 19 |
| 92 | 4.0 | 33 |
| 93 | 0.5 | 8 |
| 95 | 61.0 | 250 |
| 106 | 10.7 | 60 |
| 112 | 7.5 | 94 |
| 138 | 7.8 | 65 |
| 152 | 1.2 | 17 |
| 154 | 0.5 | 16 |
| 168 | 0.5 | 16 |
| 170 | 1.0 | 13 |

Enzyme inhibitory $IC_{50}$s have been rounded up to 1 decimal point, antiviral $IC_{50}$s have been rounded up to nearest whole number.

The compounds of the present invention, as well as their pharmaceutically usable acid addition salts, can be used as medicaments, e.g. in the form of pharmaceutical preparations. The pharmaceutical preparations can be administered orally, e.g. in the form of tablets, coated tablets, dragees, hard and soft gelatin capsules, solutions, emulsions or suspensions. The administration can, however, also be effected rectally, e.g. in the form of suppositories, or parenterally, e.g. in the form of injection solutions.

The compounds of the present invention and their pharmaceutically usable acid addition salts can be processed with pharmaceutically inert, inorganic or organic excipients for the production of tablets, coated tablets, dragees and hard gelatin capsules. Lactose, corn starch or derivatives thereof, talc, stearic acid or its salts etc. can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 2500 mg per person of a compound of formula I should be appropriate, although the above upper limit can also be exceeded when necessary.

The daily dosage can be administered as a single dosage or in divided dosages. The treatment may be in conjunction with the administration of one or more additional therapeutically active substance(s), and such administration may be concurrent or sequential with respect to that of the compounds of formula I. Thus, concurrent administration, as used herein, includes administration of the agents in conjunction or combination, together, or before or after each other.

EXAMPLES

Mass spectra were recorded under electrospray ionization conditions on one of the following instruments:

THERMOQUEST SSQ 7000 [Solvent 0.085% TFA in 90% acetonitrile/water; flow rate 100 microliters/minute; capillary 250° C.; spray voltage 5KV; sheath gas 80 psi], or LC-MS system (liquid chromatograph coupled to mass spectrum) THERMOQUEST 7000 ELECTROSPRAY or MICROMASS PLATFORM ELECTROSPRAY [gradient of 0.1% TFA in water to 0.085% TFA in acetonitrile]

With regard to the starting materials that are known compounds some of these may be purchased from commercial suppliers. Other known starting materials and their analogues can be prepared by methods well known in the art. Examples of the compounds available from commercial suppliers, and citations to the synthesis of other compounds and their analogues are provided in the following.

The following examples illustrate the present invention:

Example 1

2-[3(S) -[[N-Benzoyl-3-(methanesulfonyl)-L-valyl]amino]-2(R)-hydroxy-4-phenylbutyl]-N-benzyl-1,2,3,4,4a(S),5,6,7,8,8a(S)-decahydro-3(S)-isoquinolinecarboxamide

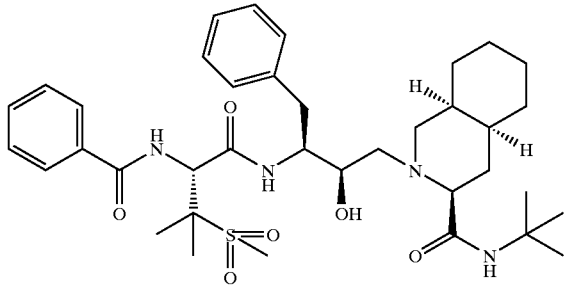

A stirred solution of 105 mg (0.13 mmol) of N-tert-butyl-2-[3(S)-[[N-[(9-fluorenyl)methoxycarbonyl]-3-(methanesulfonyl)-L-valyl]amino]-2(R) -hydroxy-4-phenylbutyl]-1,2,3,4,4a(S),5,6,7,8,8a(S)-decahydro-3(S)-isoquinolinecarboxamide in 4 ml of dry dimethylformamide at room temperature was treated with 0.4 ml (4 mmol) of piperidine. After 2.5 hours the volatiles were evaporated and the residue triturated with hexane to give N-tert-butyl-1,2,3,4,4a(S),5,5,6,7,8,8a(S)-decahydro-2-[2(R)-hydroxy-3(S) -[[3-(methanesulfonyl)-L-valyl]amino]-4-phenylbutyl]-3(S)-isoquinolinecarboxamide as a gum which was dissolved in 3 ml of dichloromethane and cooled to 0° C. 0.035 ml (0.26 mmol) of N-Ethylmorpholine (NEM) was added followed by 0.016 ml (0.13 mmol) of benzoyl chloride (Aldrich 24,054-0). After 2 hours the solution was diluted with 20 ml of dichloromethane and washed in sequence with 10% aqueous citric acid solution, saturated sodium hydrogen carbonate and brine. The solution was dried over magnesium sulfate and evaporated under reduced pressure to give a solid which was chromatographed on silica eluting with dichloromethane/methanol (37:3) to give the product 60 mg (67%) as a white solid, mp 212–18° C., [M+H]$^+$ 683.2.

The starting material was prepared as follows:

N-tert-Butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S) -decahydro-3(S)-isoquinolinecarboxamide

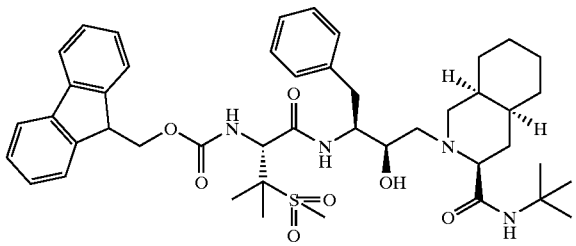

A stirred solution of 596 mg (4 mmol) of L-penicillamine (Aldrich 19,631-2) in 40 ml of water/dioxane (1:1) was treated at room temperature with 11.04 g (80 mmol) of potassium carbonate followed by 710 mg (5 mmol) of iodomethane followed, after 1 hour, by 5.39 g (20 mmol) of N-(9-fluorenylmethyloxycarbonyl)-oxysuccinimide (Advanced Chemtech RC8015). After a further 2 hours the volatiles were evaporated and the residue partitioned between water and ether. The solution was acidified with 2N hydrochloric acid, extracted with ether and the combined organic phase dried over magnesium sulfate. Evaporation to dryness afforded a yellow foam which was chromatographed on silica eluting with dichloromethane/methanol (9:1) to give 4.8 g (78%) of N-[(9-fluorenyl)methoxycarbonyl]-3-(methylthio)-L-valine as a white foam, [M+H]$^+$ 385.9.

A vigorously stirred solution of 4.8 g (12.4 mmol) of N-[(9-fluorenyl)methoxycarbonyl]-3-(methylthio)-L-valine, obtained from (A) above, in 36 ml of water containing 600 mg (15 mmol) of sodium hydroxide was treated with 8.43 g (99 mmol) of sodium hydrogen carbonate and 12 ml of acetone. 10.26 g (16.68 mmol) of OXONE® (Aldrich 22,803-6) in 36 ml of (0.0004M) EDTA solution was added dropwise and the solution stirred vigorously for 2 hours. A solution of 6.3 g of sodium metabisulfite in 12.6 ml of water was then added and the solution stirred for a further 15 minutes. Ethyl acetate was added and the aqueous phase was acidified to pH 2 with 6N hydrochloric acid, saturated with sodium chloride and extracted with ethyl acetate. The combined organic phase was washed in sequence with water and brine, dried over magnesium sulfate and evaporated under reduced pressure to give a yellow gum. Trituration with petroleum ether (bp 40–60° C.)/ether afforded a cream solid which was washed further with ether to give 3.18 g (61%) of N-[(9-fluorenyl)methoxycarbonyl]-3-(methanesulfonyl)-L-valine as a white solid, mp 189–92° C., [M+H]$^+$ 417.8.

C) A solution of 8.34 g (20 mmol) of N-[(9-fluorenyl)methoxycarbonyl]-3-(methanesulfonyl)-L-valine, obtained from (B) above, in dry tetrahydrofuran was cooled to −10° C. and 2.8 ml (20 mmol) of triethylamine was added followed by 2.6 ml (20 mmol) of isobutyl chloroformate (Aldrich 17,798-9). 8.02 g (20 mmol) of 2-(3(S)-amino-2(R)-hydroxy-4-phenylbutyl)-N-tert-butyl-1,2,3,4,4a(S),4,5,6,7,8,8a(S)-decahydro-3(S)-isoquinolinecarboxamide (prepared according to known methods, e.g. Martin, Joseph Armstrong; Redshaw, Sally; EP 432695 A2) was then added and the mixture stirred at −10° C. for a further 2 hours and then allowed to warm to room temperature overnight. The volatiles were evaporated and the residue partitioned between 100 ml of dichloromethane and 100 ml of 10% citric acid solution. The aqueous phase was extracted with dichloromethane and the combined organic phase was washed with saturated sodium hydrogen carbonate and brine, dried over magnesium sulfate and evaporated under reduced pressure to give a solid which was triturated with ether followed by ether/ethyl acetate (10:1) to give 10.84 g (68%) of N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide as a white solid, [M+H]⁺ 801.4.

Example 2

N-tert-Butyl-2-[3(S)-[[N-(N-ethyl-N-methylglycyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide

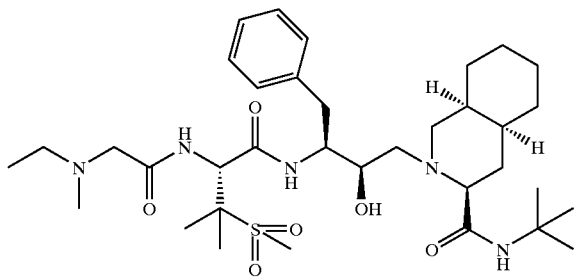

A solution of 38 mg (0.2 mmol) of N-ethyl-N-methylglycine hydrobromide and 116 mg (0.2 mmol) of N-tert-butyl-1,2,3,4,4a(S),5,5,6,7,8,8a(S)-decahydro-2-[2(R)-hydroxy-3(S)-[[3-(methanesulfonyl)-L-valyl]amino]-4-phenylbutyl]-3(S)-isoquinolinecarboxamide in 5 ml of dichloromethane was treated with 28 mg (0.2 mmol) of 1-hydroxy-7-azabenzotriazole (HOAT), 0.05 ml (0.4 mmol) of N-ethylmorpholine (NEM) and 38 mg (0.2 mmol) of N-ethyl-N'(3-dimethylaminopropyl)carbodiimide hydrochloride (EDAC.HCl) at 0° C. and allowed to warm to room temperature overnight. The reaction mixture was diluted with dichloromethane, washed with saturated sodium hydrogen carbonate and brine, dried over magnesium sulfate and evaporated under reduced pressure to give a gum which was chromatographed on silica eluting with dichloromethane/methanol (19:1) to give 65 mg of N-tert-butyl-2-[3(S)-[[N-(N-ethyl-N-methylglycyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide as a white foam, [M+H]⁺ 678.4.

The starting material N-ethyl-N-methylglycine hydrobromide (1:1) was prepared as follows A stirred solution of 0.6 ml (7 mmol) of N-ethylmethylamine and 0.97 ml (7 mmol) of triethylamine in 7 ml of dichloromethane was treated with 1 ml (7 mmol) of tert-butyl bromoacetate (Aldrich 12,423-0) and stirred overnight. The volatiles were evaporated and the residue triturated with ethyl acetate and the solid was removed by filtration. The solvent was evaporated to give 459 mg of a yellow oil which was treated at room temperature with 2 ml of 45% hydrobromic acid in acetic acid, and stirred for 6 hours. The volatiles were evaporated under reduced pressure and the residue was triturated extensively with ethyl acetate to give 413 mg N-ethyl-N-methylglycine hydrobromide as a white solid.

Example 3

N-tert-Butyl-1,2,3,4,4a(S),5,6,7,8a(S)-decahydro-2-[2(R)-hydroxy-3(S)-[[3-(methanesulfonyl)-N-[2-(3-pyridyloxy)acetyl]-L-valyl]amino]-4-phenylbutyl]-3(S)-isoquinolinecarboxamide

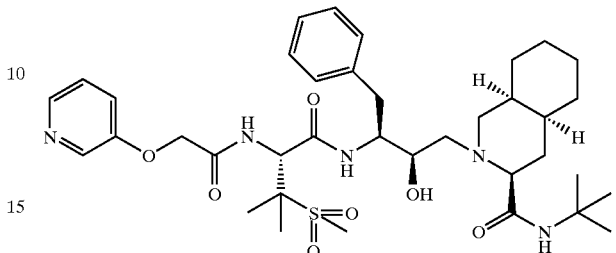

Example 3, [M+H]⁺ 714.4, was prepared in a manner analogous to that described in Example 2 but starting from 2-(3-pyridyloxy)acetic acid trifluoroacetate.

The starting material 2-(3-pyridyloxy)acetic acid trifluoroacetate was prepared as follows:

A solution of 9.5 g (0.1 mol) of 3-hydroxypyridine in 50 ml of dry dimethylformamide at 0° C. was treated portionwise with a slurry of sodium hydride in hexane (prepared by washing 4 g of sodium hydride (60% dispersion of in mineral oil) with hexane). After 30 minutes 19.4 g (0.1 mol) of tert-butyl bromoacetate was added dropwise and the solution stirred overnight. The volatiles were evaporated and the residue partitioned between dichloromethane and water. The organic phase was washed with water, dried over magnesium sulfate and evaporatedunder reduced pressure to give an oil which was chromatographed on silica eluting with dichloromethane to give 8.9 g of a green-brown oil. The oil was dissolved in dichloromethane, cooled to 0° C. and treated with 18 ml of trifluoroacetic acid and allowed to warm to room temperature overnight. The volatiles were evaporated and the residue triturated with ether to give 9.2 g of 2-(3-pyridyloxy)acetic acid trifluoroacetate as a light brown solid.

Example 4

N-tert-Butyl-1,2,3,4,4a(S),5,6,7,8,8a(S)-decahydro-2-[2(R)-hydroxy-3(S)-[[3-(methanesulfonyl)-N-(methoxycarbonyl)-L-valyl]amino]-4-phenylbutyl]-3(S)-isoquinolinecarboxamide

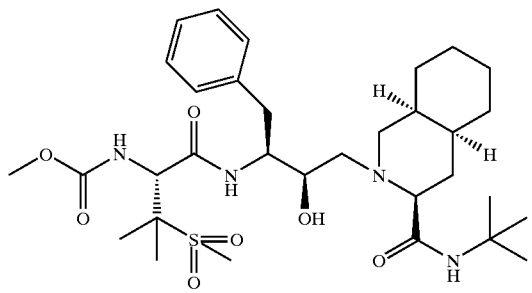

A stirred solution of 200 mg (0.25 mmol) of N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide in 5 ml of dry dimethylformamide at room temperature was treated with 0.63 ml (6.3 mmol) of piperidine. After 2.5 hours the volatiles were evaporated and the residue triturated with hexane to give N-tert-butyl-1,2,3,4,4a(S),5,5,6,7,8,8a(S)-decahydro-2-[2(R)-hydroxy-3(S)-[[3-(methanesulfonyl)-L-valyl]amino]-4-phenylbutyl]-3(S)-isoquinolinecarboxamide as a gum which was dissolved in 5 ml of dichloromethane and treated with 0.2 ml (1.5 mmol) of N-ethylmorpholine (NEM) and 0.02 ml (0.25 mmol) of methylchloroformate (Aldrich, M3,530-4) and stirred overnight. A further 0.02 ml (0.25 mmol) of methylchloroformate was added and the reaction stirred for a further 3 hours. The solution was diluted with dichloromethane, and then washed with 10% citric acid solution, saturated sodium hydrogen carbonate and brine. The citric acid solution was made basic by the addition of solid sodium hydrogen carbonate and extracted with dichloromethane. The combined organic phase was dried over magnesium sulfate and evaporated under reduced pressure to give a residue which was chromatographed on silica eluting with dichloromethane/methanol (19:1) and triturated with ether to give 75 mg of N-tert-Butyl-1,2,3,4,4a(S),5,6,7,8,8a(S)-decahydro-2-[2(R)-hydroxy-3(S)-[[3-(methanesulfonyl)-N-(methoxycarbonyl)-L-valyl]amino]-4-phenylbutyl]-3(S)-isoquinolinecarboxamide as a white solid, mp 190–194° C., [M+H]$^+$ 637.4.

Example 5

2-[3(S)-[[N,3-Bis(methanesulfonyl)-L-valyl]amino]-2(R)-hydroxy-4-phenylbutyl]-N-tert-butyl-1,2,3,4,4a(S),5,6,7,8a(S)-decahydro-3(S)-isoquinolinecarboxamide

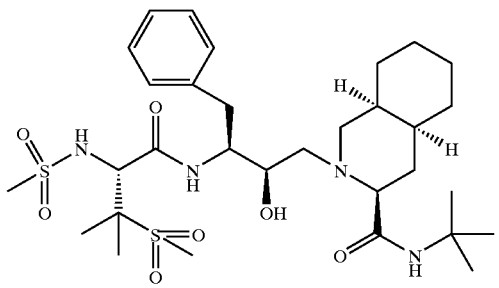

A stirred solution of 200 mg (0.25 mmol) of N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide in 5 ml of dry dimethylformamide at room temperature was treated with 0.63 ml (6.3 mmol) of piperidine. After 2.5 hours the volatiles were evaporated and the residue triturated with hexane to give N-tert-butyl-1,2,3,4,4a(S),5,5,6,7,8,8a(S)-decahydro-2-[2(R)-hydroxy-3(S)-[[3-(methanesulfonyl)-L-valyl]amino]-4-phenylbutyl]-3(S)-isoquinolinecarboxamide as a gum which was dissolved in 5 ml of dichloromethane and treated with 0.12 ml (1.5 mmol) of pyridine followed by 0.02 ml (0.25 mmol) of methanesulfonyl chloride. After 2 hours the solution was diluted with dichloromethane, washed with saturated sodium hydrogen carbonate and brine, dried over magnesium sulfate and evaporated under reduced pressure to give a gum which was triturated with ether and then chromatographed on silica eluting with dichloromethane/methanol (19:1) to give 105 mg of 2-[3(S)-[[N,3-bis(methanesulfonyl)-L-valyl]amino]-2(R)-hydroxy-4-phenylbutyl]-N-tert-butyl-1,2,3,4,4a(S),5,6,7,8a(S)-decahydro-3(S)-isoquinolinecarboxamide as a white solid, mp 135–160° C. foams, re-melts 230–235° C. (dec.), [M+H]$^+$ 657.2.

In a manner analogous to that described for Example 1, the compounds shown in Table 1 were also prepared. Examples 6, 7, 8, 9, 10 were prepared from N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide and examples 11 and 12 were prepared in an analogous manner to Example 1 but using iodoethane in place of iodomethane in part A). The acid chlorides used as starting materials were all purchased from commercial sources such as Aldrich and Lancaster.

TABLE 1

| name | structure | [M + H]$^+$ | Ex. No. |
| --- | --- | --- | --- |
| 2-[3(S)-[[N-Acetyl-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 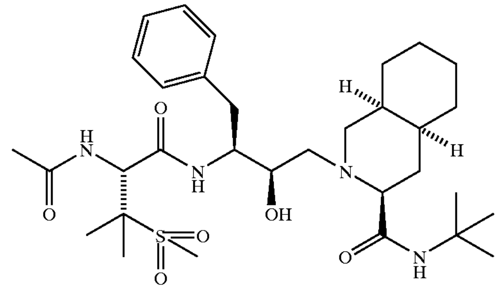 | 621.1 | 6 |

TABLE 1-continued

| name | structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-[(3-pyridyl)carbonyl]-L-valyl]amino]-4-phenylbutyl]-3(S)-isoquinolinecarboxamide | 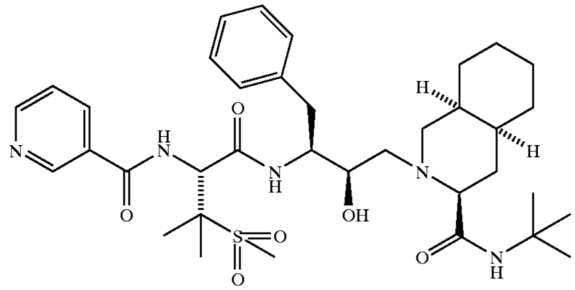 | 684.2 | 7 |
| N-tert-Butyl-1,2,3,4,4a(S),5,6,7,8,8a(S)-decahydro-2-[2(R)-hydroxy-3(S)-[[3-(methanesulfonyl)-N-propionyl-L-valyl]amino]-4-phenylbutyl]-3(S)-isoquinolinecarboxamide | 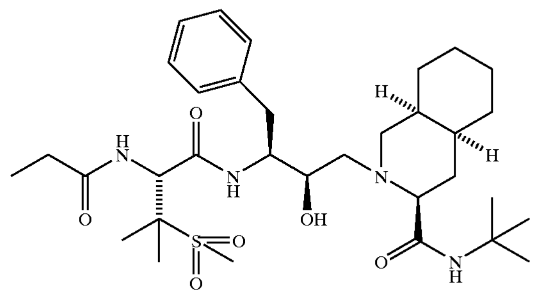 | 635.3 | 8 |
| 2-[3(S)-[[N-Butyryl-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 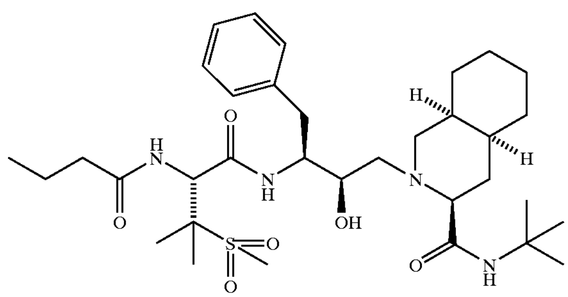 | 649.3 | 9 |
| N-tert-Butyl-1,2,3,4,4a(S),5,6,7,8,8a(S)-decahydro-2-[2(R)-hydroxy-3(S)-[[N-isobutyryl-3-(methanesulfonyl)-L-valyl]amino]-4-phenylbutyl]-3(S)-isoquinolinecarboxamide | 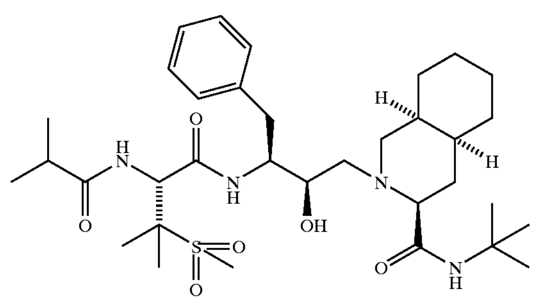 | 649.3 | 10 |
| 2-[3(S)-[[N-Benzoyl-3-(ethanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 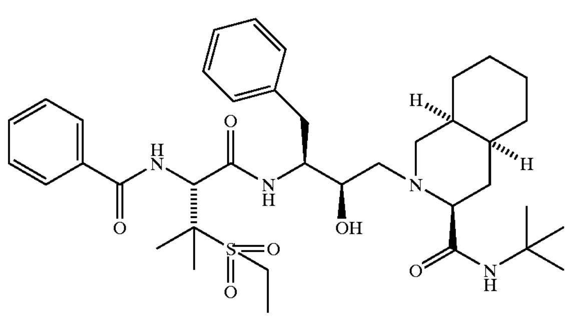 | 697.2 | 11 |

TABLE 1-continued

| name | structure | [M + H]+ | Ex. No. |
|---|---|---|---|
| 2-[3(S)-[[N-Acetyl-3-(ethanesulfonyl)-L-valyl]amino]-2(R)-hydroxy-4-phenylbutyl]-N-tert-butyl-1,2,3,4,4a(S),5,6,7,8a(S)-decahydro-3(S)-isoquinolinecarboxamide | | 635.2 | 12 |

In a manner analogous to that described for Examples 2 and 3, the compounds in Table 2 were prepared starting from N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide.

Other reagents used in the synthesis of the compounds in Table 2 were obtained from commercial sources such as Aldrich, Lancaster, and Maybridge Int. or were prepared using methods described in the art or analogous to those described in the art.

For example phenoxyacetic acid (Example 14), 3-furoic acid (Example 28),2-ethyl-2-hydroxybutyric acid (Example 23) and 5-bromo-2-furoic acid (Example 32) were purchased from Aldrich (cat. Nos. 15,851-8; 16,339-2; 13,843-6; B6,740-6), 4,5-dimethyl-2-furoic acid (Example 33) and 5-(trifluoromethyl)-2-furoic acid (Example 34) were purchased from Maybridge Int. (cat. Nos. BTB 08890; PC8012) and thiophene-3-carboxylic acid (Example 68) and 5-chlorothiophene-2-carboxylic acid (Example 36) were purchased from Lancaster (cat. Nos. 1089; 5453).

Thiazole-5-carboxylic acid (Example 69) was prepared according to the method described in WO97/14687, and 5-methyl-thiazole-2-carboxylic acid (Example 61) was prepared analogously. 2-Methyl-thiazole-4-carboxylic acid (Example 74) was prepared by analogy to the method of W. R. Tully et al, J. Med. Chem; 1991, 34, 2060. 2-Isopropoxyacetic acid (Example 72) was prepared according to the method described in J. Chem. Soc., 1969, 2698. 2-Methyl-2-phenoxypropionic acid (Example 80) was prepared according to the method described in the Romanian patent RO 69-61256.

Other aryloxy acetic acids were prepared by analogy to the method of Mertes et al, J. Heterocycl. Chem., 1968, 5, 281, or by the method described for Example 3A for the preparation of 2-(3-pyridyloxy)acetic acid trifluoroacetate. Similarly 2-(1-pyrrolyl)acetic acid (example 62), pyrazole-1-acetic acid (example 64), 1-pyrrolidinylacetic acid (example 66) etc were prepared by analogy to the method described in example 2A for the preparation of N-ethyl-N-methylglycine hydrobromide

TABLE 2

| Name | Structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-(2-thenoyl-L-valyl]amino]-4-phenylbutyl]-3(S)-isoquinolinecarboxamide | 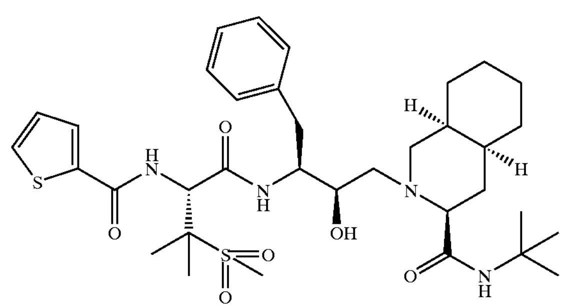 | 689.4 | 13 |

TABLE 2-continued

| Name | Structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-[(2-phenoxyacetyl)-L-valyl]amino]-4-phenylbutyl]-3(S)-isoquinolinecarboxamide | 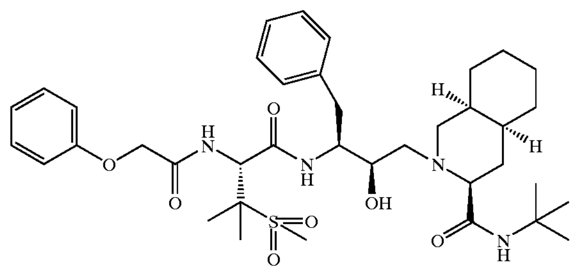 | 713 | 14 |
| N-tert-Butyl-1,2,3,4,4a(S),5,6,7,8,8a(S)-decahydro-2-[2(R)-hydroxy-3(S)-[[3-(methanesulfonyl)-N-[(2-pyrazinyl)carbonyl-L-valyl]amino]-4-phenylbutyl]-3(S)-isoquinolinecarboxamide | 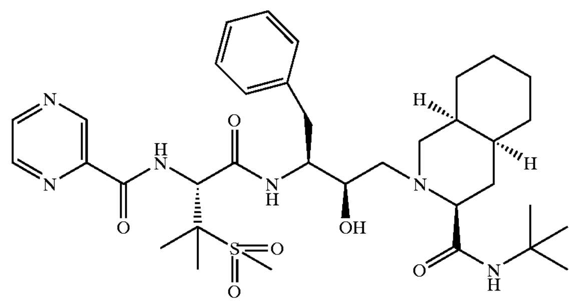 | 685.4 | 15 |
| N-tert-Butyl-2-[3-(S)-[[N-[(6-chloro-3-pyridyl)carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 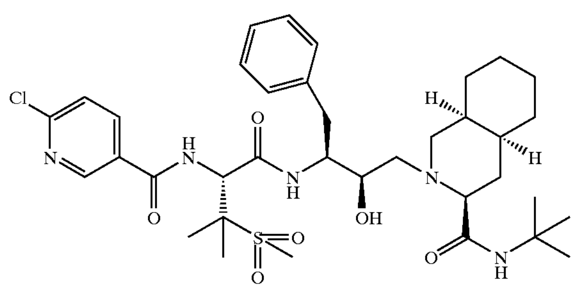 | 718.3 | 16 |
| N-tert-Butyl-1,2,3,4,4a(S),5,6,7,8,8a(S)-decahydro-2-[2(R)-hydroxy-3(S)-[[N-[(1-hydroxy-1-cyclopropyl)carbonyl]-3-(methanesulfonyl)-N-(2-thenoyl-L-valyl]amino]-4-phenylbutyl]-3(S)-isoquinolinecarboxamide | 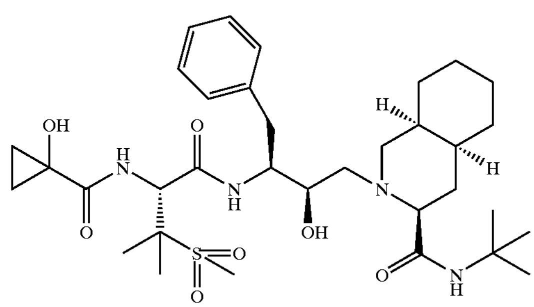 | 663.4 | 17 |
| N-tert-Butyl-1,2,3,4,4a(S),5,6,7,8,8a(S)-decahydro-2-[2(R)-hydroxy-3(S)-[[3-(methanesulfonyl)-N-[(1,2,3-thiadiazol-4-yl)carbonyl]-L-valyl]amino]-4-phenylbutyl]-3(S)-isoquinolinecarboxamide | 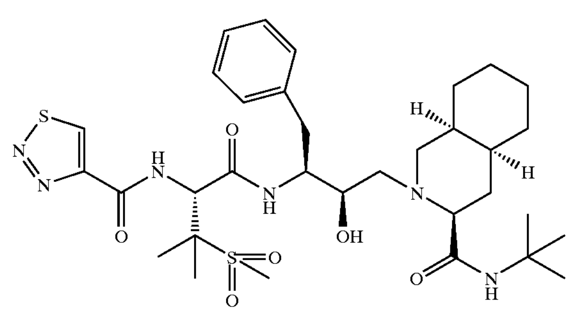 | 688.4 | 18 |

TABLE 2-continued

| Name | Structure | [M + H]+ | Ex. No. |
|---|---|---|---|
| N-tert-Butyl-2-[3-(S)-[[N-(5-chloro-2-furoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 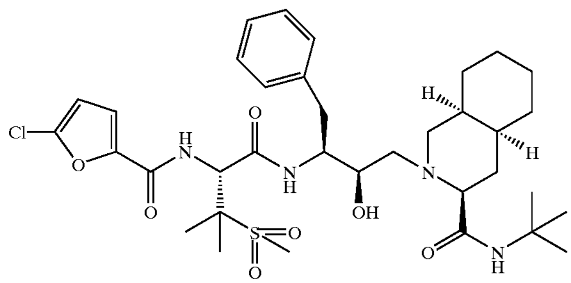 | 707 | 19 |
| N-tert-Butyl-1,2,3,4,4a(S),5,6,7,8,8a(S)-decahydro-2-[2(R)-hydroxy-3(S)-[[3-(methanesulfonyl)-N-[(5-isoxazolyl)carbonyl]-L-valyl]amino]-4-phenylbutyl]-3(S)-isoquinolinecarboxamide | 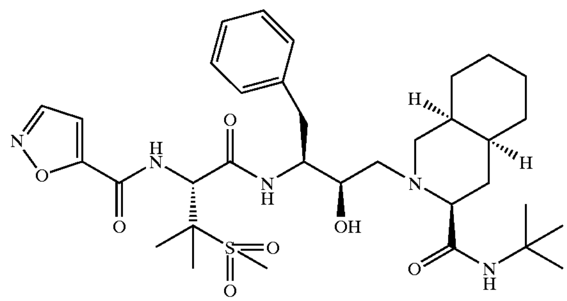 | 674.3 | 20 |
| N-tert-Butyl-1,2,3,4,4a(S),5,6,7,8,8a(S)-decahydro-2-[2(R)-hydroxy-3(S)-[[3-(methanesulfonyl)-N-[(3-methyl-4-isoxazolyl)carbonyl-L-valyl]amino]-4-phenylbutyl]-3(S)-isoquinolinecarboxamide | 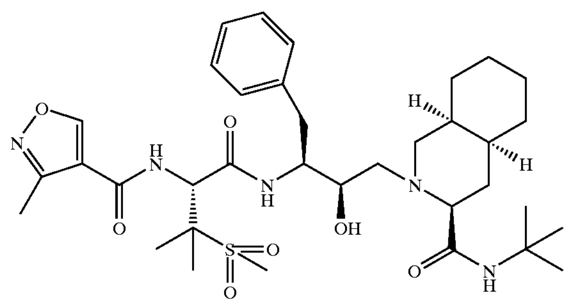 | 688.4 | 21 |
| N-tert-Butyl-1,2,3,4,4a(S),5,6,7,8,8a(S)-decahydro-2-[2(R)-hydroxy-3(S)-[[3-(methanesulfonyl)-N-[(5-methyl-3-isoxazolyl)carbonyl]-L-valyl]amino]-4-phenylbutyl]-3(S)-isoquinolinecarboxamide | 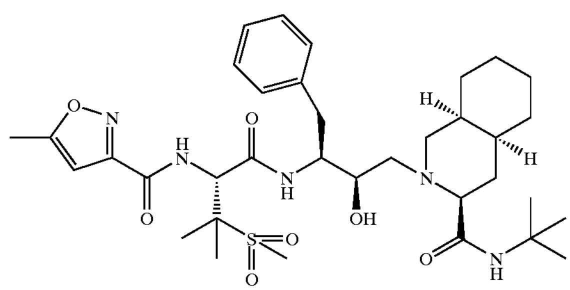 | 688.4 | 22 |
| N-tert-Butyl-1,2,3,4,4a(S),5,6,7,8,8a(S)-decahydro-2-[2(R)-hydroxy-3(S)-[[N-(2-hydroxy-2-ethylbutyryl)-3-(methanesulfonyl)-L-valyl]amino]-4-phenylbutyl]-3(S)-isoquinolinecarboxamide | 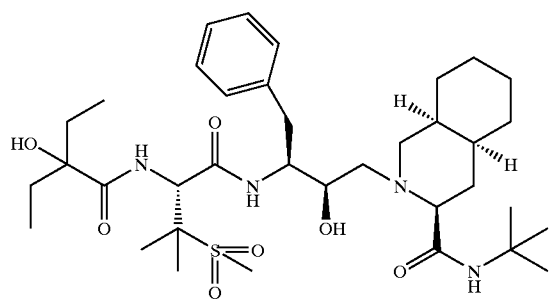 | 693.4 | 23 |

TABLE 2-continued

| Name | Structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-(2-methoxyacetyl))-L-valyl]amino]-4-phenylbutyl]-3(S)-isoquinolinecarboxamide | 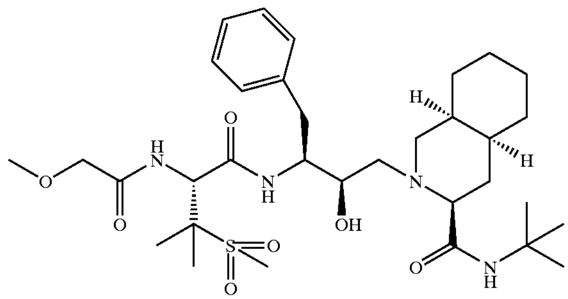 | 651.3 | 24 |
| N-tert-Butyl-2-[3-(S)-[[N-(2[isoxazolyl)carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 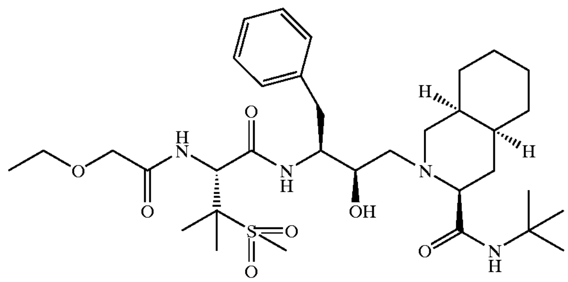 | 665.4 | 25 |
| N-tert-Butyl-1,2,3,4,4a(S),5,6,7,8,8a(S)-decahydro-2-[2(R)-hydroxy-3(S)-[[N-(2-hydroxyacetyl)-3-(methanesulfonyl)-L-valyl]amino]-4-phenylbutyl]-3(S)-isoquinolinecarboxamide | 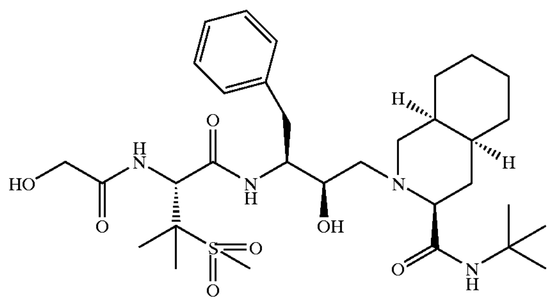 | 637.2 | 26 |
| N-tert-Butyl-1,2,3,4,4a(S),5,6,7,8,8a(S)-decahydro-2-[2(R)-hydroxy-3(S)-[[N-(2-hydroxy-2-methylpropionyl)-3-(methanesulfonyl)-L-valyl]amino]-4-phenylbutyl]-3(S)-isoquinolinecarboxamide | 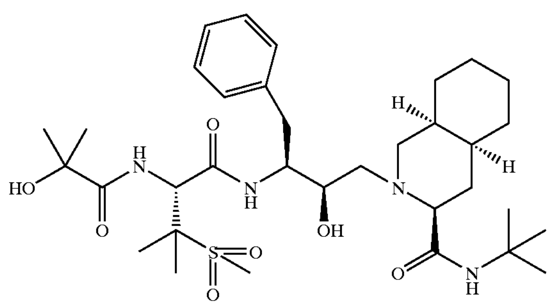 | 665.4 | 27 |
| N-tert-Butyl-2-[3-(S)-[[N-(3-furoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 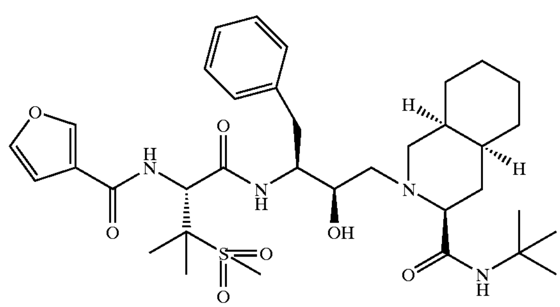 | 673.3 | 28 |

TABLE 2-continued

| Name | Structure | [M + H]+ | Ex. No. |
|------|-----------|----------|---------|
| N-tert-Butyl-1,2,3,4,4a(S),5,6,7,8,8a(S)-decahydro-2-[2(R)-hydroxy-3(S)-[[3-(methanesulfonyl)-N-[(4-pyridyl)carbonyl]-L-valyl]amino]-4-phenylbutyl]-3(S)-isoquinolinecarboxamide | 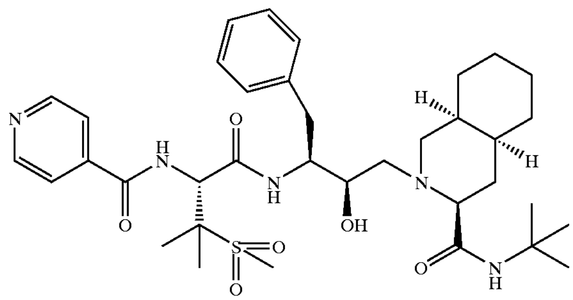 | 684.3 | 29 |
| N-tert-Butyl-1,2,3,4,4a(S),5,6,7,8,8a(S)-decahydro-2-[2(R)-hydroxy-3(S)-[[N-(2(S)-hydroxypropionyl)-3-(methanesulfonyl)-N-(2-thenoyl-L-valyl]amino]-4-phenylbutyl]-3(S)-isoquinolinecarboxamide | 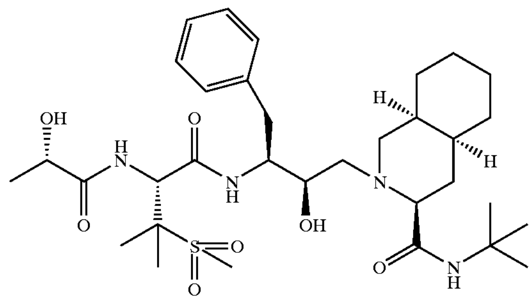 | 651.4 | 30 |
| N-tert-Butyl-1,2,3,4,4a(S),5,6,7,8,8a(S)-decahydro-2-[2(R)-hydroxy-3(S)-[[N-(2(R)-hydroxypropionyl)-3-(methanesulfonyl)-N-(2-thenoyl-L-valyl]amino]-4-phenylbutyl]-3(S)-isoquinolinecarboxamide | 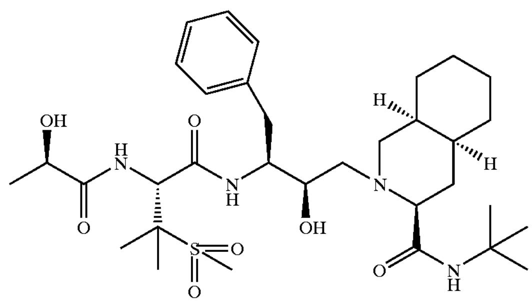 | 651.3 | 31 |
| 2-[3(S)-[[N-(5-Bromo-2-furoyl)-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 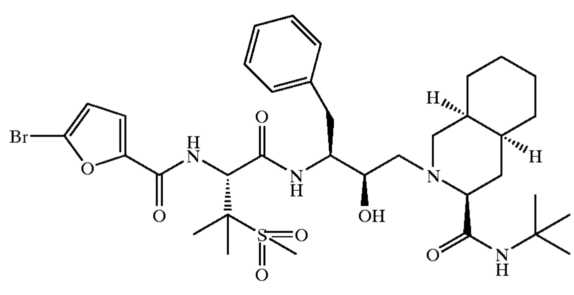 | 751.6 | 32 |
| N-tert-Butyl-1,2,3,4,4a(S),5,6,7,8,8a(S)-decahydro-2-[2(R)-hydroxy-3(S)-[[3-(methanesulfonyl)-N-(4,5-dimethyl-2-furoyl)-L-valyl]amino]-4-phenylbutyl]-3(S)-isoquinolinecarboxamide | 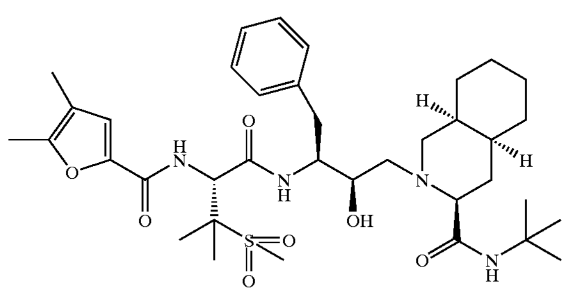 | 701.6 | 33 |

TABLE 2-continued

| Name | Structure | [M + H]+ | Ex. No. |
|---|---|---|---|
| N-tert-Butyl-2-[3-(S)-[[N-[[5-trifluoromethyl)-2-furoyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 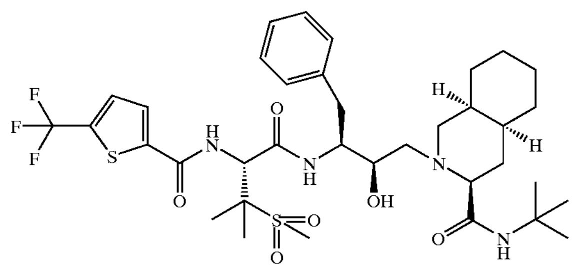 | 741.6 | 34 |
| N-tert-Butyl-1,2,3,4,4a(S),5,6,7,8,8a(S)-decahydro-2-[2(R)-hydroxy-3(S)-[[3-(methanesulfonyl)-N-(5-methyl-2-thenoyl-L-valyl]amino]-4-phenylbutyl]-3(S)-isoquinolinecarboxamide | 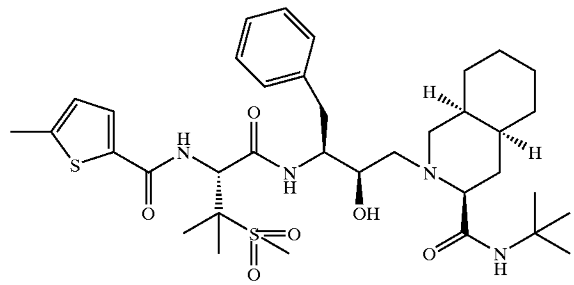 | 703.6 | 35 |
| N-tert-Butyl-2-[3-(S)-[[N-(5-chloro-2-thenoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 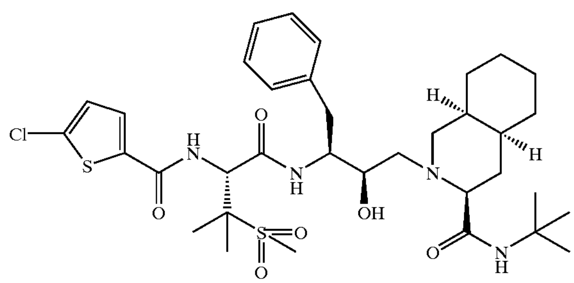 | 723.4 | 36 |
| 2-[3(S)-[[N-(5-Acetyl-2-thenoyl)-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 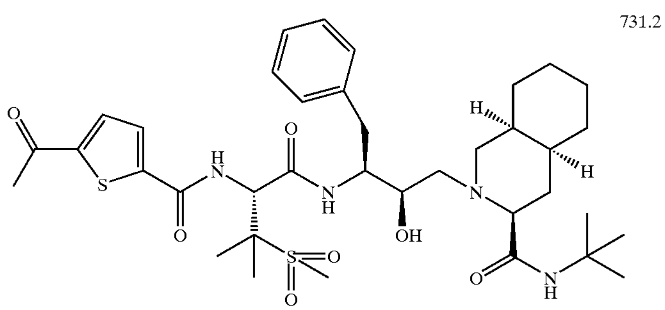 | 731.2 | 37 |
| N-tert-Butyl-2-[3-(S)-[[N-(5-tert-butyl-2-thenoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 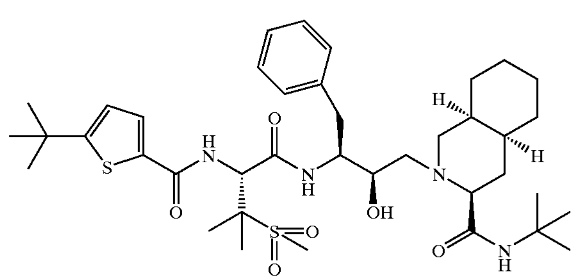 | 745.6 | 38 |

TABLE 2-continued

| Name | Structure | [M + H]+ | Ex. No. |
|---|---|---|---|
| N-tert-Butyl-2-[3-(S)-[[N-(3-cyanobenzoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 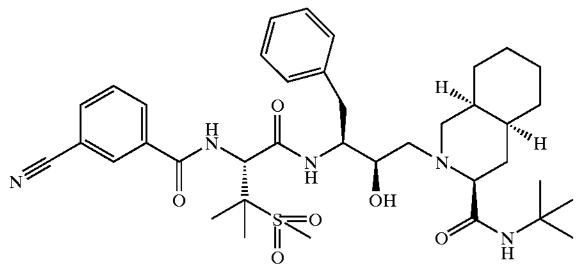 | 708.6 | 39 |
| N-tert-Butyl-2-[3-(S)-[[N-(3-fluorobenzoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 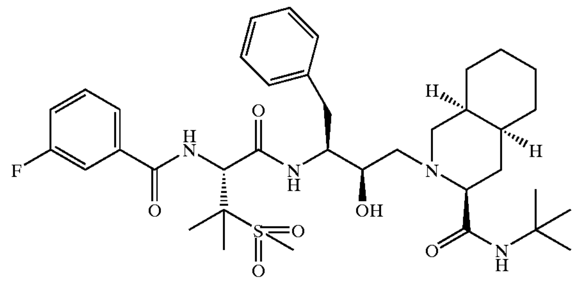 | 701.4 | 40 |
| N-tert-Butyl-2-[3-(S)-[[N-(4-cyanobenzoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 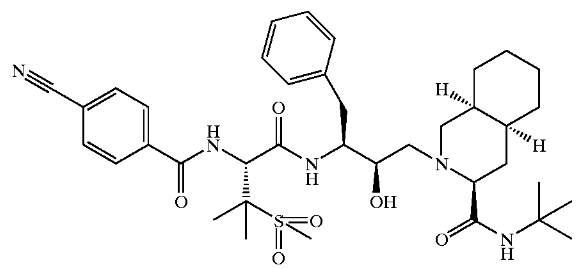 | 708.6 | 41 |
| N-tert-Butyl-2-[3-(S)-[[N-(4-fluorobenzyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 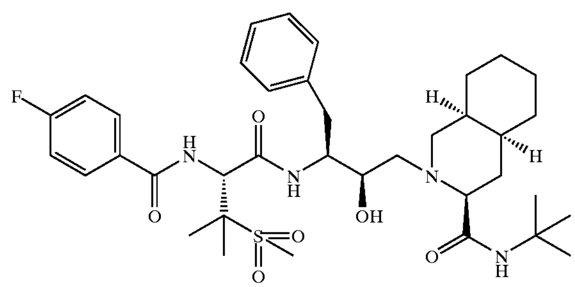 | 701.6 | 42 |
| N-tert-Butyl-2-[3-(S)-[[N-[[6-(trifluoromethyl)-3-pyridyl]carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 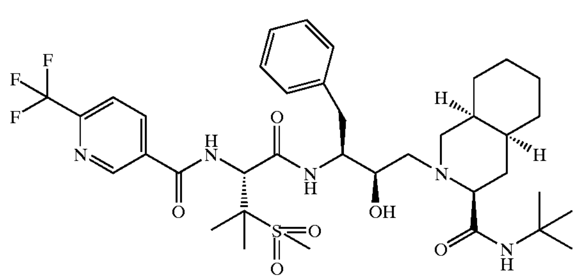 | 752.8 | 43 |

TABLE 2-continued

| Name | Structure | [M + H]+ | Ex. No. |
|---|---|---|---|
| N-tert-Butyl-2-[3-(S)-[[N-[(6-cyano-3-pyridyl)carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 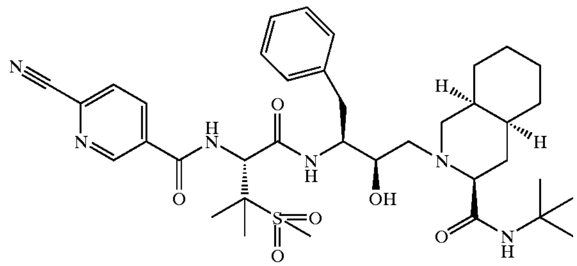 | 709.6 | 44 |
| N-tert-Butyl-1,2,3,4,4a(S),5,6,7,8,8a(S)-decahydro-2-[2(R)-hydroxy-3(S)-[[3-(methanesulfonyl)-N-[(1,5-dimethyl-3-pyrazolyl)carbonyl]-L-valyl]amino]-4-phenylbutyl]-3(S)-isoquinolinecarboxamide | 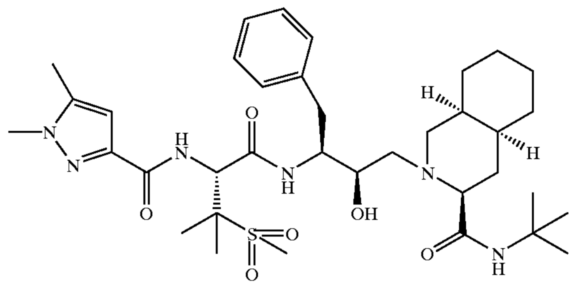 | 701.6 | 45 |
| N-tert-Butyl-2-[3-(S)-[[N-[(1-tert butyl-5-methyl-3-pyrazolyl)carbonyl]3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 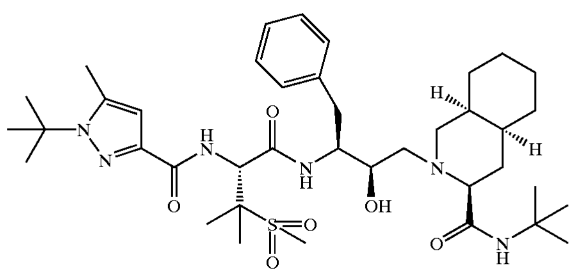 | 743.6 | 46 |
| N-tert-Butyl-2-[3-(S)-[[N-(cyclopropylcarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 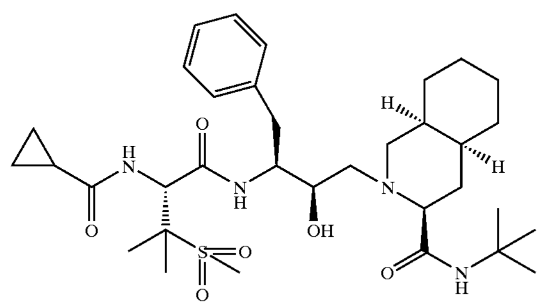 | 647.6 | 47 |
| N-tert-Butyl-2-[3-(S)-[[N-(cyclobutylcarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 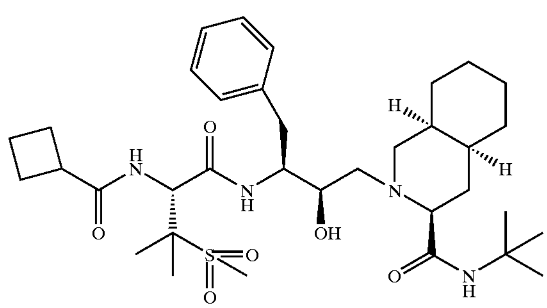 | 661.6 | 48 |

TABLE 2-continued

| Name | Structure | [M + H]+ | Ex. No. |
|---|---|---|---|
| N-tert-Butyl-2-[3-(S)-[[N-(cyclohexylcarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 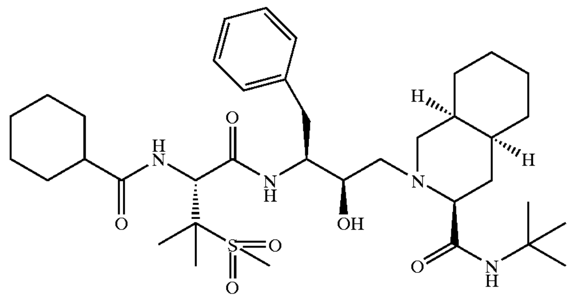 | 689.4 | 49 |
| N-tert-Butyl-1,2,3,4,4a(S),5,6,7,8,8a(S)-decahydro-2-[3(S)-[[N-(tetrahydro-3(RS)-furoyl)-3-(methanesulfonyl)-L-valyl]amino]-2(R)-hydroxy-4-phenylbutyl]-3(S)-isoquinolinecarboxamide(1:1 mixture of diastereoisomers) | 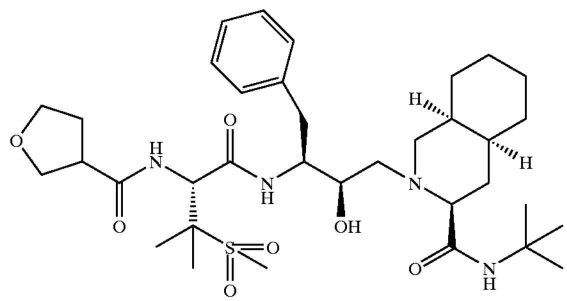 | 677.6 | 50 |
| N-tert-Butyl-2-[3-(S)-[[N-[(2-chloro-6-methyl-4-pyridyl)carbonyl]-3-(S)-[[3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 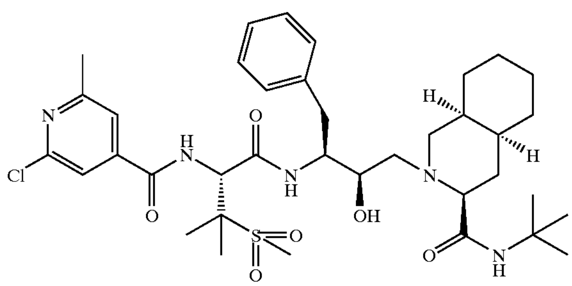 | 732.4 | 51 |
| N-tert-Butyl-2-[3-(S)-[[N-[(2-chloro-4-pyridyl)carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 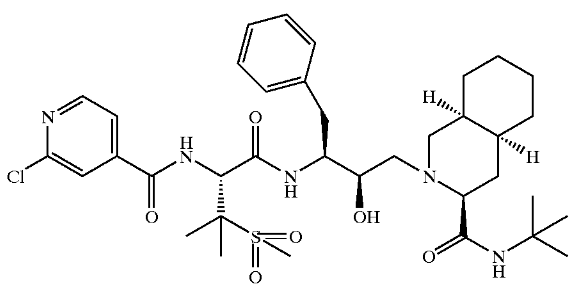 | 718.4 | 52 |
| N-tert-Butyl-2-[N-(2-furoyl)-3(S)-[[3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 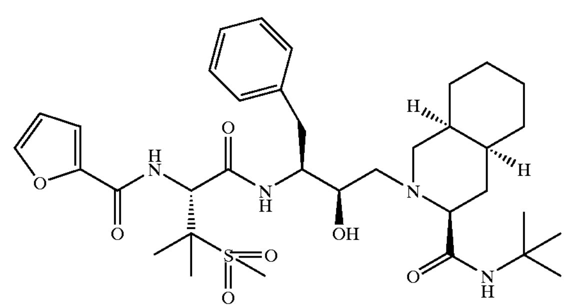 | 673.8 | 53 |

TABLE 2-continued

| Name | Structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-(3-methylbenzoyl)-L-valyl]amino]-4-phenylbutyl]-3(S)-isoquinolinecarboxamide | 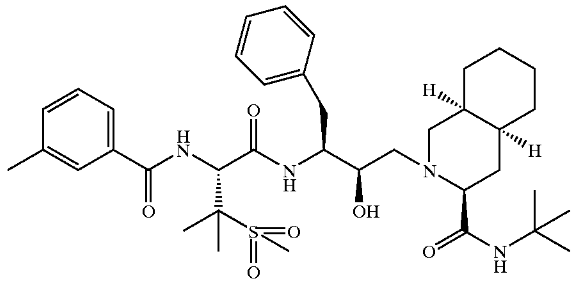 | 697.6 | 54 |
| N-tert-Butyl-1,2,3,4,4a(S),5,6,7,8,8a(S)-decahydro-2-[2(R)-hydroxy-3(S)-[[3-(methanesulfonyl)-N-(4-methoxylbenzoyl)-L-valyl]amino]-4-phenylbutyl]-3(S)-isoquinolinecarboxamide | 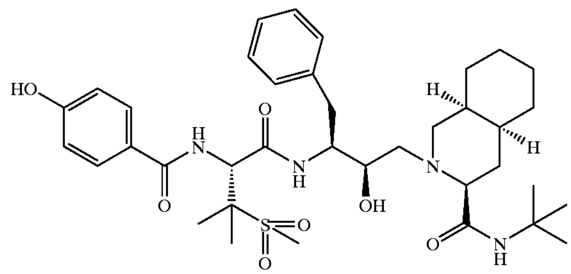 | 701.6 | 55 |
| N-tert-Butyl-1,2,3,4,4a(S),5,6,7,8,8a(S)-decahydro-2-[2(R)-hydroxy-3(S)-[[3-(methanesulfonyl)-N-(4-methylbenzoyl)-L-valyl]amino]-4-phenylbutyl]-3(S)-isoquinolinecarboxamide | 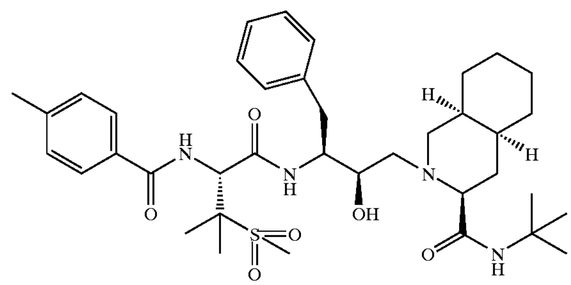 | 697.6 | 56 |
| N-tert-Butyl-1,2,3,4,4a(S),5,6,7,8,8a(S)-decahydro-2-[2(R)-hydroxy-3(S)-[[3-(methanesulfonyl)-N-[(5-methyl-3-pyridyl)carbonyl]-L-valyl]amino]-4-phenylbutyl]-3(S)-isoquinolinecarboxamide | 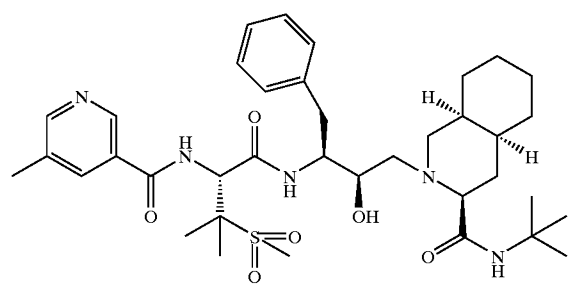 | 698.6 | 57 |
| N-tert-Butyl-2-[3-(S)-[[N-(cyclopentylcarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 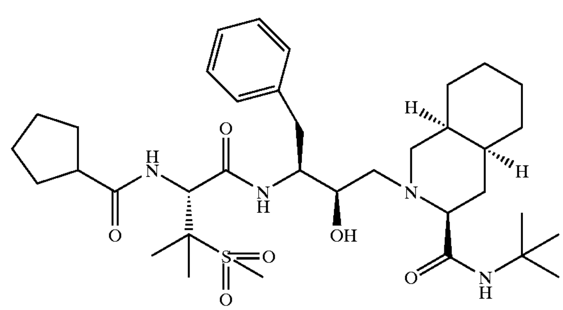 | 675.5 | 58 |

TABLE 2-continued

| Name | Structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-[(2,5-dimethyl-3-pyrazolyl)carbonyl]-L-valyl]amino]-4-phenylbutyl]-3(S)-isoquinolinecarboxamide | 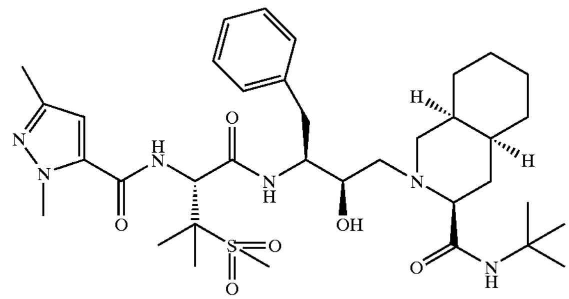 | 701.6 | 59 |
| N-tert-Butyl-1,2,3,4,4a(S),5,6,7,8,8a(S)-decahydro-2-[2(R)-hydroxy-3(S)-[[3-(methanesulfonyl)-N-pivaloyl-L-valyl]amino]-4-phenylbutyl]-3(S)-isoquinolinecarboxamide | 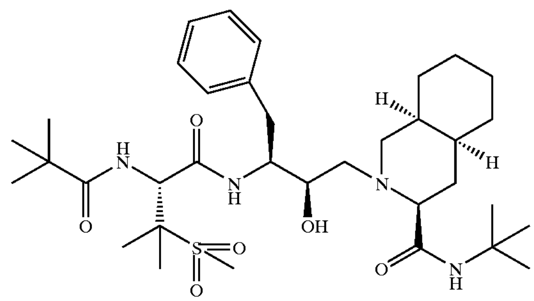 | 663.4 | 60 |
| N-tert-Butyl-1,2,3,4,4a(S),5,6,7,8,8a(S)-decahydro-2-[2(R)-hydroxy-3(S)-[[3-(methanesulfonyl)-N-[(4-methyl-2-thiazolyl)carbonyl]-L-valyl]amino]-4-phenylbutyl]-3(S)-isoquinolinecarboxamide | 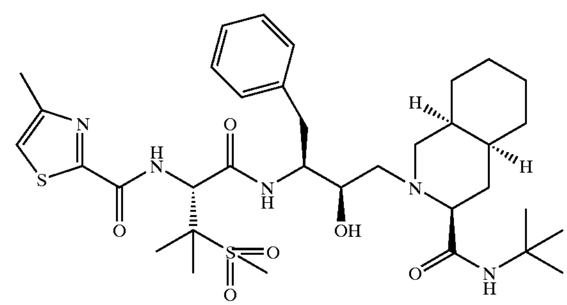 | 704 | 61 |
| N-tert-Butyl-1,2,3,4,4a(S),5,6,7,8,8a(S)-decahydro-2-[2(R)-hydroxy-3(S)-[[3-(methanesulfonyl)-3-methyl-N-[2-(1-pyrrolyl)acetyl]-L-valyl]amino]-4-phenylbutyl]-3(S)-isoquinolinecarboxamide | 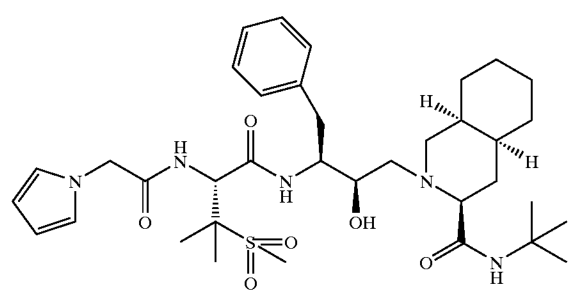 | 686.2 | 62 |
| N-tert-Butyl-2-[3-(S)-[[N-[2-(diethylamino)acetyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 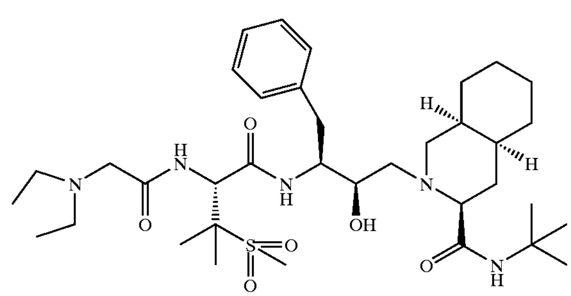 | 692.3 | 63 |

TABLE 2-continued

| Name | Structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-3-methyl-N-[2-(1-pyrazolyl)acetyl]-L-valyl]amino]-4-phenylbutyl]-3(S)-isoquinolinecarboxamide | 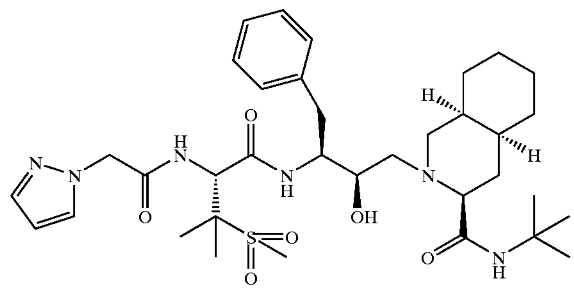 | 687.3 | 64 |
| N-tert-Butyl-1,2,3,4,4a(S),5,6,7,8,8a(S)-decahydro-2-[2(R)-hydroxy-3(S)-[[N-[2-(1-imidazolyl)acetyl]3-(methanesulfonyl)-3-methyl-L-valyl]amino]-4-phenylbutyl]-3(S)-isoquinolinecarboxamide | 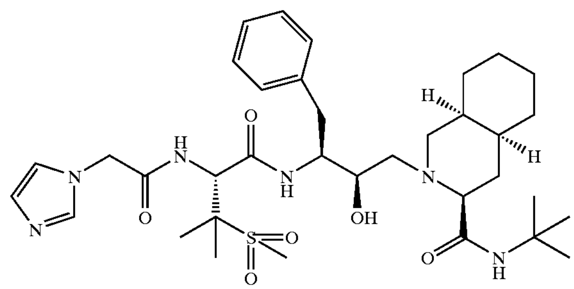 | 687.2 | 65 |
| N-tert-Butyl-1,2,3,4,4a(S),5,6,7,8,8a(S)-decahydro-2-[2(R)-hydroxy-3(S)-[[3-(methanesulfonyl)-N-[2-(1-pyrrolidinyl)acetyl]-L-valyl]amino]-4-phenylbutyl]-3(S)-isoquinolinecarboxamide | 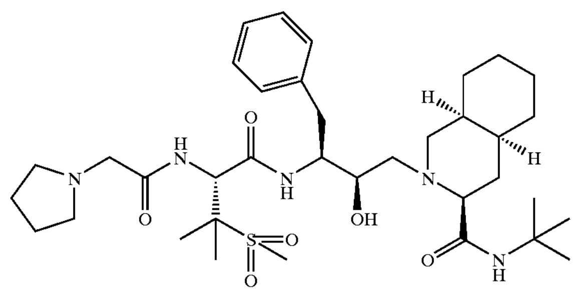 | 690.3 | 66 |
| N-tert-Butyl-1,2,3,4,4a(S),5,6,7,8,8a(S)-decahydro-2-[2(R)-hydroxy-3(S)-[[3-(methanesulfonyl)-N-(2-morpholinoacetyl)-L-valyl]amino]-4-phenylbutyl]-3(S)-isoquinolinecarboxamide | 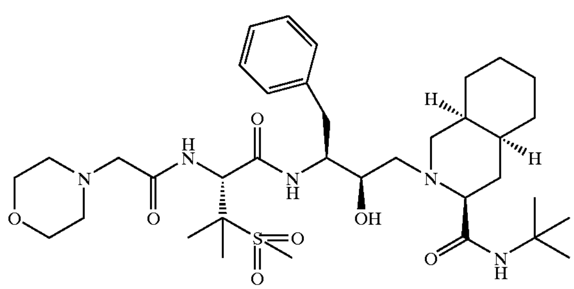 | 706.2 | 67 |
| N-tert-Butyl-1,2,3,4,4a(S),5,6,7,8,8a(S)-decahydro-2-[2(R)-hydroxy-3(S)-[[3-(methanesulfonyl)-N-(3-thenoyl-L-valyl]amino]-4-phenylbutyl]-3(S)-isoquinolinecarboxamide | 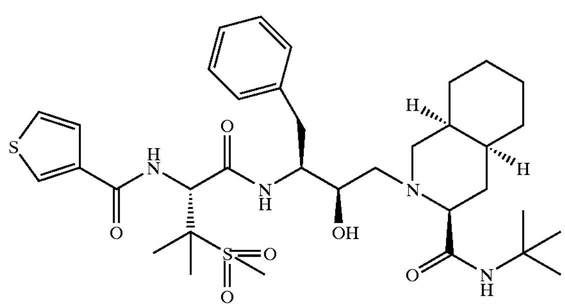 | 689.2 | 68 |

TABLE 2-continued

| Name | Structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-[(5-thiazolyl)carbonyl]-L-valyl]amino]-4-phenylbutyl]-3(S)-isoquinolinecarboxamide | 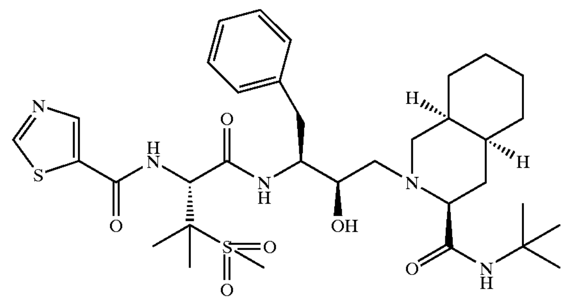 | 690.3 | 69 |
| N-tert-Butyl-1,2,3,4,4a(S),5,6,7,8,8a(S)-decahydro-2-[2(R)-hydroxy-3(S)-[[3-(methanesulfonyl)-N-[(6-methyl-3-pyridyl)carbonyl]-L-valyl]amino]-4-phenylbutyl]-3(S)-isoquinolinecarboxamide | | 698.3 | 70 |
| N-tert-Butyl-1,2,3,4,4a(S),5,6,7,8,8a(S)-decahydro-2-[2(R)-hydroxy-3(S)-[[3-(methanesulfonyl)-N-[N-methyl-N-phenylglycyl]-L-valyl]amino]-4-phenylbutyl]-3(S)-isoquinolinecarboxamide | 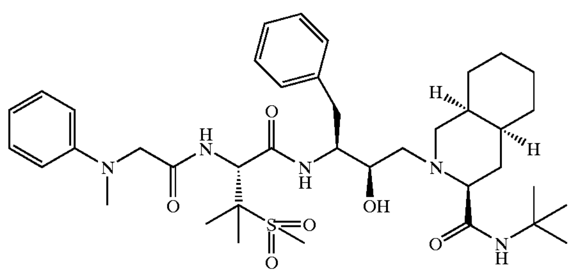 | 726.4 | 71 |
| N-tert-Butyl-1,2,3,4,4a(S),5,6,7,8,8a(S)-decahydro-2-[2(R)-hydroxy-3(S)-[[N-(2-isopropoxyacetyl)-3-(methanesulfonyl)-N-(2-thenoyl-L-valyl]amino]-4-phenylbutyl]-3(S)-isoquinolinecarboxamide | 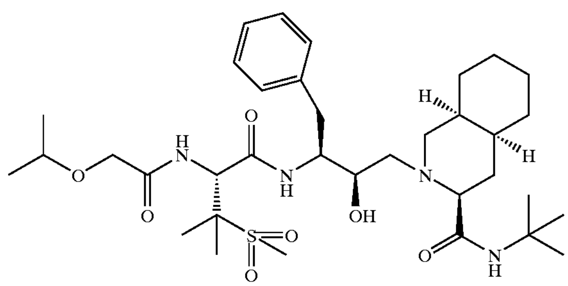 | 679.3 | 72 |
| N-tert-Butyl-1,2,3,4,4a(S),5,6,7,8,8a(S)-decahydro-2-[2(R)-hydroxy-3(S)-[[3-(methanesulfonyl)-N-[(2-pyridyl)carbonyl]-L-valyl]amino]-4-phenylbutyl]-3(S)-isoquinolinecarboxamide | 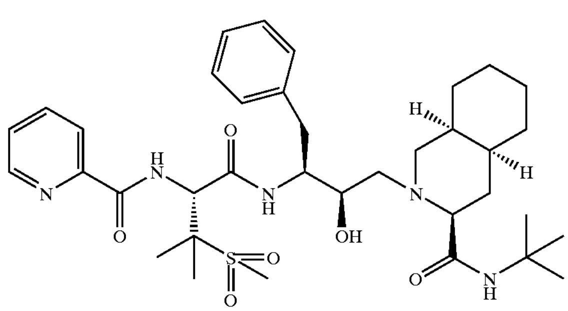 | 684.3 | 73 |

TABLE 2-continued

| Name | Structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-[(2-methyl-4-thiazolyl)carbonyl]-L-valyl]amino]-4-phenylbutyl]-3(S)-isoquinolinecarboxamide | 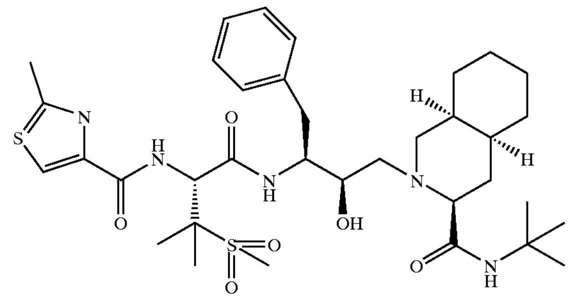 | 704 | 74 |
| N-tert-Butyl-1,2,3,4,4a(S),5,6,7,8,8a(S)-decahydro-2-[2(R)-hydroxy-3(S)-[[3-(methanesulfonyl)-N-(3-phenylpropionyl)-L-valyl]amino]-4-phenylbutyl]-3(S)-isoquinolinecarboxamide | 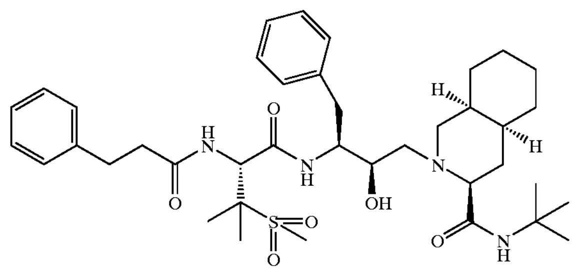 | 711.4 | 75 |
| (E)-N-tert-Butyl-1,2,3,4,4a(S),5,6,7,8,8a(S)-decahydro-2-[2(R)-hydroxy-3(S)-[[3-(methanesulfonyl)-N-(3-phenylacryloyl-L-valyl]amino]-4-phenylbutyl]-3(S)-isoquinolinecarboxamide | 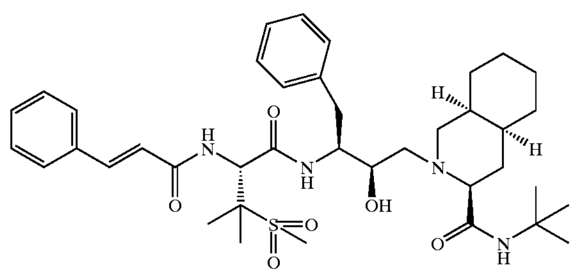 | 709.4 | 76 |
| N-tert-Butyl-2-[3-(S)-[[N-[2-(pentafluorophenyoxy)acetyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 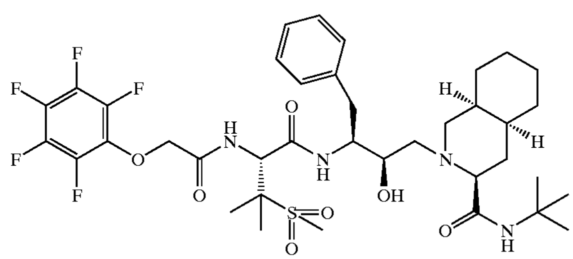 | 803.3 | 77 |
| 2-[3(S)-[[N-[[(2-Benzofuryl)carbonyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 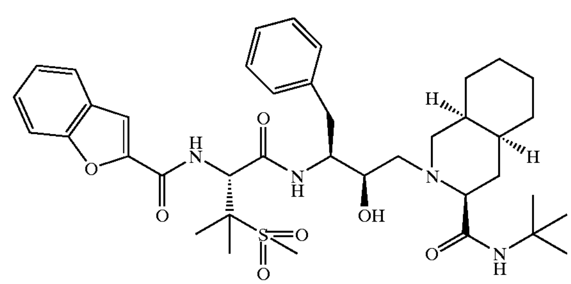 | 723.4 | 78 |

TABLE 2-continued

| Name | Structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-[2-(phenylthio)acetyl]-L-valyl]amino]-4-phenylbutyl]-3(S)-isoquinolinecarboxamide | 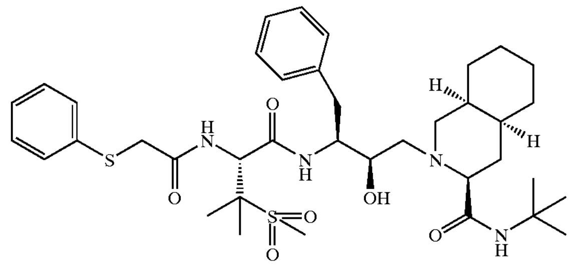 | 729.4 | 79 |
| N-tert-Butyl-1,2,3,4,4a(S),5,6,7,8,8a(S)-decahydro-2-[2(R)-hydroxy-3(S)-[[3-(methanesulfonyl)-N-(2-methyl-2-phenoxypropionyl)-L-valyl]amino]-4-phenylbutyl]-3(S)-isoquinolinecarboxamide | 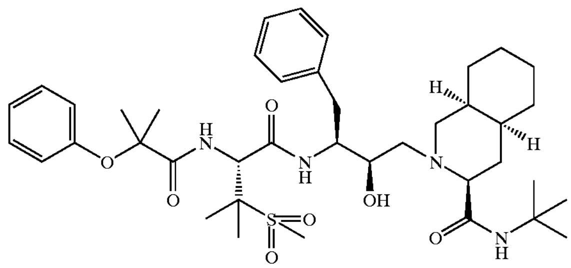 | 741.4 | 80 |
| N-tert-Butyl-1,2,3,4,4a(S),5,6,7,8,8a(S)-decahydro-2-[2(R)-hydroxy-3(S)-[[3-(methanesulfonyl)-N-[2-(2-naphthyloxy)acetyl]-L-valyl]amino]-4-phenylbutyl]-3(S)-isoquinolinecarboxamide | 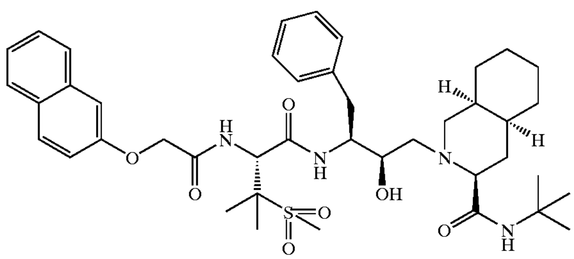 | 763.4 | 81 |
| N-tert-Butyl-1,2,3,4,4a(S),5,6,7,8,8a(S)-decahydro-2-[2(R)-hydroxy-3(S)-[[3-(methanesulfonyl)-N-[2-(1-naphthyloxy)acetylamino]-L-valyl]amino]-4-phenylbutyl]-3(S)-isoquinolinecarboxamide | 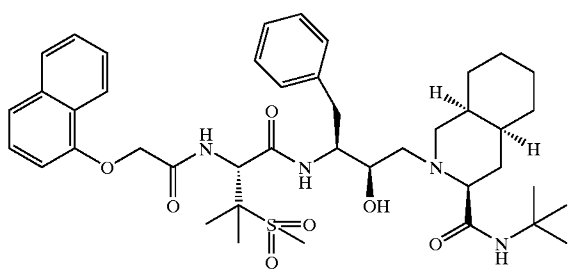 | 763.4 | 82 |
| N-tert-Butyl-1,2,3,4,4a(S),5,6,7,8,8a(S)-decahydro-2-[2(R)-hydroxy-3(S)-[[3-(methanesulfonyl)-N-(5-methyl-2-furoyl)-L-valyl]amino]-4-phenylbutyl]-3(S)-isoquinolinecarboxamide | 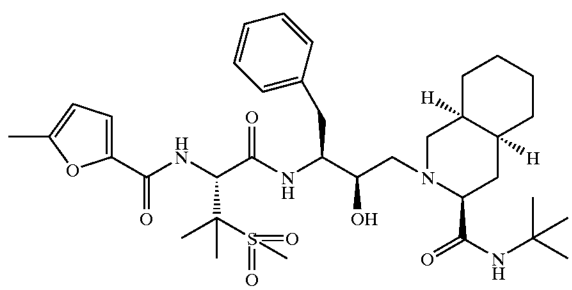 | 687.5 | 83 |

TABLE 2-continued

| Name | Structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[2-[2-(dimethylamino)acetyl]-3-(methanesulfonyl)-L-valyl]amino]-4-phenylbutyl]-3(S)-isoquinolinecarboxamide | 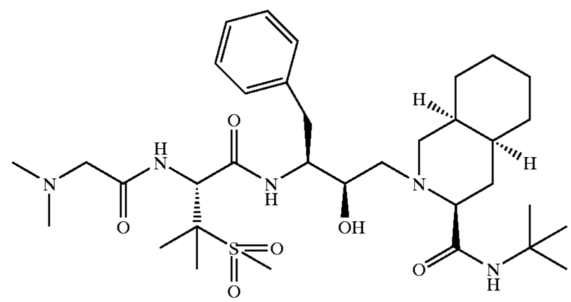 | 664.5 | 84 |
| N-tert-Butyl-1,2,3,4,4a(S),5,6,7,8,8a(S)-decahydro-2-[2(R)-hydroxy-3(S)-[[3-(methanesulfonyl)-N-(3,5-dimethoxybenzoyl)-L-valyl]amino]-4-phenylbutyl]-3(S)-isoquinolinecarboxamide | 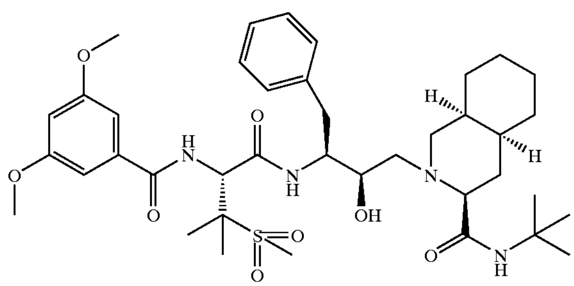 | 743.4 | 85 |
| N-tert-Butyl-1,2,3,4,4a(S),5,6,7,8,8a(S)-decahydro-2-[2(R)-hydroxy-N-[(2-indolyl)carbonyl]-3(S)-[[3-(methanesulfonyl)-L-valyl]amino]-4-phenylbutyl]-3(S)-isoquinolinecarboxamide | 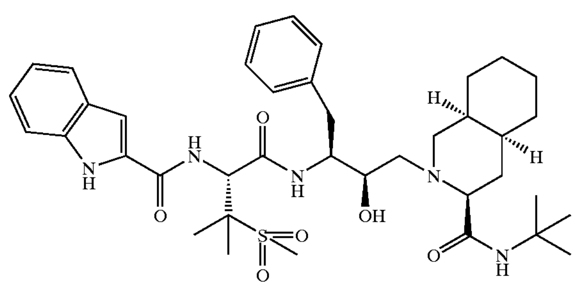 | 722.4 | 86 |
| N-tert-Butyl-1,2,3,4,4a(S),5,6,7,8,8a(S)-decahydro-2-[2(R)-hydroxy-3(S)-[[3-(methanesulfonyl)-N-[1-methyl-2-indolyl]carbonyl]-L-valyl]amino]-4-phenylbutyl]-3(S)-isoquinolinecarboxamide | | 736.4 | 87 |
| 2-[3(S)-[[N-[(1-Benzothiphen-2-yl)carbonyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 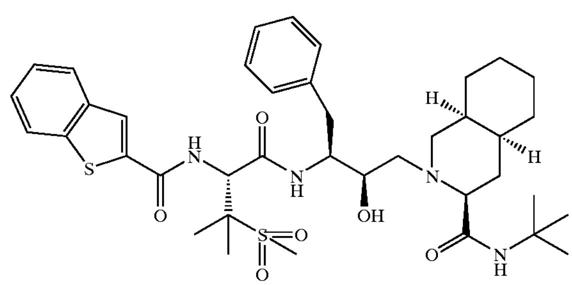 | 739.3 | 88 |

In a manner analogous to that described for Example 4 the compounds in Table 3 were prepared starting from N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide and commercially available chloroformates.

TABLE 3

| name | structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-(propoxycarbonyl)-L-valyl]amino]-4-phenylbutyl]-3(S)-isoquinolinecarboxamide | 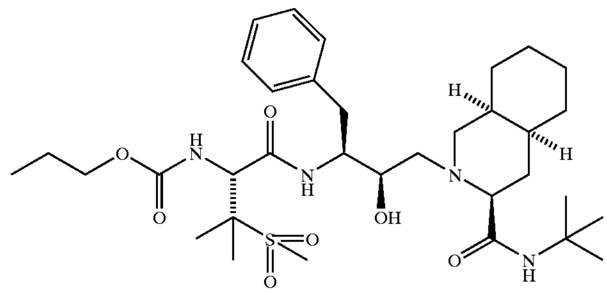 | 665.3 | 89 |
| N-tert-Butyl-1,2,3,4,4a(S),5,6,7,8,8a(S)-decahydro-2-[2(R)-hydroxy-3(S)-[[N-(isopropoxycarbonyl)-3-(methanesulfonyl)-L-valyl]amino]-4-phenylbutyl]-3(S)-isoquinolinecarboxamide | | 665.3 | 90 |
| N-tert-Butyl-2-[3(S)-[[N-(ethoxycarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 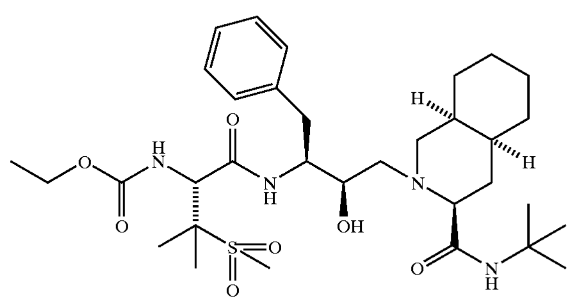 | 651.3 | 91 |

Example 92

N-tert-Butyl-1,2,3,4,4a(S),5,6,7,8,8a(S)-decahydro-2-[2(R)-hydroxy-3(S)-[[N-[2-(isopropylamino)acetyl]-3-(methanesulfonyl)-L-valyl]amino]-4-phenylbutyl]-3(S)-isoquinolinecarboxamide

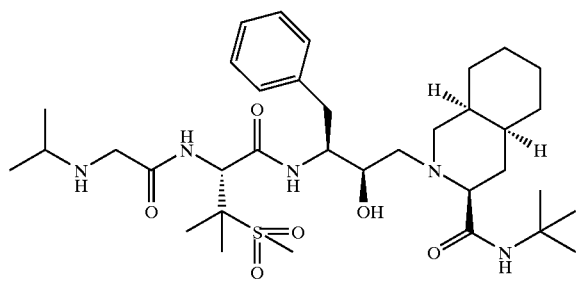

A solution of 0.123 g of 2-[3(S)-[[N-[N-(benzyloxycarbonyl)-N-isopropylglycyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide in 30 ml of ethanol was treated with 10% palladium on carbon and hydrogenated under a hydrogen atmosphere overnight.

The catalyst was removed by filtration and the volatiles evaporated under reduced pressure to give a colourless glass which was chromatographed on silica eluting with dichloromethane/methanol (25:1) followed by dichloromethane/methanol (10:1) to give an oil. The oil was triturated with petroleum ether/ether (bp 40–60° C.) to give 29 mg of N-tert-butyl-1,2,3,4,4a(S),5,6,7,8,8a(S)-decahydro-2-[2(R)-hydroxy-3(S)-[[N-[2-(isopropylamino)acetyl]-3-(methanesulfonyl)-L-valyl]amino]-4-phenylbutyl]-3(S)-isoquinolinecarboxamide as a white solid, [M+H]$^+$ 678.5.

The starting material was prepared as follows:

A solution of 1.04 ml (7.6 mmol) of glycine tert-butyl ester and 0.11 ml (8.38 mmol) of acetone in 30 ml of ethanol was treated with 10% palladium on carbon (Fluka) and hydrogenated under a hydrogen atmosphere overnight. The catalyst was removed by filtration and the volatiles evaporated under reduced pressure to give 1.08 g (82%) a cloudy mobile oil which was treated at 0° C. with 7 ml of trifluoroacetic acid and allowed to warm to room temperature. After 5 hours the volatiles were evaporated to give 2.65 g of a pale yellow oil, a 1.44 g portion of which was dissolved in 10 ml of 2M sodium hydroxide solution at 0° C. and treated simultaneously with 0.89 ml (6.23 mmol) of benzyl chloroformate and 10 ml of 2M sodium hydroxide solution. The reaction mixture was allowed to warm to room temperature overnight and was washed with ether. The solution was acidified and extracted with ethyl acetate and the combined organic phase was washed with water, dried over magnesium sulfate and evaporated under reduced pressure to give 0.338 g of N-(benzyloxycarbonyl)-N-isopropylglycine as a colourless oil. A 0.043 g portion of the oil was reacted with 0.1 g (1.73 mmol) of N-tert-butyl-1,2,3,4,4a(S),5,5,6,7,8,8a(S)-decahydro-2-[2(R)-hydroxy-3(S)-[[3-(methanesulfonyl)-L-valyl]amino]-4-phenylbutyl]-3(S)-isoquinolinecarboxamide in a manner analogous to that described for Example 2 to give 0.123 g of 2-[3(S)-[[N-[N-(benzyloxycarbonyl)-N-isopropylglycyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide as a yellow glass.

Example 93

N-tert-Butyl-1,2,3,4,4a(S),5,6,7,8,8a(S)-decahydro-2-[2(R)-hydroxy-3(S)-[3-(methanesulfonyl)-N-(N-phenylglycyl)-L-valyl]amino]-4-phenylbutyl -3(S)-isoquinolinecarboxamide

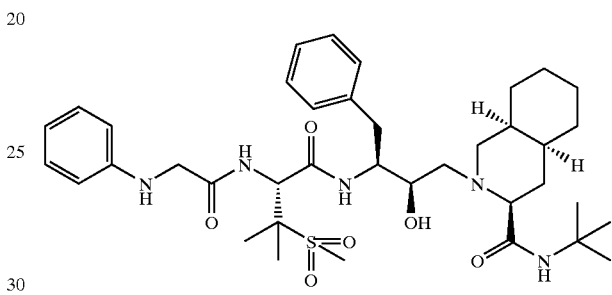

Example 93, [M+H]$^+$ 712.5, was prepared in a manner analogous to that described for Example 92 starting from N-phenylglycine (Aldrich 33,046-9).

Example 94

N-tert-Butyl-1,2,3,4,4a(S),5,6,7,8,8a(S)-decahydro-2-[2(R)-hydroxy-3(S)-[[3-(methanesulfonyl)-N-(N-methylglycyl)-L-valyl]amino]-4-phenylbutyl]-3(S)-isoquinolinecarboxamide

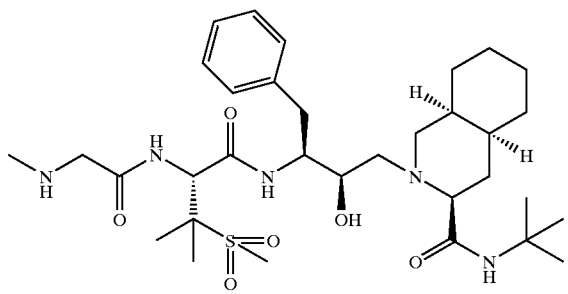

Example 94, [M+H]$^+$ 650.4, was prepared in a manner analogous to that described for Example 92 starting from N-(benzyloxycarbonyl)sarcosine (Bachem C-2570) but omitting the protection step in the preparation of the starting material.

Example 95

N-tert-Butyl-1,2,3,4,4a(S),5,6,7,8,8a(S)-decahydro-1-[2(R)-hydroxy-3(S)-[3-(methanesulfonyl)butyramido]-4-phenylbutyl]-2(S)-piperazinecarboxamide

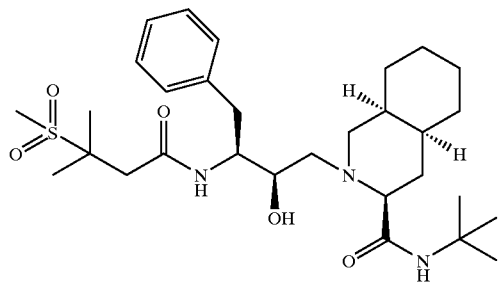

3-(Methanesulfonyl)-3-methylbutyric acid was reacted with 2-(3(S)-amino-2(R)-hydroxy-4-phenylbutyl)-N-tert-butyl-1,2,3,4,4a(S),4,5,6,7,8,8a(S)-decahydro-3(S)-isoquinolinecarboxamide in a manner analogous to that described for Example 2 to give the product as a white solid, mp 95–110° C. (foams), [M+H]+ 564.3.

The starting material 3-(methanesulfonyl)-3-methylbutyric acid was prepared as follows:

A stirred solution of 0.81 g (6 mmol) of 3-mercapto-3-methylbutanoic acid, prepared from 3,3-dimethylacrylic acid (Aldrich D13,860-6) according to the method described by G. Pattenden et al, J. Chem. Soc. Perkin Trans. 1, 1992, 10, 1215–21, in 25 ml of dioxane/water (3:2) was treated with 4.14 g (30 mmol) of potassium carbonate in 25 ml of water followed by 1.14 g (8 mmol) of iodomethane.

After 4 hours the volatiles were evaporated and water added. The aqueous phase was extracted with ether and then acidified. The acidified aqueous phase was then extracted with ether and the organic phase dried over magnesium sulfate and evaporated under reduced pressure to give 0.57 g (64%) of 3-methyl-3-(methylthio)butyric acid as a pale orange oil. The oil was dissolved in 12 ml of water containing 188 mg (4.63 mmol) of sodium hydroxide and treated with 2.59 g (31 mmol) of sodium hydrogen carbonate and 4 ml of acetone, followed by 3.16 g (5.13 mmol) of OXONE® (Aldrich 17,798-9) dissolved in 12 ml of 0.0004M EDTA solution by dropwise addition. After 2 hours, 2 g of sodium metabisulfite in 4 ml of water was added and the solution stirred for 15 minutes. The solution was acidified to pH 2 and extracted with ethyl acetate. The organic phase was washed with water and brine, dried over magnesium sulfate and evaporated under reduced pressure to give 585 mg of a colourless oil, [M+H]+ 181 (CI+ive),

Example 96

2-[3(S)-[3-(Ethanesulfonyl)-3-methylbutyramido]-2(R)-hydroxy-4-phenylbutyl]-1,2,3,4,4a(S),5,6,7,8,8a(S)-decahydro-3(S)-isoquinolinecarboxamide

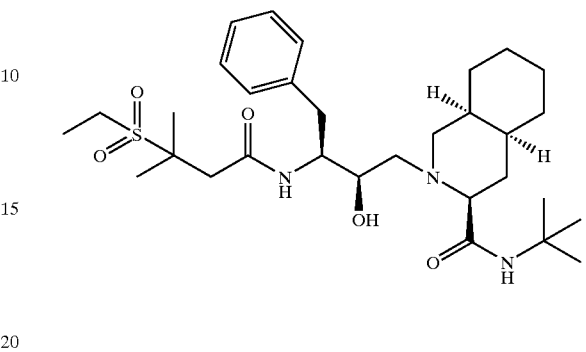

Example 96, [M+H]+ 578.2, was prepared in a manner analogous to that described for Example 2 by reacting 3-(ethanesulfonyl)-3-methylbutyric acid with 2-(3(S)-amino-2(R)-hydroxy-4-phenylbutyl)-N-tert-butyl-1,2,3,4,4a(S),4,5,6,7,8,8a(S)-decahydro-3(S)-isoquinolinecarboxamide.

The starting material 3-(ethanesulfonyl)-3-methylbutyric acid was prepared in a manner analogous to that described for the preparation of 3-(methanesulfonyl)-3-methylbutyric acid, the starting material usedfor Example 95, using iodoethane in place of iodomethane.

Example 97

2-[3(S)-[3-(Benzenesulfonyl)-3-methylbutyramido]-2(R)-hydroxy-4-phenylbutyl]-N-tert-butyl-1,2,3,4,4a(S),5,6,7,8,8a(S)-decahydro-3(S )-isoquinolinecarboxamide

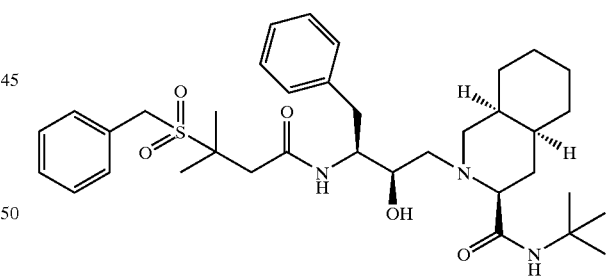

Example 97, [M+H]+ 640, was prepared in a manner analogous to that described for Example 2 by reacting 3-(benzylsulfonyl)-3-methylbutyric acid with 2-(3(S)-amino-2(R)-hydroxy-4-phenylbutyl)-N-tert-butyl-1,2,3,4,4a(S),4,5,6,7,8,8a(S)-decahydro-3(S)-isoquinolinecarboxamide.

The starting material 3-(benzylsulfonyl)-3-methylbutyric acid was prepared from 3-(benzylthio)-3-methylbutyric acid (G. Pattenden et al, J. Chem. Soc., Perkin Trans. 1, 1992, 10, 1215–21 in a manner analogous to that described in the preparation of the starting material for Example 95.

Example 98

N-tert-Butyl-1,2,3,4,4a(S),5,6,7,8,8a(S)-decahydro-2-[3(S)-[[N-[2-(tetrahydro-2(RS)-methyl-1,1-dioxo-2-thienyl)acetyl]-3-(methanesulfonyl)-L-valyl]amino]-2(R)-hydroxy-4-phenylbutyl]-3(S)-isoquinolinecarboxamide (mixture of diastereoisomers)

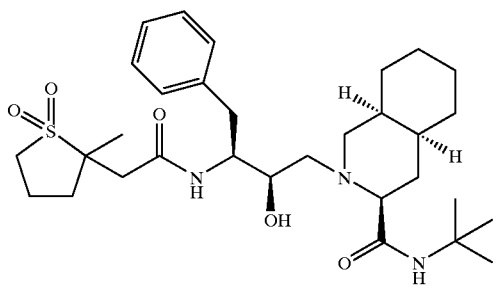

Example 98, [M+H]$^+$ 576.3, was prepared in a manner analogous to that described for Example 2 by reacting tetrahydro-2(RS)-methyl-2-thiopheneacetic acid S,S-dioxide with 2-(3(S)-amino-2(R)-hydroxy-4-phenylbutyl)-N-tert-butyl-1,2,3,4,4a(S),4,5,6,7,8,8a(S)-decahydro-3(S)-isoquinolinecarboxamide.

The starting material tetrahydro-2(RS)-methyl-2-thiopheneacetic acid S,S-dioxide was prepared from tetrahydro-2-methyl-thiopheneacetic acid (R. A. Bunce et al, J. Org. Chem. 1992, 57(6), 1727–33) in a manner analogous to that described in the preparation of the starting material for Example 95.

Example 99

N-tert-Butyl-1,2,3,4,4a(S),5,6,7,8,8a(S)-decahydro-2-[2(R)-hydroxy-3(S)-[2(R)-hydroxy-3-(methanesulfonyl)-3-methylbutyramido]-4-phenylbutyl]-3(S)-isoquinolinecarboxamide

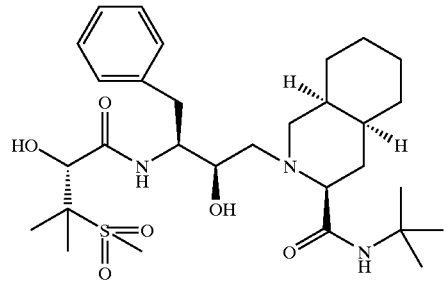

Example 99, [M+H]$^+$ 580.4, was prepared in a manner analogous to that described for Example 2 by reacting 2(R)-Hydroxy-3-(methanesulfonyl)-3-methylbutyric acid with 2-(3(S)-amino-2(R)-hydroxy-4-phenylbutyl)-N-tert-butyl-1,2,3,4,4a(S),4,5,6,7,8,8a(S)-decahydro-3(S)-isoquinolinecarboxamide.

The starting material 2(R)-hydroxy-3-(methanesulfonyl)-3-methylbutyric acid was prepared as follows:

A stirred solution of 2.25 g (5.3 mmol) of the protected amino acid from example 1 part (B), in 20 ml dry dimethylformamide was treated with 1.1 ml (11 mmol) piperidine. After 1 hour the volatiles were evaporated and the residue triturated with ether followed by ethyl acetate to give 1 g of a gum which was dissolved in 8 ml of 10% v/v sulfuric acid and heated to 50° C. 1.3 g of sodium nitrite in 3 ml of water was added dropwise and, after 30 minutes, a further 0.7 g of sodium nitrite in 2 ml of water was added. The reaction mixture was cooled and extracted with ethyl acetate and the combined organic phase was washed with water and brine, dried over magnesium sulfate and evaporated under reduced pressure to give 200 mg of 2(R)-hydroxy-3-(methanesulfonyl)-3-methylbutyric acid as a gum.

Example 100

N-tert-Butyl-1,2,3,4,4a(S),5,6,7,8,8a(S)-decahydro-2-[2(R)-hydroxy-3(S)-[[N-(dimethylcarbamoyl-3-(methanesulfonyl)-L-valyl]amino]-4-phenylbutyl]-3(S)-isoquinolinecarboxamide

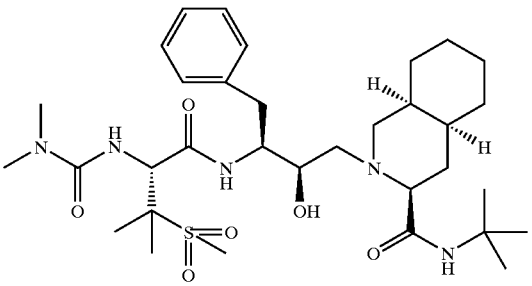

A stirred solution of 0.4 g (0.5 mmol) of N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide in 10 ml dry dimethylformamide at room temperature was treated with 1 ml (10 mmol) of piperidine. After 1 hour the volatiles were evaporated and the residue triturated with hexane to give N-tert-butyl-1,2,3,4,4a(S),5,5,6,7,8,8a(S)-decahydro-2-[2(R)-hydroxy-3(S)-[[3-(methanesulfonyl)-L-valyl]amino]-4-phenylbutyl]-3(S)-isoquinolinecarboxamide as a gum which was dissolved in 5 ml of acetonitrile and treated with 100 mg (0.5 mmol) of p-nitrophenylchloroformate (Aldrich 16,021-0) followed by 84 mg (1 mmol) of solid sodium hydrogen carbonate. After 15 minutes, 0.25 ml of 2M dimethylamine in tetrahydrofuran (Aldrich 39,195-6) and 0.14 ml of triethylamine were added and the reaction mixture was stirred for 2 hours. The volatiles were evaporated under reduced pressure and the residue was partitioned between water and dichloromethane and the aqueous phase extracted with dichloromethane. The combined organic phase was washed with brine, dried over magnesium sulfate and evaporated under reduced pressure to give an oil which was chromatographed on silica eluting with dichloromethane/methanol (19:1) to give 62 mg (20%) of N-tert-butyl-1,2,3,4,4a(S),5,6,7,8,8a(S)-decahydro-2-[2(R)-hydroxy-3(S)-[[N-(dimethylcarbamoyl-3-(methanesulfonyl)-L-valyl]amino]-4-phenylbutyl]-3(S)-isoquinolinecarboxamide as a white solid, [M+H]$^+$ 650.4.

In a manner analogous to that described for Example 100, starting from N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide the compounds shown in Table 4 were also prepared. Other reagents used in the synthesis of the compounds in Table 4 were obtained from commercial sources such as Aldrich and Lancaster.

TABLE 4

| Name | Structure | [M + H]+ | Ex. No. |
|---|---|---|---|
| N-tert-Butyl-2-[3(S)-[[N-(diethylcarbamoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 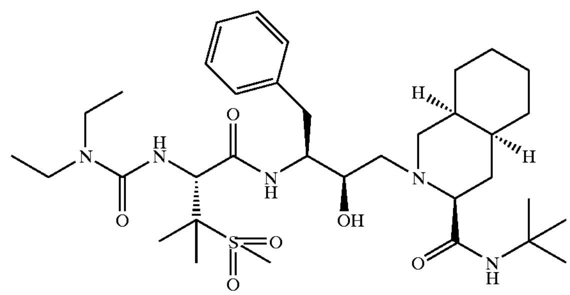 | 678.4 | 101 |
| N-tert-Butyl-2-[3(S)-[[N-(N-ethyl-N-methylcarbamoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 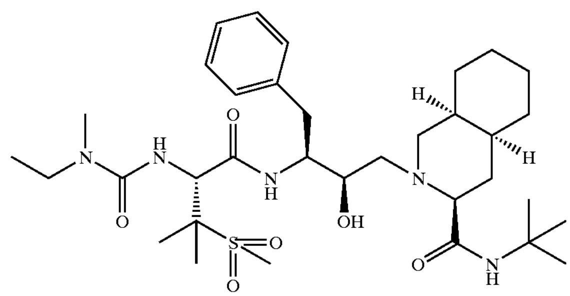 | 664.3 | 102 |
| N-tert-Butyl-1,2,3,4,4a(S),5,6,7,8,8a(S)-decahydro-2-[2(R)-hydroxy-3(S)-[[3-(methanesulfonyl)-N-(N-methyl-N-propylcarbamoyl)-L-valyl]amino]-4-phenylbutyl]-3(S)-isoquinolinecarboxamide | 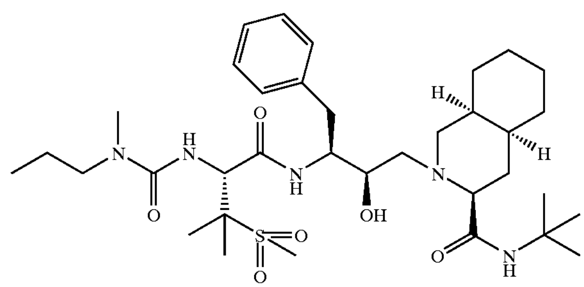 | 678.3 | 103 |
| N-tert-Butyl-1,2,3,4,4a(S),5,6,7,8,8a(S)-decahydro-2-[2(R)-hydroxy-3(S)-[[3-(methanesulfonyl)-N-[(1-pyrrolidinyl)carbonyl]-L-valyl]amino]-4-phenylbutyl]-3(S)-isoquinolinecarboxamide | 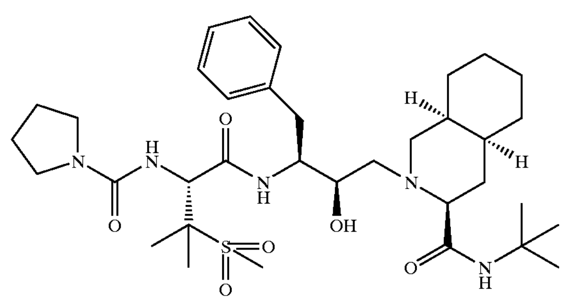 | 676.3 | 104 |
| N-tert-Butyl-1,2,3,4,4a(S),5,6,7,8,8a(S)-decahydro-2-[2(R)-hydroxy-3(S)-[[3-(methanesulfonyl)-N-(piperidinocarbonyl)-L-valyl]amino]-4-phenylbutyl]-3(S)-isoquinolinecarboxamide | 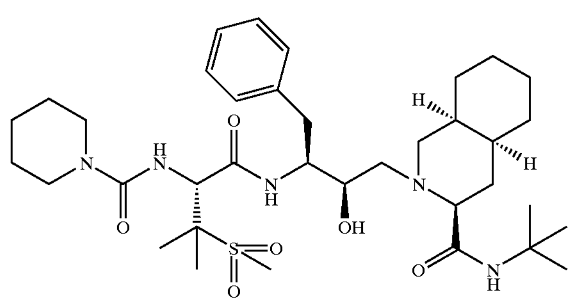 | 690.3 | 105 |

TABLE 4-continued

| Name | Structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-(morpholinocarbonyl)-L-valyl]amino]-4 phenylbutyl]-3(S)-isoquinolinecarboxamide | 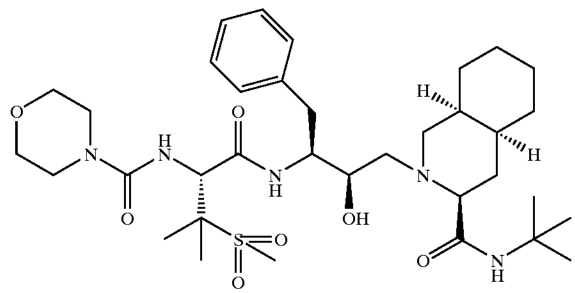 | 692.2 | 106 |
| N-tert-Butyl-1,2,3,4,4a(S),5,6,7,8,8a(S)-decahydro-2-[2(R)-hydroxy-3(S)-[[3-(methanesulfonyl)-N-[(1-piperazinyl)carbonyl]-L-valyl]amino]-4 phenylbutyl]-3(S)-isoquinolinecarboxamide | 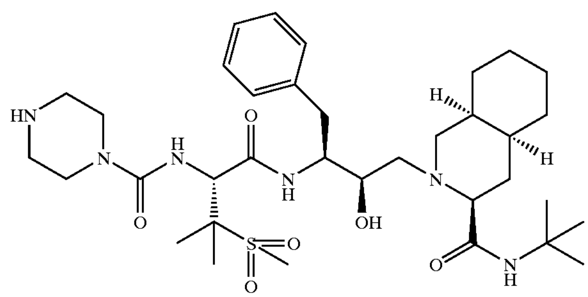 | 691.3 | 107 |
| N-tert-Butyl-1,2,3,4,4a(S),5,6,7,8,8a(S)-decahydro-2-[2(R)-hydroxy-3(S)-[[3-(methanesulfonyl)-N-[(4-methyl-1-piperazinyl)carbonyl]-L-valyl]amino]-4-phenylbutyl]-3(S)-isoquinolinecarboxamide | 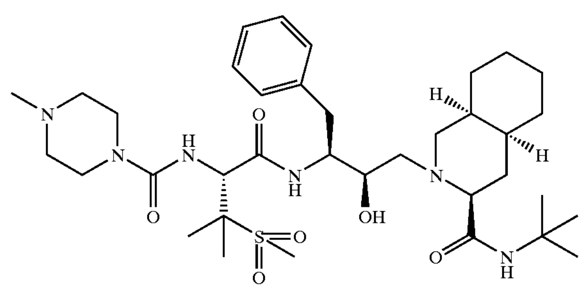 | 705.3 | 108 |
| N-tert-Butyl-1,2,3,4,4a(S),5,6,7,8,8a(S)-decahydro-2-[3(S)-[[N-[(tetrahydro-1,4-thiazin-4-yl)carbonyl]-3-(methanesulfonyl)-L-valyl]amino]-2(R)-hydroxy-4-phenylbutyl]-3(S)-isoquinolinecarboxamide | 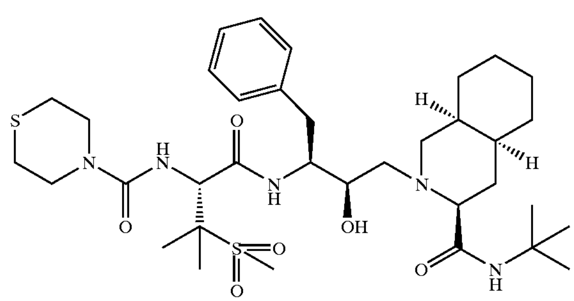 | 708 | 109 |

Example 110

N-tert-Butyl-1,2,3,4,4,4a(S),5,6,7,8,8a(S)-decahydro-2-[2(R)-hydroxy-3(S)-[[N-isopropyl-3-(methanesulfonyl)-L-valyl]amino]-4-phenylbutyl]-3(S)-isoquinolinecarboxamide

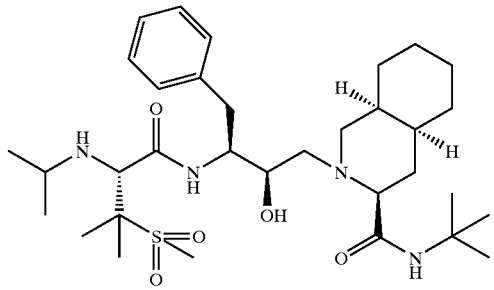

A stirred solution of 0.4 g (0.5 mmol) of N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide in 10 ml dry dimethylformamide at room temperature was treated with 1 ml (10 mmol) of piperidine. After 1 hour the volatiles were evaporated and the residue triturated with hexane to give N-tert-butyl-1,2,3,4,4a(S),5,5,6,7,8,8a(S)-decahydro-2-[2(R)-hydroxy-3(S)-[[3-(methanesulfonyl)-L-valyl]amino]-4-phenylbutyl]-3(S)-isoquinolinecarboxamide as a gum which was dissolved in 8 ml dichloroethane and treated under nitrogen with 0.037 ml (0.5 mmol) of acetone, 0.028 ml (0.5 mmol) glacial acetic acid and 160 mg (0.75 mmol) sodium triacetoxyborohydride. The reaction mixture was stirred overnight and the volatiles were then evaporated. The residue was partitioned between dichloromethane and water and extracted with dichloromethane. The combined organic phase was washed with brine, dried over magnesium sulfate and evaporated under reduced pressure to give a gum which was chromatographed on silica eluting with ethyl acetate/hexane (4:1) and then triturated with hexane to give 127 mg (41%) of N-tert-butyl-1,2,3,4,4,4a(S),5,6,7,8,8a(S)-decahydro-2-[2(R)-hydroxy-3(S)-[[N-isopropyl-3-(methanesulfonyl)-L-valyl]amino]-4-phenylbutyl]-3(S)-isoquinolinecarboxamide as a white solid. $[M+H]^+$ 621.3

In a manner analogous to that described for example 110, starting from N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide the compounds shown in Table 5 were also prepared. Other reagents used in the synthesis of the compounds in Table 5 were obtained from commercial sources such as Aldrich, Lancaster and Maybridge Int, for example e.g. furfural (example 114) and 2-fluorobenzaldehyde (example 116) were purchased from Aldrich, cat. nos.(31,991-0), (F480-7), 4(5)-formyl-2-methylimidazole (example 134) was purchased from Maybridge Int. (SB 01361)

TABLE 5

| name | structure | $[M + H]^+$ | Ex. No. |
|---|---|---|---|
| N-tert-Butyl-2-[3(S)-[[N-ethyl-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 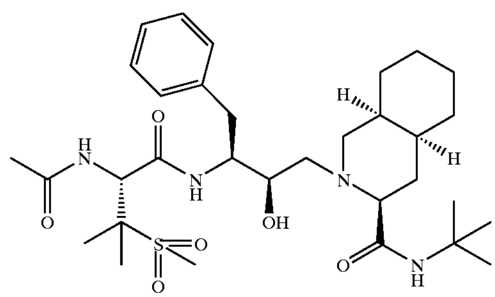 | 607.3 | 111 |
| 2-[3(S)-[[N-Benzyl-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 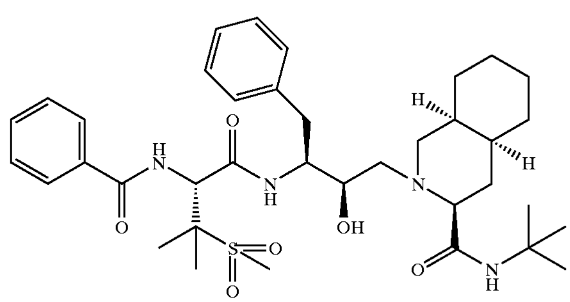 | 669.3 | 112 |

TABLE 5-continued

| name | structure | [M + H]⁺ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-methyl-L-valyl]amino]-4-phenylbutyl]-3(S)-isoquinolinecarboxamide | 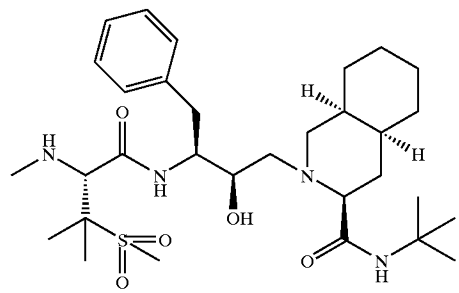 | 593.2 | 113 |
| N-tert-Butyl-2-[3(S)-[[N-(2-furfuryl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 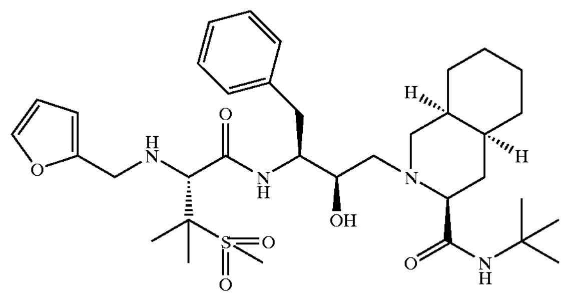 | 659.2 | 114 |
| N-tert-Butyl-1,2,3,4,4a(S),5,6,7,8,8a(S)-decahydro-2-[2(R)-hydroxy-3(S)-[[3-(methanesulfonyl)-N-(5-methyl-2-furfuryl)-L-valyl]amino]-4-phenylbutyl]-3(S)-isoquinolinecarboxamide | 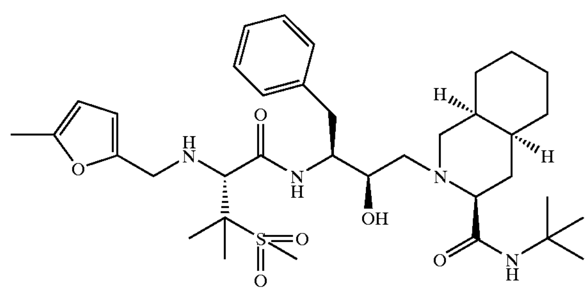 | 673.3 | 115 |
| N-tert-Butyl-2-[3(S)-[[N-(2-fluorobenzyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 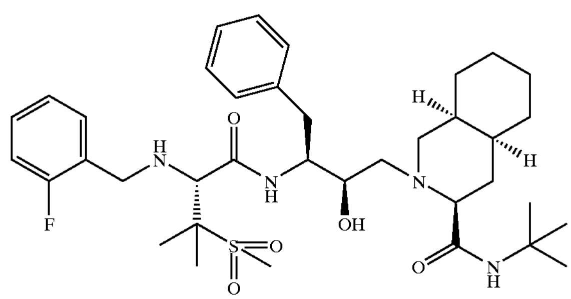 | 687.2 | 116 |
| N-tert-Butyl-2-[3(S)-[[N-(2-chlorobenzyl)-3-(methanesulfonyl)-L-valyl]amino]-3(R)-hydroxy-4-phenylbutyl]-1,2,3,4,4a(S),5,6,7,8,8a(S)-decahydro-3(S)-isoquinolinecarboxamide | 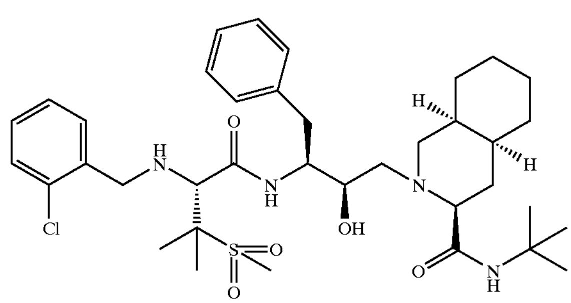 | 703.2 | 117 |

TABLE 5-continued

| name | structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-(2-methoxybenzyl)-L-valyl]amino]-4-phenylbutyl]-3(S)-isoquinolinecarboxamide | 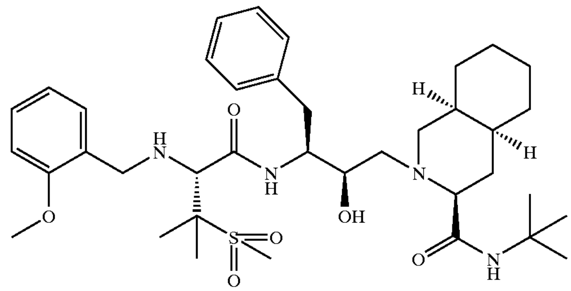 | 699.2 | 118 |
| N-tert-Butyl-1,2,3,4,4a(S),5,6,7,8,8a(S)-decahydro-2-[2(R)-hydroxy-3(S)-[[N-(2-hydroxybenzyl)-3-(methanesulfonyl)-L-valyl]amino]-4-phenylbutyl]-3(S)-isoquinolinecarboxamide | 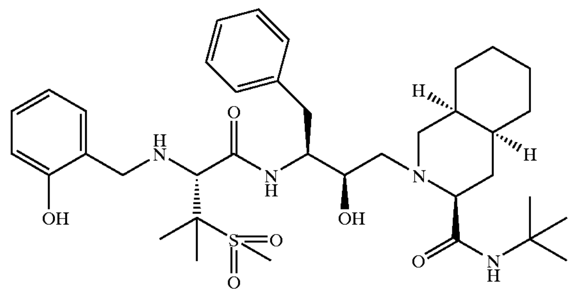 | 685.2 | 119 |
| N-tert-Butyl-1,2,3,4,4a(S),5,6,7,8,8a(S)-decahydro-2-[2(R)-hydroxy-3(S)-[[3-(methanesulfonyl)-N-(2-methylbenzyl)-L-valyl]amino]-4-phenylbutyl]-3(S)-isoquinolinecarboxamide | 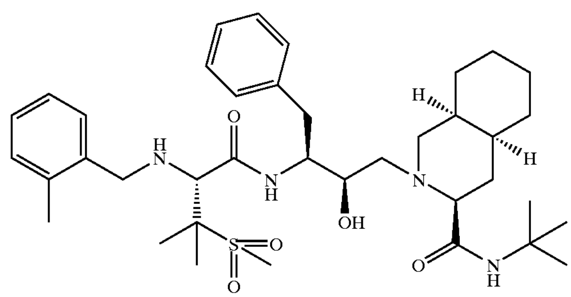 | 683.3 | 120 |
| N-tert-Butyl-2-(3(S)-[[N-(3-fluorobenzyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 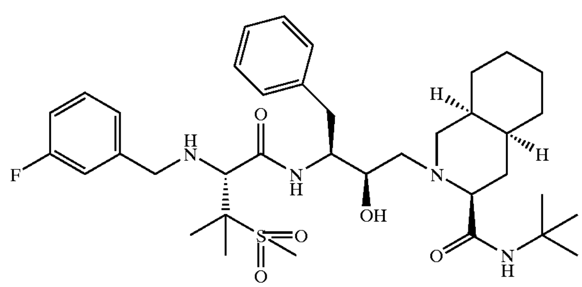 | 687.2 | 121 |
| N-tert-Butyl-2-[3(S)-[[N-(3-chlorobenzyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 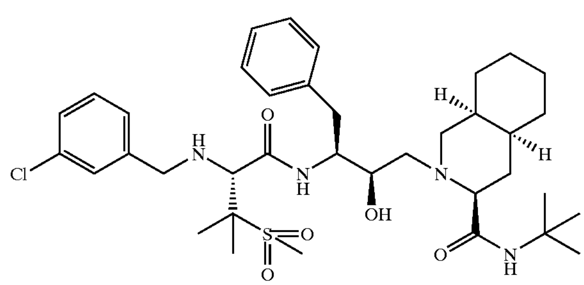 | 703.2 | 122 |

TABLE 5-continued

| name | structure | [M + H]⁺ | Ex. No. |
|---|---|---|---|
| N-tert-Butyl-1,2,3,4,4a(S),5,6,7,8,8a(S)-decahydro-2-[2(R)-hydroxy-3(S)-[[N-(3-hydroxybenzyl)-3-(methanesulfonyl)-L-valyl]amino]-4-phenylbutyl]-3(S)-isoquinolinecarboxamide | 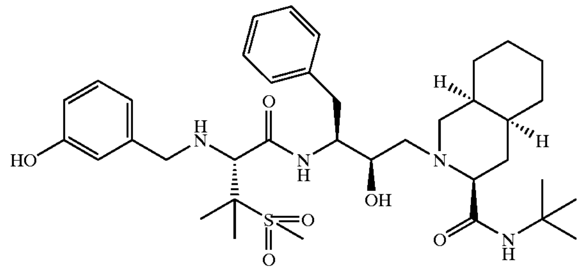 | 685.3 | 123 |
| N-tert-Butyl-1,2,3,4,4a(S),5,6,7,8,8a(S)-decahydro-2-[2(R)-hydroxy-3(S)-[[3-(methanesulfonyl)-N-(5-methyl-2-thenyl)-L-valyl]amino]-4-phenylbutyl]-3(S)-isoquinolinecarboxamide | 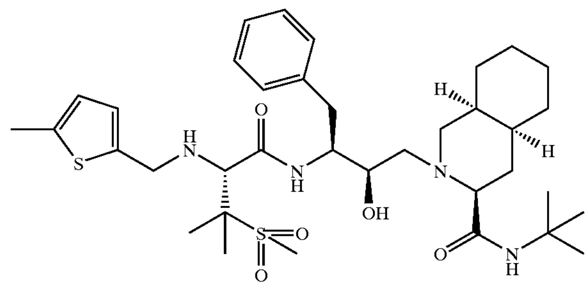 | 689.2 | 124 |
| N-tert-Butyl-1,2,3,4,4a(S),5,6,7,8,8a(S)-decahydro-2-[2(R)-hydroxy-3(S)-[[3-(methanesulfonyl)-N-[(2-pyridyl)methyl]-L-valyl]amino]-4-phenylbutyl]-3(S)-isoquinolinecarboxamide | 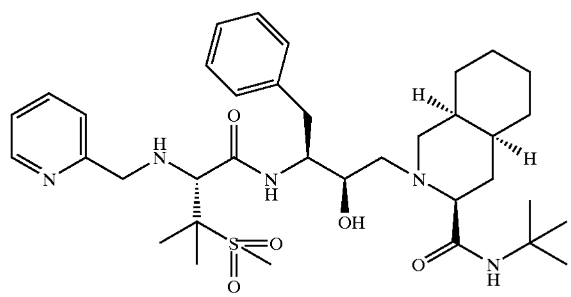 | 670.3 | 125 |
| N-tert-Butyl-1,2,3,4,4a(S),5,6,7,8,8a(S)-decahydro-2-[2(R)-hydroxy-3(S)-[[N-(4-hydroxybenzyl)-3-(methanesulfonyl)-L-valyl]amino]-4-phenylbutyl]-3(S)-isoquinolinecarboxamide | 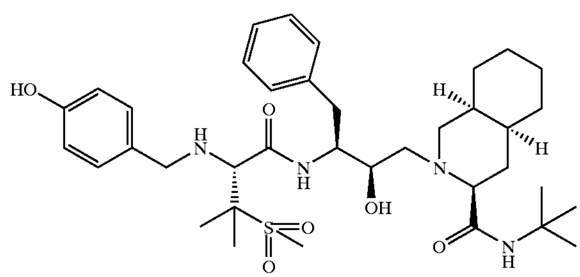 | 685.2 | 126 |
| N-tert-Butyl-1,2,3,4,4a(S),5,6,7,8,8a(S)-decahydro-2-[2(R)-hydroxy-3(S)-[[3-(methanesulfonyl)-N-(4-methylbenzyl)-L-valyl]amino]-4-phenylbutyl]-3(S)-isoquinolinecarboxamide | 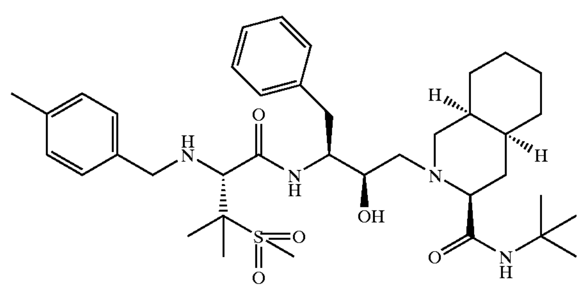 | 683.3 | 127 |

TABLE 5-continued

| name | structure | [M + H]⁺ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-[(2-pyridyl)methyl]-L-valyl]amino]-4-phenylbutyl]-3(S)-isoquinolinecarboxamide | 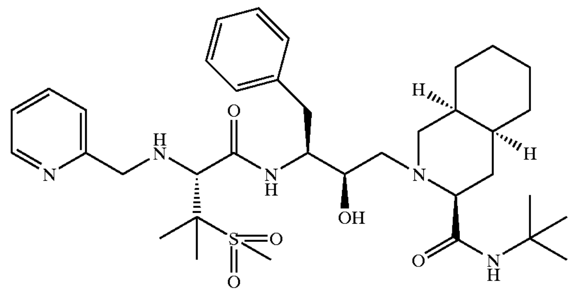 | 670.3 | 125 |
| N-tert-Butyl-1,2,3,4,4a(S),5,6,7,8,8a(S)-decahydro-2-[2(R)-hydroxy-3(S)-[[N-(4-hydroxybenzyl)-3-(methanesulfonyl)-L-valyl]amino]-4-phenylbutyl]-3(S)-isoquinolinecarboxamide | 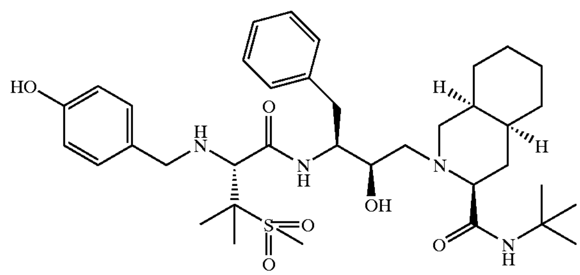 | 685.2 | 126 |
| N-tert-Butyl-1,2,3,4,4a(S),5,6,7,8,8a(S)-decahydro-2-[2(R)-hydroxy-3(S)-[[3-(methanesulfonyl)-N-(4-methylbenzyl)-L-valyl]amino]-4-phenylbutyl]-3(S)-isoquinolinecarboxamide | 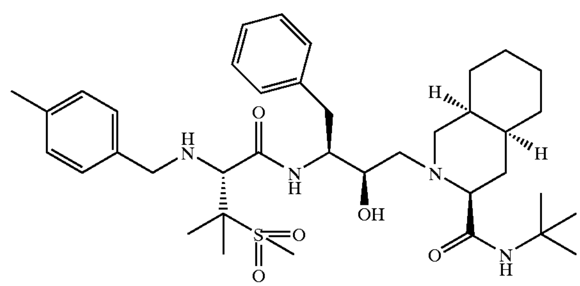 | 683.3 | 127 |
| N-tert-Butyl-1,2,3,4,4a(S),5,6,7,8,8a(S)-decahydro-2-[2(R)-hydroxy-3(S)-[[N-isobutyl-3-(methanesulfonyl)-L-valyl]amino]-4-phenylbutyl]-3(S)-isoquinolinecarboxamide | 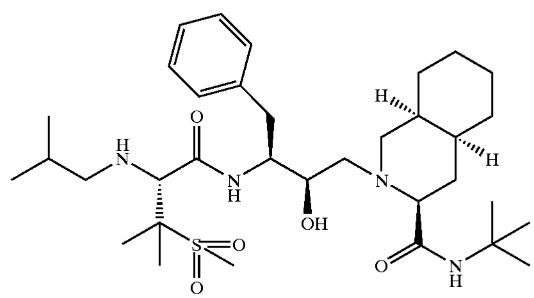 | 635.2 | 129 |
| N-tert-Butyl-1,2,3,4,4a(S),5,6,7,8,8a(S)-decahydro-2-[2(R)-hydroxy-3(S)-[[3-(methanesulfonyl)-N-(2-phenylethylyl))-L-valyl]amino]-4-phenylbutyl]-3(S)-isoquinolinecarboxamide | 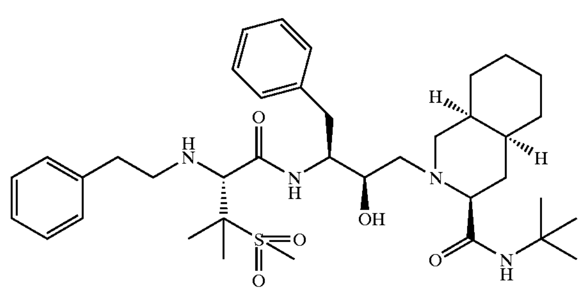 | 683.3 | 130 |

TABLE 5-continued

| name | structure | [M + H]+ | Ex. No. |
|---|---|---|---|
| N-tert-Butyl-2-[3(S)-[[N-(2,6-difluorobenzyl)-3-(methanesulfonyl)-N-L-valyl]amino]-2(R)-hydroxy-4-phenylbutyl]-1,2,3,4,4a(S),5,6,7,8,8a(S)-decahydro-3(S)-isoquinolinecarboxamide | 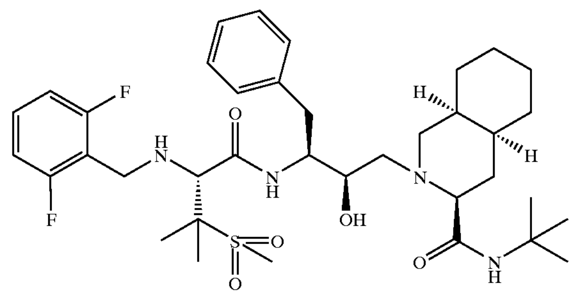 | 705.2 | 131 |
| N-tert-Butyl-2-[3(S)-[[N-(3-furfuryl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 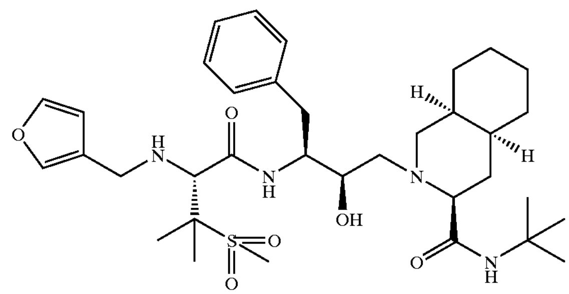 | 659.2 | 132 |
| N-tert-Butyl-2-[3(S)-[[N-(cyclopropylmethyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 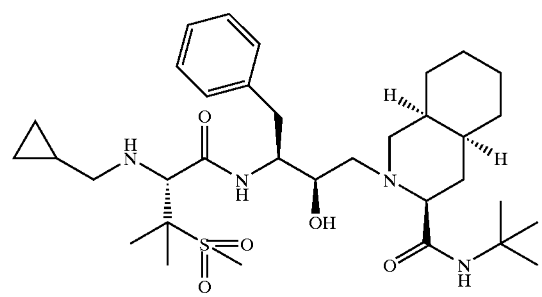 | 633.3 | 133 |
| N-tert-Butyl-1,2,3,4,4a(S),5,6,7,8,8a(S)-decahydro-2-[2(R)-hydroxy-3(S)-[[3-(methanesulfonyl)-N-[(2-methyl-4-imidazolyl)methyl]-L-valyl]amino]-4-phenylbutyl]-3(S)-isoquinolinecarboxamide | 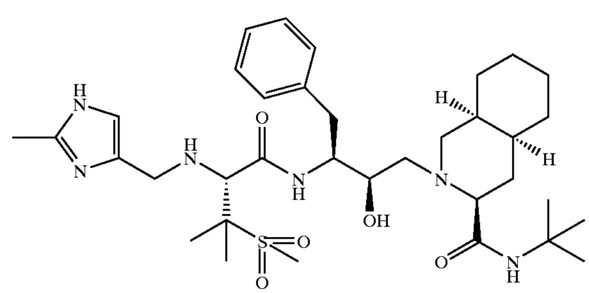 | 673.3 | 134 |
| N-tert-Butyl-1,2,3,4,4a(S),5,6,7,8,8a(S)-decahydro-2-[2(R)-hydroxy-3(S)-[[3-(methanesulfonyl)-N-[(5-methyl-4-imidazolyl)methyl]-L-valyl]amino]-4-phenylbutyl]-3(S)-isoquinolinecarboxamide | 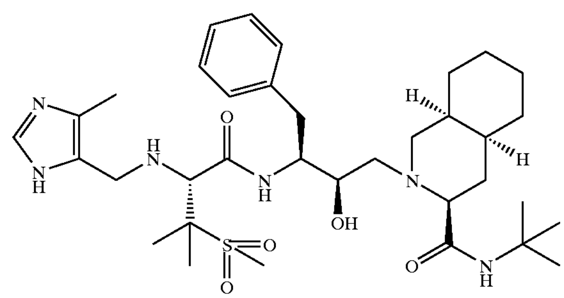 | 673.3 | 135 |

TABLE 5-continued

| name | structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-[(1-methyl-2-imidazolyl)methyl]-L-valyl]amino]-4-phenylbutyl]-3(S)-isoquinolinecarboxamide | 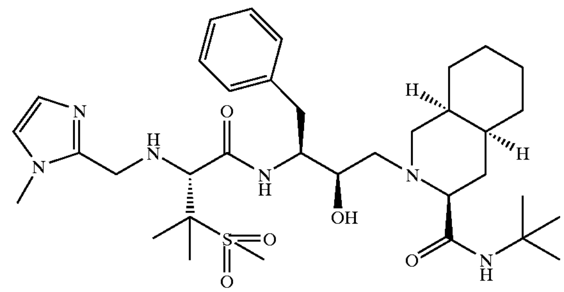 | 673.3 | 136 |

Example 137

N-tert-Butyl-1,2,3,4,4a(S),5,6,7,8,8a(S)-decahydro-2-[2(R)-hydroxy-3(S)-[[3-(methanesulfonyl)-N-(2-thiazolyl)-L-valyl]amino]-4-phenylbutyl]-3(S)-isoquinolinecarboxamide

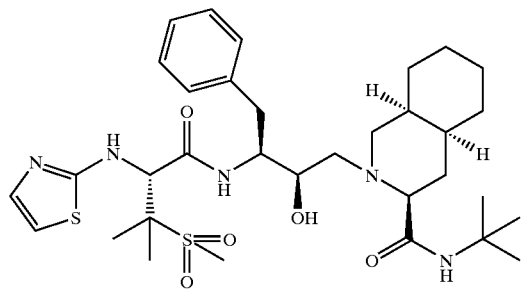

A stirred solution of 255 mg (0.4 mmol) of N-tert-butyl-1,2,3,4,4a(S),5,6,7,8,8a(S)-decahydro-2-[2(R)-hydroxy-3(S)-[[3-(methanesulfonyl)-N-(thiocarbamoyl)-L-valyl]amino]-4-phenylbutyl]-3(S)-isoquinolinecarboxamide in 5 ml of ethanol was treated with 0.1 ml of chloroacetaldehyde (50% solution in water) and heated at reflux for 4 hours. The volatiles were evaporated and the residue partitioned between dichloromethane and saturated aqueous sodium hydrogen carbonate. The aqueous phase was extracted with dichloromethane and the combined organic phase was washed with brine, dried over magnesium sulfate and evaporated under reduced pressure to give a solid which was chromatographed on silica eluting with dichloromethane/methanol (19:1) to give 100 mg (38%) of N-tert-butyl-1,2,3,4,4a(S),5,6,7,8,8a(S)-decahydro-2-[2(R)-hydroxy-3(S)-[[3-(methanesulfonyl)-N-(2-thiazolyl)-L-valyl]amino]-4-phenylbutyl]-3(S)-isoquinolinecarboxamide as a white solid, [M+H]+ 662.2.

The starting material N-tert-butyl-1,2,3,4,4a(S),5,6,7,8,8a(S)-decahydro-2-[2(R)-hydroxy-3(S)-[[3-(methanesulfonyl)-N-(thiocarbamoyl)-L-valyl]amino]-4-phenylbutyl]-3(S)-isoquinolinecarboxamide was prepared as follows:

A stirred solution of 1.6 g (2 mmol) of N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide in 40 ml of dry dimethylformamide at room temperature was treated with 4 ml (40 mmol) of piperidine. After 1 hour the volatiles were evaporated and the residue triturated with hexane to give N-tert-butyl-1,2,3,4,4a(S),5,6,7,8,8a(S)-decahydro-2-[2(R)-hydroxy-3(S)-[[3-(methanesulfonyl)-L-valyl]amino]-4-phenylbutyl]-3(S)-isoquinolinecarboxamide as a gum which was dissolved in 5 ml of acetone and treated with 0.28 ml (2.1 mmol) of benzoyl isothiocyanate (Aldrich 26,165-3). The stirred reaction mixture was heated at reflux for 4 hours and then cooled. The volatiles were evaporated under reduced pressure and the residue was triturated with hexane to give a gum which was then chromatographed on silica eluting with ethyl acetate/hexane (2:1) to give 765 mg (52%) of 2-[3(S)-[[N-(benzoylthiocarbamoyl)-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide as a fawn foam, [M+H]+ 742.3, which was combined with another batch of material and used in the next step.

A stirred solution of 850 mg (1.15 mmol) of 2-[3(S)-[[N-(benzoylthiocarbamoyl)-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide from (A) above, in 6 ml of methanol/acetone (1:1) was treated with 115 mg (1.15 mmol) of potassium hydrogen carbonate and 0.5 ml of water. After 5 hours 1 ml of acetic acid was added and the mixture stirred for a further 10 minutes.

The volatiles were evaporated under reduced pressure and the remaining water was removed by repeated re-evaporation with ethanol to give a gummy oil which was chromatographed on silica eluting with dichloromethane/methanol (19:1) to give 710 mg (97%) of N-tert-butyl-1,2,3,4,4a(S),5,6,7,8,8a(S)-decahydro-2-[2(R)-hydroxy-3(S)-[[3-(methanesulfonyl)-N-(thiocarbamoyl)-L-valyl]amino]-4-phenylbutyl]-3(S)-isoquinolinecarboxamide as a white foam, [M+H]+ 638.

In a manner analogous to that described for Example 137, starting from N-tert-butyl-1,2,3,4,4a(S),5,6,7,8,8a(S)-decahydro-2-[2(R)-hydroxy-3(S)-[[3-(methanesulfonyl)-N-(thiocarbamoyl)-L-valyl]amino]-4-phenylbutyl]-3(S)-isoquinolinecarboxamide, the compounds shown in Table 6 were also prepared. Other reagents were obtained from commercial sources.

TABLE 6

| Name | Structure | [M + H]+ | Ex. No. |
|---|---|---|---|
| N-tert-Butyl-1,2,3,4,4a(S),5,6,7,8,8a(S)-decahydro-2-[2(R)-hydroxy-3(S)-[[3-(methanesulfonyl)-N-(4-methyl-2-thiazolyl)-L-valyl]amino]-4-phenylbutyl]-3(S)-isoquinolinecarboxamide | 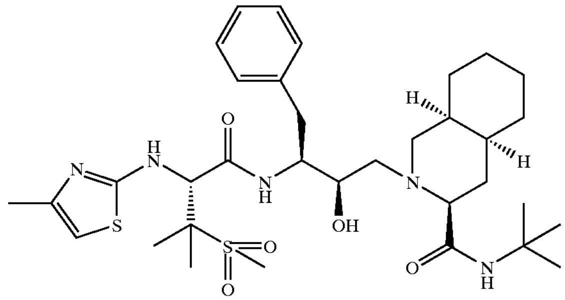 | 676 | 138 |
| N-tert-Butyl-1,2,3,4,4a(S),5,6,7,8,8a(S)-decahydro-2-[2(R)-hydroxy-3(S)-[[3-(methanesulfonyl)-N-(4-phenyl-2-thiazolyl)-L-valyl]amino]-4-phenylbutyl]-3(S)-isoquinolinecarboxamide | 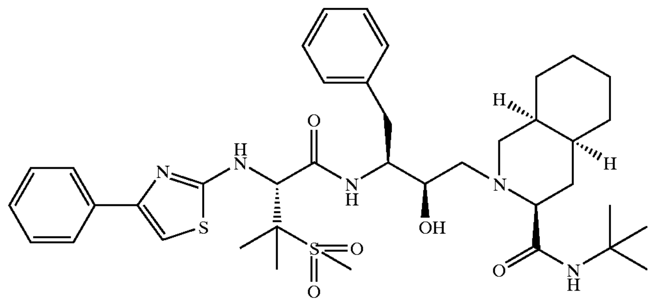 | 738 | 139 |
| N-tert-Butyl-2-[3(S)-[[N-[4-(ethoxycarbonyl)-2-thiazolyl]-3-(methanesulfonyl)-L-valyl]amino]-2(R)-hydroxy-4-phenylbutyl]-1,2,3,4,4a(S),5,6,7,8,8a(S)-decahydro3(S)-isoquinolinecarboxamide | 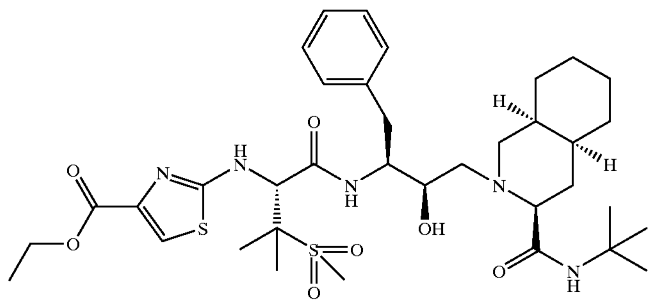 | 734 | 140 |
| 2-[3(S)-[[N-[4-(Acetoxymethyl)-2-thiazolyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 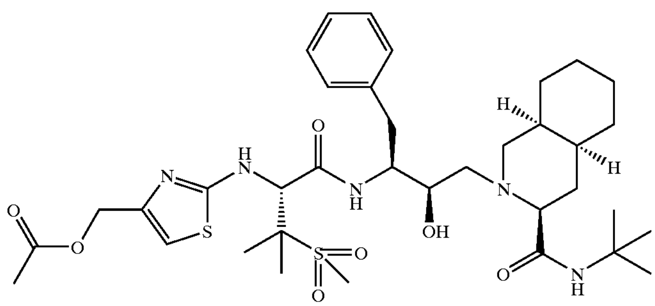 | 734 | 141 |
| N-tert-Butyl-1,2,3,4,4a(S),5,6,7,8,8a(S)-decahydro-2-[2(R)-hydroxy-3(S)-[[3-(methanesulfonyl)-N-[4-[(methoxycarbonyl)methyl]-2-thiazolyl]-L-valyl]amino]-4-phenylbutyl]-3(S)-isoquinolinecarboxamide | 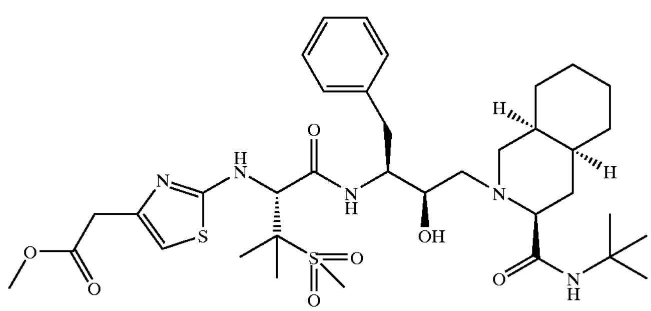 | 734 | 142 |

Example 143

N-tert-Butyl-1,2,3,4,4a(S),5,6,7,8,8a(S)-decahydro-2-[2(R)-hydroxy-3(S)-[[N-[4-(hydroxymethyl)-2-thiazolyl]-3-(methanesulfonyl)-L-valyl]amino]-4-phenylbutyl]-3(S)-isoquinolinecarboxamide

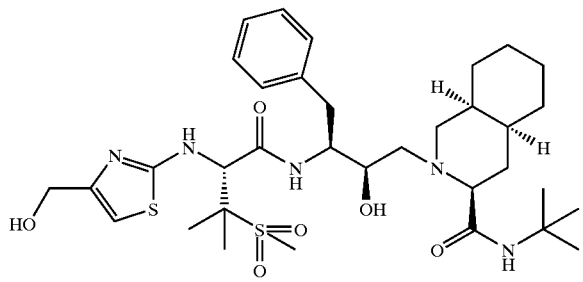

A stirred solution of 73 mg (0.1 mmol) of 2-[3(S)-[[N-[4-(acetoxymethyl)-2-thiazolyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide (Example 141) in 7 ml of methanol/water (5:2) was treated with 700 mg of potassium carbonate. After 1.5 hours the volatiles were evaporated and the residue partitioned between ethyl acetate and water. The aqueous phase was extracted with ethyl acetate and the combined organic phase was washed with brine, dried over magnesium sulfate and evaporated under reduced pressure to give a gum which was chromatographed on silica eluting with dichloromethane/methanol (40:3) to give 32 mg (48%) of N-tert-butyl-1,2,3,4,4a(S),5,6,7,8,8a(S)-decahydro-2-[2(R)-hydroxy-3(S)-[[N-[4-(hydroxymethyl)-2-thiazolyl]-3-(methanesulfonyl)-L-valyl]amino]-4-phenylbutyl]-3(S)-isoquinolinecarboxamide as a solid, mp 126° C., [M+H]+ 692.

Example 144

N-tert-Butyl-1,2,3,4,4a(S),5,6,7,8,8a(S)-decahydro-2-[3(S)-[2(R)-(2,3-dihydro-2-oxo-1H-imidazol-2-yl)-3-(methanesulfonyl)-3-methylbutyramido]-2(R)-hydroxy-4-phenylbutyl]-3(S)-isoquinolinecarboxamide

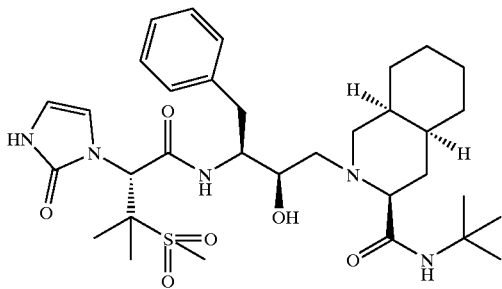

A stirred solution of 0.578 g (1 mmol) of N-tert-butyl-1,2,3,4,4a(S),5,5,6,7,8,8a(S)-decahydro-2-[2(R)-hydroxy-3(S)-[[3-(methanesulfonyl)-L-valyl]amino]-4-phenylbutyl]-3(S)-isoquinolinecarboxamide was dissolved in 20 ml of acetonitrile and treated with 201 mg (1 mmol) of p-nitrophenyl chloroformate followed by 168 mg (2 mmol) of sodium hydrogen carbonate. After 15 minutes, 0.11 ml of aminoacetaldehyde dimethyl acetal (Lancaster 7520) and 0.28 ml (2 mmol) of triethylamine were added and the reaction mixture was stirred for 2 hours. The volatiles were evaporated under reduced pressure and the residue partitioned between water and dichloromethane. The aqueous phase was extracted with dichloromethane and the combined organic phase was washed with brine, dried over magnesium sulfate and evaporated under reduced pressure to give a yellow gum which was triturated with hexane followed by ethyl acetate to give 466 mg (66%) of a cream solid mp 228–30° C., [M+H]+ 710. 420 mg (0.59 mmol) Of the solid was dissolved in 20 ml of acetone and treated with 5 ml of 10% hydrochloric acid solution and stirred overnight. The solution was treated with saturated sodium hydrogen carbonate solution and partially evaporated. The solution was extracted with dichloromethane and the combined organic phase washed with brine, dried over magnesium sulfate and evaporated to give a cream solid which was chromatographed on silica eluting with dichloromethane/methanol (38:1) to give 50 mg (13%) of N-tert-butyl-1,2,3,4,4a(S),5,6,7,8,8a(S)-decahydro-2-[3(S)-[2(R)-(2,3-dihydro-2-oxo-1H-imidazol-2-yl)-3-(methanesulfonyl)-3-methylbutyramido]-2(R)-hydroxy-4-phenylbutyl]-3(S)-isoquinolinecarboxamide as a white solid, [M+H]+ 646.

Example 145

N-Benzyl-1,2,3,4,4a(S),5,6,7,8,8a(S)-decahydro-2-[2(R)-hydroxy-3(S)-[[3-(methanesulfonyl)-N-(methoxycarbonyl)-L-valyl]amino]-4-phenylbutyl]-3(S)-isoquinolinecarboxamide

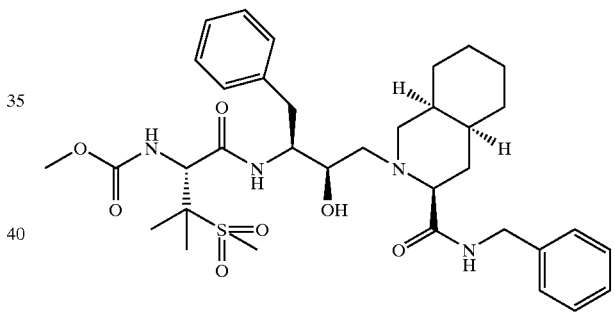

A solution of 0.13 ml (1.2 mmol) of benzylamine in 5 ml of dichloromethane was treated with 0.6 ml of trimethylaluminium (2M in toluene) and stirred at room temperature for 15 minutes. A solution of 68 mg of the lactone N1-[1(S)-(1,3,4,6,6a(S),7,8,9,10,10a(S),11,11a(S)-dodecahydro-1-oxo-1,4-oxazino[4,3-b]isoquinolin-3(R)-yl)-2-phenylethyl]-3-(methanesulfonyl)-N2-(methoxycarbonyl)-L-valinamide, dissolved in 5 ml of dichloromethane was added dropwise followed by 5 ml of toluene and the solution was stirred overnight. Dilute hydrochloric acid was added dropwise and the solution was extracted with dichloromethane.

The combined organic phase was washed with dilute hydrochloric acid and brine, dried over magnesium sulphate and evaporated under reduced pressure to give a residue which was crystallised from dichloromethane/hexane to give 15 mg of N-benzyl-1,2,3,4,4a(S),5,6,7,8,8a(S)-decahydro-2-[2(R)-hydroxy-3(S)-[[3-(methanesulfonyl)-N-(methoxycarbonyl)-L-valyl]amino]-4-phenylbutyl]-3(S)-isoquinolinecarboxamide as a white solid, [M+H]+ 671.

The starting material N1-[1(S)-(1,3,4,6,6a(S),7,8,9,10,10a(S),11,11a(S)-dodecahydro-1-oxo-1,4-oxazino[(4,3-b]

isoquinolin-3(R)-yl]-2-phenylethyl]-3-(methanesulfonyl)-N2-(methoxycarbonyl)-L-valinamide was prepared as follows: 23.8 g (0.1M) of N-tert-butyl-1,2,3,4,4a(S),4,5,6,7,8,8a(S)-decahydro-3(S)-isoquinolinecarboxamide prepared according to known procedures e.g. Martin, Joseph Armstrong; Redshaw, Sally, EP 432695 A2, was suspended in 100 ml of 6N hydrochloric acid and stirred at reflux for 23 hours. The reaction mixture was evaporated to dryness to give 23.1 g of a white solid which was dissolved in 200 ml of water and treated with 30 ml of 4N sodium hydroxide solution. The solution was cooled to 4° C. and stirred vigorously as 15.5 ml (0.11 mol) of benzyl chloroformate and 4.4 g (0.11 mol) of sodium hydroxide in 15 ml of water were added simultaneously. The reaction was stirred for a further 1 hour adjusting the pH to pH 9 by the addition of 4N sodium hydroxide and was then warmed to room temperature. After a further 2 hours the solution was diluted with water and extracted with hexane. The aqueous phase was acidified with concentrated hydrochloric acid and extracted with ethyl acetate. The combined organic phase was washed with water and brine, dried over magnesium sulfate and evaporated under reduced pressure to give 29.6 g of a gum which was dissolved in 300 ml of ethyl acetate and stirred vigorously as 10.7 ml (0.093 mol) of cyclohexylamine was added dropwise. A further 200 ml of ethyl acetate was added and the mixture stirred overnight and then filtered to give a 28.9 g of a solid which was combined with another 10.4 g batch of the same material and partitioned between 400 ml of ethyl acetate and 250 ml of 2N hydrochloric acid. The organic phase was washed with water and brine, dried over magnesium sulfate and evaporated to give a gum. A stirred solution of the gum in 50 ml of dichloromethane was treated with a solution of 41.3 g (0.18 mol) of tert-butyl trichloroacetimidate (Aldrich) in 400 ml of cyclohexane followed by 1.9 ml of borontrifluoride diethyl etherate (Fluka). The mixture was stirred overnight and sodium hydrogen carbonate was added and the solution filtered after 30 minutes. The volatiles were evaporated to give a gum which was dissolved in 500 ml of ethyl acetate and washed with 2N sodium carbonate, water and brine, dried over magnesium sulfate and evaporated under reduced pressure to give 28 g of a gum. A solution of 18.8 g of the gum in 500 ml of ethanol was hydrogenated over 1.9 g of 5% palladium on carbon (Fluka). The catalyst was removed by filtration and the volatiles evaporated under reduced pressure to give a white solid which was partitioned between 300 ml of methyl tert-butyl ether and 250 ml of saturated sodium hydrogen carbonate solution. The organic phase was washed with water and brine, dried over magnesium sulfate and evaporated under reduced pressure to give 10 g (0.042 mol) of a pale yellow gum which was dissolved in 200 ml of ethanol. 12.43 g (0.042 mol) of 2(S)-[1(S)-(Benzyloxyformamido)-2-phenylethyl]oxirane (prepared according to known methods (EP 346847 A2)) was added and the mixture heated at reflux for 10 hours. The volatiles were evaporated and the residue was chromatographed on silica eluting with ethyl acetate/hexane (1:2) to give 19.5 g of a cream solid, 1.072 g (2.0 mmol) of which was dissolved in 5 ml glacial acetic acid and treated with 10 ml 45% hydrogen bromide in acetic acid and stirred for 1.5 hours. The volatiles were evaporated almost to dryness and the solid filtered and washed with glacial acetic acid followed by ether. The solid was partitioned between ethyl acetate and aqueous sodium carbonate and the organic phase was washed with water and brine, dried over magnesium sulfate and evaporated under reduced pressure to give 493 mg of 3(R)-(1(S)-amino-2-phenylethyl)-3,4,6a(S),7,8,9,10,10a(S),11,11a(S)-decahydro-1,4-oxazino[4,3-b]isoquinolin-1(6H)-one hydrobromide as a white foam, [M+H]⁺ 329.0.

A stirred suspension of 417 mg (1 mmol) of N-[(9-fluorenyl)methoxycarbonyl]-3-(methanesulfonyl)-L-valine obtained in example 1 (B) above, in 5 ml of tetrahydrofuran was treated with 115 mg (1 mmol) of N-ethylmorpholine (NEM) and cooled to 0° C. under nitrogen. 0.13 ml (1 mmol) of isobutyl chloroformate was added and the reaction mixture stirred for 15 minutes. A solution of 295 mg (0.9 mmol) of 3(R)-(1(S)-amino-2-phenylethyl)-3,4,6a(S),7,8,9,10,10a(S),11,11a(S)-decahydro-1,4-oxazino[4,3-b]isoquinolin-1(6H)-one hydrobromide, from (A) above, in 5 ml of tetrahydrofuran was added and the solution was allowed to warm to room temperature overnight. The solution was partitioned between ethyl acetate and water and the organic phase was washed with 10% citric acid solution, aqueous sodium hydrogen carbonate and brine, dried over magnesium sulfate and evaporated under reduced pressure to give a yellow gum. The gum was chromatographed on silica eluting with ethyl acetate/hexane (1:1) to give 281 mg of a product, [M+H]⁺ 729, which was dissolved in 5 ml of dichloromethane and treated with 1 ml of piperidine and stirred at room temperature for 2 hours. The solution was diluted with hexane and filtered and the filtrate evaporated under reduced pressure. The residue was chromatographed on silica eluting with dichloromethane/methanol (19:1) and then crystallised from ether/hexane to give 120 mg (0.24 mmol) of a white solid, [M+H ⁺ 506, which was dissolved in 4 ml dioxane/water (1:1) and treated with 66 mg of potassium carbonate and 0.19 ml of methyl chloroformate. The solution was stirred overnight and then partitioned between ethyl acetate and water. The organic phase was washed with aqueous sodium hydrogen carbonate and brine, dried over magnesium sulfate and evaporated under reduced pressure to give the 68 mg of N1-[1(S)-(1,3,4,6,6a(S),7,8,9,10,10a(S),11,11a(S)-dodecahydro-1-oxo-1,4-oxazino[4,3-b]isoquinolin-3(R)-yl]-2-phenylethyl]-3-(methanesulfonyl)-N2-(methoxycarbonyl)-L-valinamide as a white solid, [M+H]⁺ 564.

Example 146

N-tert-Butyl-1,2,3,4,4s(S),5,6,7,8,8a(S)-decahydro-2-[2(R)-(isobutyryloxy)-3(S)-[[3-(methanesulfonyl)-N-[(3-pyridyl)carbonyl]-L-valyl]amino]-4-phenylbutyl]-3(S)-isoquinolinecarboxamide

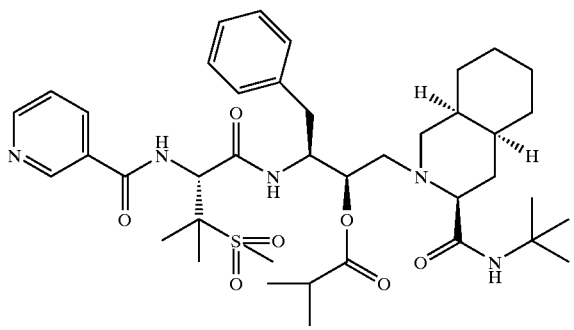

A solution of 0.15 g (0.21 mmol) of N-tert-butyl-1,2,3,4,4a(S),5,6,7,8,8a(S)-decahydro-2-[2(R)-hydroxy-3(S)-[[3-(methanesulfonyl)-N-[(3-pyridyl)carbonyl]-L-valyl]amino]-4-phenylbutyl]-3(S)-isoquinolinecarboxamide (Example 7) in 1 ml of pyridine was treated with 0.092 ml (0.21 mmol) of isobutyryl chloride at 0° C. and allowed to reach room temperature overnight. The volatiles were evaporated and the residue partitioned between dichloromethane and saturated sodium hydrogen carbonate solution. The organic phase was dried over sodium sulfate and evaporated under reduced pressure to give a gum which was chromatographed on silica eluting with dichloromethane/methanol (25:1) and triturated with ether/petroleum ether bp 40–60° C. to give 83 mg of N-tert-butyl-1,2,3,4,4s(S),5,6,7,8,8a(S)-decahydro-2-[2(R)-(isobutyryloxy)-3(S)-[[3-(methanesulfonyl)-N-[(3-pyridyl)carbonyl]-L-valyl]amino]-4-phenylbutyl]-3(S)-isoquinolinecarboxamide as a white solid, [M+H]+ 754.5.

Example 147

N-tert-Butyl-1,2,3,4,4a(S),5,6,7,8,8a(S)-decahydro-2-[2(R)-(isobutyryloxy)-3(S)-[[3-(methanesulfonyl)-N-[2-(3-pyridyloxy)acetyl]-L-valyl]amino]-4-phenylbutyl]-3(S)-isoquinolinecarboxamide

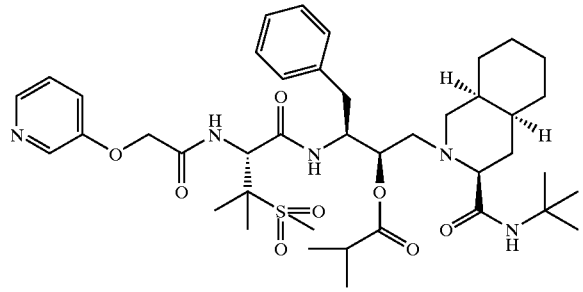

A stirred solution of 190 mg (2.66 mmol) of N-tert-butyl-1,2,3,4,4a(S),5,6,7,8a(S)-decahydro-2-[2(R)-hydroxy-3(S)-[[3-(methanesulfonyl)-N-[2-(3-pyridyloxy)acetyl]-L-valyl]amino]-4-phenylbutyl]-3(S)-isoquinolinecarboxamide (Example 3) and 26 mg (2.66 mmol) of isobutyric acid in 3 ml of dichloromethane was treated with 36 mg (2.92 mmol) of 4-(dimethylamino)pyridine (DMAP) and 56 mg (2.92 mmol) of EDAC.HCl and left at room temperature overnight. A further 26 mg of isobutyric acid, 36 mg of DMAP and 56 mg of EDAC.HCl were added and the reaction stirred for a further 2 hours. The solution was diluted with dichloromethane and the organic phase was washed with saturated sodium hydrogen carbonate solution and brine, dried over magnesium sulfate and evaporated under reduced pressure to give a colourless glass which was chromatographed on silica eluting with dichloromethane/methanol (97:3) to give 153 mg of N-tert-butyl-1,2,3,4,4a(S),5,6,7,8,8a(S)-decahydro-2-[2(R)-(isobutyryloxy)-3(S)-[[3-(methanesulfonyl)-N-[2-(3-pyridyloxy)acetyl]-L-valyl]amino]-4-phenylbutyl]-3(S)-isoquinolinecarboxamide as a white foam, [M+H+ 784.6.

Example 148

N-tert-Butyl-1,2,3,4,4a(S),4,5,6,8,8(a)-decahydro-2-[3(S)-[[3-(methanesulfonyl)-N-[(3-pyridyl)carbonyl]-L-valyl]amino]-4-phenyl-2(R)-(L-valyloxy)butyl]-3(S)-isoquinolinecarboxamide

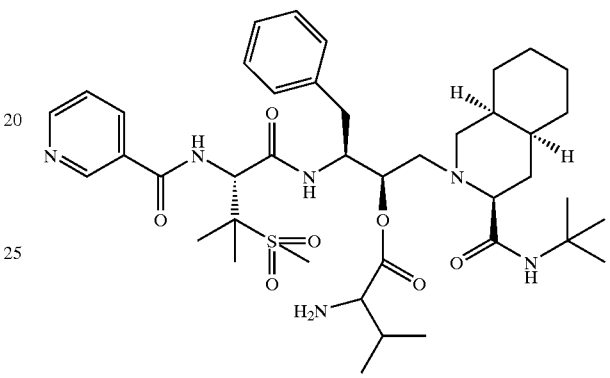

A stirred solution of 150 mg (2.19 mmol) of N-tert-butyl-1,2,3,4,4a(S),5,6,7,8,8a(S)-decahydro-2-[2(R)-hydroxy-3(S)-[[3-(methanesulfonyl)-N-[(3-pyridyl)carbonyl]-L-valyl]amino]-4-phenylbutyl]-3(S)-isoquinolinecarboxamide (Example 7), 61 mg (2.41 mmol) of carbobenzyloxy-L-valine (BACHEM C-2805) and 33 mg (2.41 mmol) of HOBT in 2 ml of dichloromethane was treated with 0.026 ml (2.1 mmol) of NEM and 46 mg (2.41 mmol) of EDAC.HCl. Further equivalent portions of carbobenzyloxy-L-valine, HOBT, NEM and EDAC.HCl were added daily over a period of 11 days. The solution was diluted with dichloromethane and washed with saturated sodium hydrogen carbonate solutionand brine, dried over magnesium sulfate and evaporated under reduced pressure to give an orange gum which was chromatographed on silica eluting with dichloromethane/methanol (97:3) to give 137 mg of an off white foam. The foam was dissolved in 20 ml of ethanol and treated with 10% palladium on carbon and hydrogenated under a hydrogen atmosphere for 1 hour. The catalyst was removed by filtration and the volatiles were evaporated under reduced pressure to give a white solid which was chromatographed on silica eluting with dichloromethane/methanol (47:2) and triturated with ether/petroleum ether bp 40–60° C. to give 14 mg of N-tert-butyl-1,2,3,4,4a(S),4,5,6,8,8(a)-decahydro-2-[3(S)-[[3-(methanesulfonyl)-N-[(3-pyridyl)carbonyl]-L-valyl]amino]-4-phenyl-2(R)-(L-valyloxy)butyl]-3(S)-isoquinolinecarboxamide as a white solid, [M+H]+ 783.5.

Example 149

N-tert-Butyl-1,2,3,4,4a(S),5,6,7,8,8a(S)-decahydro-2-[3(S)-[[N-[(2-indolyl)carbonyl]-3-(methanesulfonyl)-L-valyl]amino]-2(R)-[4-(morpholinomethyl)benzoyloxy]-4-phenylbutyl]-3(S)-isoquinolinecarboxamide

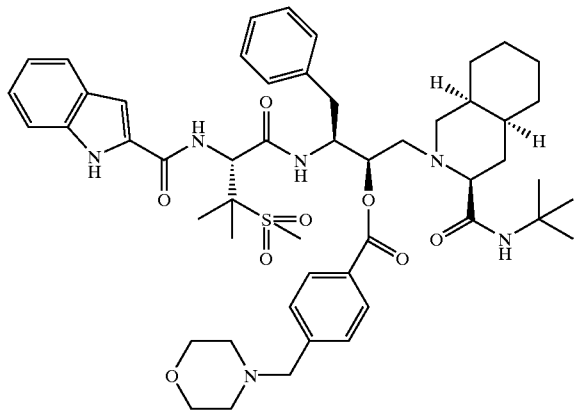

Example 159, [M+H]⁺ 925.6, was prepared in a manner analogous to Example 157 starting from N-tert-butyl-1,2,3,4,4a(S),5,6,7,8,8a(S)-decahydro-2-[2(R)-hydroxy-N-[(2-indolyl)carbonyl]-3(S)-[[3-(methanesulfonyl)-L-valyl]amino]-4-phenylbutyl]-3(S)-isoquinolinecarboxamide (Example 86) and 4-(morpholinomethyl)benzoic acid which was prepared according to the method described by H. Bundgaard et al, J. Med. Chem. 1989, 32, 2503.

Example 150

N-tert-Butyl-2-[3(S)-[[N-(3-cyanobenzoyl)-3-(methanesulfonyl)-L-valyl]amino]-2(R)-[2-[2-(2-methoxyethoxy)ethoxy]acetoxy]-4-phenylbutyl]-1,2,3,4,4a(S),5,6,7,8,8a(S)-decahydro-3(S)-isoquinolinecarboxamide

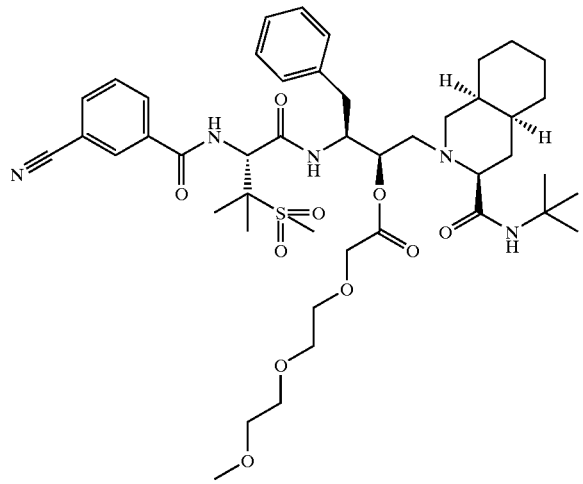

Example 160, [M+H]⁺ 868.5, was prepared in a manner analogous to Example 147 starting from N-tert-butyl-2-[3(S)-[[N-(3-cyanobenzoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide (Example 39) and 2-[2-(2-methoxyethoxy)ethoxy]acetic acid (Aldrich 40,7000-3).

Example 151

N-tert-Butyl-2-[2(R)-(3-carboxypropionyloxy)-3(S)-[[3-(methanesulfonyl)-N-[(3-pyridyl)carbonyl]-L-valyl]amino]-4-phenylbutyl]-1,2,3,4,4a(S),5,6,7,8,8a(S)decahydro-3(S)-isoquinolinecarboxamide

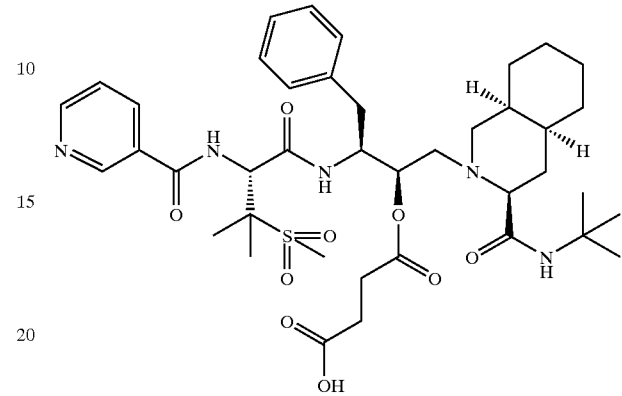

A solution of 68 mg (0.1 mmol) of N-tert-butyl-1,2,3,4,4a(S),5,6,7,8,8a(S)-decahydro-2-[2(R)-hydroxy-3(S)-[[3-(methanesulfonyl)-N-[(3-pyridyl)carbonyl]-L-valyl]amino]-4-phenylbutyl]-3(S)-isoquinolinecarboxamide (example 7) in 10 ml of tetrahydrofuran was treated with 10 mg (1 mmol) of succinic anhydride (Aldrich 23,960-0) and heated at reflux overnight. The volatiles were evaporated under reduced pressure and the residue chromatographed on silica eluting with dichloromethane/methanol (19:1) to give 53 mg of N-tert-butyl-2-[2(R)-(3-carboxypropionyloxy)-3(S)-[[3-(methanesulfonyl)-N-[(3-pyridyl)carbonyl]-L-valyl]amino]-4-phenylbutyl]-1,2,3,4,4a(S),5,6,7,8,8a(S)decahydro-3(S)-isoquinolinecarboxamide as a foam, [M+H]⁺ 784.5.

Example 152

N-tert-Butyl-1,2,3,4,4a(S),5,6,7,8,8a(S)-decahydro-2-[2(R)-hydroxy-3(S)-[[3-(methanesulfonyl)-N-[2-(2-pyridyloxy)acetyl]-L-valyl]amino]-4-phenylbutyl-3(S)-isoquinolinecarboxamide

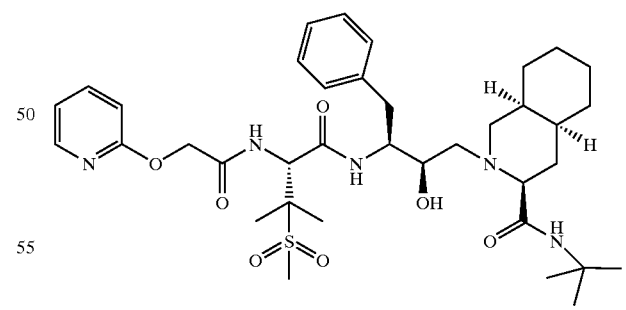

Example 152, [M+H]⁺ 714 was prepared in a manner analogous to that described in Example 2 but starting from 2-(2-pyridyloxy)acetic acid.

The starting material 2-(2-pyridyloxy)acetic acid was prepared by methods described in the art. For example following the methods of Hill and Mc Graw, J. Org. Chem., 1949, 14, 783–787 and Maas et al, Red. Trav. Chim. Pays-Bas, 1955, 74, 175–179.

Example 153

N-tert-Butyl-1,2,3,4,4a(S),5,6,7,8,8a(S)-decahydro-2-[2(R)-hydroxy-3(S)-[[3-(methanesulfonyl )-N-[2-(6-methyl-3-pyridyloxy)acetyl]-L-valyl]amino]-4-phenylbutyl]-3(S)-isoquinolinecarboxamide

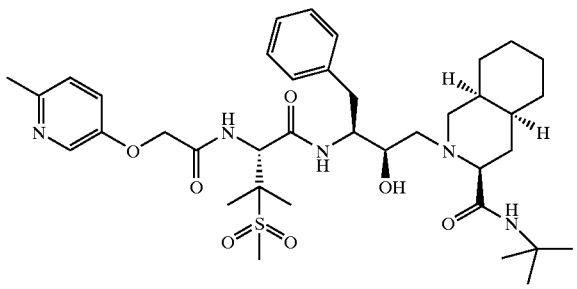

Example 153, [M+H]$^+$ 728 was prepared in a manner analogous to that described in Example 2 but starting from 2-(6-methyl-3-pyridyloxy)acetic acid hydrobromide.

The starting material 2-(6-methyl-3-pyridyloxy)acetic acid hydrobromide was prepared as follows:

1.09 g (0.01 mol) of 3-hydroxy-6-methylpyridine was added to a stirred suspension of 440 mg sodium hydride (60% dispersion in mineral oil) in 20 ml of dry dimethylformamide at 0° C. under nitrogen. After effervescence had subsided 1.94 g (0.01 mol) of tert-butyl bromoacetate was added dropwise and the solution stirred overnight. The volatiles were evaporated and the residue partitioned between dichloromethane and 10% citric acid solution. The organic phase was washed with saturated sodium hydrogen carbonate and brine. The combined organic phase was dried over magnesium sulfate and evaporated under reduced pressure to give 1.8 g of a gum, [M+H]$^+$ 224 which was treated with 3 ml of 45% hydrobromic acid in acetic acid at 0° C. 5 ml of acetic acid was added and the suspension was stirred overnight. The volatiles were evaporated and the residue was triturated with petroleum ether bp 40–60° C. to give 1.5 g of 2-(6-methyl-3-pyridyloxy)acetic acid hydrobromide as a fawn solid.

Example 154

N-tert-Butyl-1,2,3,4,4a(S),5,6,7,8,8a(S)-decahydro-2-[2(R)-hydroxy-3(S)-[[3-(methanesulfonyl)-N-[2-(3-pyrazinyloxy)acetyl]-L-valyl]amino]-4-phenylbutyl]-3(S)-isoquinolinecarboxamide

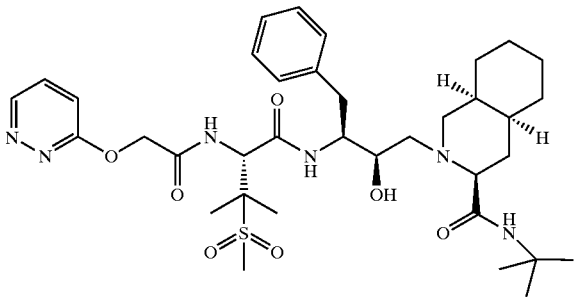

Example 154, [M+H]$^+$ 715 was prepared in a manner analogous to that described in Example 2 but starting from 2-(3-pyrazinyloxy)acetic acid trifluoroacetate.

The starting material 2-(3-pyrazinyloxy)acetic acid trifluoroacetate was prepared as follows:

A stirred suspension of 88 mg (2.2 mmol) sodium hydride (60% dispersion in mineral oil) in 5 ml of dry dimethylformamide at –5° C. under nitrogen was treated with 264 mg (2 mmol) tert-butylglycolate. After 10 minutes 298 mg (2 mmol) of 3,6-dichloropyridazine (Aldrich D7, 320-0) was added and the solution was allowed to warm to room temperature and was stirred overnight. The volatiles were evaporated under reduced pressure and the residue was chromatographed on silica eluting with ethyl acetate/hexane (1:2) to give 210 mg of a gum that was dissolved in 20 ml of ethanol and treated with 10% palladium on carbon (Fluka) and hydrogenated under a hydrogen atmosphere overnight. The catalyst was removed by filtration and the volatiles were evaporated under reduced pressure to give a gum that was chromatographed on silica eluting with ethyl acetate/hexane (1:2) followed by ethyl acetate to give 50 mg of a gum [M+H+MeCN]$^+$ 252. The gum was dissolved in 2 ml of dichloromethane and treated with 1 ml of trifluoroacetic acid. After 10 minutes the volatiles were evaporated and the residue triturated with toluene and re-evaportated to give a gum that was further triturated with petroleum ether bp 40–60° C. to give 2-(3-pyrazinyloxy)acetic acid trifluoroacetate.

Example 155

N-tert-Butyl-1,2,3,4,4a(S),5,6,7,8,8a(S)-decahydro-2-[2(R)-hydroxy-3(S)-[3-(methanesulfonyl)-N-[2-(2-pyrimidinyloxy)acetyl]-L-valyl]amino]-4-phenylbutyl]-3(S)-isoquinolinecarboxamide

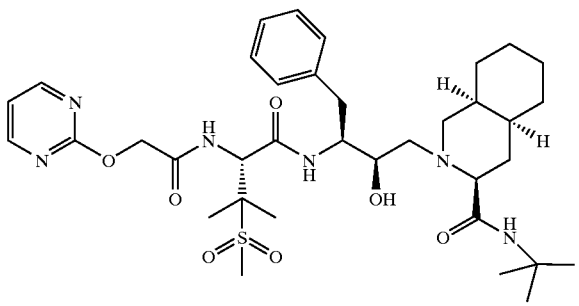

Example 155, [M+H]$^+$ 715 was prepared in a manner analogous to that described in Example 2 but starting from 2-(pyrimidin-2-yloxy)acetic acid trifluoroacetate.

The starting material 2-(pyrimidin-2-yloxy)acetic acid trifluoroacetate was prepared as follows:

A stirred suspension of 88 mg (2.2 mmol) sodium hydride (60% dispersion in mineral oil) in 5 ml of dry dimethylformamide at –5° C. under nitrogen was treated with 264 mg (2 mmol) tert-butylglycolate. After 30 minutes 318 mg (2 mmol) of 2-bromopyrimidine was added and the solution was allowed to warm to room temperature and was stirred overnight. The volatiles were evaporated and the residue partitioned between dichloromethane and 10% citric acid solution. The organic phase was washed with saturated sodium hydrogen carbonate and brine. The combined organic phase was dried over magnesium sulfate and evaporated under reduced pressure to give 360 mg of a gum. The gum was chromatographed on silica eluting with ethyl acetate/hexane (1:1) to give 105 mg of a gum that was dissolved in 3 ml of dichloromethane and treated with 1.5 ml of trifluoroacetic acid. After 1.5 hours the volatiles were evaporated and the residue triturated with toluene and re-evaportated to give a gum that was further triturated with petroleum ether bp 40–60° C. to give 60 mg of 2-(pyrimidin-2-yloxy)acetic acid trifluoroacetate as an of white solid.

Example 156

N-tert-Butyl-2-[3(S)-[[N-[2-(3-fluorophenoxy) acetyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide

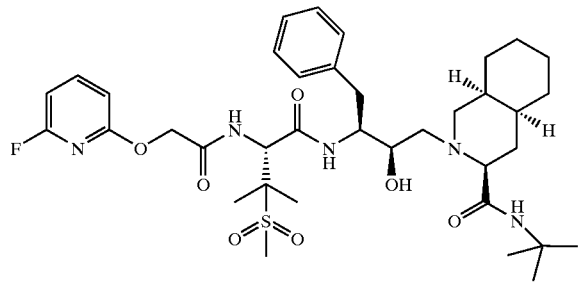

Example 156, [M+H]+ 731.6 mp 197–199° C. was prepared in a manner analogous to that described in Example 3 but starting from 3-fluorophenol in place of 3-hydroxypyridine.

Example 157

N-tert-Butyl-2-[3(S)-[[N-[2-(4-Fluorophenoxy)-acetyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide

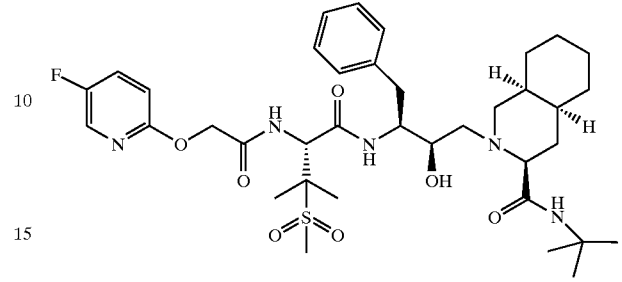

Example 157, [M+H]+ 731 was prepared in manner analogous to that described in Example 3 but starting from 4-fluorophenol in place of 3-hydroxypyridine.

In a manner analogous to that described for Examples 2 and 3, the compounds in Table 7 were prepared starting from N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide.

Other reagents used in the synthesis of the compounds in Table 7 were obtained from commercial sources such as Aldrich, Lancaster, and Maybridge Int. or were prepared using methods described in the art or analogous to those described in the art.

TABLE 7

| Name | Structure | [M + H]+ | Ex. No. |
|---|---|---|---|
| (E)-N-tert-Butyl-1,2,3,4,4a(S),5,6,7,8,8a(S)-decahydro-2-[2(R)-hydroxy-3(S)-[[3-(methanesulfonyl)-N-[3-(4-pyridyl)acroyl]-L-valyl]amino]-4-phenylbutyl]-3(S)-isoquinolinecarboxamide | 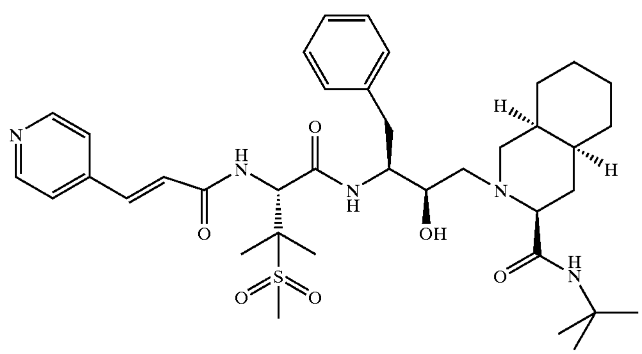 | 710 | 158 |
| N-tert-Butyl-1,2,3,4,4a(S),5,6,7,8,8a(S)-decahydro-2-[2(R)-hydroxy-3(S)-[[3-(methanesulfonyl)-N-[(6-quinolinyl)carbonyl]-L-valyl]amino]-4-phenylbutyl]-3(S)-isoquinolinecarboxamide | 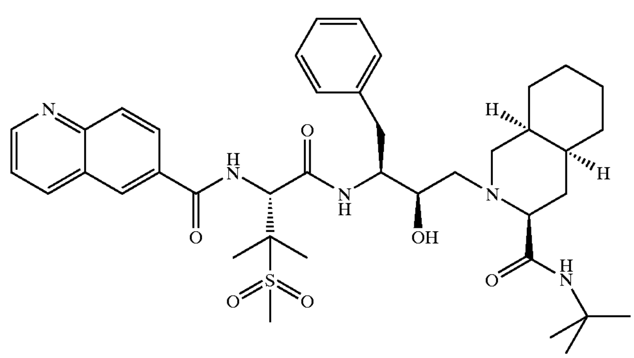 | 734 | 159 |

TABLE 7-continued

| Name | Structure | [M + H]+ | Ex. No. |
|---|---|---|---|
| 2-[3(S)-[[N-[(6-Benzothiazolyl)carbonyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 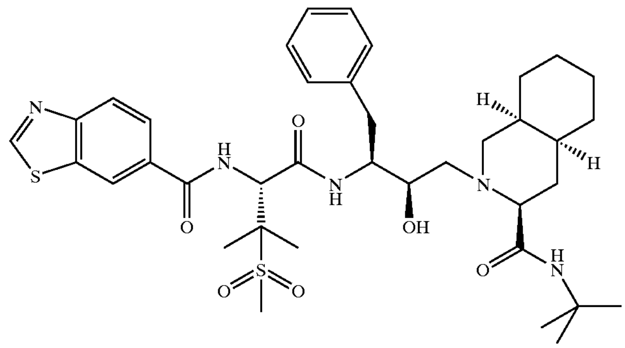 | 740 | 160 |
| (E)-N-tert-Butyl-1,2,3,4,4a(S),5,6,7,8,8a(S)-decahydro-2-[2(R)-hydroxy-3(S)-[[3-(methanesulfonyl)-N-[3-(2-pyridyl)acroyl]-L-valyl]amino]-4-phenylbutyl]-3(S)-isoquinolinecarboxamide | 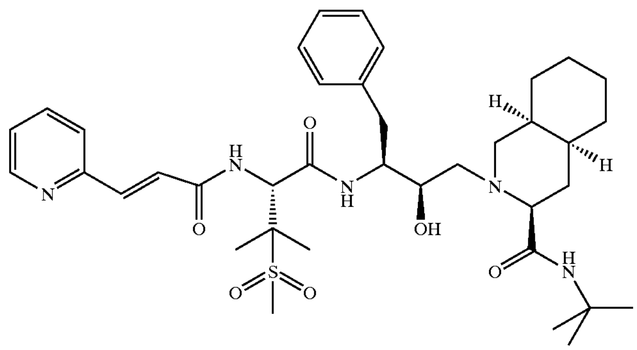 | 710 | 161 |
| (E)-N-tert-Butyl-1,2,3,4,4a(S),5,6,7,8,8a(S)-decahydro-2-[2(R)-hydroxy-3(S)-[[3-(methanesulfonyl)-N-[3-(3-pyridyl)acroyl]-L-valyl]amino]-4-phenylbutyl]-3(S)-isoquinolinecarboxamide | 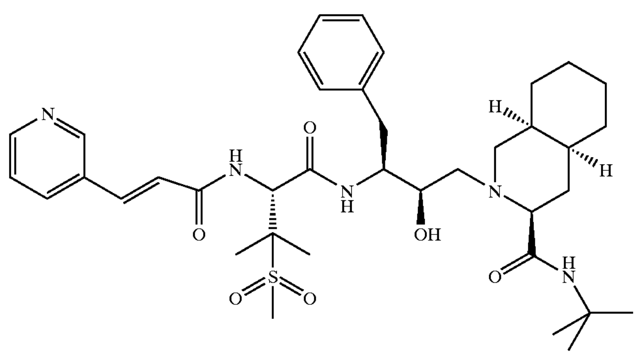 | 710 | 162 |
| N-tert-Butyl-1,2,3,4,4a(S),5,6,7,8,8a(S)-decahydro-2-[2(R)-hydroxy-3(S)-[[3-(methanesulfonyl)-N-[(2-quinoxalinyl)carbonyl]-L-valyl]amino]-4-phenylbutyl]-3(S)-isoquinolinecarboxamide | 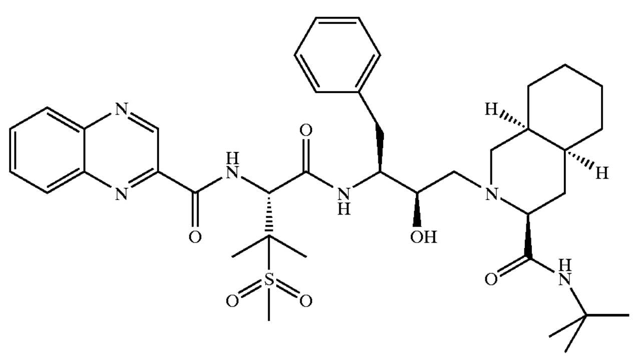 | 735 | 163 |

TABLE 7-continued

| Name | Structure | [M + H]+ | Ex. No. |
|------|-----------|----------|---------|
| N-tert-Butyl-1,2,3,4,4a(S),5,6,7,8,8a(S)-decahydro-2-[2(R)-hydroxy-3(S)-[[3-(methanesulfonyl)-N-[(pyrido[4,3-b]pyridin-2-yl)carbonyl]-L-valyl]amino]-4-phenylbutyl]-3(S)-isoquinolinecarboxamide | 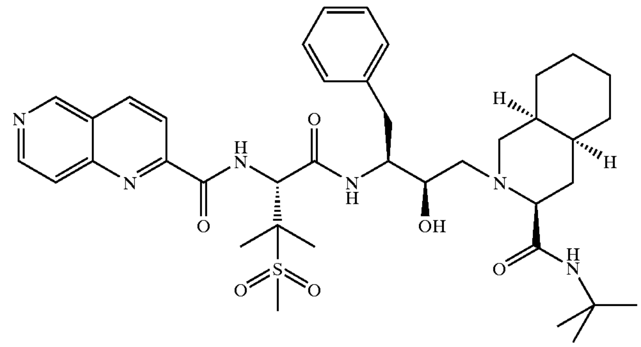 | 735 | 164 |
| (E)-N-tert-Butyl-1,2,3,4,4a(S),5,6,7,8,8a(S)-decahydro-2-[2(R)-hydroxy-3(S)-[[N-[3-(3-indolyl)acroyl]-3-(methanesulfonyl)-L-valyl]amino]-4-phenylbutyl]-3(S)-isoquinolinecarboxamide | 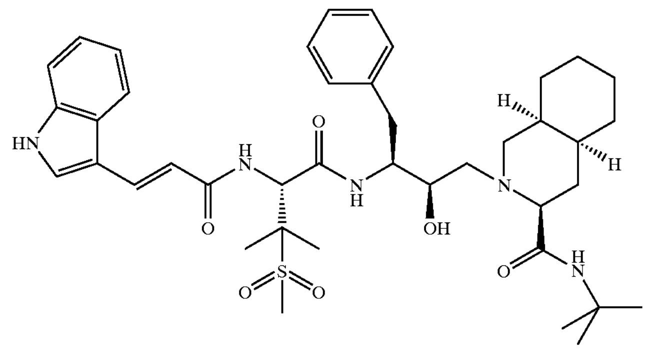 | 748 | 165 |
| (E)-2-[3(S)-[[N-[3-(1,3-Benzodioxol-5-yl)acroyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 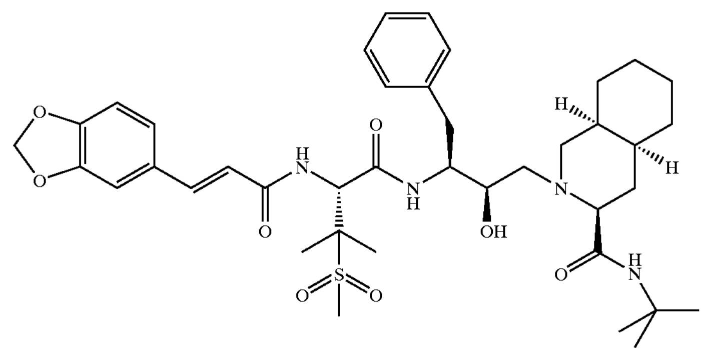 | 753 | 166 |
| N-tert-Butyl-1,2,3,4,4a(S),5,6,7,8,8a(S)-decahydro-2-[2(R)-hydroxy-3(S)-[[3-(methanesulfonyl)-N-[(3-quinolyl)carbonyl]-L-valyl]amino]-4-phenylbutyl]-3(S)-isoquinolinecarboxamide | 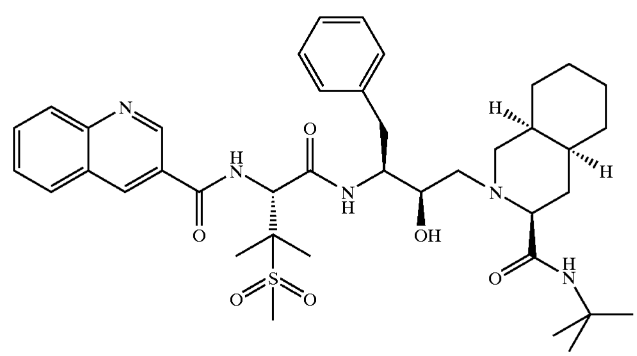 | 734 | 167 |

In a manner analogous to that described for Example 100, starting from N-tert-butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide the compounds shown in Table 8 were also prepared. Other reagents used in the synthesis of the compounds in Table 8 were obtained from commercial sources such as Aldrich and Lancaster or were prepared using methods described in the art or analogous to those described in the art.

TABLE 8

| Name | Structure | [M + H]+ | Ex. No. |
|---|---|---|---|
| 2-[3(S)-[[N-(Benzylcarbamoyl)-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 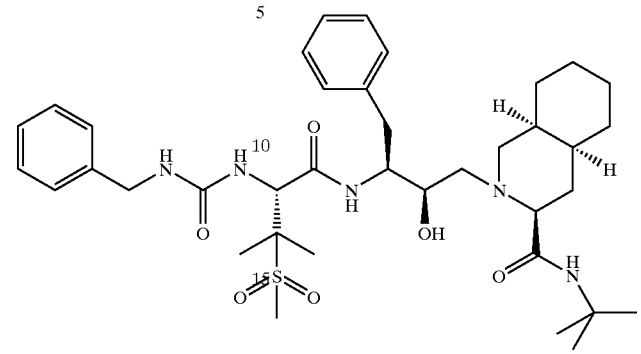 | 712 | 168 |
| N-tert-Butyl-1,2,3,4,4a(S),5,6,7,8,8a(S)-decahydro-2-[2(R)-hydroxy-3(S)-[[3-(methanesulfonyl)-N-[N-methyl-N-[(4-pyridyl)methyl]carbamoyl]-L-valyl]amino]-4-phenylbutyl]-3(S)-isoquinolinecarboxamide | 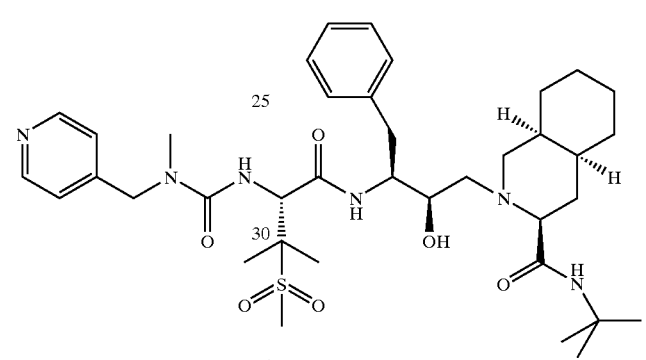 | 727 | 169 |
| N-tert-Butyl-1,2,3,4,4a(S),5,6,7,8,8a(S)-decahydro-2-[2(R)-hydroxy-3(S)-[[3-(methanesulfonyl)-N-[N-methyl-N-[(3-pyridyl)methyl]carbamoyl]-L-valyl]amino]-4-phenylbutyl]-3(S)-isoquinolinecarboxamide | 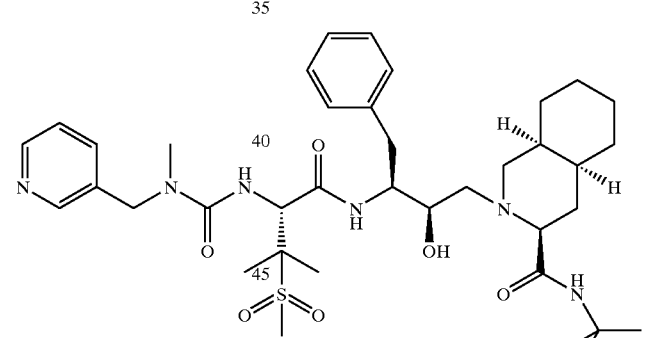 | 727 | 170 |
| N-tert-Butyl-1,2,3,4,4a(S),5,6,7,8,8a(S)-decahydro-2-[2(R)-hydroxy-3(S)-[[3-(methanesulfonyl)-N-[(5-methyl-2-furfuryl)carbamoyl]-L-valyl]amino]-4-phenylbutyl]-3(S)-isoquinolinecarboxamide | 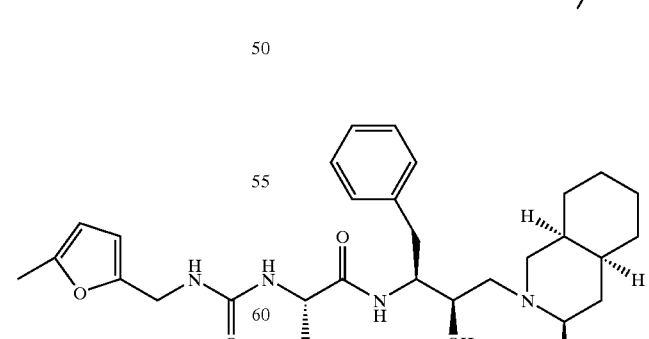 | 716 | 171 |

Example 172

N-tert-butyl-2-[3(S)-[[N-[2-(4-fluorobenzylamino)acetyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide

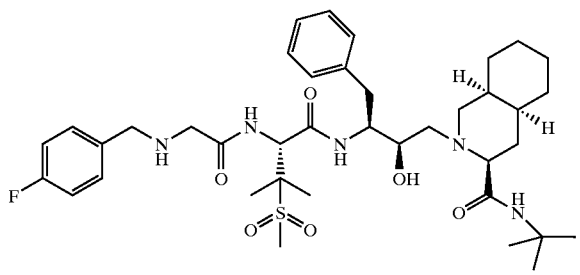

Example 172, [M+H]$^+$ 744, was prepared in a manner analogous to that described for Example 121 starting from 4-fluorobenzaldehyde and N-tert-butyl-2-[3(S)-[[N-glycyl-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide.

The starting material N-tert-butyl-2-(3(S)-[[N-glycyl-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide was prepared in a manner analogous to that described for example 94 starting from n-(benzyloxycarbonyl)glycine

Example 173

2-[3(S)-[[N-[2-(Benzylamino)acetyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide

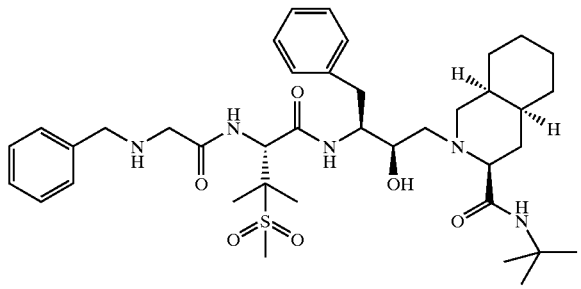

Example 173, [M+H]$^+$ 726, was prepared in a manner analogous to that described for example 172 starting with benzaldehyde in place of 4-fluorobenzaldehyde

What is claimed is:
1. Compounds of the formula

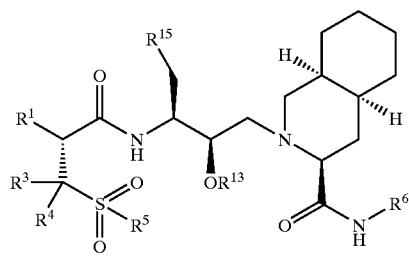

I and pharmaceutically acceptable salts thereof
wherein $R^1$ is H, hydroxy or $NHR^2$
wherein $R^2$ is H, alkyl, alkenyl, alkynyl, arylalkyl, heterocyclylalkyl, cycloalkyl, alkyl carbonyl, cycloalkyl carbonyl, aryl carbonyl, heterocyclyl carbonyl, aryl alkyl carbonyl, heterocyclyl alkyl carbonyl, alkyl oxy carbonyl, aryl alkyl oxy carbonyl, heterocyclyl alkyl oxy carbonyl, aryl, heterocyclyl, sulfonyl, alkyl sulfonyl, aryl sulfonyl, heterocyclyl sulfonyl or a group of the formula

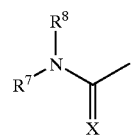

wherein X is O or S and
$R^7$ and $R^8$ independently are H, alkyl, aryl, heterocyclyl, aryl alkyl, heterocyclyl alkyl or $R^7$ and $R^8$ together with the nitrogen atom to which they are attached form a saturated ring optionally containing a further hetero atom or a group

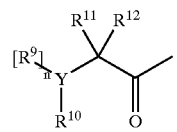

wherein when n=0, Y represents O or S and $R^{10}$ is H, alkyl, aryl alkyl, heterocyclyl alkyl, aryl, heterocyclyl or when n=1, Y represents N, $R^9$ is H or alkyl and $R^{10}$ is H, alkyl, aryl alkyl, heterocyclyl alkyl, aryl, heterocyclyl
or $R^9$ and $R^{10}$ taken together with the hetero atom to which they are attached form a heterocycle, $R^{11}$ and $R^{12}$ independently are H or alkyl
or $R^{11}$ and $R^{12}$ taken together with the carbon atom to which they are attached form a cycle,
$R^3$, $R^4$ independently are alkyl or taken together with the carbon atom to which they are attached form a carbocycle,
$R^5$ is alkyl, aryl alkyl, heterocyclyl alkyl or $R^4$ and $R^5$ taken together with the carbon and sulfur atom to which they are attached form a heterocycle and
$R^6$ is alkyl, aryl alkyl, heterocyclyl alkyl, alkyl oxy alkyl, hydroxy alkyl, amino alkyl, fluoro alkyl and
$R^{13}$ is H or the residue of an inorganic or an organic ester and
$R^{15}$ is aryl,
with the proviso that, if $R^3$, $R^4$ and $R^5$ are methyl, $R^6$ is tert-butyl, $R^{13}$ is H and $R^{15}$ is phenyl, $R^2$ is not benzyl oxycarbonyl and not 2-quinoline carbonyl.

2. The compound according to claim 1 of the formula

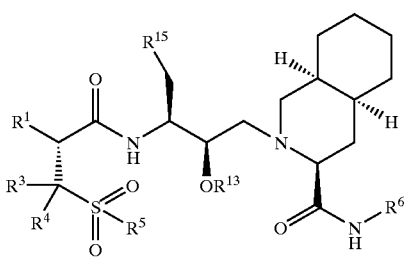

I and pharmaceutically acceptable salts thereof
wherein $R^1$ is H, hydroxy or $NHR^2$
wherein $R^2$ is H, alkyl, alkenyl, alkynyl, arylalkyl, heterocyclylalkyl cycloalkyl, alkyl carbonyl, cycloalkyl carbonyl, aryl carbonyl, heterocyclyl carbonyl, aryl alkyl carbonyl, heterocyclyl alkyl carbonyl, alkyl oxy carbonyl, aryl alkyl oxy carbonyl, heterocyclyl alkyl oxy carbonyl, aryl, heterocyclyl, sulfonyl, alkyl sulfonyl, aryl sulfonyl, heterocyclyl sulfonyl or a group of the formula

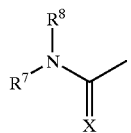

wherein X is O or S and
$R^7$ and $R^8$ independently are H, alkyl, aryl, heterocyclyl, aryl alkyl, heterocyclyl alkyl or $R^7$ and $R^8$ together with the nitrogen atom to which they are attached form a saturated ring optionally containing a further hetero atom or a group

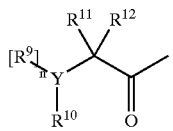

wherein when n=0, Y represents O or S
and $R^{10}$ is H, alkyl, aryl, heterocyclyl
or when n=1, Y represents N, $R^9$ is H or alkyl and $R^{10}$ is H, alkyl, aryl, heterocyclyl
or $R^9$ and $R^{10}$ taken together with the hetero atom to which they are attached form a heterocycle,
$R^{11}$ and $R^{12}$ independently are H or alkyl
or $R^{11}$ and $R^{12}$ taken together with the carbon atom to which they are attached form a cycle,
$R^3$, $R^4$ independently are alkyl or taken together with the carbon atom to which they are attached form a carbocycle,
$R^5$ is alkyl, aryl alkyl, heterocyclyl alkyl or $R^4$ and $R^5$ taken together with the carbon and sulfur atom to which they are attached form a heterocycle and
$R^6$ is alkyl, aryl alkyl, heterocyclyl alkyl, alkyl oxy alkyl, hydroxy alkyl, amino alkyl, fluoro alkyl and
$R^{13}$ is H or the residue of an inorganic or an organic ester and
$R^{15}$ is aryl,
with the proviso that, if $R^3$, $R^4$ and $R^5$ are methyl, $R^6$ is tert-butyl, $R^{13}$ is H and $R^{15}$ is phenyl, $R^2$ is not benzyl oxycarbonyl and not 2-quinoline carbonyl.

3. The compound according to claim 1 having the formula

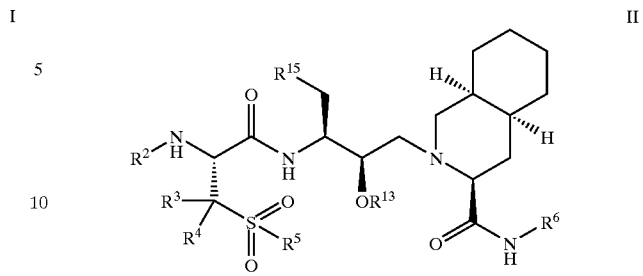

II

4. The compound according to claim 1 wherein $R^3$, $R^4$ and $R^5$ are methyl, $R^6$ is tert-butyl or and $R^{15}$ is phenyl.

5. The compound according to claim 1 wherein $R^2$ is alkyl carbonyl, cycloalkyl carbonyl, aryl carbonyl, heterocyclyl carbonyl, heterocyclyl alkyl carbonyl or a group of the formula

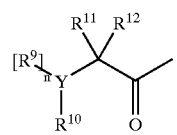

wherein when n=0, Y represents O or S
and $R^{10}$ is alkyl, aryl alkyl, heterocyclyl alkyl, aryl, heterocyclyl
or when n=1, Y represents N, $R^9$ is H and $R^{10}$ is alkyl, aryl alkyl, heterocyclyl alkyl, aryl or heterocyclyl,
and wherein $R^{11}$ and $R^{12}$ independently are H.

6. The compound according to claim 1 wherein $R^3$, $R^4$ and $R^5$ are methyl, $R^6$ is tert-butyl, $R^{15}$ is phenyl and $R^2$ is alkyl carbonyl, cycloalkyl carbonyl, aryl carbonyl, heterocyclyl carbonyl, heterocyclyl alkyl carbonyl or a group of the formula

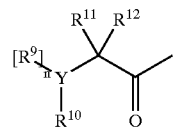

wherein when n=0, Y represents O or S
and $R^{10}$ is alkyl, aryl alkyl, heterocyclyl alkyl, aryl, heterocyclyl
or when n=1, Y represents N, $R^9$ is H and $R^{10}$ is alkyl, aryl alkyl, heterocyclyl, alkyl, aryl or heterocyclyl,
and wherein $R^{11}$ and $R^{12}$ independently are H.

7. The compound according to claim 1 wherein $R^3$, $R^4$ and $R^5$ are methyl, $R^6$ is tert-butyl, $R^{15}$ is phenyl and $R^2$ is aryl carbonyl, heterocyclyl carbonyl, or a group of the formula

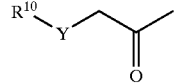

wherein Y represents O, NH, S, $CH_2$
and $R^{10}$ is aryl or heterocyclyl.

8. The compound according to claim 1 wherein $R^{13}$ is H.

9. The compound according to claim 1 selected from the group consisting of:

| Name | Structures |
|---|---|
| 2-[3(S)-[[N-Benzoyl-3-(methanesulfonyl)-L-valyl]amino]-2(R)-hydroxy-4-phenylbutyl]-N-benzyl-1,2,3,4,4a(S),5,6,7,8,8a(S)-decahydro-3(S)-isoquinolinecarboxamide | 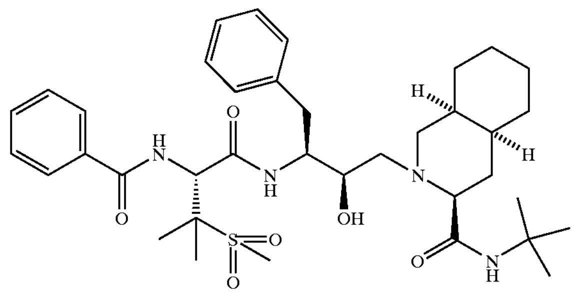 |
| N-tert-Butyl-2-[3(S)-[[N-[(9-fluorenyl)methoxycarbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 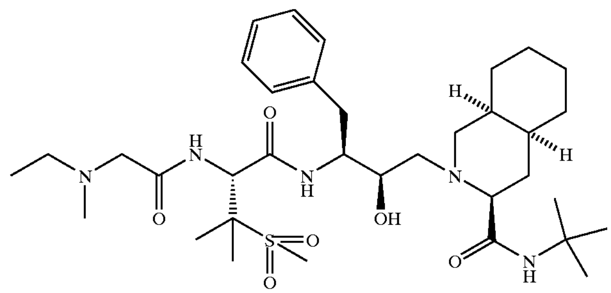 |
| N-tert-Butyl-1,2,3,4,4a(S),5,6,7,8,8a(S)-decahydro-2-[2(R)-hydroxy-3(S)-[[3-(methanesulfonyl)-N-[2-(3-pyridyloxy)acetyl]-L-valyl]amino]-4-phenylbutyl]-3(S)-isoquinolinecarboxamide | |
| N-tert-Butyl-1,2,3,4,4a(S),5,6,7,8,8a(S)-decahydro-2-[2(R)-hydroxy-3(S)-[[3-(methanesulfonyl)-N-(methoxycarbonyl)-L-valyl]amino]-4-phenylbutyl]-3(S)-isoquinolinecarboxamide | 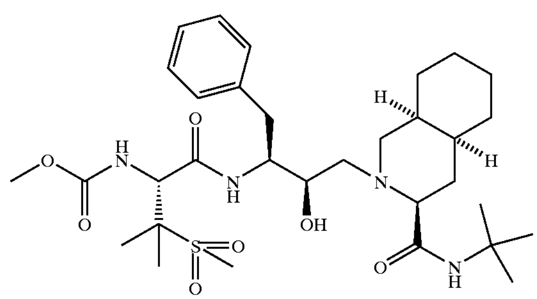 |
| 2-[3(S)-[[N,3-Bis(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | |

-continued

| Name | Structures |
|---|---|
| 2[3(S)-[[N-Acetyl-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 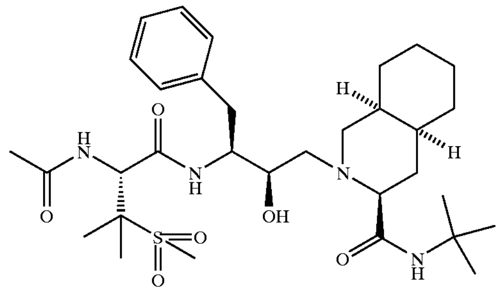 |
| N-tert-Butyl-1,2,3,4,4a(S),5,6,7,8,8a(S)-decahydro-2-[2(R)-hydroxy-3(S)-[[3-(methanesulfonyl)-N-[(3-pyridyl)carbonyl]-L-valyl]amino]-4-phenylbutyl]-3(S)-isoquinolinecarboxamide | 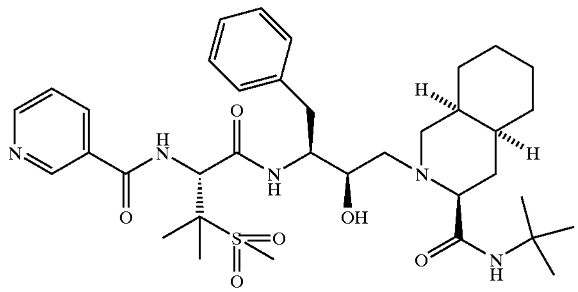 |
| N-tert-Butyl-1,2,3,4,4a(S),5,6,7,8,8a(S)-decahydro-2-[2(R)-hydroxy-3(S)-[[3-(methanesulfonyl)-N-propionyl-L-valyl]amino]-4-phenylbutyl]-3(S)-isoquinolinecarboxamide | 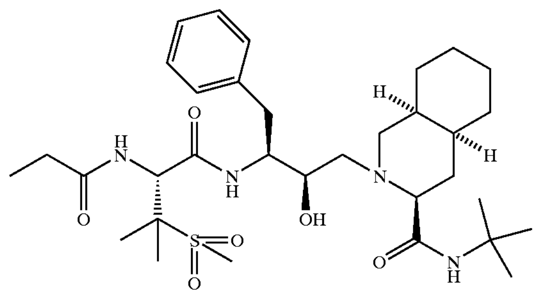 |
| 2-[3(S)-[[N-Butyryl-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 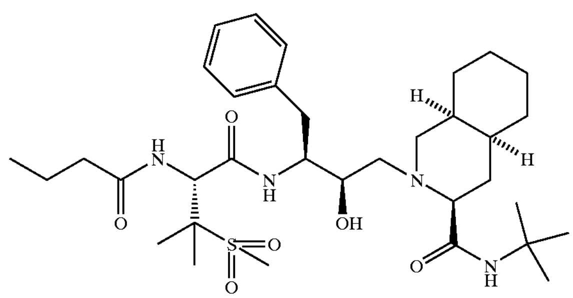 |
| N-tert-Butyl-1,2,3,4,4a(S),5,6,7,8,8a(S)-decahydro-2-[2(R)-hydroxy-3(S)-[[N-isobutyryl-3-(methanesulfonyl)-L-valyl]amino]-4-phenylbutyl]-3(S)-isoquinolinecarboxamide | 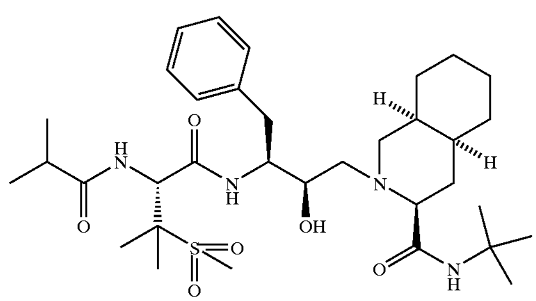 |

-continued

| Name | Structures |
|---|---|
| 2-[3(S)-[[N-Benzoyl-3-(ethanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 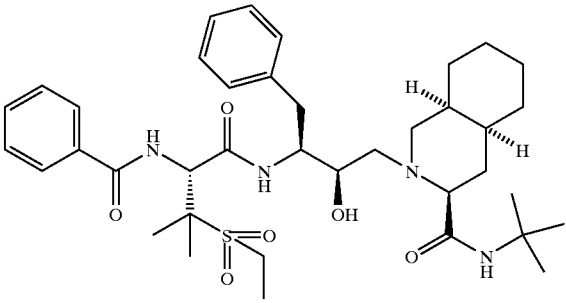 |
| 2-[3(S)-[[N-Acetyl-3-(ethanesulfonyl)-L-valyl]amino]-2(R)-hydroxy-4-phenylbutyl]-N-tert-butyl-1,2,3,4,4a(S),5,6,7,8a(S)-decahydro-3(S)-isoquinolinecarboxamide | 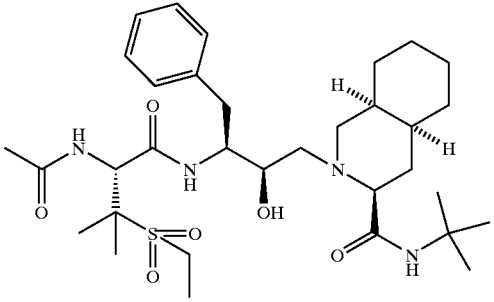 |
| N-tert-Butyl-1,2,3,4,4a(S),5,6,7,8,8a(S)-decahydro-2-[2(R)-hydroxy-3(S)-[[3-(methanesulfonyl)-N-(2-thenoyl)-L-valyl]amino]-4-phenylbutyl]-3(S)-isoquinolinecarboxamide | 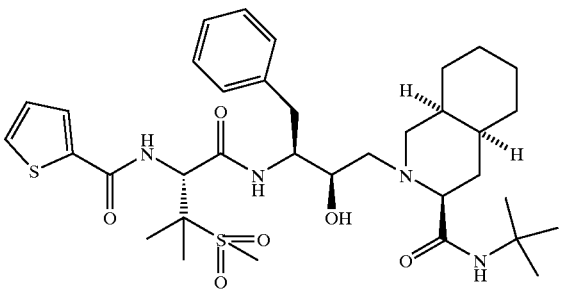 |
| N-tert-Butyl-1,2,3,4,4a(S),5,6,7,8,8a(S)-decahydro-2-[2(R)-hydroxy-3(S)-[[3-(methanesulfonyl)-N-(2-phenoxyacetyl)-L-valyl]amino]-4-phenylbutyl]-3(S)-isoquinolinecarboxamide | 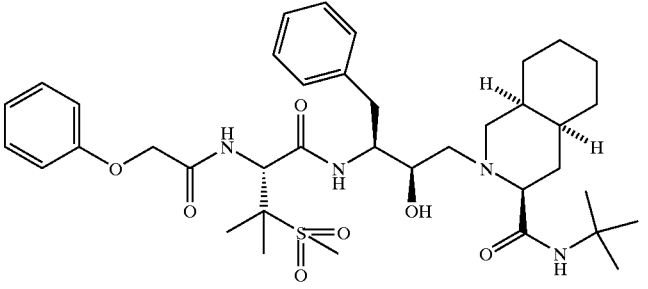 |
| N-tert-Butyl-1,2,3,4,4a(S),5,6,7,8,8a(S)-decahydro-2-[2(R)-hydroxy-3(S)-[[3-(methanesulfonyl)-N-[(2-pyrazinyl)carbonyl]-L-valyl]amino]-4-phenylbutyl]-3(S)-isoquinolinecarboxamide | 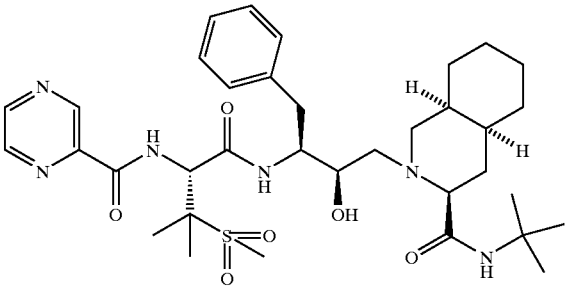 |

| Name | Structures |
|---|---|
| N-tert-Butyl-2-[3(S)-[[N-[(6-chloro-3-pyridyl)carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 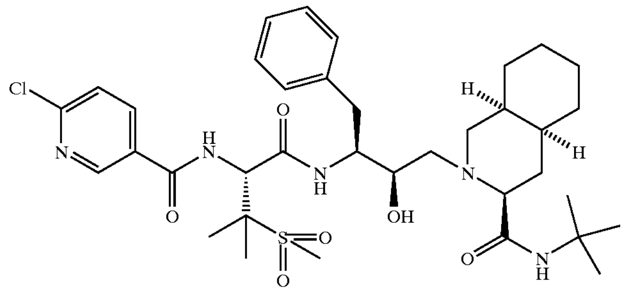 |
| N-tert-Butyl-1,2,3,4,4a(S),5,6,7,8,8a(S)-decahydro-2-[2(R)-hydroxy-3(S)-[[N-[(1-hydroxy-1-cyclopropyl)carbonyl]-3-(methanesulfonyl)-L-valyl]amino]-4-phenylbutyl]-3(S)-isoquinolinecarboxamide | 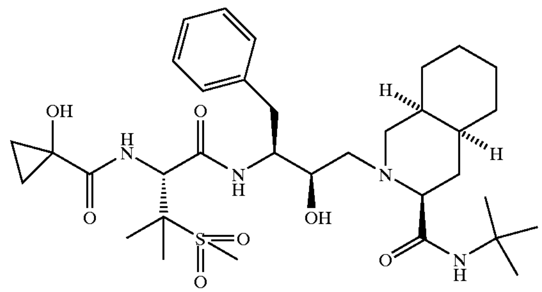 |
| N-tert-Butyl-1,2,3,4,4a(S),5,6,7,8,8a(S)-decahydro-2-[2(R)-hydroxy-3(S)-[[3-(methanesulfonyl)-N-[(1,2,3-thiadiazol-4-yl)carbonyl]-L-valyl]amino]-4-phenylbutyl]-3(S)-isoquinolinecarboxamide | 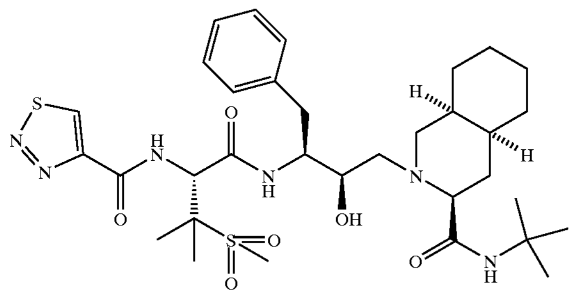 |
| N-tert-Butyl-2-[3(S)-[[N-(5-chloro-2-furoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 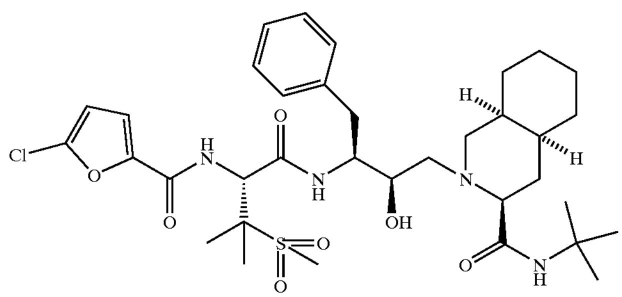 |
| N-tert-Butyl-1,2,3,4,4a(S),5,6,7,8,8a(S)-decahydro-2-[2(R)-hydroxy-3(S)-[[3-(methanesulfonyl)-N-[(5-isoxazolyl)carbonyl]-L-valyl]amino]-4-phenylbutyl]-3(S)-isoquinolinecarboxamide | 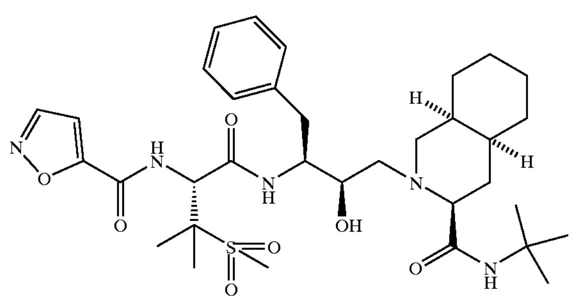 |

-continued

| Name | Structures |
|---|---|
| N-tert-Butyl-1,2,3,4,4a(S),5,6,7,8,8a(S)-decahydro-2-[2(R)-hydroxy-3(S)-[[3-(methanesulfonyl)-N-[(3-methyl-4-isoxazolyl)carbonyl]-L-valyl]amino]-4-phenylbutyl]-3(S)-isoquinolinecarboxamide | 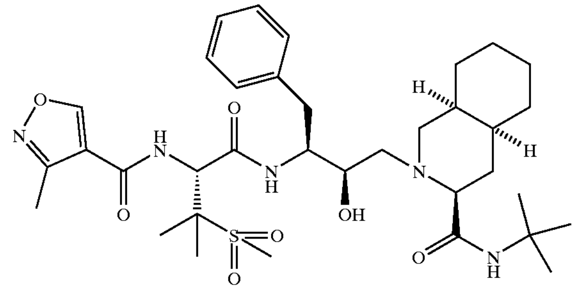 |
| N-tert-Butyl-1,2,3,4,4a(S),5,6,7,8,8a(S)-decahydro-2-[2(R)-hydroxy-3(S)-[[3-(methanesulfonyl)-N-[(5-methyl-3-isoxazolyl)carbonyl]-L-valyl]amino]-4-phenylbutyl]-3(S)-isoquinolinecarboxamide | 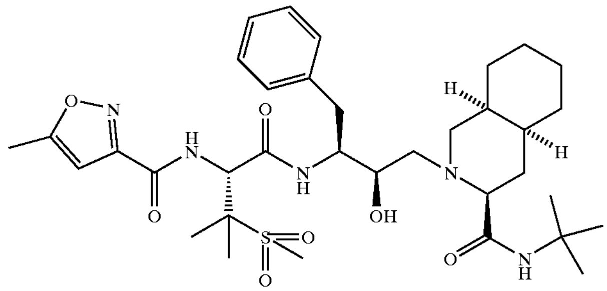 |
| N-tert-Butyl-1,2,3,4,4a(S),5,6,7,8,8a(S)-decahydro-2-[2(R)-hydroxy-3(S)-[[N-(2-hydroxy-2-ethylbutyryl)-3-(methanesulfonyl)-L-valyl]amino]-4-phenylbutyl]-3(S)-isoquinolinecarboxamide | 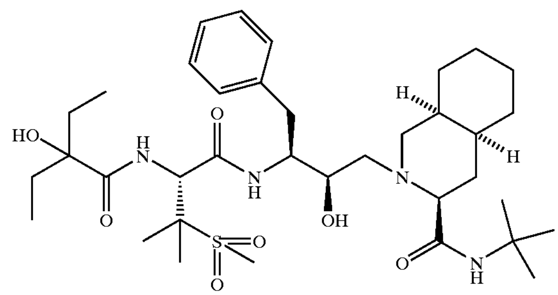 |
| N-tert-Butyl-1,2,3,4,4a(S),5,6,7,8,8a(S)-decahydro-2-[2(R)-hydroxy-3(S)-[[3-(methanesulfonyl)-N-(2-methoxyacetyl))-L-valyl]amino]-4-phenylbutyl]-3(S)-isoquinolinecarboxamide | 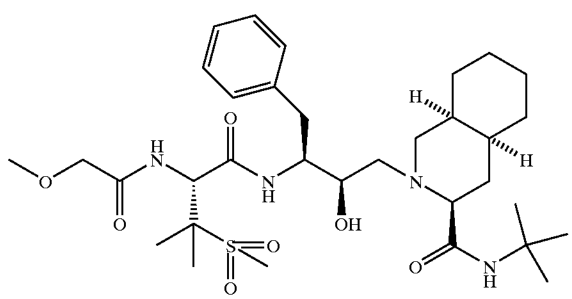 |
| N-tert-Butyl-2-[3(S)-[[N-(2-ethoxyacetyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 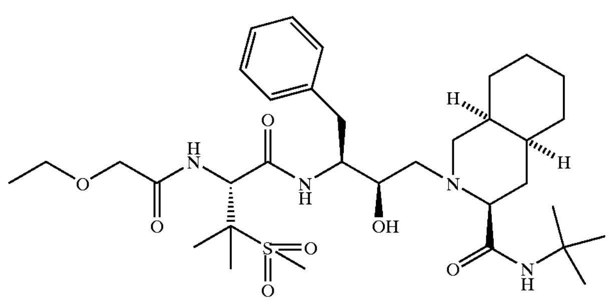 |

-continued

| Name | Structures |
|---|---|
| N-tert-Butyl-1,2,3,4,4a(S),5,6,7,8,8a(S)-decahydro-2-[2(R)-hydroxy-3(S)-[[N-(2-hydroxyacetyl)-3-(methanesulfonyl)-L-valyl]amino]-4-phenylbutyl]-3(S)-isoquinolinecarboxamide | 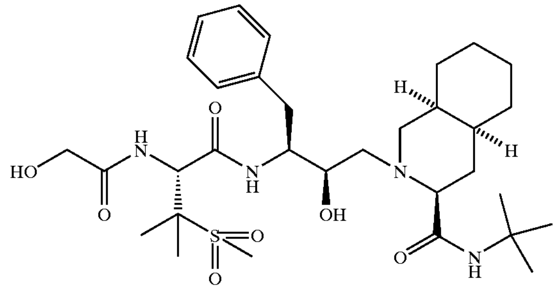 |
| N-tert-Butyl-1,2,3,4,4a(S),5,6,7,8,8a(S)-decahydro-2-[2(R)-hydroxy-3(S)-[[N-(2-hydroxy-2-methylpropionyl)-3-(methanesulfonyl)-L-valyl]amino]-4-phenylbutyl]-3(S)-isoquinolinecarboxamide | 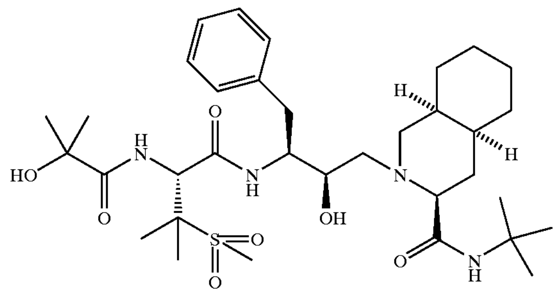 |
| N-tert-Butyl-2-[3(S)-[[N-(3-furoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 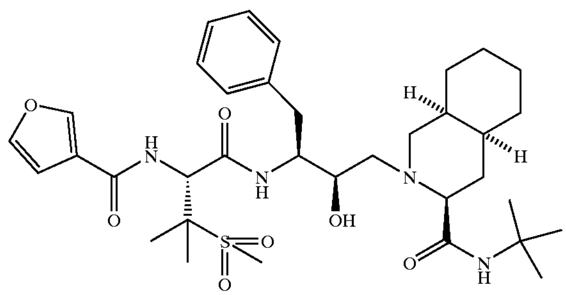 |
| N-tert-Butyl-1,2,3,4,4a(S),5,6,7,8,8a(S)-decahydro-2-[2(R)-hydroxy-3(S)-[[3-(methanesulfonyl)-N-[(4-pyridyl)carbonyl]-L-valyl]amino]-4-phenylbutyl]-3(S)-isoquinolinecarboxamide | 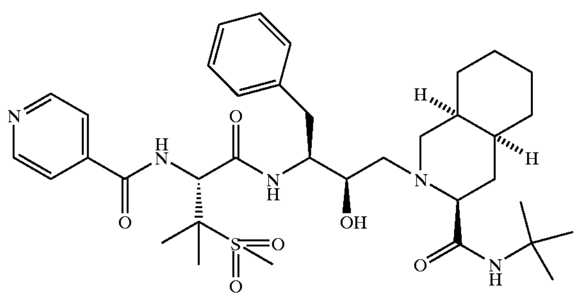 |
| N-tert-Butyl-1,2,3,4,4a(S),5,6,7,8,8a(S)-decahydro-2-[2(R)-hydroxy-3(S)-[[N-(2(S)-hydroxypropionyl)-3-(methanesulfonyl)-L-valyl]amino]-4-phenylbutyl]-3(S)-isoquinolinecarboxamide | 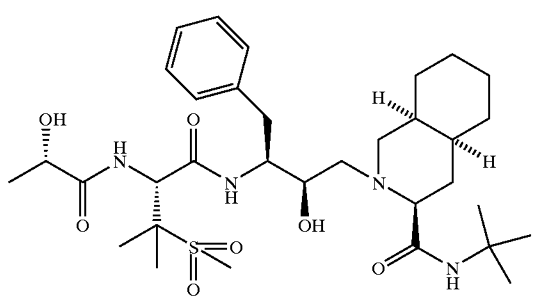 |

-continued

| Name | Structures |
|---|---|
| N-tert-Butyl-1,2,3,4,4a(S),5,6,7,8,8a(S)-decahydro-2-[2(R)-hydroxy-3(S)-[[N-(2(R)-hydroxypropionyl)-3-(methanesulfonyl)-L-valyl]amino]-4-phenylbutyl]-3(S)-isoquinolinecarboxamide | 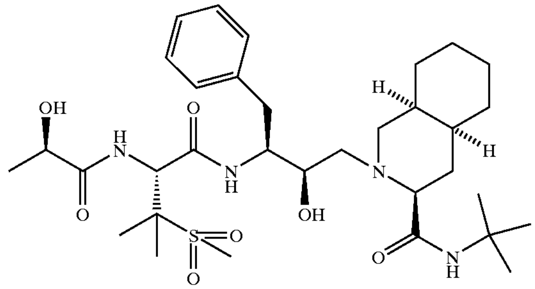 |
| 2-[3(S)-[[N-(5-Bromo-2-furoyl)-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 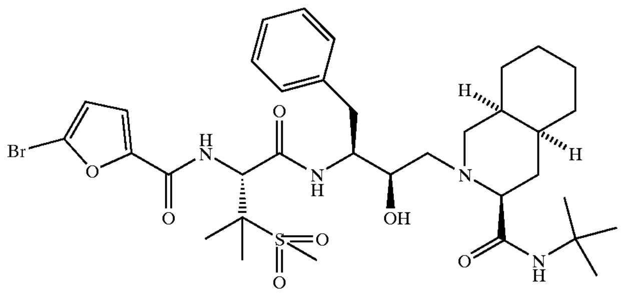 |
| N-tert-Butyl-1,2,3,4,4a(S),5,6,7,8,8a(S)-decahydro-2-[2(R)-hydroxy-3(S)-[[3-(methanesulfonyl)-N-(4,5-dimethyl-2-furoyl)-L-valyl]amino]-4-phenylbutyl]-3(S)-isoquinolinecarboxamide | 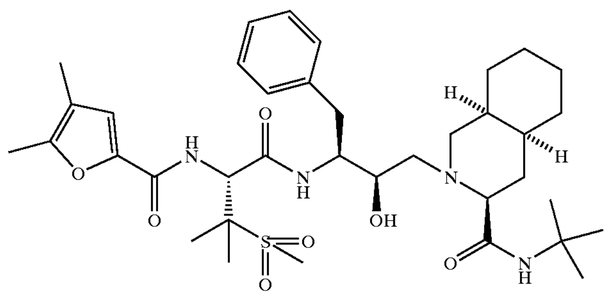 |
| N-tert-Butyl-2-[3(S)-[[N-[5-(trifluoromethyl)-2-furoyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 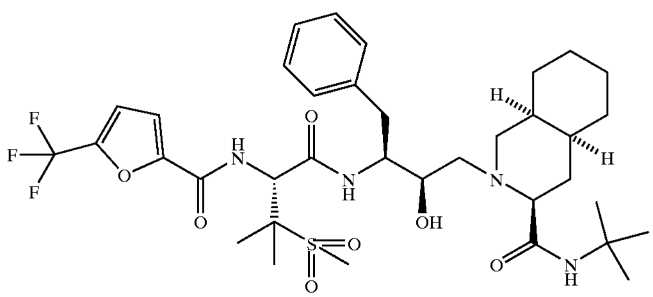 |
| N-tert-Butyl-1,2,3,4,4a(S),5,6,7,8,8a(S)-decahydro-2-[2(R)-hydroxy-3(S)-[[3-(methanesulfonyl-N-(5-methyl-2-thenoyl)-L-valyl]amino]-4-phenylbutyl]-3(S)-isoquinolinecarboxamide | 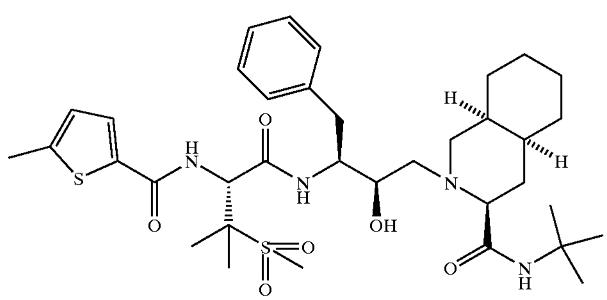 |

| Name | Structures |
|---|---|
| N-tert-Butyl-2-[3(S)-[[N-(5-chloro-2-thenoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 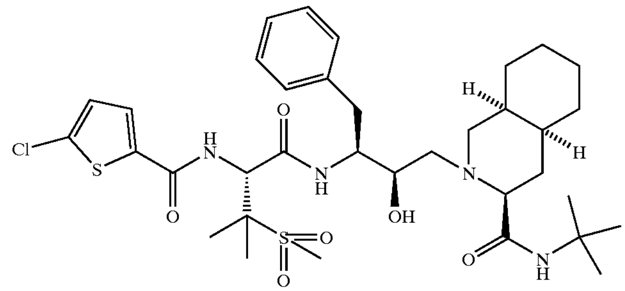 |
| 2-[3(S)-[[N-(5-Acetyl-2-thenoyl)-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 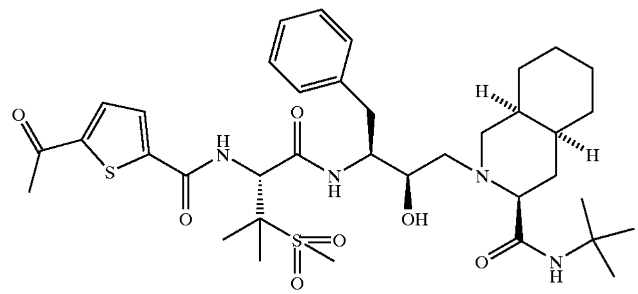 |
| N-tert-Butyl-2-[3(S)-[[N-(5-tert-butyl-2-thenoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 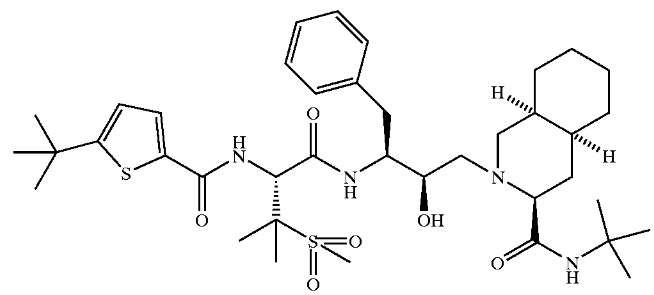 |
| N-tert-Butyl-2-[3(S)-[[N-(3-cyanobenzoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 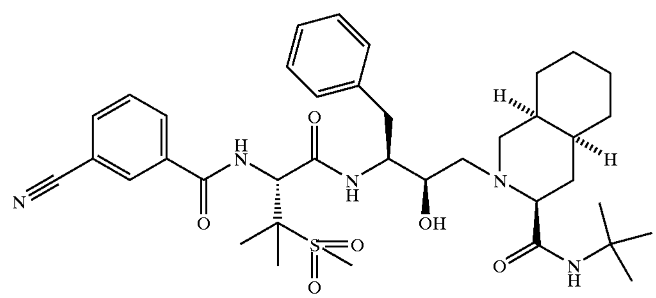 |
| N-tert-Butyl-2-[3(S)-[[N-(3-fluorobenzoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 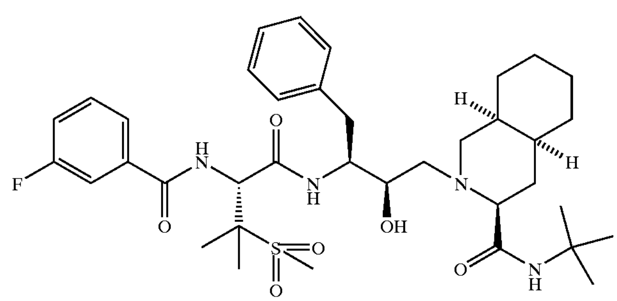 |

-continued

| Name | Structures |
|------|------------|
| N-tert-Butyl-2-[3(S)-[[N-(4-cyanobenzoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 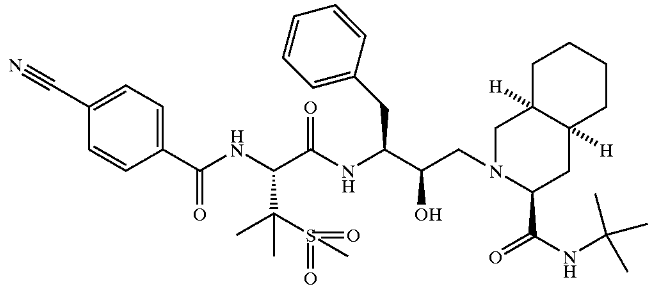 |
| N-tert-Butyl-2-[3(S)-[[N-(4-fluorobenzyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 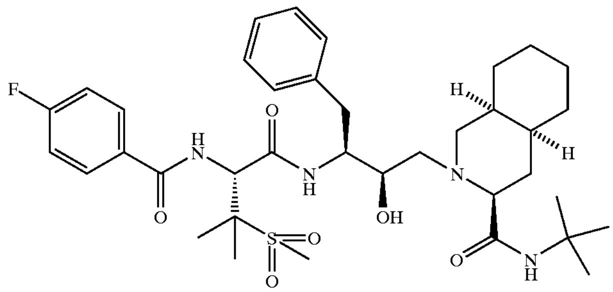 |
| N-tert-Butyl-2-[3(S)-[[N-[[6-(trifluoromethyl)-3-pyridyl]carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 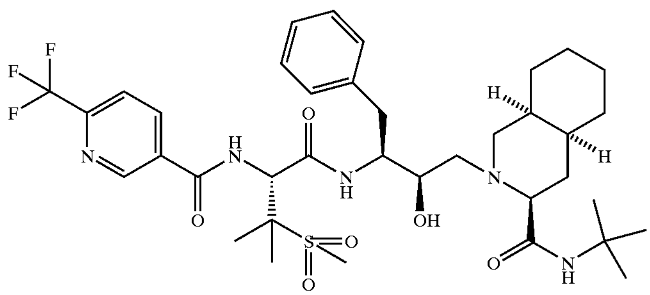 |
| N-tert-Butyl-2-[3(S)-[[N-[(6-cyano-3-pyridyl)carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 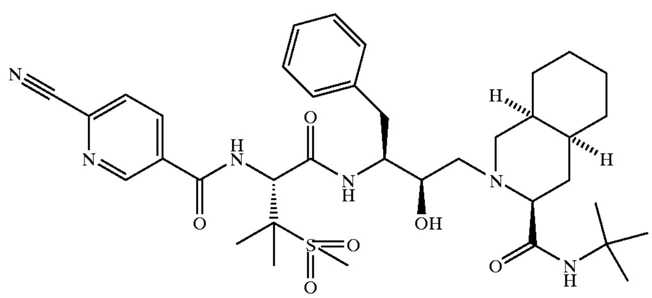 |
| N-tert-Butyl-1,2,3,4,4a(S),5,6,7,8,8a(S)-decahydro-2-[2(R)-hydroxy-3(S)-[[3-(methanesulfonyl)-N-[(1,5-dimethyl-3-pyrazolyl)carbonyl]-L-valyl]amino]-4-phenylbutyl]-3(S)-isoquinolinecarboxamide | 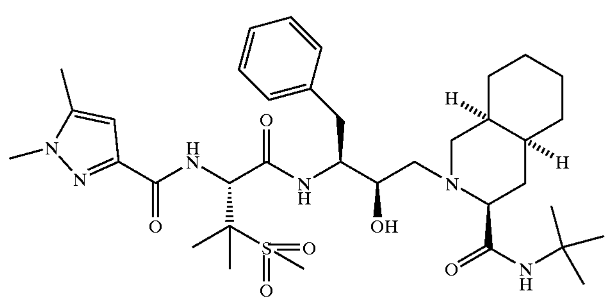 |

-continued

| Name | Structures |
|---|---|
| N-tert-Butyl-2-[3(S)-[[N-[(1-tert-butyl-5-methyl-3-pyrazolyl)carbonyl]3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 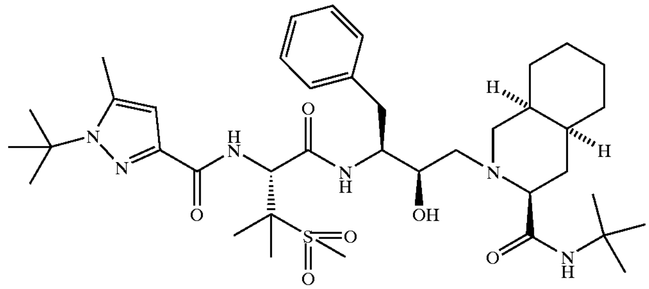 |
| N-tert-Butyl-2-[3(S)-[[N-(cyclopropylcarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 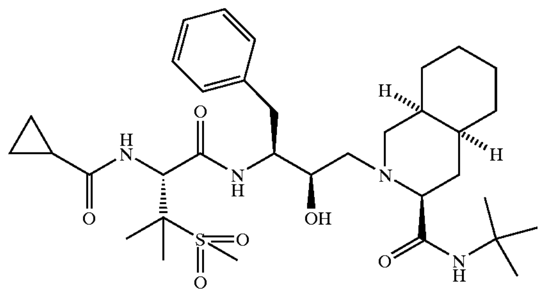 |
| N-tert-Butyl-2-[3(S)-[[N-(cyclobutylcarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 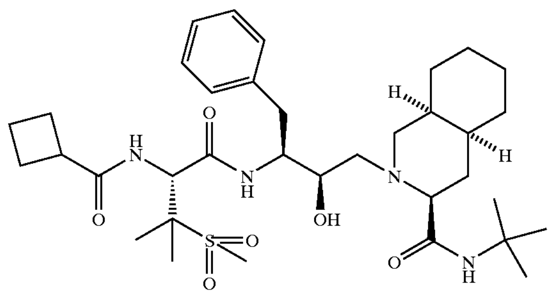 |
| N-tert-Butyl-2-[3(S)-[[N-(cyclohexylcarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 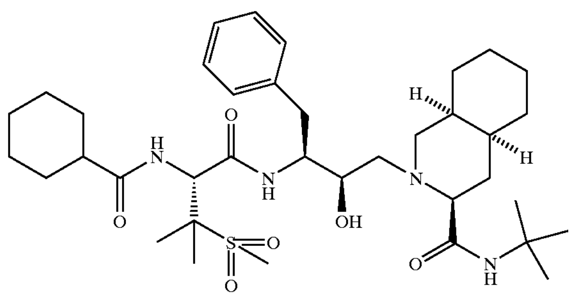 |
| N-tert-Butyl-1,2,3,4,4a(S),5,6,7,8,8a(S)-decahydro-2-[3(S)-[[N-(tetrahydro-3(RS)-furoyl)-3-(methanesulfonyl)-L-valyl]amino]-2(R)-hydroxy-4-phenylbutyl]-3(S)-isoquinolinecarboxamide (1:1 mixture of diastereoisomers) | 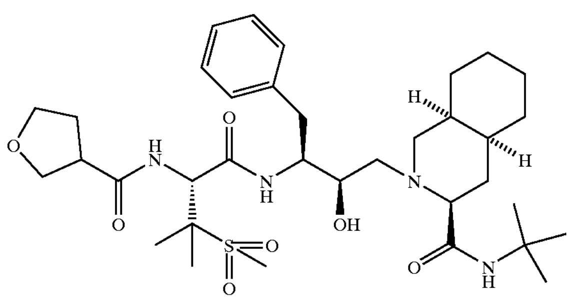 |

-continued

| Name | Structures |
|---|---|
| N-tert-Butyl-2-[N-[(2-chloro-6-methyl-4-pyridyl)carbonyl]-3(S)-[[3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 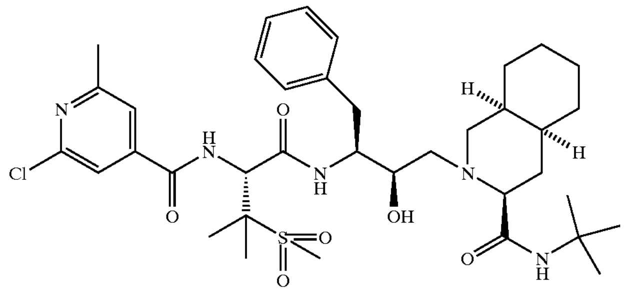 |
| N-tert-Butyl-2-[3(S)-[[N-[(2-chloro-4-pyridyl)carbonyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 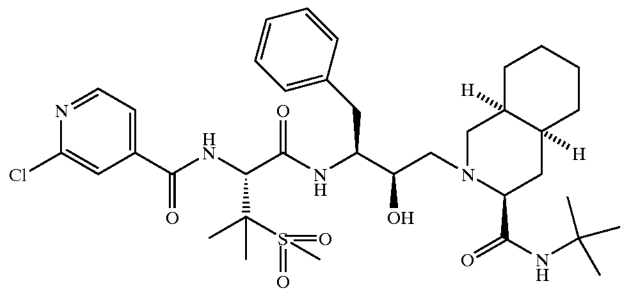 |
| N-tert-Butyl-2-[N-(2-furoyl)-3(S)-[[3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 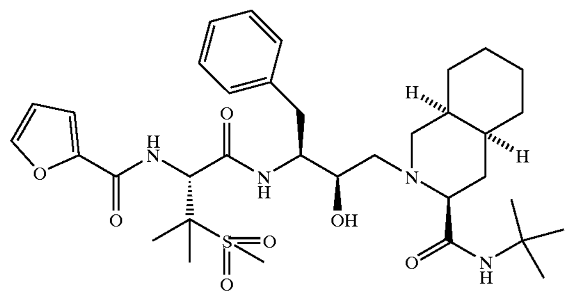 |
| N-tert-Butyl-1,2,3,4,4a(S),5,6,7,8,8a(S)-decahydro-2-[2(R)-hydroxy-3(S)-[[3-(methanesulfonyl)-N-(3-methylbenzoyl)-L-valyl]amino]-4-phenylbutyl]-3(S)-isoquinolinecarboxamide | 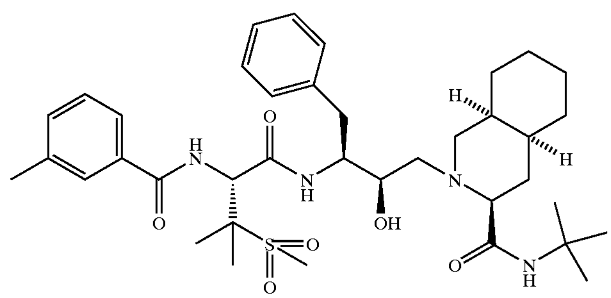 |
| N-tert-Butyl-1,2,3,4,4a(S),5,6,7,8,8a(S)-decahydro-2-[2(R)-hydroxy-3(S)-[[3-(methanesulfonyl)-N-(4-methoxybenzoyl)-L-valyl]amino]-4-phenylbutyl]-3(S)-isoquinolinecarboxamide | 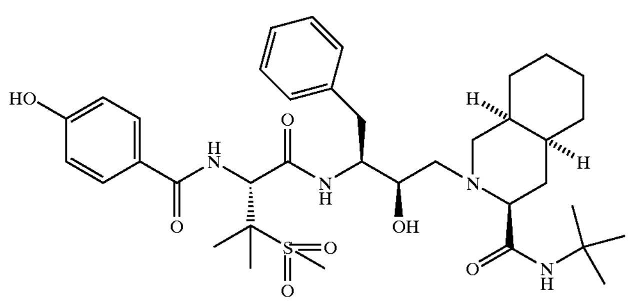 |

-continued

| Name | Structures |
|---|---|
| N-tert-Butyl-1,2,3,4,4a(S),5,6,7,8,8a(S)-decahydro-2-[2(R)-hydroxy-3(S)-[[3-(methanesulfonyl)-N-(4-methylbenzoyl)-L-valyl]amino]-4-phenylbutyl]-3(S)-isoquinolinecarboxamide | 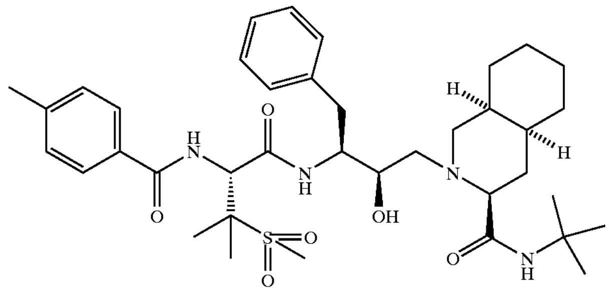 |
| N-tert-Butyl-1,2,3,4,4a(S),5,6,7,8,8a(S)-decahydro-2-[2(R)-hydroxy-3(S)-[[3-(methanesulfonyl)-N-[(5-methyl-3-pyridyl)carbonyl]-L-valyl]amino]-4-phenylbutyl]-3(S)-isoquinolinecarboxamide | 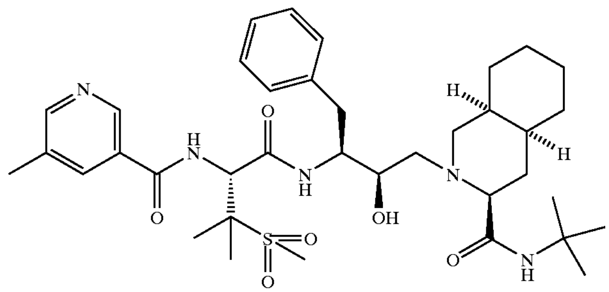 |
| N-tert-Butyl-2-[3(S)-[[N-(cyclopentylcarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 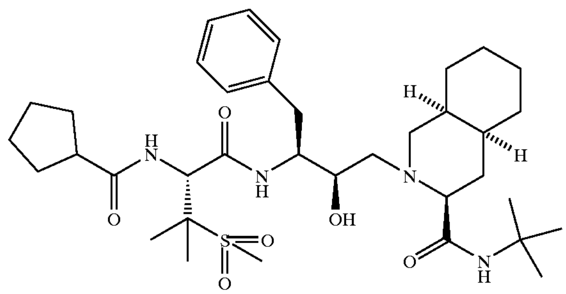 |
| N-tert-Butyl-1,2,3,4,4a(S),5,6,7,8,8a(S)-decahydro-2-[2(R)-hydroxy-3(S)-[[3-(methanesulfonyl)-N-[(2,5-dimethyl-3-pyrazolyl)carbonyl]-L-valyl]amino]-4-phenylbutyl]-3(S)-isoquinolinecarboxamide | 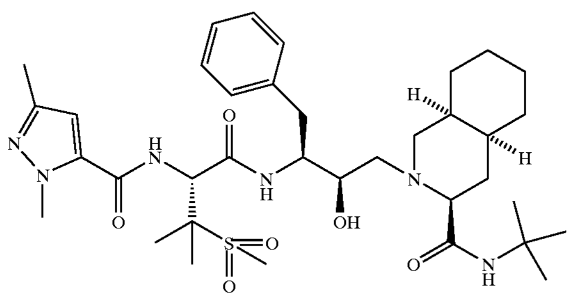 |
| N-tert-Butyl-1,2,3,4,4a(S),5,6,7,8,8a(S)-decahydro-2-[2(R)-hydroxy-3(S)-[[3-(methanesulfonyl)-N-pivaloyl-L-valyl]amino]-4-phenylbutyl]-3(S)-isoquinolinecarboxamide | 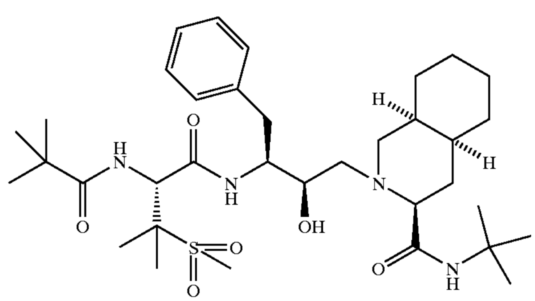 |

| Name | Structures |
|---|---|
| N-tert-Butyl-1,2,3,4,4a(S),5,6,7,8,8a(S)-decahydro-2-[2(R)-hydroxy-3(S)-[[3-(methanesulfonyl)-N-[(4-methyl-2-thiazolyl)carbonyl]-L-valyl]amino]-4-phenylbutyl]-3(S)-isoquinolinecarboxamide | 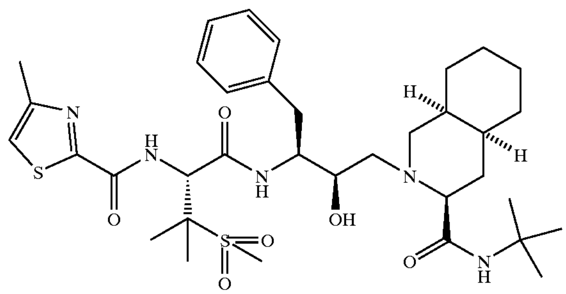 |
| N-tert-Butyl-1,2,3,4,4a(S),5,6,7,8,8a(S)-decahydro-2-[2(R)-hydroxy-3(S)-[[3-(methanesulfonyl)-3-methyl-N-[2-(1-pyrrolyl)acetyl]-L-valyl]amino]-4-phenylbutyl]-3(S)-isoquinolinecarboxamide | 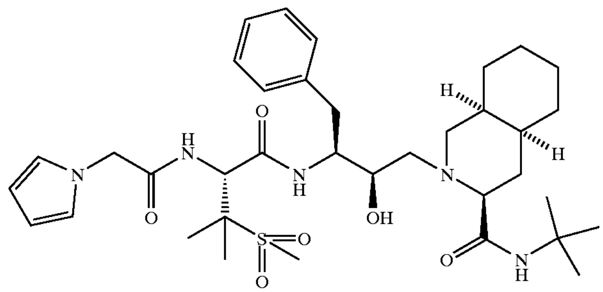 |
| N-tert-Butyl-2-[3(S)-[[N-[2-(diethylamino)acetyl]-3-(methanesulfonyl)-3-methyl-L-valyl]amino]-2(R)-hydroxy-4-phenylbutyl]-1,2,3,4,4a(S),5,6,7,8,8a(S)-decahydro3(S)-isoquinolinecarboxamide | 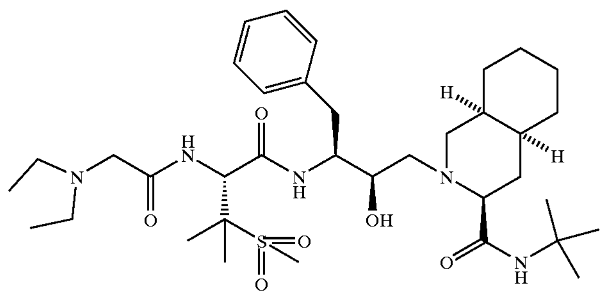 |
| N-tert-Butyl-1,2,3,4,4a(S),5,6,7,8,8a(S)-decahydro-2-[2(R)-hydroxy-3(S)-[[3-(methanesulfonyl)-3-methyl-N-[2-(1-pyrazolyl)acetyl]-L-valyl]amino]-4-phenylbutyl]-3(S)-isoquinolinecarboxamide | 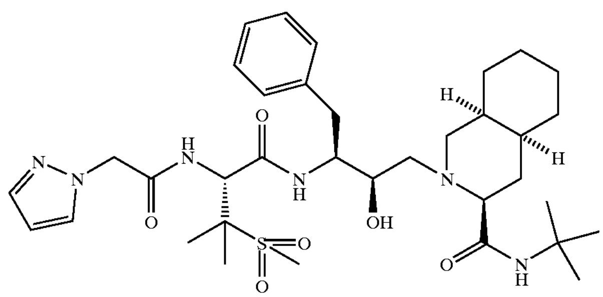 |
| N-tert-Butyl-1,2,3,4,4a(S),5,6,7,8,8a(S)-decahydro-2-[2(R)-hydroxy-3(S)-[[N-[2-(1-imidazolyl)acetyl]-3-(methanesulfonyl)-3-methyl-L-valyl]amino]-4-phenylbutyl]-3(S)-isoquinolinecarboxamide | 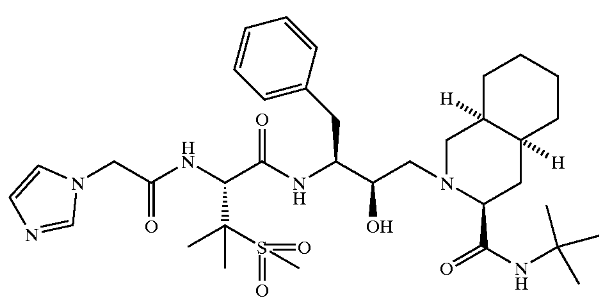 |

| Name | Structures |
|---|---|
| N-tert-Butyl-1,2,3,4,4a(S),5,6,7,8,8a(S)-decahydro-2-[2(R)-hydroxy-3(S)-[[3-(methanesulfonyl)-N-[2-(1-pyrrolidinyl)acetyl]-L-valyl]amino]-4-phenylbutyl]-3(S)-isoquinolinecarboxamide | |
| N-tert-Butyl-1,2,3,4,4a(S),5,6,7,8,8a(S)-decahydro-2-[2(R)-hydroxy-3(S)-[[3-(methanesulfonyl)-N-(2-morpholinoacetyl)-L-valyl]amino]-4-phenylbutyl]-3(S)-isoquinolinecarboxamide | 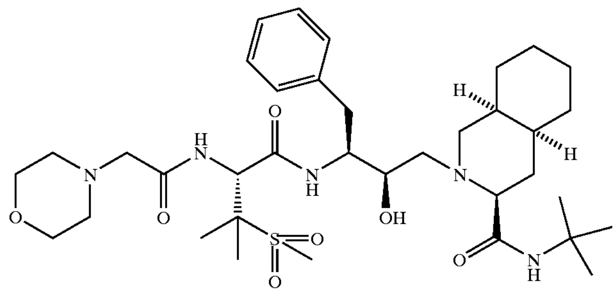 |
| N-tert-Butyl-1,2,3,4,4a(S),5,6,7,8,8a(S)-decahydro-2-[2(R)-hydroxy-3(S)-[[3-(methanesulfonyl)-N-(3-thenoyl)-L-valyl]amino]-4-phenylbutyl]-3(S)-isoquinolinecarboxamide | 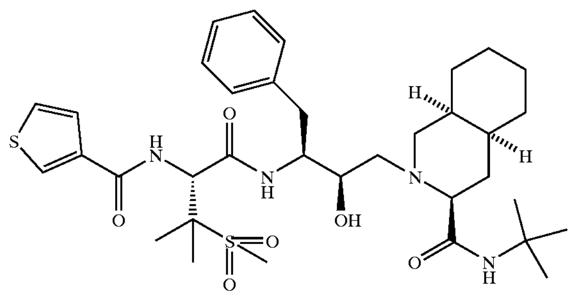 |
| N-tert-Butyl-1,2,3,4,4a(S),5,6,7,8,8a(S)-decahydro-2-[2(R)-hydroxy-3(S)-[[3-(methanesulfonyl)-N-[(5-thiazolyl)carbonyl]-L-valyl]amino]-4-phenylbutyl]-3(S)-isoquinolinecarboxamide | 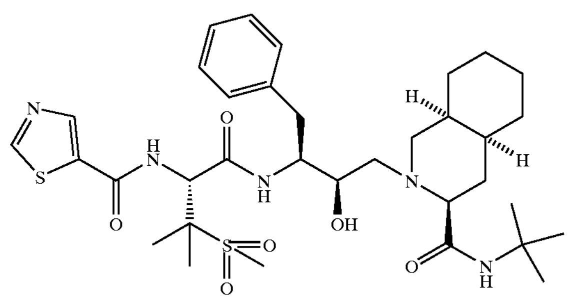 |
| N-tert-Butyl-1,2,3,4,4a(S),5,6,7,8,8a(S)-decahydro-2-[2(R)-hydroxy-3(S)-[[3-(methanesulfonyl)-N-[(6-methyl-3-pyridyl)carbonyl]-L-valyl]amino]-4-phenylbutyl]-3(S)-isoquinolinecarboxamide | 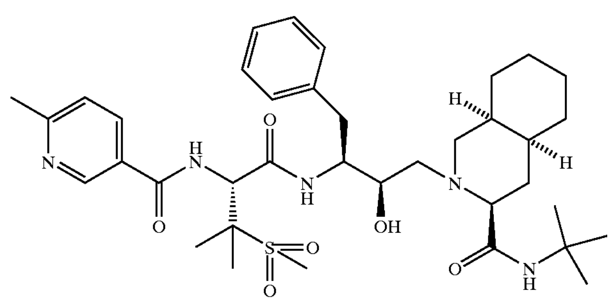 |

| Name | Structures |
|---|---|
| N-tert-Butyl-1,2,3,4,4a(S),5,6,7,8,8a(S)-decahydro-2-[2(R)-hydroxy-3(S)-[[3-(methanesulfonyl)-N-[N-methyl-N-phenylglycyl]-L-valyl]amino]-4-phenylbutyl]-3(S)-isoquinolinecarboxamide | 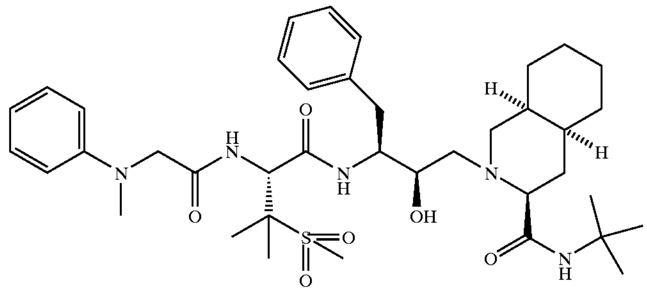 |
| N-tert-Butyl-1,2,3,4,4a(S),5,6,7,8,8a(S)-decahydro-2-[2(R)-hydroxy-3(S)-[[N-(2-isopropoxyacetyl)-3-(methanesulfonyl)-L-valyl]amino]-4-phenylbutyl]-3(S)-isoquinolinecarboxamide | 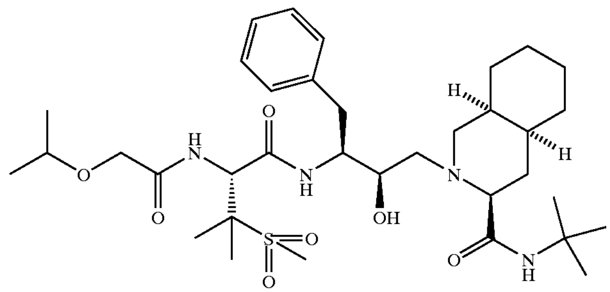 |
| N-tert-Butyl-1,2,3,4,4a(S),5,6,7,8,8a(S)-decahydro-2-[2(R)-hydroxy-3(S)-[[3-(methanesulfonyl)-N-[(2-pyridyl)carbonyl]-L-valyl]amino]-4-phenylbutyl]-3(S)-isoquinolinecarboxamide | 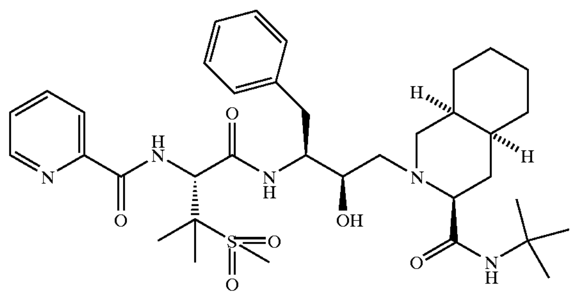 |
| N-tert-Butyl-1,2,3,4,4a(S),5,6,7,8,8a(S)-decahydro-2-[2(R)-hydroxy-3(S)-[[3-(methanesulfonyl)-N-[(2-methyl-4-thiazolyl)carbonyl]-L-valyl]amino]-4-phenylbutyl]-3(S)-isoquinolinecarboxamide | 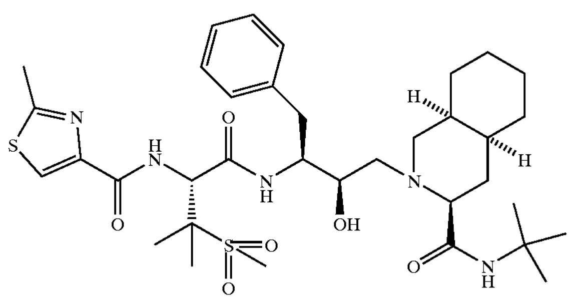 |
| N-tert-Butyl-1,2,3,4,4a(S),5,6,7,8,8a(S)-decahydro-2-[2(R)-hydroxy-3(S)-[[3-(methanesulfonyl)-N-(3-phenylpropionyl)-L-valyl]amino]-4-phenylbutyl]-3(S)-isoquinolinecarboxamide | 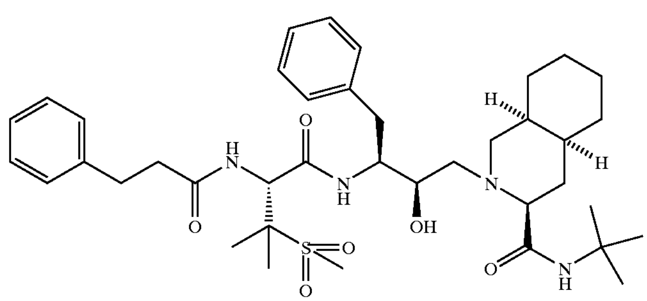 |

| Name | Structures |
|---|---|
| (E)-N-tert-Butyl-1,2,3,4,4a(S),5,6,7,8,8a(S)-decahydro-2-[2(R)-hydroxy-3(S)-[[3-(methanesulfonyl)-N-(3-phenylacryloyl)-L-valyl]amino]-4-phenylbutyl]-3(S)-isoquinolinecarboxamide | 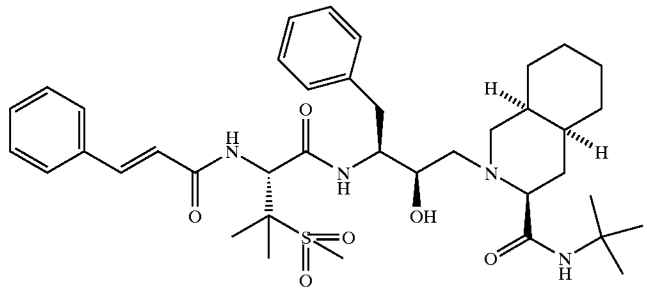 |
| N-tert-Butyl-2-[3(S)-[[N-[2-(pentafluorophenoxy)acetyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 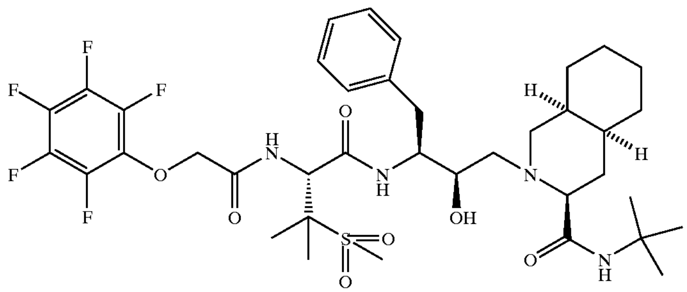 |
| 2-[3(S)-[[N-[[(2-Benzofuryl)carbonyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 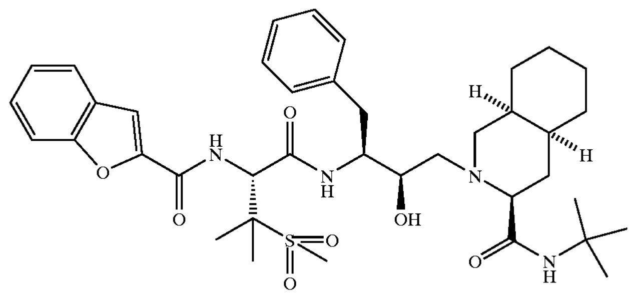 |
| N-tert-Butyl-1,2,3,4,4a(S),5,6,7,8,8a(S)-decahydro-2-[2(R)-hydroxy-3(S)-[[3-(methanesulfonyl)-N-[2-(phenylthio)acetyl]-L-valyl]amino]-4-phenylbutyl]-3(S)-isoquinolinecarboxamide | 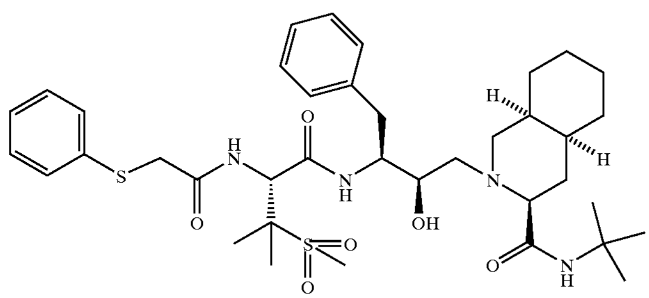 |
| N-tert-Butyl-1,2,3,4,4a(S),5,6,7,8,8a(S)-decahydro-2-[2(R)-hydroxy-3(S)-[[3-(methanesulfonyl)-N-(2-methyl-2-phenoxypropionyl)-L-valyl]amino]-4-phenylbutyl]-3(S)-isoquinolinecarboxamide | 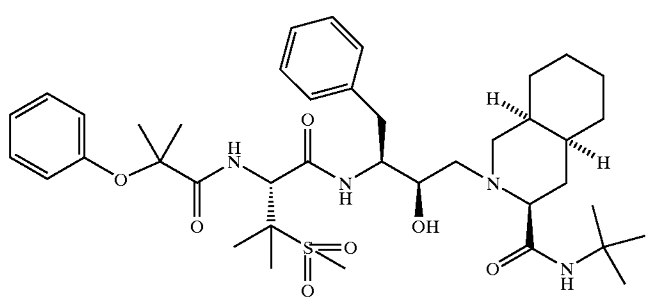 |

-continued

| Name | Structures |
|---|---|
| N-tert-Butyl-1,2,3,4,4a(S),5,6,7,8,8a(S)-decahydro-2-[2(R)-hydroxy-3(S)-[[3-(methanesulfonyl)-N-[2-(2-naphthyloxy)acetyl]-L-valyl]amino]-4-phenylbutyl]-3(S)-isoquinolinecarboxamide | 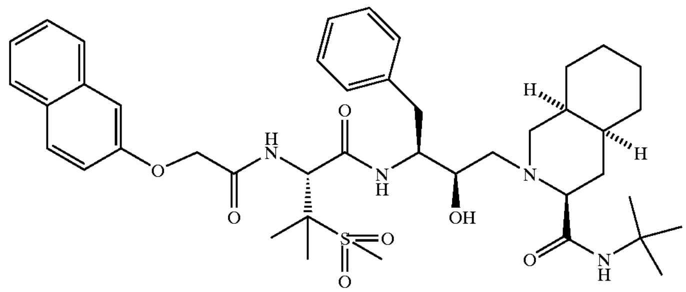 |
| N-tert-Butyl-1,2,3,4,4a(S),5,6,7,8,8a(S)-decahydro-2-[2(R)-hydroxy-3(S)-[[3-(methanesulfonyl)-N-[2-(1-naphthyloxy)acetylamino]-L-valyl]amino]-4-phenylbutyl]-3(S)-isoquinolinecarboxamide | 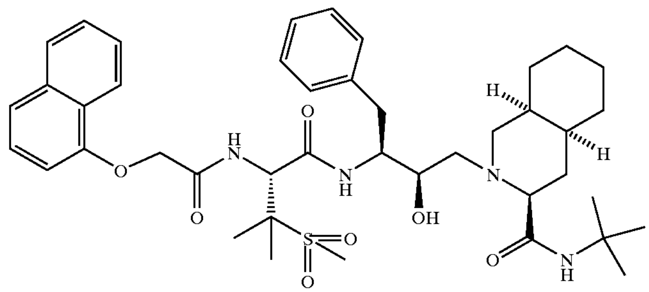 |
| N-tert-Butyl-1,2,3,4,4a(S),5,6,7,8,8a(S)-decahydro-2-[2(R)-hydroxy-3(S)-[[3-(methanesulfonyl)-N-(5-methyl-2-furoyl)-L-valyl]amino]-4-phenylbutyl]-3(S)-isoquinolinecarboxamide | 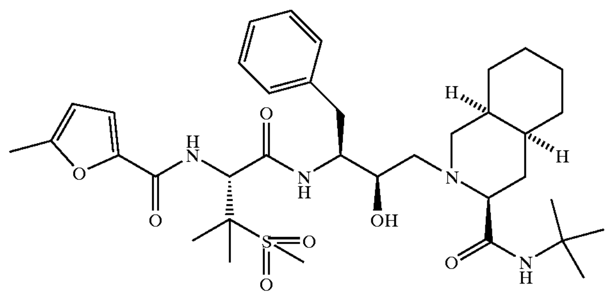 |
| N-tert-Butyl-1,2,3,4,4a(S),5,6,7,8,8a(S)-decahydro-2-[2(R)-hydroxy-3(S)-[[2-[2-(dimethylamino)acetyl]-3-(methanesulfonyl)-L-valyl]amino]-4-phenylbutyl]-3(S)-isoquinolinecarboxamide | 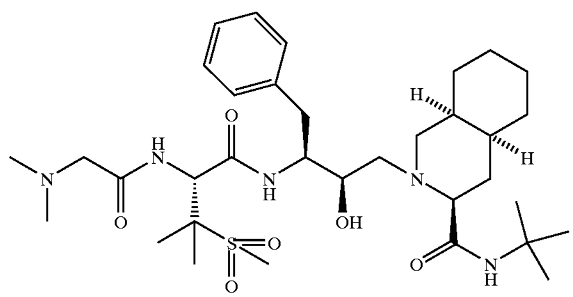 |
| N-tert-Butyl-1,2,3,4,4a(S),5,6,7,8,8a(S)-decahydro-2-[2(R)-hydroxy-3(S)-[[3-(methanesulfonyl)-N-(3,5-dimethoxybenzoyl)-L-valyl]amino]-4-phenylbutyl]-3(S)-isoquinolinecarboxamide | 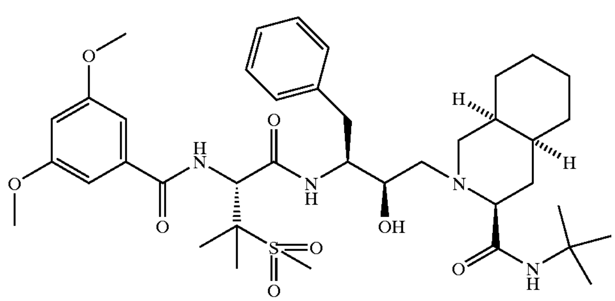 |

| Name | Structures |
|---|---|
| N-tert-Butyl-1,2,3,4,4a(S),5,6,7,8,8a(S)-decahydro-2-[2(R)-hydroxy-N-[(2-indolyl)carbonyl]-3(S)-[[3-(methanesulfonyl)-L-valyl]amino]-4-phenylbutyl]-3(S)-isoquinolinecarboxamide | 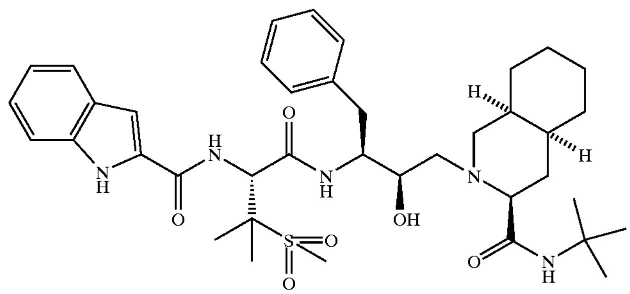 |
| N-tert-Butyl-1,2,3,4,4a(S),5,6,7,8,8a(S)-decahydro-2-[2(R)-hydroxy-3(S)-[[-3-(methanesulfonyl)-N-[1-methyl-2-indolyl)carbonyl]-L-valyl]amino]-4-phenylbutyl]-3(S)-isoquinolinecarboxamide | 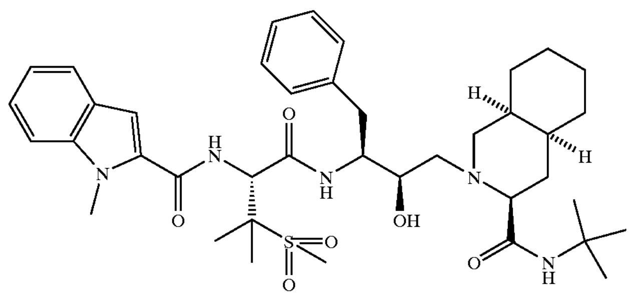 |
| 2-[3(S)-[[N-[(1-Benzothiophen-2-yl)carbonyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 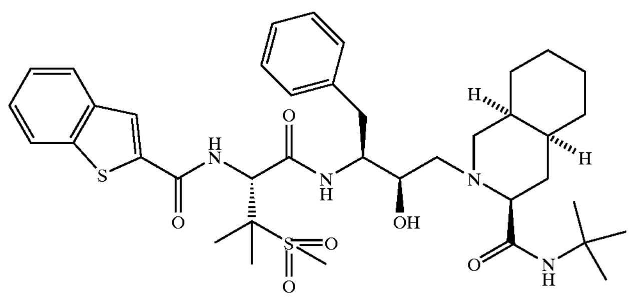 |
| N-tert-Butyl-1,2,3,4,4a(S),5,6,7,8,8a(S)-decahydro-2-[2(R)-hydroxy-3(S)-[[3-(methanesulfonyl)-N-(propoxycarbonyl)-L-valyl]amino]-4-phenylbutyl]-3(S)-isoquinolinecarboxamide | 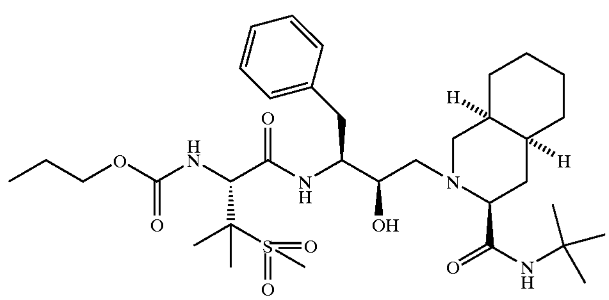 |
| N-tert-Butyl-1,2,3,4,4a(S),5,6,7,8a(S)-decahydro-2-[2(R)-hydroxy-3(S)-[[N-(isopropoxycarbonyl)-3-(methanesulfonyl)-L-valyl]amino]-4-phenylbutyl]-3(S)-isoquinolinecarboxamide | 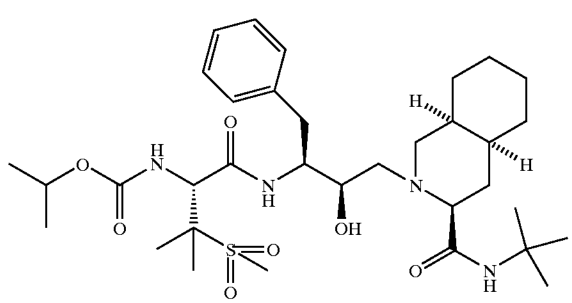 |

-continued

| Name | Structures |
|---|---|
| N-tert-Butyl-2-[3(S)-[[N-(ethoxycarbonyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 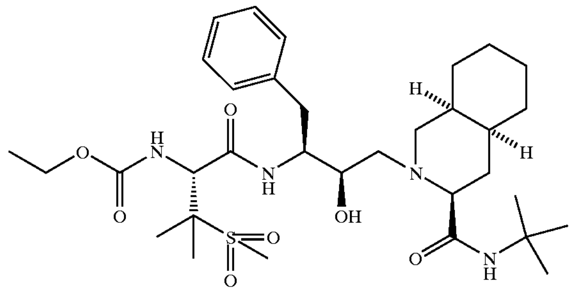 |
| N-tert-Butyl-1,2,3,4,4a(S),5,6,7,8,8a(S)-decahydro-2-[2(R)-hydroxy-3(S)-[[N-[2-(isopropylamino)acetyl]-3-(methanesulfonyl)-L-valyl]amino]-4-phenylbutyl]-3(S)-isoquinolinecarboxamide | 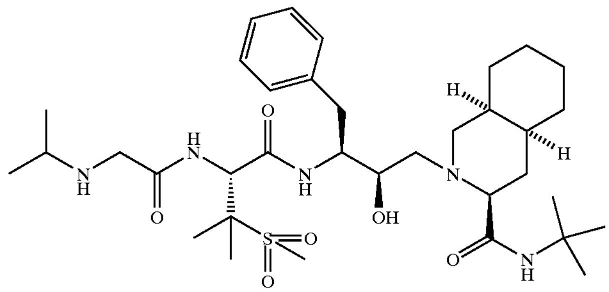 |
| N-tert-Butyl-1,2,3,4,4a(S),5,6,7,8,8a(S)-decahydro-2-[2(R)-hydroxy-3(S)-[[3-(methanesulfonyl)-N-(N-phenylglycyl)-L-valyl]amino]-4-phenylbutyl]-3(S)-isoquinolinecarboxamide | 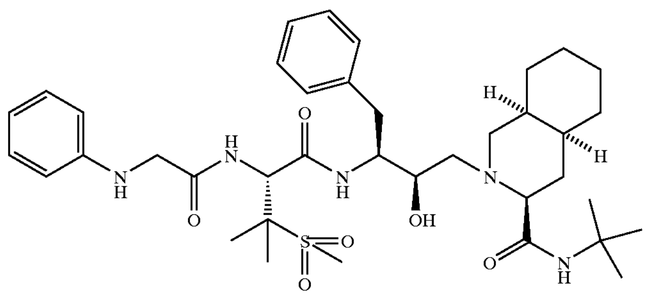 |
| N-tert-Butyl-1,2,3,4,4a(S),5,6,7,8,8a(S)-decahydro-2-[2(R)-hydroxy-3(S)-[[3-(methanesulfonyl)-N-(N-methylglycyl)-L-valyl]amino]-4-phenylbutyl]-3(S)-isoquinolinecarboxamide | 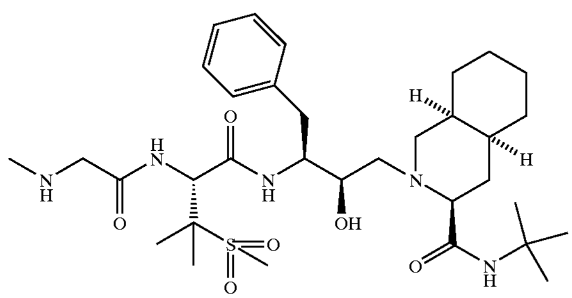 |
| N-tert-Butyl-1,2,3,4,4a(S),5,6,7,8,8a(S)-decahydro-1-[2(R)-hydroxy-3(S)-[3-(methanesulfonyl)butyramido]-4-phenylbutyl]-2(S)-piperazinecarboxamide | 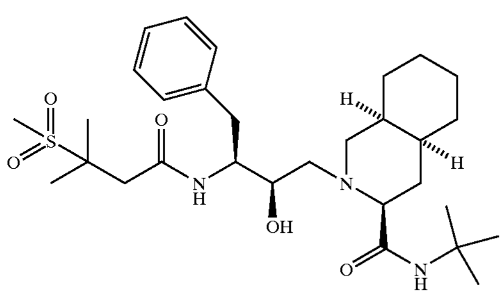 |

-continued

| Name | Structures |
|---|---|
| 2-[3(S)-[3-(Ethanesulfonyl)-3-methylbutyramido]-2(R)-hydroxy-4-phenylbutyl]-1,2,3,4,4a(S),5,6,7,8,8a(S)-decahydro-3(S)-isoquinolinecarboxamide | 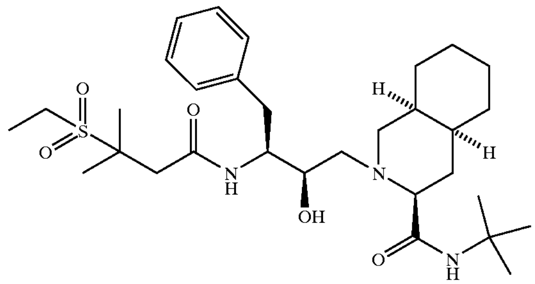 |
| 2-[3(S)-[3-(Benzenesulfonyl)-3-methylbutyramido]-2(R)-hydroxy-4-phenylbutyl]-N-tert-butyl-1,2,3,4,4a(S),5,6,7,8,8a(S)-decahydro-3(S)-isoquinolinecarboxamide | 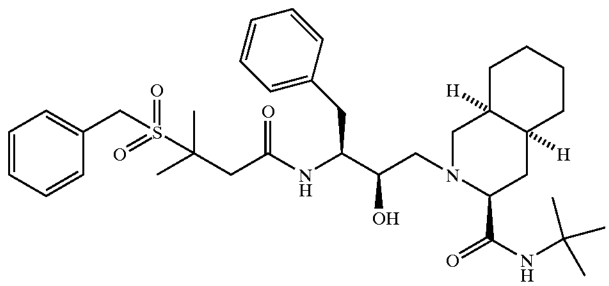 |
| N-tert-Butyl-1,2,3,4,4a(S),5,6,7,8,8a(S)-decahydro-2-[3(S)-[[N-[2-(tetrahydro-2(RS)-methyl-1,1-dioxo-2-thienyl)acetyl]-3-(methanesulfonyl)-L-valyl]amino]-2(R)-hydroxy-4-phenylbutyl]-3(S)-isoquinolinecarboxamide (mixture of diastereoisomers) | 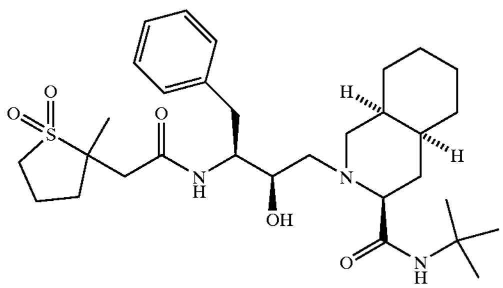 |
| N-tert-Butyl-1,2,3,4,4a(S),5,6,7,8,8a(S)-decahydro-2-[2(R)-hydroxy-3(S)-[2(R)-hydroxy-3-(methanesulfonyl)-3-methylbutyramido]-4-phenylbutyl]-3(S)-isoquinolinecarboxamide | 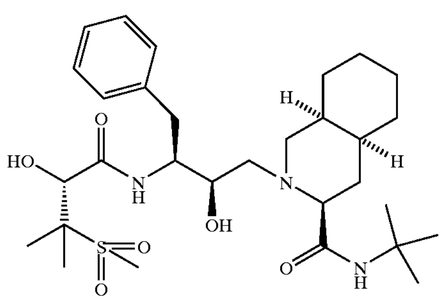 |
| N-tert-Butyl-1,2,3,4,4a(S),5,6,7,8,8a(S)-decahydro-2-[2(R)-hydroxy-3(S)-[[N-(dimethylcarbamoyl)-3-(methanesulfonyl)-L-valyl]amino]-4-phenylbutyl]-3(S)-isoquinolinecarboxamide | |

| Name | Structures |
|---|---|
| N-tert-Butyl-2-[3(S)-[[N-(diethylcarbamoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 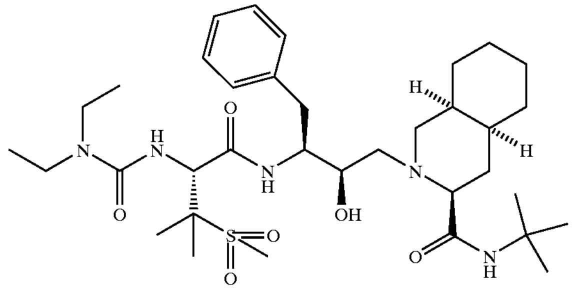 |
| N-tert-Butyl-2-[3(S)-[[N-(N-ethyl-N-methylcarbamoyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 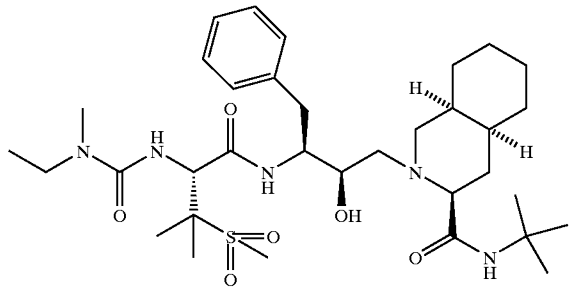 |
| N-tert-Butyl-1,2,3,4,4a(S),5,6,7,8,8a(S)-decahydro-2-[2(R)-hydroxy-3(S)-[[3-(methanesulfonyl)-N-(N-methyl-N-propylcarbamoyl)-L-valyl]amino]-4-phenylbutyl]-3(S)-isoquinolinecarboxamide | 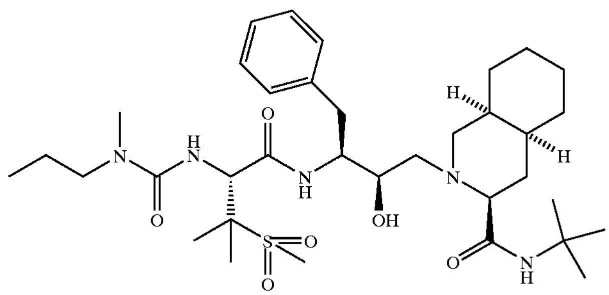 |
| N-tert-Butyl-1,2,3,4,4a(S),5,6,7,8,8a(S)-decahydro-2-[2(R)-hydroxy-3(S)-[[3-(methanesulfonyl)-N-[(1-pyrrolidinyl)carbonyl]-L-valyl]amino]-4-phenylbutyl]-3(S)-isoquinolinecarboxamide | 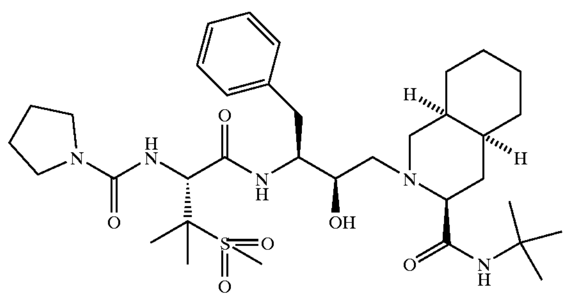 |
| N-tert-Butyl-1,2,3,4,4a(S),5,6,7,8,8a(S)-decahydro-2-[2(R)-hydroxy-3(S)-[[3-(methanesulfonyl)-N-(piperidinocarbonyl)-L-valyl]amino]-4-phenylbutyl]-3(S)-isoquinolinecarboxamide | 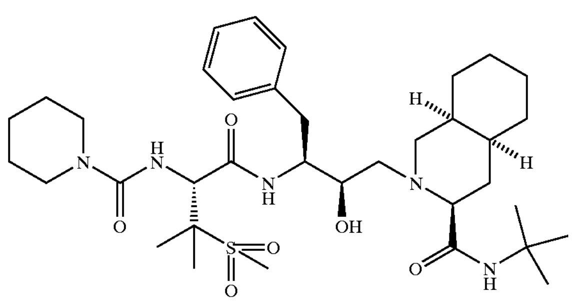 |

| Name | Structures |
|---|---|
| N-tert-Butyl-1,2,3,4,4a(S),5,6,7,8,8a(S)-decahydro-2-[2(R)-hydroxy-3(S)-[[3-(methanesulfonyl)-N-(morpholinocarbonyl)-L-valyl]amino]-4-phenylbutyl]-3(S)-isoquinolinecarboxamide | 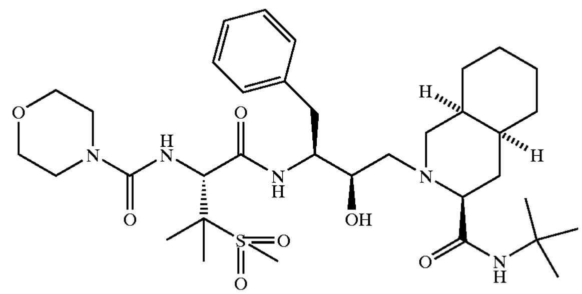 |
| N-tert-Butyl-1,2,3,4,4a(S),5,6,7,8,8a(S)-decahydro-2-[2(R)-hydroxy-3(S)-[[3-(methanesulfonyl)-N-[(1-piperazinyl)carbonyl]-L-valyl]amino]-4-phenylbutyl]-3(S)-isoquinolinecarboxamide | 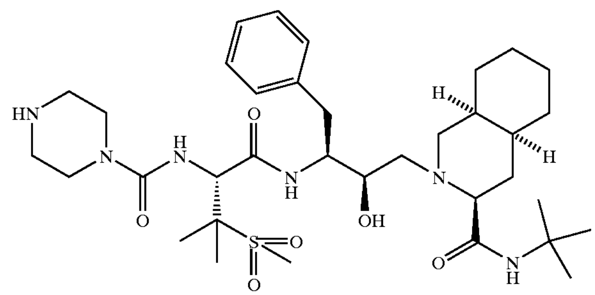 |
| N-tert-Butyl-1,2,3,4,4a(S),5,6,7,8,8a(S)-decahydro-2-[2(R)-hydroxy-3(S)-[[3-(methanesulfonyl)-N-[(4-methyl-1-piperazinyl)carbonyl]-L-valyl]amino]-4-phenylbutyl]-3(S)-isoquinolinecarboxamide | 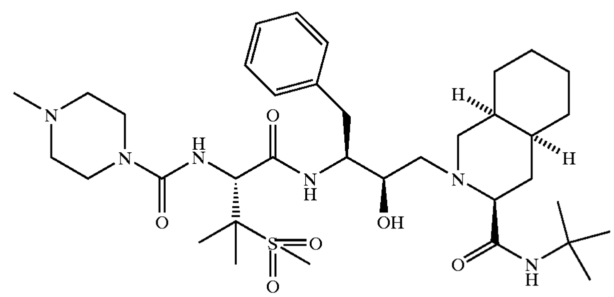 |
| N-tert-Butyl-1,2,3,4,4a(S),5,6,7,8,8a(S)-decahydro-2-[3(S)-[[N-[(tetrahydro-1,4-thiazin-4-yl)carbonyl]-3-(methanesulfonyl)-L-valyl]amino]-2(R)-hydroxy-4-phenylbutyl]-3(S)-isoquinolinecarboxamide | 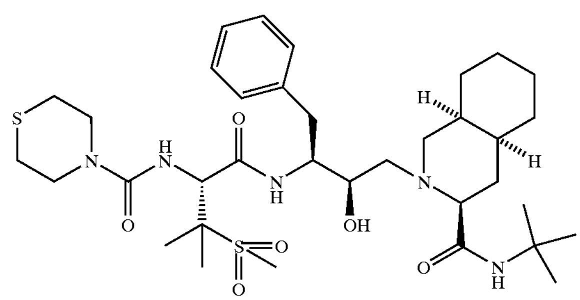 |
| N-tert-Butyl-1,2,3,4,4a(S),5,6,7,8,8a(S)-decahydro-2-[2(R)-hydroxy-3(S)-[[N-isopropyl-3-(methanesulfonyl)-L-valyl]amino]-4-phenylbutyl]-3(S)-isoquinolinecarboxamide | |

-continued

| Name | Structures |
|---|---|
| N-tert-Butyl-2-[3(S)-[[N-ethyl-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 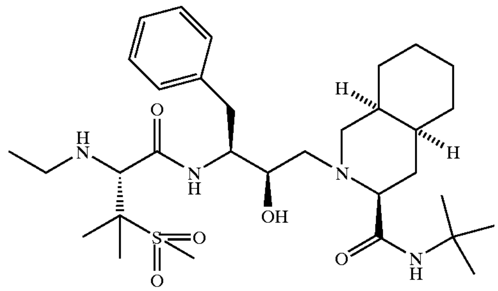 |
| 2-[3(S)-[[N-Benzyl-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 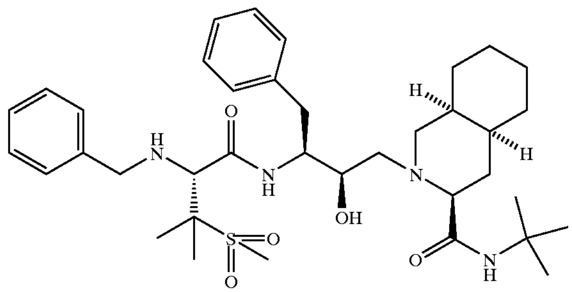 |
| N-tert-Butyl-1,2,3,4,4a(S),5,6,7,8,8a(S)-decahydro-2-[2(R)-hydroxy-3(S)-[[3-(methanesulfonyl)-N-methyl-L-valyl]amino]-4-phenylbutyl]-3(S)-isoquinolinecarboxamide | 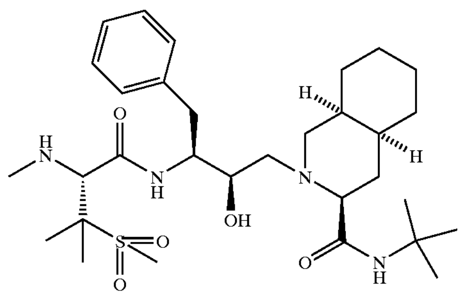 |
| N-tert-Butyl-2-[3(S)-[[N-(2-furfuryl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 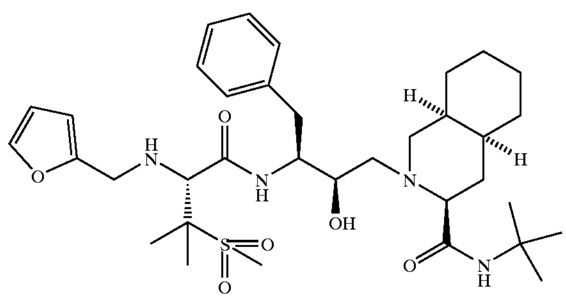 |
| N-tert-Butyl-1,2,3,4,4a(S),5,6,7,8,8a(S)-decahydro-2-[2(R)-hydroxy-3(S)-[[3-(methanesulfonyl)-N-(5-methyl-2-furfuryl)-L-valyl]amino]-4-phenylbutyl]-3(S)-isoquinolinecarboxamide | 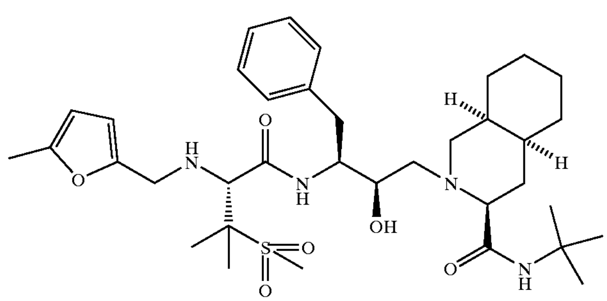 |

-continued

| Name | Structures |
|------|------------|
| N-tert-Butyl-2-[3(S)-[[N-(2-fluorobenzyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 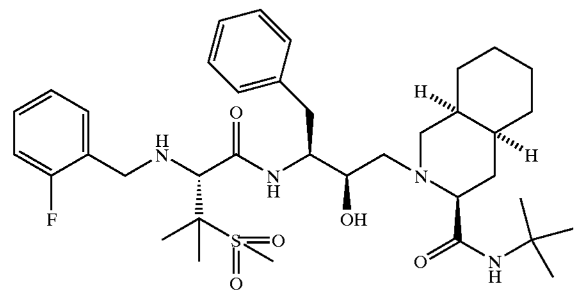 |
| N-tert-Butyl-2-[3(S)-[[N-(2-chlorobenzyl)-3-(methanesulfonyl)-L-valyl]amino]-3(R)-hydroxy-4-phenylbutyl]-1,2,3,4,4a(S),5,6,7,8,8a(S)-decahydro-3(S)-isoquinolinecarboxamide | 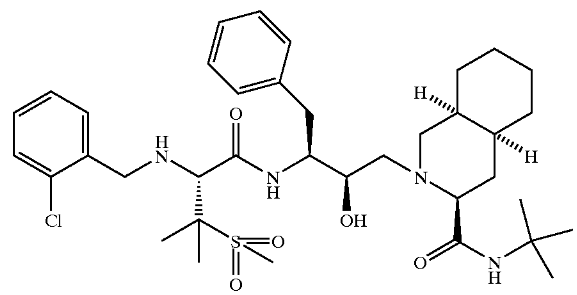 |
| N-tert-Butyl-1,2,3,4,4a(S),5,6,7,8,8a(S)-decahydro-2-[2(R)-hydroxy-3(S)-[[3-(methanesulfonyl)-N-(2-methoxybenzyl)-L-valyl]amino]-4-phenylbutyl]-3(S)-isoquinolinecarboxamide | 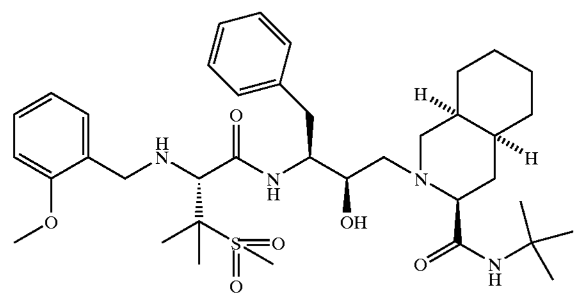 |
| N-tert-Butyl-1,2,3,4,4a(S),5,6,7,8,8a(S)-decahydro-2-[2(R)-hydroxy-3(S)-[[N-(2-hydroxybenzyl)-3-(methanesulfonyl)-L-valyl]amino]-4-phenylbutyl]-3(S)-isoquinolinecarboxamide | 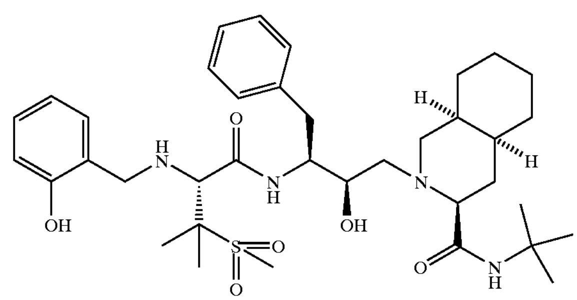 |
| N-tert-Butyl-1,2,3,4,4a(S),5,6,7,8,8a(S)-decahydro-2-[2(R)-hydroxy-3(S)-[[3-(methanesulfonyl)-N-(2-methylbenzyl)-L-valyl]amino]-4-phenylbutyl]-3(S)-isoquinolinecarboxamide | 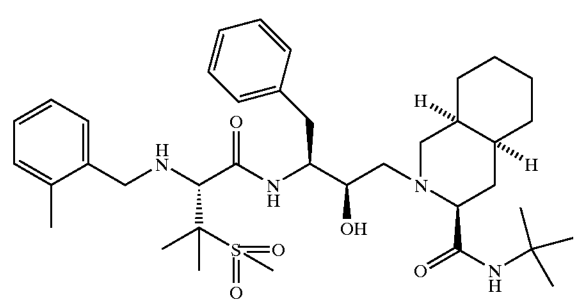 |

-continued

| Name | Structures |
|---|---|
| N-tert-Butyl-2-[3(S)-[[N-(3-fluorobenzyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 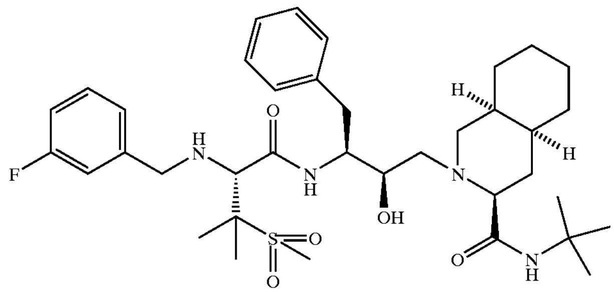 |
| N-tert-Butyl-2-[3(S)-[[N-(3-chlorobenzyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 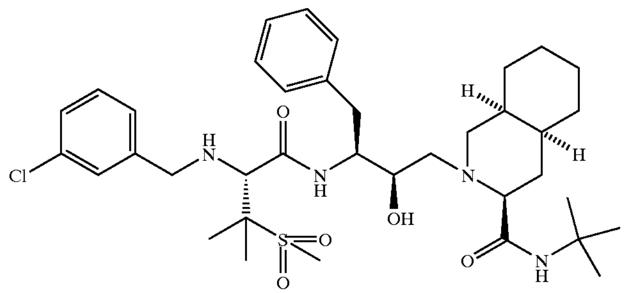 |
| N-tert-Butyl-1,2,3,4,4a(S),5,6,7,8,8a(S)-decahydro-2-[2(R)-hydroxy-3(S)-[[N-(3-hydroxybenzyl)-3-(methanesulfonyl)-L-valyl]amino]-4-phenylbutyl]-3(S)-isoquinolinecarboxamide | 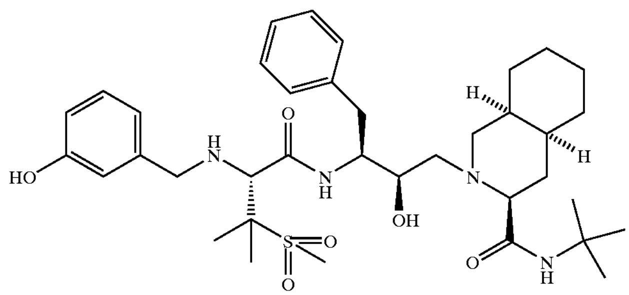 |
| N-tert-Butyl-1,2,3,4,4a(S),5,6,7,8,8a(S)-decahydro-2-[2(R)-hydroxy-3(S)-[[3-(methanesulfonyl)-N-(5-methyl-2-thenyl)-L-valyl]amino]-4-phenylbutyl]-3(S)-isoquinolinecarboxamide | 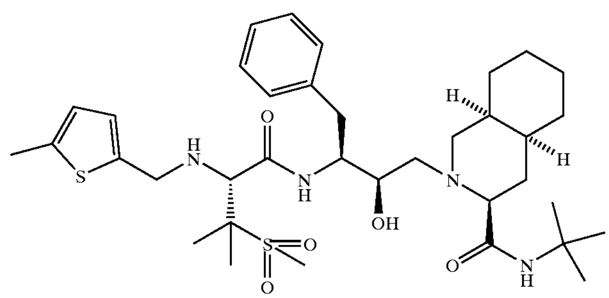 |
| N-tert-Butyl-1,2,3,4,4a(S),5,6,7,8,8a(S)-decahydro-2-[2(R)-hydroxy-3(S)-[[3-(methanesulfonyl)-N-[(2-pyridyl)methyl]-L-valyl]amino]-4-phenylbutyl]-3(S)-isoquinolinecarboxamide | 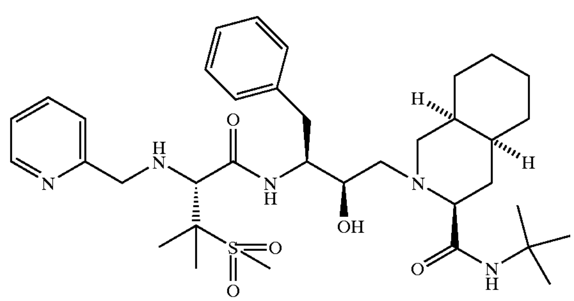 |

-continued

| Name | Structures |
|---|---|
| N-tert-Butyl-1,2,3,4,4a(S),5,6,7,8,8a(S)-decahydro-2-[2(R)-hydroxy-3(S)-[[N-(4-hydroxybenzyl)-3-(methanesulfonyl)-L-valyl]amino]-4-phenylbutyl]-3(S)-isoquinolinecarboxamide | 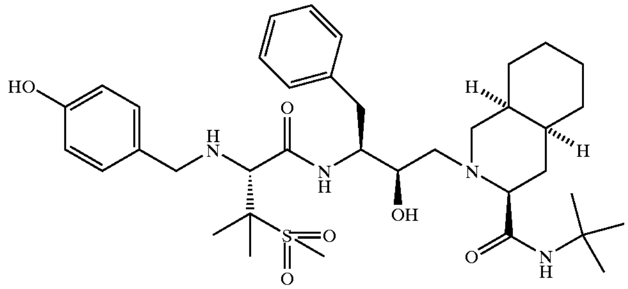 |
| N-tert-Butyl-1,2,3,4,4a(S),5,6,7,8,8a(S)-decahydro-2-[2(R)-hydroxy-3(S)-[[3-(methanesulfonyl)-N-(4-methylbenzyl)-L-valyl]amino]-4-phenylbutyl]-3(S)-isoquinolinecarboxamide | 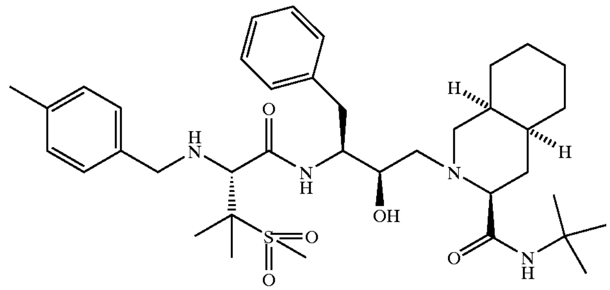 |
| N-tert-Butyl-1,2,3,4,4a(S),5,6,7,8,8a(S)-decahydro-2-[2(R)-hydroxy-3(S)-[[3-(methanesulfonyl)-N-(2,2-dimethylpropyl)-L-valyl)amino]-4-phenylbutyl]-3(S)-isoquinolinecarboxamide | 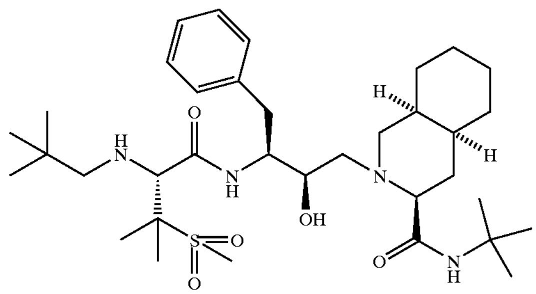 |
| N-tert-Butyl-1,2,3,4,4a(S),5,6,7,8,8a(S)-decahydro-2-[2(R)-hydroxy-3(S)-[[N-isobutyl-3-(methanesulfonyl)-L-valyl]amino]-4-phenylbutyl]-3(S)-isoquinolinecarboxamide | 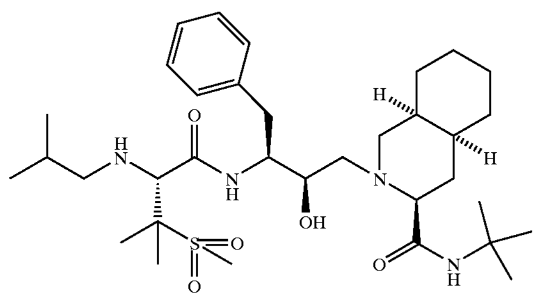 |
| N-tert-Butyl-1,2,3,4,4a(S),5,6,7,8,8a(S)-decahydro-2-[2(R)-hydroxy-3(S)-[[3-(methanesulfonyl)-N-(2-phenylethylyl))-L-valyl]amino]-4-phenylbutyl]-3(S)-isoquinolinecarboxamide | 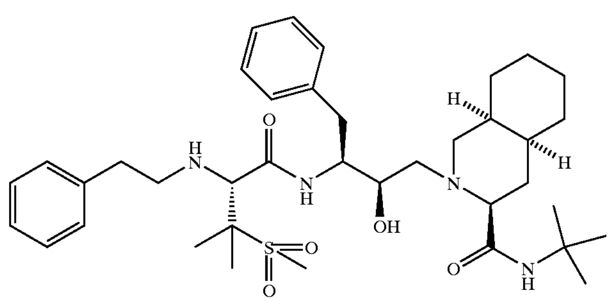 |

-continued

| Name | Structures |
|---|---|
| N-tert-Butyl-2-[3(S)-[[N-(2,6-difluorobenzyl)-3-(methanesulfonyl)-N-L-valyl]amino]-2(R)-hydroxy-4-phenylbutyl]-1,2,3,4,4a(S),5,6,7,8,8a(S)-decahydro-3(S)-isoquinolinecarboxamide | 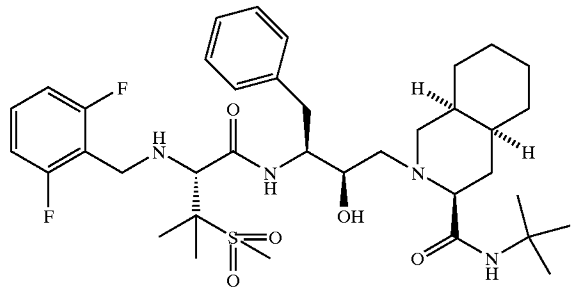 |
| N-tert-Butyl-2-[3(S)-[[N-(3-furfuryl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 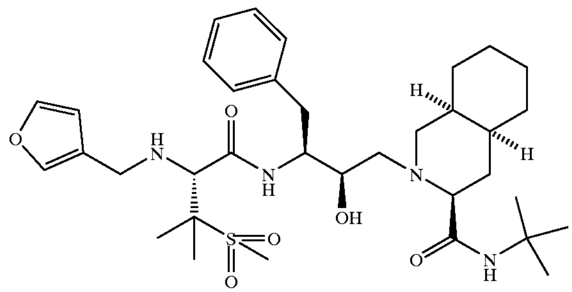 |
| N-tert-Butyl-2-[3(S)-[[N-(cyclopropylmethyl)-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 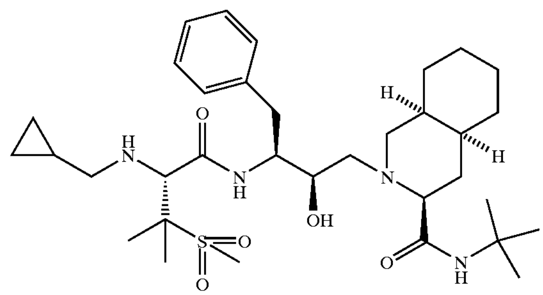 |
| N-tert-Butyl-1,2,3,4,4a(S),5,6,7,8,8a(S)-decahydro-2-[2(R)-hydroxy-3(S)-[[3-(methanesulfonyl)-N-[(2-methyl-4-imidazolyl)methyl]-L-valyl]amino]-4-phenylbutyl]-3(S)-isoquinolinecarboxamide | 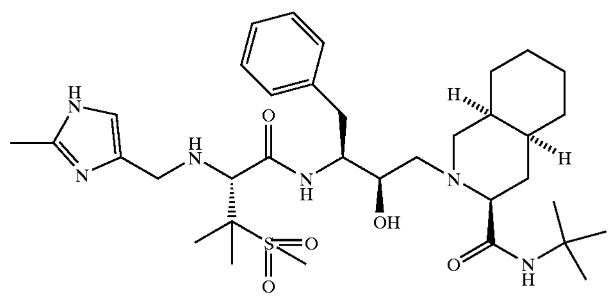 |
| N-tert-Butyl-1,2,3,4,4a(S),5,6,7,8,8a(S)-decahydro-2-[2(R)-hydroxy-3(S)-[[3-(methanesulfonyl)-N-[(5-methyl-4-imidazolyl)methyl]-L-valyl]amino]-4-phenylbutyl]-3(S)-isoquinolinecarboxamide | 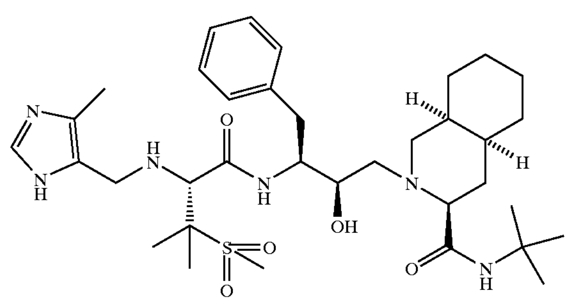 |

| Name | Structures |
|---|---|
| N-tert-Butyl-1,2,3,4,4a(S),5,6,7,8,8a(S)-decahydro-2-[2(R)-hydroxy-3(S)-[[3-(methanesulfonyl)-N-[(1-methyl-2-imidazolyl)methyl]-L-valyl]amino]-4-phenylbutyl]-3(S)-isoquinolinecarboxamide | 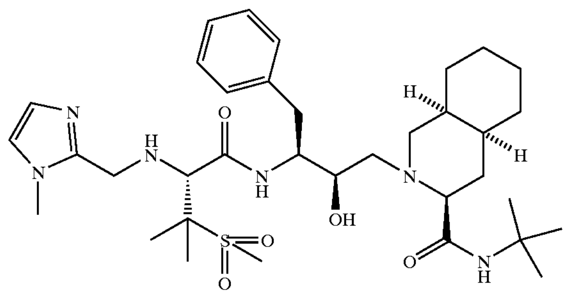 |
| N-tert-Butyl-1,2,3,4,4a(S),5,6,7,8,8a(S)-decahydro-2-[2(R)-hydroxy-3(S)-[[3-(methanesulfonyl)-N-(2-thiazolyl)-L-valyl]amino]-4-phenylbutyl]-3(S)-isoquinolinecarboxamide | 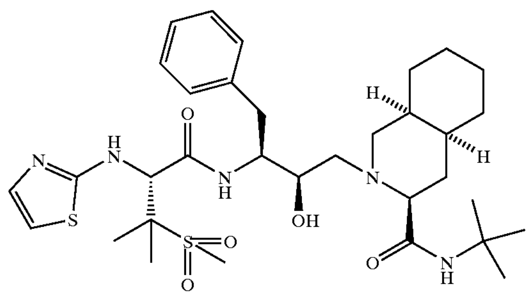 |
| N-tert-Butyl-1,2,3,4,4a(S),5,6,7,8,8a(S)-decahydro-2-[2(R)-hydroxy-3(S)-[[3-(methanesulfonyl)-N-(4-methyl-2-thiazolyl)-L-valyl]amino]-4-phenylbutyl]-3(S)-isoquinolinecarboxamide | 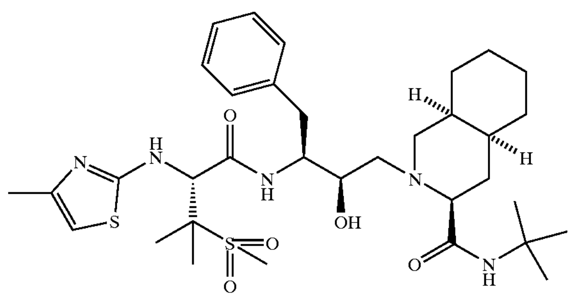 |
| N-tert-Butyl-1,2,3,4,4a(S),5,6,7,8,8a(S)-decahydro-2-[2(R)-hydroxy-3(S)-[[3-(methanesulfonyl)-N-(4-phenyl-2-thiazolyl)-L-valyl]amino]-4-phenylbutyl]-3(S)-isoquinolinecarboxamide | 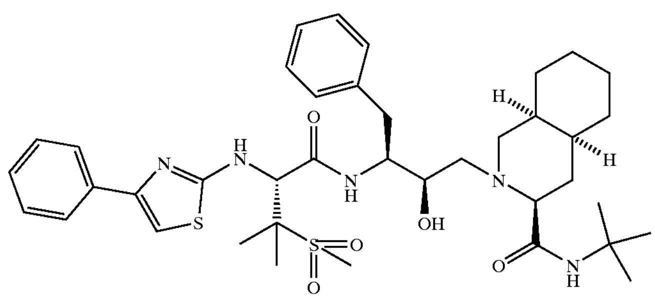 |
| N-tert-Butyl-2-[3(S)-[[N-[4-(ethoxycarbonyl)-2-thiazolyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 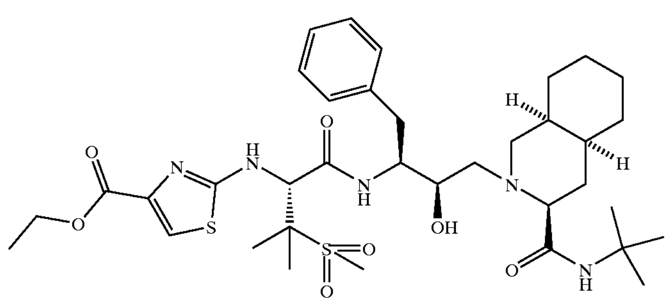 |

| Name | Structures |
|---|---|
| 2-[3(S)-[[N-[4-(Acetoxymethyl)-2-thiazolyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 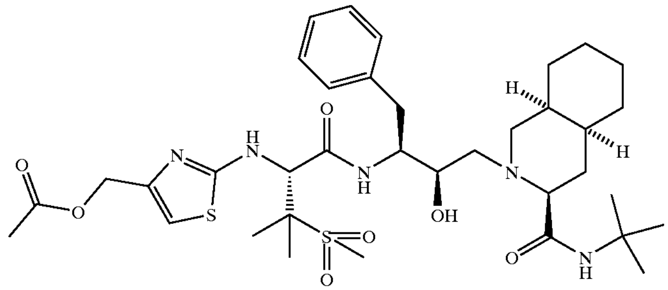 |
| N-tert-Butyl-1,2,3,4,4a(S),5,6,7,8,8a(S)-decahydro-2-[2(R)-hydroxy-3(S)-[[3-(methanesulfonyl)-N-[4-[(methoxycarbonyl)methyl]-2-thiazolyl]-L-valyl]amino]-4-phenylbutyl]-3(S)-isoquinolinecarboxamide | 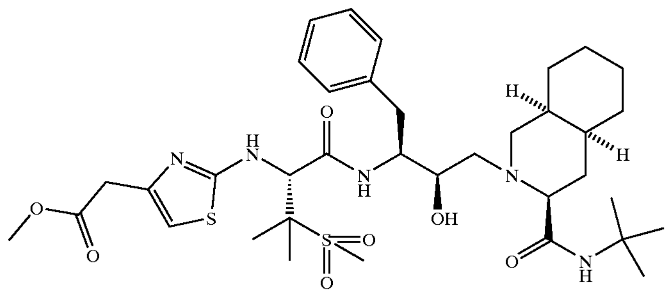 |
| N-tert-Butyl-1,2,3,4,4a(S),5,6,7,8,8a(S)-decahydro-2-[2(R)-hydroxy-3(S)-[[N-[4-(hydroxymethyl)-2-thiazolyl]-3-(methanesulfonyl)-L-valyl]amino]-4-phenylbutyl]-3(S)-isoquinolinecarboxamide | 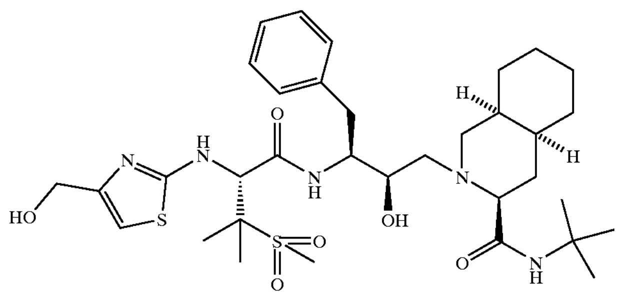 |
| N-tert-Butyl-1,2,3,4,4a(S),5,6,7,8,8a(S)-decahydro-2-[3(S)-[2(R)-(2,3-dihydro-2-oxo-1H-imidazol-2-yl)-3-(methanesulfonyl)-3-methylbutyramido]-2(R)-hydroxy-4-phenylbutyl]-3(S)-isoquinolinecarboxamide | 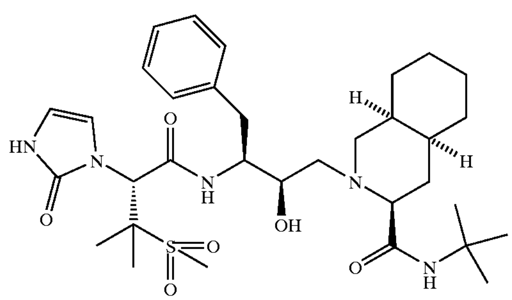 |
| N-Benzyl-1,2,3,4,4a(S),5,6,7,8,8a(S)-decahydro-2-[2(R)-hydroxy-3(S)-[[3-(methanesulfonyl)-N-(methoxycarbonyl)-L-valyl]amino]-4-phenylbutyl]-3(S)-isoquinolinecarboxamide | 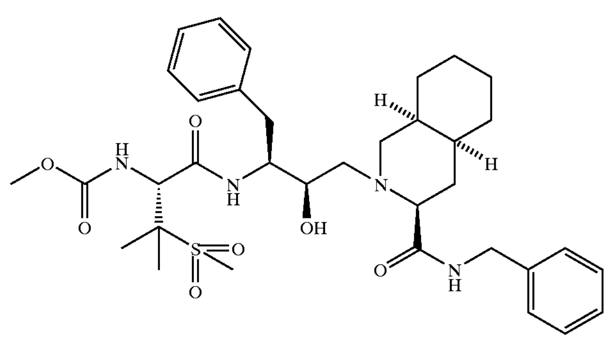 |

| Name | Structures |
|---|---|
| N-tert-Butyl-2-[3(S)-[[N-[2-(3-fluorophenoxy)acetyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 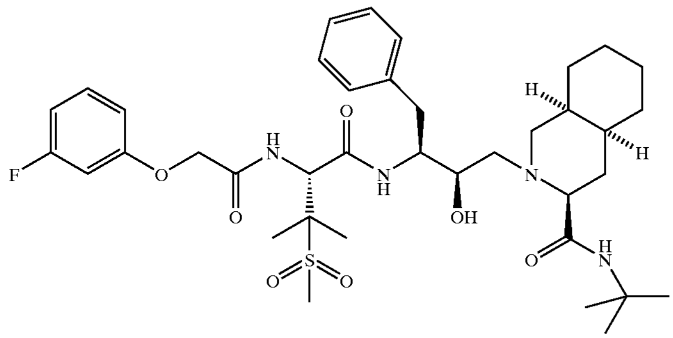 |
| N-tert-Butyl-2-[3(S)-[[N-[2-(4-Fluorophenoxy)-acetyl]-3-(methanesulfonyl)-L-valyl]amino]-2(R)-hydroxy-4-phenylbutyl]-1,2,3,4,4a(S),5,6,7,8,8a(S)-decahydro-3(S)-isoquinolinecarboxamide | 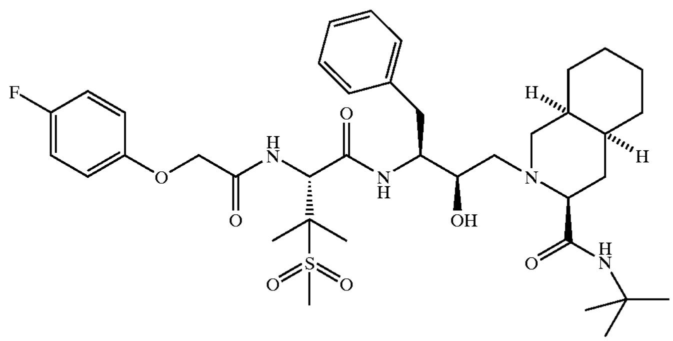 |
| (E)-N-tert-Butyl-1,2,3,4,4a(S),5,6,7,8,8a(S)-decahydro-2-[2(R)-hydroxy-3(S)-[[3-(methanesulfonyl)-N-[3-(4-pyridyl)acroyl]-L-valyl]amino]-4-phenylbutyl]-3(S)-isoquinolinecarboxamide | 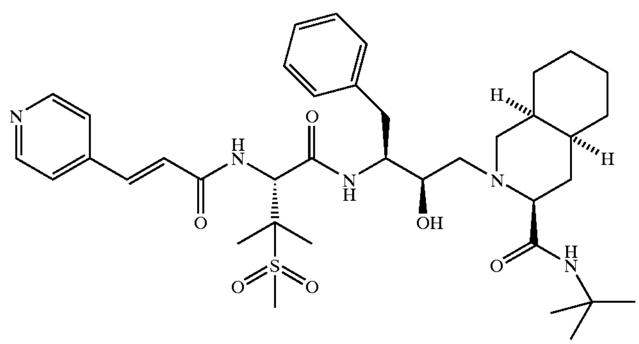 |
| N-tert-Butyl-1,2,3,4,4a(S),5,6,7,8,8a(S)-decahydro-2-[2(R)-hydroxy-3(S)-[[3-(methanesulfonyl)-N-[(6-quinolinyl)carbonyl]-L-valyl]amino]-4-phenylbutyl]-3(S)-isoquinolinecarboxamide | 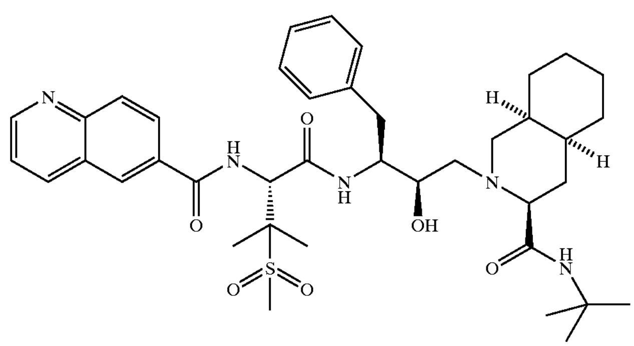 |

-continued

| Name | Structures |
|------|------------|
| 2-[3(S)-[[N-[(6-Benzothiazolyl)carbonyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 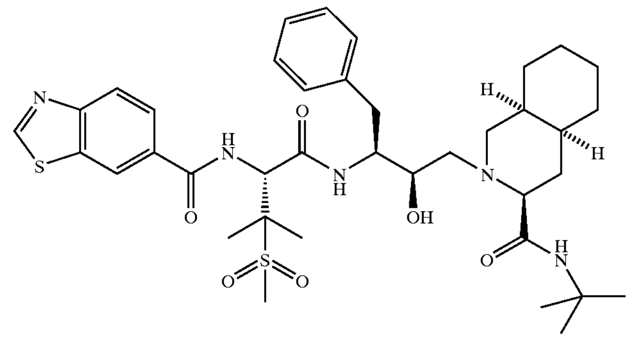 |
| (E)-N-tert-Butyl-1,2,3,4,4a(S),5,6,7,8,8a(S)-decahydro-2-[2(R)-hydroxy-3(S)-[[3-(methanesulfonyl)-N-[3-(2-pyridyl)acroyl]-L-valyl]amino]-4-phenylbutyl]-3(S)-isoquinolinecarboxamide | 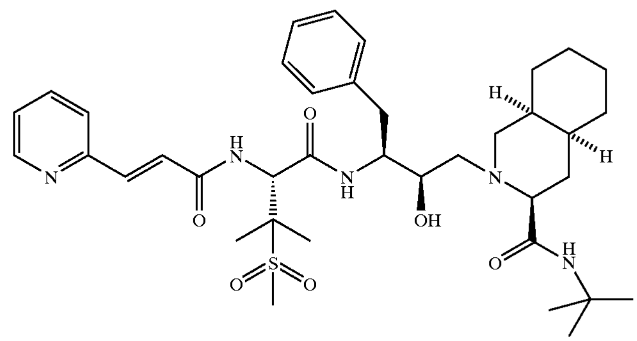 |
| (E)-N-tert-Butyl-1,2,3,4,4a(S),5,6,7,8,8a(S)-decahydro-2-[2(R)-hydroxy-3(S)-[[3-(methanesulfonyl)-N-[3-(3-pyridyl)acroyl]-L-valyl]amino]-4-phenylbutyl]-3(S)-isoquinolinecarboxamide | 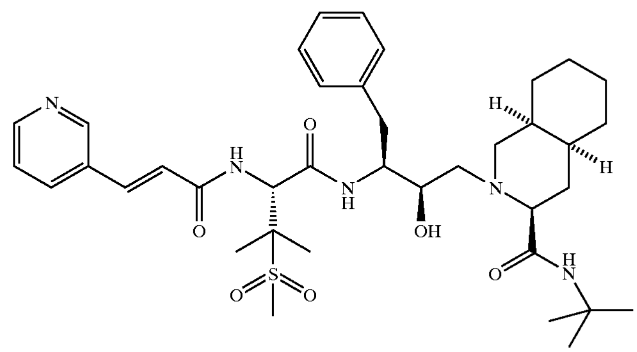 |
| N-tert-Butyl-1,2,3,4,4a(S),5,6,7,8,8a(S)-decahydro-2-[2(R)-hydroxy-3(S)-[[3-(methanesulfonyl)-N-[(2-quinoxalinyl)carbonyl]-L-valyl]amino]-4-phenylbutyl]-3(S)-isoquinolinecarboxamide | 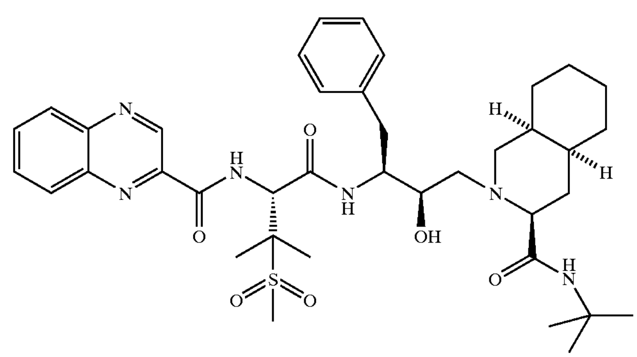 |

-continued

| Name | Structures |
|---|---|
| N-tert-Butyl-1,2,3,4,4a(S),5,6,7,8,8a(S)-decahydro-2-[2(R)-hydroxy-3(S)-[[3-(methanesulfonyl)-N-[(pyrido[4,3-b]pyridin-2-yl)carbonyl]-L-valyl]amino]-4-phenylbutyl]-3(S)-isoquinolinecarboxamide | 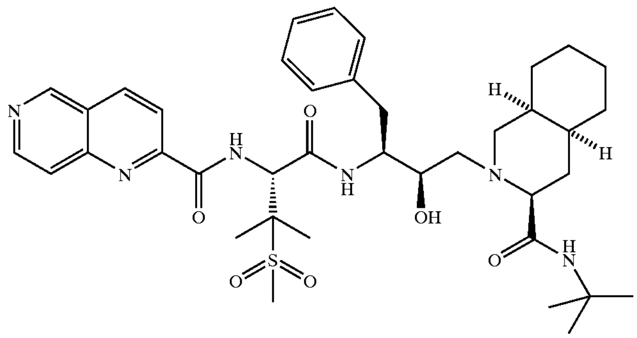 |
| (E)-N-tert-Butyl-1,2,3,4,4a(S),5,6,7,8,8a(S)-decahydro-2-[2(R)-hydroxy-3(S)-[[N-[3-(3-indolyl)acroyl]-3-(methanesulfonyl)-L-valyl]amino]-4-phenylbutyl]-3(S)-isoquinolinecarboxamide | 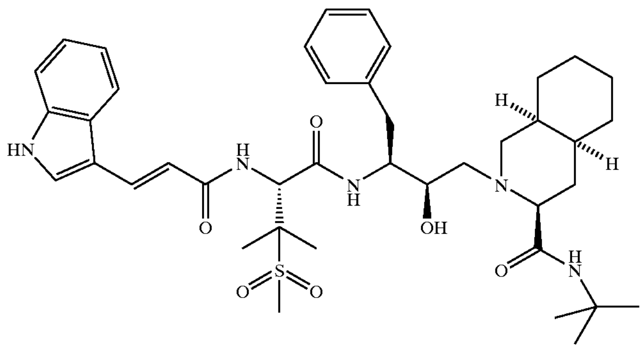 |
| (E)-2-[3(S)-[[N-[3-(1,3-Benzodioxol-5-yl)acroyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 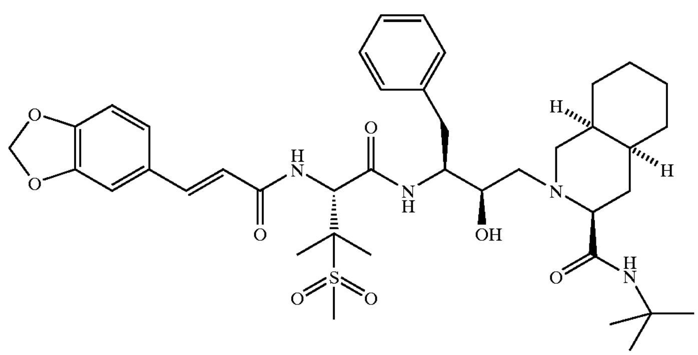 |
| N-tert-Butyl-1,2,3,4,4a(S),5,6,7,8,8a(S)-decahydro-2-[2(R)-hydroxy-3(S)-[[3-(methanesulfonyl)-N-[(3-quinolyl)carbonyl]-L-valyl]amino]-4-phenylbutyl]-3(S)-isoquinolinecarboxamide | 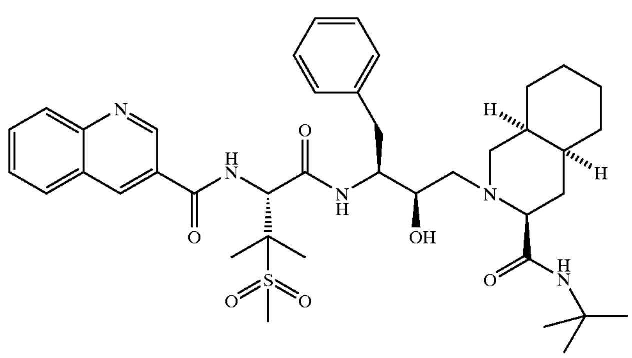 |

-continued

| Name | Structures |
|---|---|
| 2-[3(S)-[[N-(Benzylcarbamoyl)-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 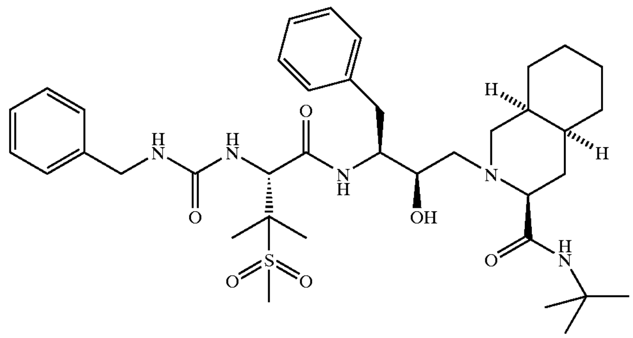 |
| N-tert-Butyl-1,2,3,4,4a(S),5,6,7,8,8a(S)-decahydro-2-[2(R)-hydroxy-3(S)-[[3-(methanesulfonyl)-N-[N-methyl-N-[(4-pyridyl)methyl]carbamoyl]-L-valyl]amino]-4-phenylbutyl]-3(S)-isoquinolinecarboxamide | 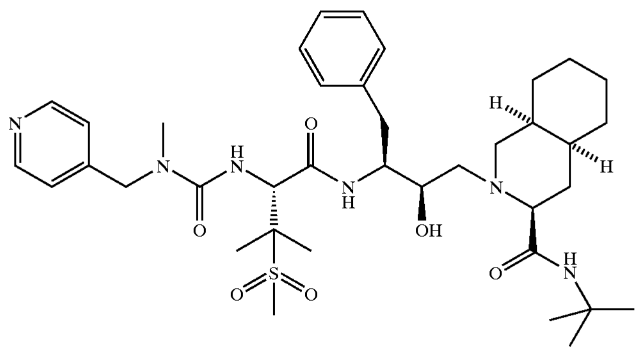 |
| N-tert-Butyl-1,2,3,4,4a(S),5,6,7,8,8a(S)-decahydro-2-[2(R)-hydroxy-3(S)-[[3-(methanesulfonyl)-N-[N-methyl-N-[(3-pyridyl)methyl]carbamoyl]-L-valyl]amino]-4-phenylbutyl]-3(S)-isoquinolinecarboxamide | 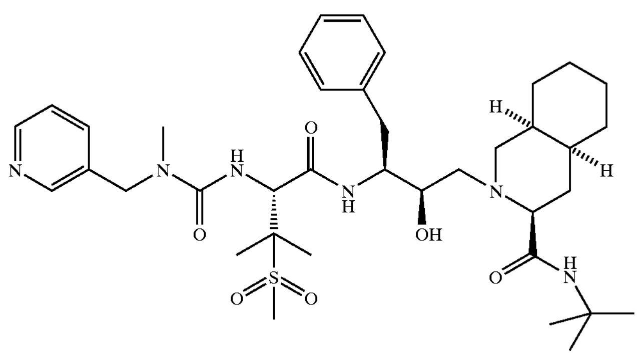 |
| N-tert-Butyl-1,2,3,4,4a(S),5,6,7,8,8a(S)-decahydro-2-[2(R)-hydroxy-3(S)-[[3-(methanesulfonyl)-N-[(5-methyl-2-furfuryl)carbamoyl]-L-valyl]amino]-4-phenylbutyl]-3(S)-isoquinolinecarboxamide | 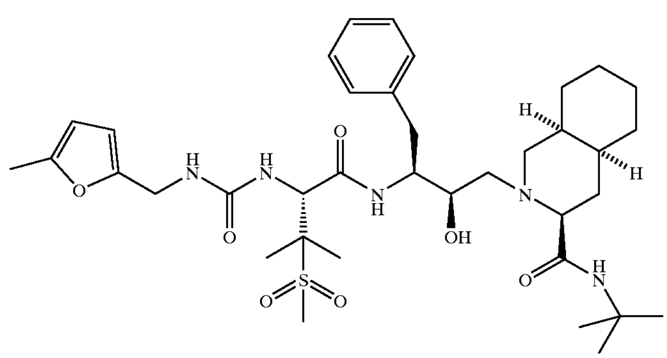 |

| Name | Structures |
|---|---|
| N-tert-Butyl-2-[3(S)-[[N-[2-(4-fluorobenzylamino)acetyl]-3-(methanesulfonyl-L-valyl]amino]-2(R)-hydroxy-4-phenylbutyl]-1,2,3,4,4a(S).5.6.7.8.8a(S)-decahydro-3(S)-isoquinolinecarboxamide | 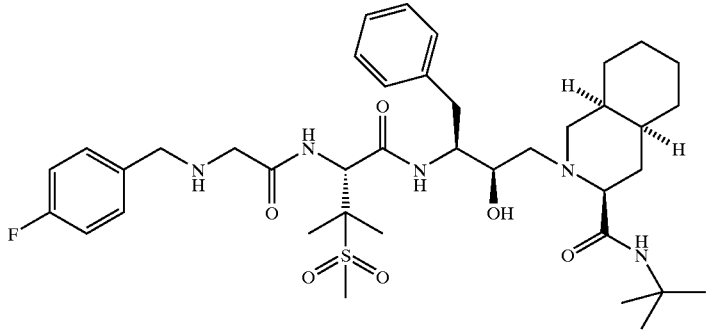 |
| 2-[3(S)-[[N-[2-(Benzylamino)acetyl]-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 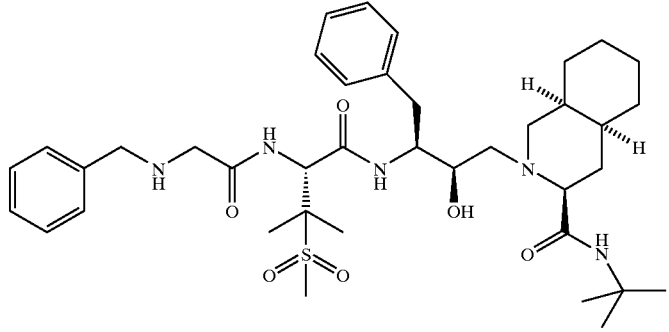 |
| 2-[3(S)-[[N-(Benzylcarbamoyl)-3-(methanesulfonyl)-L-valyl]amino]-2(R)-hydroxy-4-phenylbutyl]-N-tert-butyl-1,2,3,4,4a(S),5,6,7,8,8a(S)-decahydro-3(S)-isoquinolinecarboxamide | 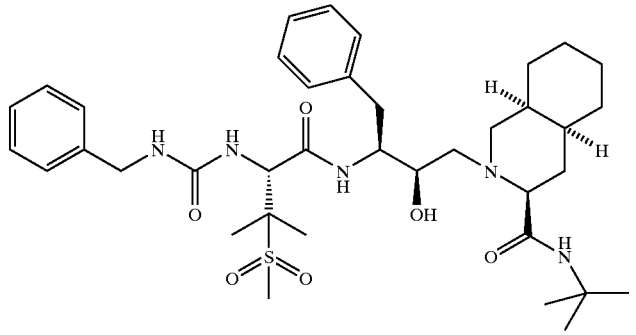 |
| N-tert-Butyl-1,2,3,4,4a(S),5,6,7,8,8a(S)-decahydro-2-[2(R)-hydroxy-3(S)-[[3-(methanesulfonyl)-N-[N-methyl-N-[(4-pyridyl)methyl]carbamoyl]-L-valyl]amino]-4-phenylbutyl]-3(S)-isoquinolinecarboxamide | 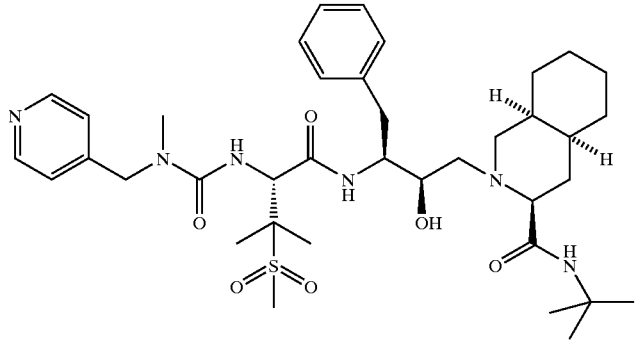 |

-continued

| Name | Structures |
|---|---|
| N-tert-Butyl-1,2,3,4,4a(S),5,6,7,8,8a(S)-decahydro-2-[2(R)-hydroxy-3(S)-[[3-(methanesulfonyl)-N-[N-methyl-N-[(3-pyridyl)methyl]carbamoyl]-L-valyl]amino]-4-phenylbutyl]-3(S)-isoquinolinecarboxamide | 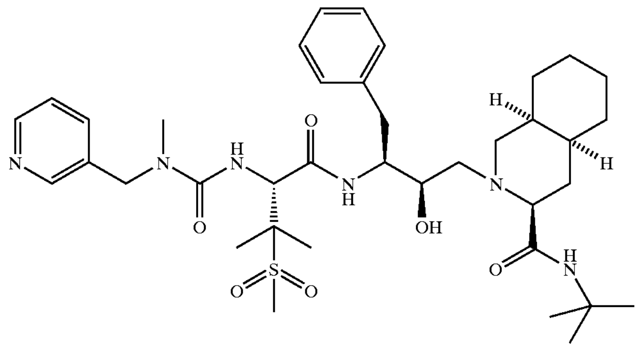 |
| N-tert-Butyl-1,2,3,4,4a(S),5,6,7,8,8a(S)-decahydro-2-[2(R)-hydroxy-3(S)-[[3-(methanesulfonyl)-N-[(5-methyl-2-furfuryl)carbamoyl]-L-valyl]amino]-4-phenylbutyl]-3(S)-isoquinolinecarboxamide | 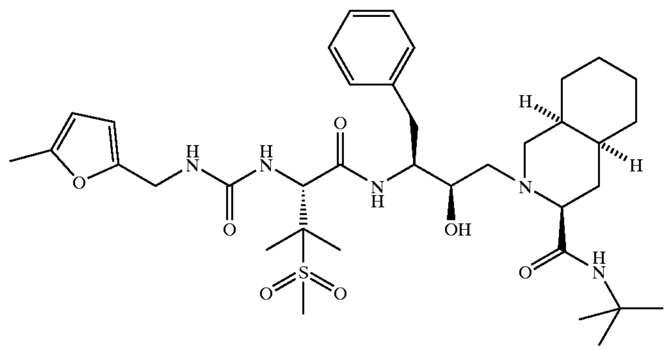 |
| N-tert-Butyl-2-[3(S)-[[N-[2-(4-fluorobenzylamino)acetyl]-3-(methanesulfonyl-L-valyl]amino]-2(R)-hydroxy-4-phenylbutyl]-1,2,3,4,4a(S).5.6.7.8.8a(S)-decahydro-3(S)-isoquinolinecarboxamide | 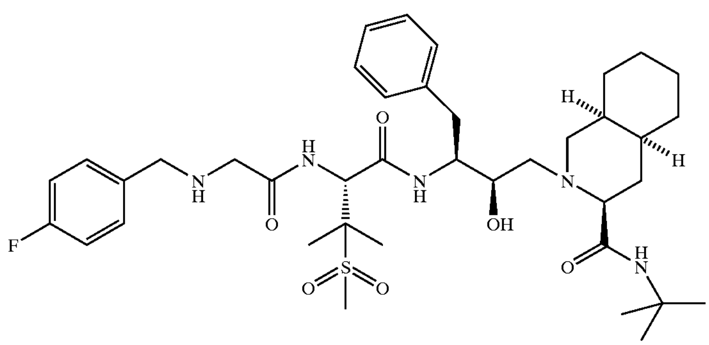 |
| 2-[3(S)-[[N-[2-(Benzylamino)acetyl]-3-(methanesulfonyl)-L-valyl]amino]-2(R)-hydroxy-4-phenylbutyl]-N-tert-butyl-1,2,3,4,4a(S).5.6.7.8.8a(S)-decahydro-3(S)-isoquinolinecarboxamide | 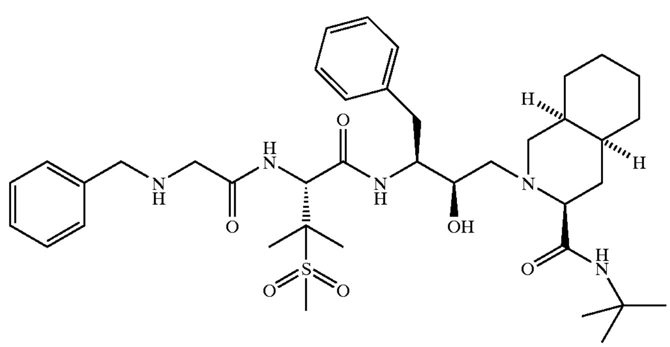 |

10. The compound according to claim 1 wherein R¹³ is —SO₂OH, —PO(OH)₂ or a group

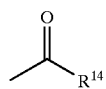

wherein R¹⁴ is alkyl, alkenyl, cycloalkyl, aryl, aryl alkyl, heterocyclyl or a group —CH₂(CH₂CH₂O)$_m$CH₃, wherein m is an integer from 0 to 10 or a carbonyl group-linked radical of an amino acid.

11. The compound according to claim 10 selected from the group consisting of:

| Name | Structures |
|---|---|
| N-tert-Butyl-1,2,3,4,4a(S),5,6,7,8,8a(S)-decahydro-2-[2(R)-(isobutyryloxy)-3(S)-[[3-(methanesulfonyl)-N-[(3-pyridyl)carbonyl]-L-valyl]amino]-4-phenylbutyl]-3(S)-isoquinolinecarboxamide | 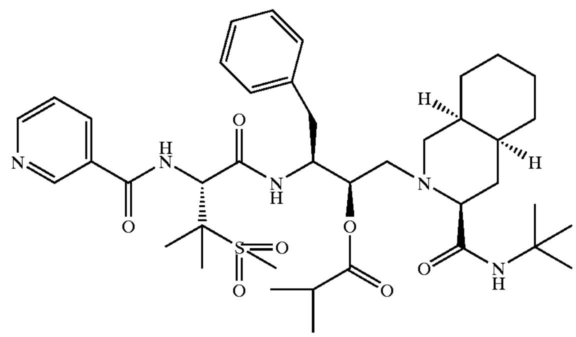 |
| N-tert-Butyl-1,2,3,4,4a(S),5,6,7,8,8a(S)-decahydro-2-[2(R)-(isobutyryloxy)-3(S)-[[3-(methanesulfonyl)-N-[2-(3-pyridyloxy)acetyl]-L-valyl]amino]-4-phenylbutyl]-3(S)-isoquinolinecarboxamide | 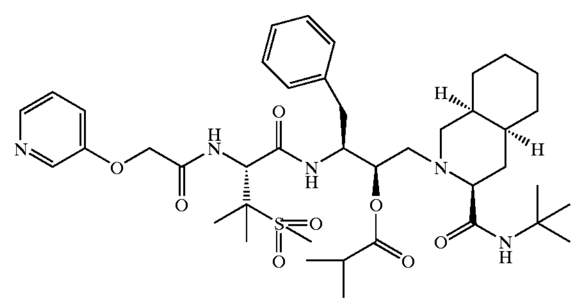 |
| N-tert-Butyl-1,2,3,4,4a(S),4,5,6,8,8(a)-decahydro-2-[3(S)-[[3-(methanesulfonyl)-N-[(3-pyridyl)carbonyl]-L-valyl]amino]-4-phenyl-2(R)-)L-valyloxy)butyl]-3(S)-isoquinolinecarboxamide | 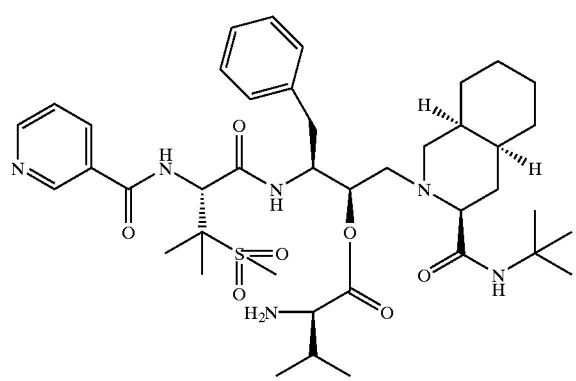 |

-continued

| Name | Structures |
|---|---|
| N-tert-Butyl-1,2,3,4,4a(S),5,6,7,8,8a(S)-decahydro-2-[3(S)-[[N-[(2-indolyl)carbonyl]-3-(methanesulfonyl)-L-valyl]amino]-2(R)-[4-(morpholinomethyl)benzoyloxy]-4-phenylbutyl]-3(S)-isoquinolinecarboxamide | 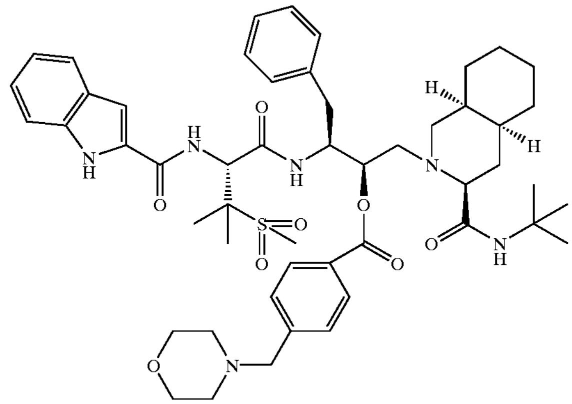 |
| N-tert-Butyl-2-[3(S)-[[N-(3-cyanobenzoyl)-3-(methanesulfonyl)-L-valyl]amino]-2(R)-[2-[2-(2-methoxyethoxy)ethoxy]acetoxy]-4-phenylbutyl]-1,2,3,4,4a(S),5,6,7,8,8a(S)-decahydro-3(S)-isoquinolinecarboxamide | 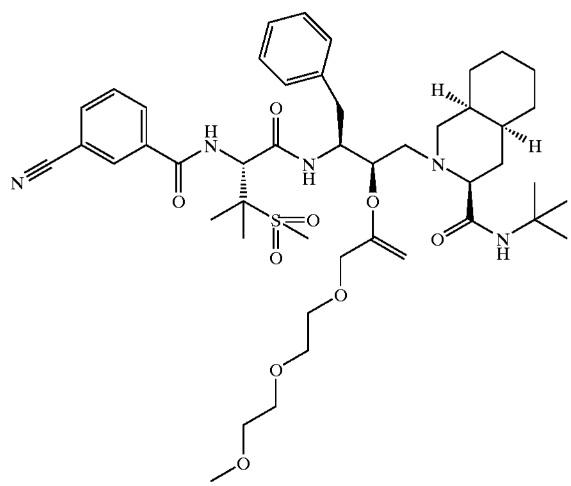 |
| N-tert-Butyl-2-∂2(R)-(3-carboxypropionyloxy)-3(S)-[[3-(methanesulfonyl)-N-[(3-pyridyl)carbonyl]-L-valyl]amino]-4-phenylbutyl]-1,2,3,4,4a(S),5,6,7,8,8a(S)decahydro-3(S)-isoquinolinecarboxamide | 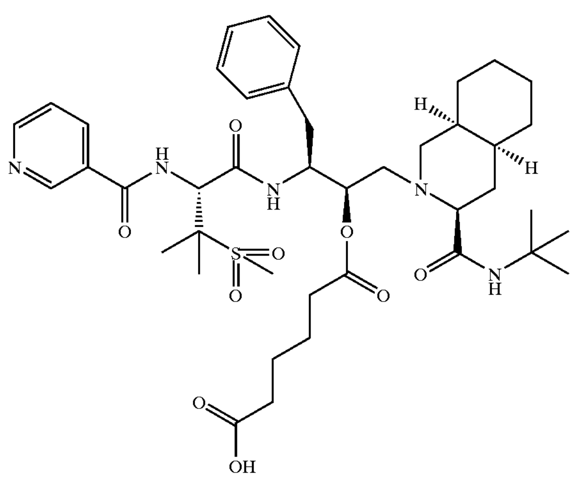 |

12. The compound according to claim 1 of the formula

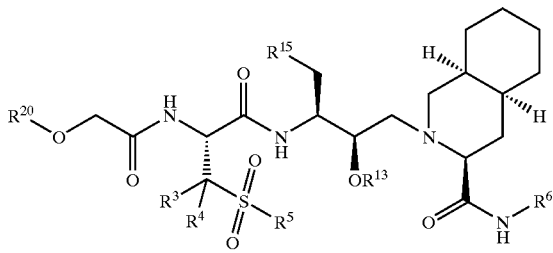

wherein R²⁰ is heterocyclyl.

13. The compound according to claim 12 wherein $R^3$, $R^4$ and $R^5$ are methyl, $R^6$ is tert-butyl, $R^{13}$ is H and $R^{15}$ is phenyl.

14. The compound according to claim 12 wherein $R^3$, $R^4$ and $R^5$ are methyl, $R^6$ is tert-butyl, $R^{15}$ is phenyl, and $R^{20}$ is pyridyl.

15. N-tert-Butyl-1,2,3,4,4a(S),5,6,7,8a(S)-decahydro-2-[2(R)-hydroxy-3(S)-[[3-methanesulfonyl)-N-[2-(3-pyridyloxy)acetyl]-L-valyl]amino]-4-phenylbutyl]-3(S)-isoquinolinecarboxamide and pharmaceutically acceptable salts thereof.

16. A pharmaceutical composition comprising as the active ingredient a pharmaceutically effective amount of a compound according to claim 1 and at least one pharmaceutically acceptable excipient.

17. A method for the treatment of HIV infection in a mammal comprising administering a therapeutically effective dosage of the pharmaceutical composition according to claim 16.

* * * * *

UNITED STATES PATENT AND TRADEMARK OFFICE
CERTIFICATE OF CORRECTION

PATENT NO.     : 6,472,404 B1
DATED          : October 29, 2002
INVENTOR(S)    : Joseph A. Martin et al.

It is certified that error appears in the above-identified patent and that said Letters Patent is hereby corrected as shown below:

Column 252, the structure of the sixth compound in claim 11 should be:

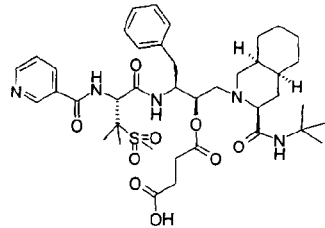

Signed and Sealed this

First Day of July, 2003

JAMES E. ROGAN
*Director of the United States Patent and Trademark Office*